United States Patent [19]
Marui et al.

[11] Patent Number: 6,030,967
[45] Date of Patent: Feb. 29, 2000

[54] NAPHTHOLACTAMS AND LACTONES AS BONE MORPHOGENETIC PROTEIN ACTIVE AGENTS

[75] Inventors: Shogo Marui, Hyogo; Masatoshi Hazama; Kohei Notoya, both of Osaka; Masaki Ogino, Hyogo, all of Japan

[73] Assignee: Takeda Chemical Industries, Ltd., Osaka, Japan

[21] Appl. No.: 08/945,631

[22] PCT Filed: Aug. 19, 1997

[86] PCT No.: PCT/JP97/02858

§ 371 Date: Oct. 30, 1997

§ 102(e) Date: Oct. 30, 1997

[87] PCT Pub. No.: WO98/07705

PCT Pub. Date: Feb. 26, 1998

[30] Foreign Application Priority Data

Aug. 20, 1996 [JP] Japan ..................... 8-218353
Apr. 24, 1997 [JP] Japan ..................... 9-107617

[51] Int. Cl.$^7$ ................ A61K 31/365; A61K 31/40; C07D 217/24; C07D 317/48
[52] U.S. Cl. ................ 514/215; 514/217; 514/232.8; 514/287; 514/290; 514/410; 514/411; 540/521; 540/522; 544/125; 544/126; 546/65; 546/110; 548/421; 548/423; 548/450; 548/451
[58] Field of Search ..................... 540/521, 522; 544/125, 126; 546/65, 110; 548/421, 423, 450, 451; 514/215, 217, 237.8, 287, 290, 410, 411

[56] References Cited

U.S. PATENT DOCUMENTS

| | | | |
|---|---|---|---|
| 3,558,632 | 1/1971 | Diebold et al. | 260/287 |
| 3,649,632 | 3/1972 | Diebold et al. | 260/279 R |
| 3,691,168 | 9/1972 | Wolf et al. | 260/283 S |
| 3,704,247 | 11/1972 | Munakata et al. | 260/340.5 |
| 3,987,047 | 10/1976 | Griss et al. | 260/287 CF |
| 4,771,072 | 9/1988 | Iwasaki et al. | 514/533 |

FOREIGN PATENT DOCUMENTS

| | | |
|---|---|---|
| 0380982 | 8/1990 | European Pat. Off. . |
| 0585913 | 3/1994 | European Pat. Off. . |
| 0634169 | 1/1995 | European Pat. Off. . |
| 2357253 | 5/1975 | Germany . |
| 62-142169 | 6/1987 | Japan . |
| 62-142170 | 6/1987 | Japan . |
| 62-207213 | 9/1987 | Japan . |
| 63-146845 | 6/1988 | Japan . |
| 2149545 | 6/1990 | Japan . |
| 2160248 | 6/1990 | Japan . |
| 2160583 | 6/1990 | Japan . |
| 3081274 | 4/1991 | Japan . |
| 4211609 | 8/1992 | Japan . |
| 4321681 | 11/1992 | Japan . |
| WO 08155 | 4/1993 | WIPO . |
| WO 25929 | 8/1996 | WIPO . |

OTHER PUBLICATIONS

Klemm et al., J. Org. Chem., vol. 41, No. 15 (1976) 2571–79.
Sakakibara et al., Chemical Abstracts, vol. 113, abstract 218225, 1990.
Aly et al., Chemical Abstracts, vol. 110, abstract 154089, 1989.
Bedair et al., Chemical Abstracts, vol. 109, abstract 128765, 1988.
Krepelka et al., Chemical Abstracts, vol. 97, abstract 38903, 1982.
Krepelka et al., Chemical Abstracts, vol. 101, abstract 130583, 1984.
Moussa, Chemical Abstracts, vol. 101, abstract 211074, 1984.
Krepelka et al., Chemical Abstracts, vol. 96, abstract 217631, 1982.
Baddar et al., Chemical Abstracts, vol. 81, abstract 37417, 1974.
Baddar et al., Chemical Abstracts, vol. 74, abstract 125247, 1971.

*Primary Examiner*—Richard L. Raymond
*Attorney, Agent, or Firm*—Fitzpatrick, Cella, Harper & Scinto

[57] ABSTRACT

A compound of the formula:

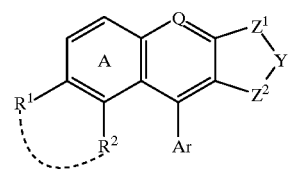

[I]

wherein
Q is an optionally substituted carbon atom or N(O)p wherein p is 0 or 1;
Y is an optionally substituted methylene group, S(O)q wherein q is an integer of 0 to 2, or an optionally substituted imino group;
$Z^1$ is a $C_{1-3}$ alkylene group which may have an oxo group or a thioxo group and may contain etherified oxygen or sulfur within the carbon chain;
$Z^2$ is an optionally substituted $C_{1-3}$ alkylene group;
Ar is an optionally substituted carbocyclic group or an optionally substituted heterocyclic group;
one of $R^1$ and $R^2$ is a hydrogen atom, a halogen atom, a hydroxyl group, an optionally substituted lower alkyl group, or an optionally substituted lower alkoxy group;
the other is a halogen atom, a hydroxyl group, an optionally substituted lower alkyl group, or an optionally substituted lower alkoxy group; or
$R^1$ and $R^2$ taken together with adjacent —c=c— form a ring; and
ring A is a benzene ring which may be substituted in addition to $R^1$ and $R^2$; or a salt thereof.

19 Claims, No Drawings

NAPHTHOLACTAMS AND LACTONES AS BONE MORPHOGENETIC PROTEIN ACTIVE AGENTS

This application is a 371 of PCT/97/02858, filed Aug. 19, 1997.

TECHNICAL FIELD

This invention relates to fused cyclic compounds having very satisfactory bone morphogenetic protein (BMP) like and/or neurotrophic factor [for example, nerve growth factor (NGF), brain-derived neurotrophic factor (BDNF), neurotrophin-3 (NT-3), and glial cell line-derived neurotrophic factor (GDNF)]-like activity or enhancing activity of BMP and/or neurotrophic factor activity, to a technology for producing the compound, and to relevant pharmaceutical compositions.

BACKGROUND ART

Bone morphogenetic proteins (BMPs) are the family of proteins isolated from demineralized bone and known to be able to induce ectopic bone formation. As such, BMP is of value as a bone formation promoting agent for bone fracture healing and bone remodeling [A. E. Wang, Trends Biotechnol., 11, 379–383, 1993].

Furthermore, since it directly promotes osteoblast differentiation, BMP is supposed to be playing the role of a coupling factor in bone remodeling and is, therefore, considered to be closely associated with bone metabolism. It has also been reported that the BMP content of bone matrix in aged animals has been considerably depressed [M. L. Urist, Bone and Mineral Research, 6 (ed by W. A. Peck), 57–112, Elsevier, 1989], indicating that BMP is closely related to the maintenance of bone mass. This finding suggests that BMP may be a promising drug for the treatment of various diseases of bone, such as osteoporosis. However, BMP usually exists only in trace amounts in the organisms, and sources of its supply were limited. Moreover, as it is a protein, the routes of administration are restricted, and therefore the spectrum of diseases which can be treated is quite limited.

It has also been reported that BMP has neurotrophic factor-like activity [V. M. Paralkar et al., J. Cell Biol., 119, 1721–1728, 1992]. Also known is an intense expression of the BMP gene in the brain tissue [E. Ozkaynak et al., Biochem. Biophys. Res. Commun., 179, 116–123, 1991]. It has also been suggested that BMP is playing an important role in the formation of the neural tube during embryonic development [K. Basler et al., Cell, 73, 687–702, 1993]. It is, therefore, believed that BMP is closely involved in the differentiation or functional maintenance of nerve cells.

Neurotrophic factor (NTF) is a family of proteins playing important roles in the maintenance of neuron and functional expression of neurons and includes nerve growth factor (NGF), brain-derived neurotrophic factor (BDNF), neurotrophin-3 (NT-3), and glial cell line-derived neurotrophin factor (GDNF), among others. NGF in the peripheral nervous system promotes the differentiation and maturation of the neural crest sympathetic ganglion and dorsal root ganglion cells [A. M. Davies & R. M. Lindsay, Dev. Biol., 111, 62–72, 1985; R. Levi-Montalcini, EMBO J., 6, 1145–1154, 1987] and in the central nervous system acts on the cholinergic neurons of septa (forebrain basal ganglia) [H. Gnahn et al, Dev. Brain Res., 9, 45–52, 1983; H. Hatanaka & H. Tsukui, Dev. Brain Res., 30, 47–56, 1986; F. Hefti, J. Neurosci., 6, 2155–2162, 1986]. NGF is necessary for the maintenance of nerve function even after completion of differentiation of neurons. BDNF in the peripheral nervous system acts on the dorsal root ganglion and nodular ganglion cells but does not act on sympathetic ganglion cells [R. M. Lindsay & H. Rohrer, Dev. Biol., 112, 30–48, 1985; R. M. Lindsay et al., Dev. Biol., 112, 319–328, 1985; A. M. Davies et al., J. Neurosci., 6, 1897–1904, 1986]. In the central nervous system, BDNF acts on the cholinergic neurons and GABA (γ-aminobutyric acid)-nergic neurons of septa and the dopaminergic neurons of midbrain [R. F. Alderson et al., Neuron, 5, 297–306, 1990; C. Hyman et al., Nature, 350, 230–232, 1991; B. Knusel et al., Proc. Natl. Acad. Sci. USA, 88, 961–965, 1991]. The activites of NT-3 on the peripheral nervous system are similar to that of NGF and BDNF, however NT-3 characteristically acts strongly on neural placodes-derived sensory neurons [P. Ernfors et al., Proc. Natl. Acad. Sci. USA, 87, 5454–5458, 1990; A. Rosenthal et al., Neuron, 4, 767–773, 1990]. In the central nervous system, however, there is not known a nerve cell responsive to NT-3.

GDNF promotes the survival and morphelogical differentiation of dopaminergic neurons and increases their high affinity dopamine uptake [L-F. H. Lin et al., Science, 260, 1130–1132 (1993)].

In Alzheimer type dementia, the degeneration and exfoliation of cholinergic neurons of the forebrain basal ganglia inclusive of septa and an extensive lesion and exfoliation of cerebrocortical neurons have been observed. The NGF and neurotrophic factors discovered more recently are considered among candidate therapeutic drugs for this disease [F. Hefti & W. J. Weiner, Annu. Neurol., 20, 275–281, 1986]. Furthermore, in Parkinson's disease which is a syndrome involving the degeneration and exfoliation of dopaminergic neurons of midbrain, BDNF and GDNF as neurotrophic factors for the associated neurons have been considered to be a promising therapeutic drugs. However, since those neurotrophic factors are proteins,. their applicability is limited.

As compounds in the lactone series which are of use as synthetic intermediates for the fused cyclic compound [I] of the present invention, the following compounds have been disclosed.

(1) Helioxanthin, which has the following formula

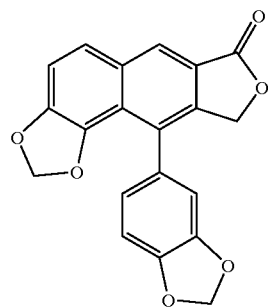

[R. S. Burden et al., J. Chem. Soc. (C), 693–701, 1969]

(2) Compounds of the following formulas

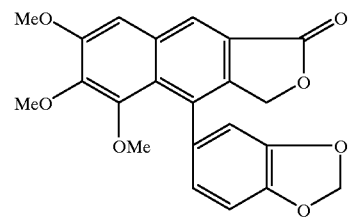

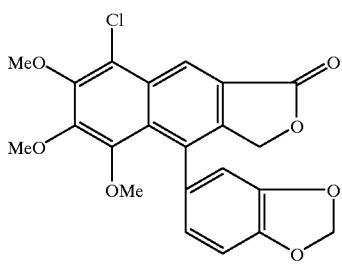
[Arch. Pharmacol., 328 (9), 640–644, 1995]
(3) Compounds of the following formulas
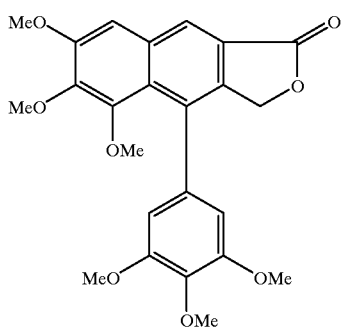
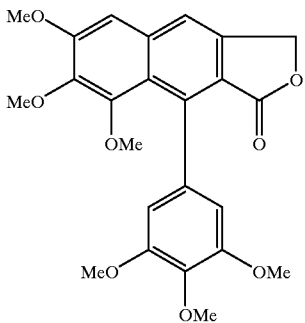
[Indian J. Chem., Sect. B: Org. Chem. Include. Med. Chem., 33B (9), 839–846, 1994]
(4) Compounds of the following formulas
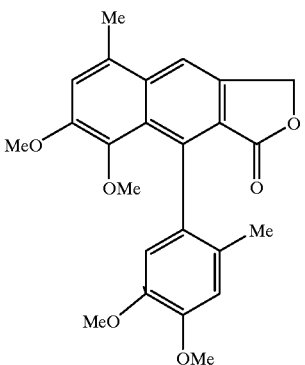
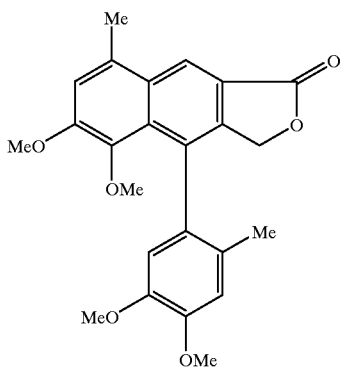
[Indian J. Chem. Sect. B: 31B (7), 401–406, 1992]
(5) Compounds of the following formulas
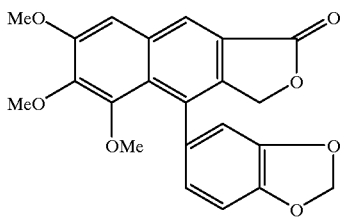
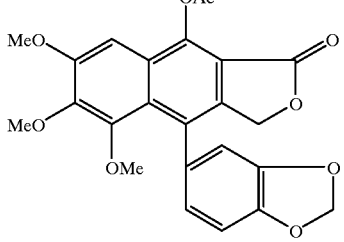
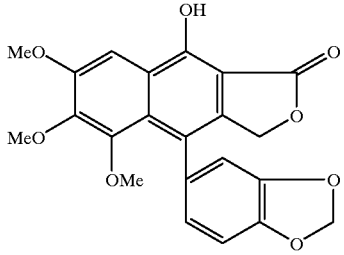
[Chem. Pharm. Bull., 32 (1), 31–7, 1984]
(6) Compounds of the following formulas
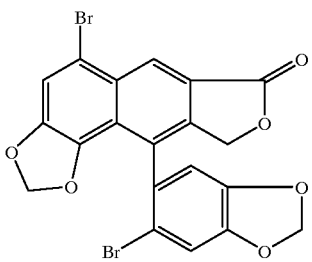

-continued
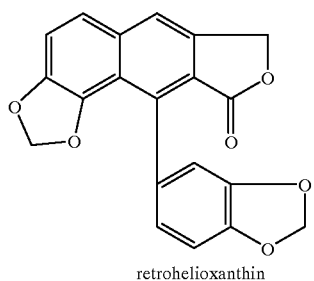
retrohelioxanthin
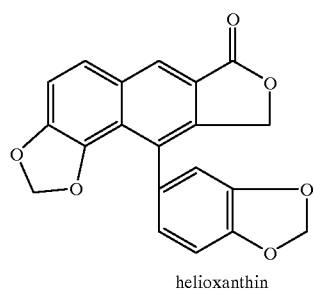
helioxanthin
[J. Chem. Soc. B, (11), 2091–2094, 1971]
(7) Compounds of the following formula
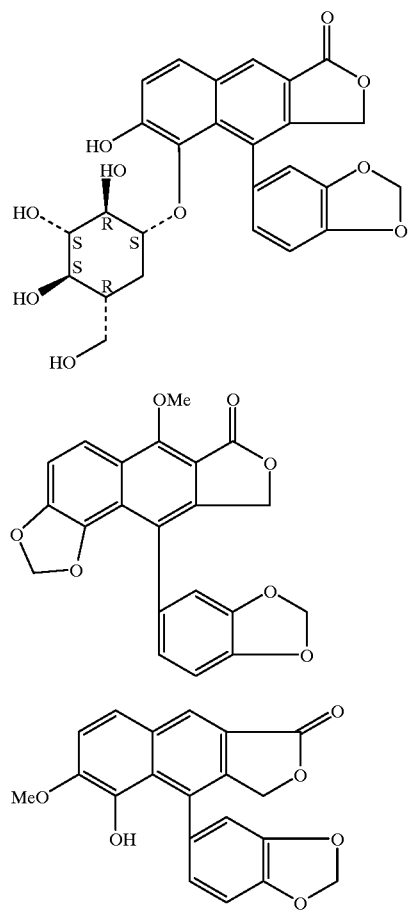
-continued
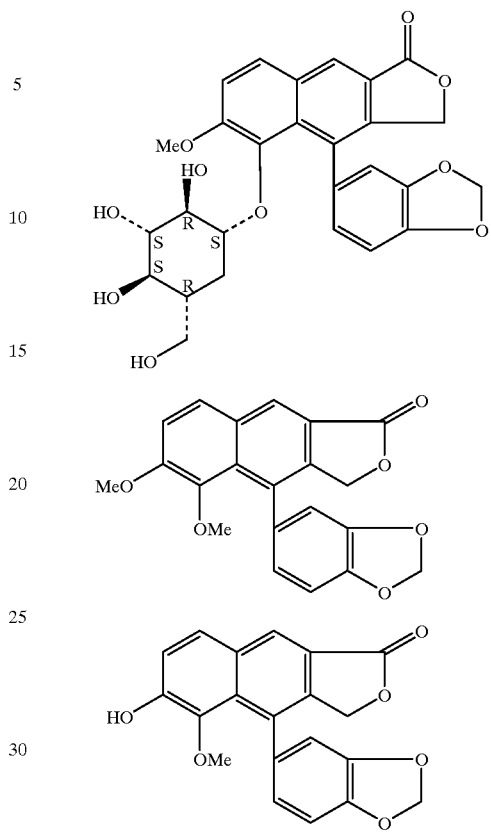
[Phytochemistry, 29 (9), 2991–2993, 1990]
(8) Compounds of the following formulas
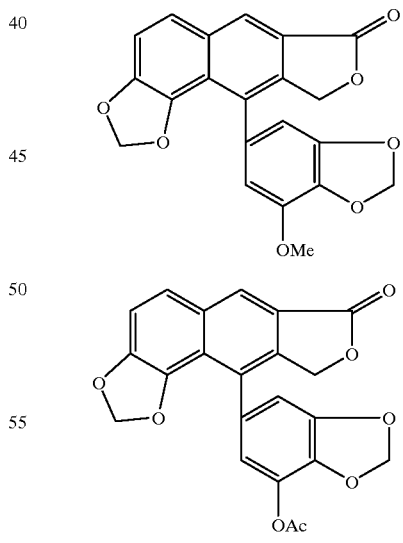

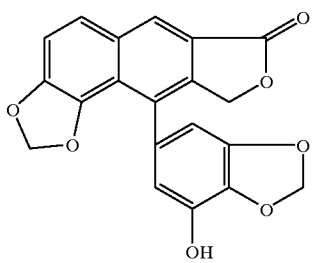

[Journal of Natural Products, 43 (4), 482–486, 1980]
(9) A compound of the following formula

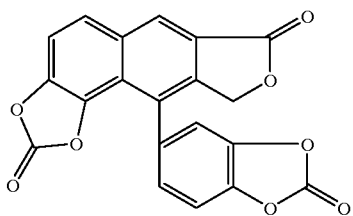

[J. Chem. Soc. C, (5), 693–701, 1969]

However, none of the above publications disclosing those lactone compounds (1) through (9) mention or even. suggest the excellent activities of the fused cyclic compounds of the present invention as cell differentiation inducing factors, such as bone morphogenetic protein (BMP) or neurotrophic factor (NTF), or activity of enhancing the cell differentiation inducing factor.

The foregoing suggests that compounds which enhance the activities of BMP can enhance the activities of BMP in vivo, whether endogenous or exogenous, and as such would be of value as a therapeutic agent for the above-mentioned diseases of bone. The substances reported to date as having such enhancing effects on BMP activities are retinoic acid, vitamin D3, estrogen, and glucocorticoids [V. Rosen & R. S. Thies, Trends Genet., 8, 97–102, 1992; Y. Takuwa et al., Biochem. Biophys. Res. Commun., 174, 96–101, 1991]. However, it is known that when administered, those substances promote bone resorption and/or cause such adverse reactions as hypercalcemia and ovarian cancer, and are thus not fully satisfactory as therapeutic drugs for diseases of bone.

Meanwhile, any compound capable of enhancing NTF activity should be able to enhance the activities of NTF in vivo, whether endogenous or exogenous, and be of value as a therapeutic drug for dementia and peripheral nervous disorders. As compounds enhancing activities of NGF, sabeluzole (4-(2-benzothiazolylmethylamino)-α-(p-fluorophenoxy)methyl]-1-(piperidine)ethanol) has been reported [New Current, 4, 26, 14, 1993]. However, its mechanism of action is not known and because such adverse reactions as headache, dizziness, and fatigue have been reported in clinical trials, this compound is not necessarily a suitable therapeutic drug for nerve diseases. Aside from the above, SR57746A [Neuroscience, 55, 629, 1993], T-588 [JP Kokai H4-95070], and MS430 [J. UOEN, 17, 131, 1995] are also claimed have NGF-like activity. SR57746A and T-588 are currently under clinical investigation in Alzheimer's disease but their efficacy in humans has not been established. As to MS430, its activity is suspected to be insufficient. As compounds up-regulating endogenous NGF, steroids, catechols, and cytokines have been reported [Experimental Neurology, 124, 36–42, 1993]. However, some of those compounds are neurotoxic or have pharmacologically unfavorable actions that compromise immunological potency or cause hypercalcemia, accelerated bone resorption, etc. and because no clear line of demarcation can be drawn in the state of the art between the NGF secretion inducing effect and the adverse effect on tissues other than the nervous system, those compounds are not fully satisfactory for clinical application.

Furthermore, since cell differentiation inducing factors represented by BMP and neurotrophic factors are proteins, their administration to the living body is limited. Thus, compounds which enhance the cell differentiation inducing factors, whether endogenous or exogenous, are preferably of low molecular weight.

Assuming that a compound itself has cell differentiation inducing activity which is typically possessed by BMP and neurotrophic factors, it is considered that, if its molecular weight is low, the compound can be used with greater advantage than BMP and neurotrophic factors for application to the living body as a drug for promoting bone formation and bone remodeling or a therapeutic drug for dementia and peripheral nerve diseases.

As low molecular-weight compounds known to promote the proliferation and differentiation of osteoblasts, iprifla-vone [K. Notoya et al., J. Bone Miner. Res., 9, 395–400, 1994], vitamin K2 (Y. Akedo et al., Biochem. Biophys. Res. Commun., 187, 814–820, 1992], etc. are known but none of those known substances have ectopic osteoinductive activity like BMP.

As compounds having neurotrophic factor-like activities such as neurite sprouting activity and promotion of the survival of neurons lactacystin [S. Omura et al., J. Antibiot., 40, 113–117, 1991], retionic acid [M. Minana et al., Prod. Natl. Acad. Sci. USA, 87, 4335–4339, 1990], staurosporine [T. B. Shea et al., J. Neurosci. Res., 33, 398–407, 1990], K252a [G. D. Borasio et al., Neuroscience Letters, 108, 207–212, 1990], and MS818 [A. Awaya et al., Biol. Pharm. Bull., 16, 248–253, 1993], among others, are known. It is reported that above-mentioned SR57746A and MS430 have not only enhancing activity but also neurotrophic factor-like activity by themselves, too. However, as to SR57746A, among them, its efficacy in humans has not been established as pointed out above, while the other compounds are not fully satisfactory for clinical application, either, in terms of the levels of activity and toxicological risk. Therefore, there has been a real need for development of a compound having satisfactory BMP or neurotrophic activity or the corresponding agonist activity from among compounds structurally different from the above known substances.

In view of the above state of the art and for the purpose of developing a low-molecular-weight drug substance having BMP- or neurotrophic factor-like activity or the specific enhancing effect on the differentiation of osteoblasts and neurons and promotion of the survival of neurons, the inventors of the present invention explored for low molecular compounds which would exhibit cell differentiation inducing factors activity or enhancing effect on these factors. As a consequence, the inventors succeeded for the first time in the creation of a novel compound of the following formula [I], inclusive of its salt.

[I]

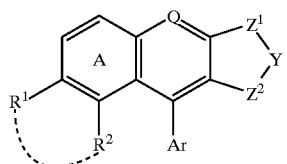

wherein
Q is an optionally substituted carbon atom or N(O)p wherein p is 0 or 1;
Y is an optionally substituted methylene group, S(O)q wherein q is an integer of 0 to 2, or an optionally substituted imino group;
$Z^1$ is a $C_{1-3}$ alkylene group which may have an oxo group or a thioxo group;
$Z^2$ is an optionally substituted $C_{1-3}$ alkylene group;
Ar is an optionally substituted carbocyclic group or an optionally substituted heterocyclic group;
one of $R^1$ and $R^2$ is a hydrogen atom, a halogen atom, a hydroxyl group, an optionally substituted lower alkyl group, or an optionally substituted lower alkoxy group;
the other is a halogen atom, a hydroxyl group, an optionally substituted lower alkyl group, or an optionally substituted lower alkoxy group; or
$R^1$ and $R^2$ taken together with adjacent —c=c— form a ring; and
ring A is a benzene ring which may have a substituent in addition to $R^1$ and $R^2$; or a salt thereof. The inventors further found that the above compound [I] and its salt have unexpectedly high BMP-like activity, neurotrophic factor-like activity or the corresponding enhancing activity and are well qualified as medicines. The present invention has been developed on the basis of the above finding.

DISCLOSURE OF INVENTION

The present invention, therefore, is directed to:
1. A compound of the formula:

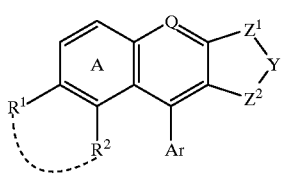

[I]

wherein
Q is an optionally substituted carbon atom or N(O)p wherein p is 0 or 1;
Y is an optionally substituted methylene group, S(O)q wherein q is an integer of 0 to 2, or an optionally substituted imino group;
$Z^1$ is a $C_{1-3}$ alkylene group which may have an oxo group or a thioxo group and may contain etherified oxygen or sulfur within the carbon chain;
$Z^2$ is an optionally substituted $C_{1-3}$ alkylene group;
Ar is an optionally substituted carbocyclic group or an optionally substituted heterocyclic group;
one of $R^1$ and $R^2$ is a hydrogen atom, a halogen atom, a hydroxyl group, an optionally substituted lower alkyl group, or an optionally substituted lower alkoxy group;
the other is a halogen atom, a hydroxyl group, an optionally substituted lower alkyl group, or an optionally substituted lower alkoxy group; or
$R^1$ and $R^2$ taken together with adjacent —c=c— form a ring; and
ring A is a benzene ring which may be substituted in addition to $R^1$ and $R^2$; or a salt thereof,
2. A compound as described in the above item 1, wherein Q is (A) $CR^4$ wherein $R^4$ is (1) a hydrogen atom, (2) a halogen atom, (3) a $C_{1-16}$ acyclic or cyclic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{3-6}$ cycloalkyl, (vii) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (viii) a $C_{1-6}$ alkylthio optionally having 1 to 3 halogen atoms, (ix) a hydroxyl, (x) an amino, (xi) a mono-$C_{1-6}$ alkylamino, (xii) a di-$C_{1-6}$ alkylamino, (xiii) a $C_{1-6}$ alkyl-carbonyl, (xiv) a $C_{1-6}$ alkyl-carbonyloxy, (xv) a $C_{1-6}$ alkyl-carbonyloxy-$C_{1-3}$ alkyl, (xvi) a carboxyl, (xvii) a $C_{1-6}$ alkoxy-carbonyl, (xviii) a mono-$C_{1-6}$ alkylamino-carbonyl, (xix) a di-$C_{1-6}$ alkylamino-carbonyl, (xx) a carbamoyl, (xxi) a mono-$C_{1-6}$ alkyl-carbamoyl, (xxii) a di-$C_{1-6}$ alkyl-carbamoyl, (xxiii) a sulfo, (xxiv) a $C_{1-6}$ alkylsulfonyl, (xxv) a $C_{6-10}$ aryl, (xxvi) a $C_{6-10}$ aryloxy, (xxvii) a 5- to 7-membered heterocyclic group having 1 to 4 hetero atoms selected from nitrogen, oxygen and sulfur in addition to carbon atoms, said heterocyclic group being optionally fused with a benzene ring, (xxviii) thiocarbamoyl, (xxix) mono-$C_{1-6}$ alkylthio-carbamoyl, (xxx) di-$C_{1-6}$ alkylthio-carbamoyl, (xxxi) $C_{6-10}$ aryl-carbamoyl and (xxxii) $C_{6-10}$ aryl-thiocarbamoyl, or (4) a hydroxyl group which may be substituted with a $C_{1-16}$ acyclic or cyclic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{3-6}$ cycloalkyl, (vii) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (viii) a $C_{1-6}$ alkylthio optionally having 1 to 3 halogen atoms, (ix) a hydroxyl, (x) an amino, (xi) a mono-$C_{1-6}$ alkylamino, (xii) a di-$C_{1-6}$ alkylamino, (xiii) a $C_{1-6}$ alkyl-carbonyl, (xiv) a $C_{1-6}$ alkyl-carbonyloxy, (xv) a $C_{1-6}$ alkyl-carbonyloxy-$C_{1-3}$ alkyl, (xvi) a carboxyl, (xvii) a $C_{1-6}$ alkoxy-carbonyl, (xviii) a mono-$C_{1-6}$ alkylamino-carbonyl, (xix) a di-$C_{1-6}$ alkylamino-carbonyl, (xx) a carbamoyl, (xxi) a mono-$C_{1-6}$ alkyl-carbamoyl, (xxii) a di-$C_{1-6}$ alkyl-carbamoyl, (xxiii) a sulfo, (xxiv) a $C_{1-6}$ alkylsulfonyl, (xxv) a $C_{6-10}$ aryl, (xxvi) a $C_{6-10}$ aryloxy, (xxvii) a 5- to 7-membered heterocyclic group having 1 to 4 hetero atoms selected from nitrogen, oxygen and sulfur in addition to carbon atoms, said heterocyclic group being optionally fused with a benzene ring, (xxviii) thiocarbamoyl, (xxix) mono-$C_{1-6}$ alkylthio-carbamoyl, (xxx) di-$C_{1-6}$ alkylthio-carbamoyl, (xxxi) $C_{6-10}$ aryl-carbamoyl and (xxxii):$C_{6-10}$ aryl-thiocarbamoyl;
or (B) N(O)p wherein p is 0 or 1;
Y is (1) a group of the formula:

wherein $R^9$ and $R^{9'}$ may be the same or different and each is (i) a hydrogen, (ii) a $C_{1-6}$ alkyl which may be substituted with amino, mono- or di-$C_{1-6}$ alkylamino or $C_{1-6}$ alkoxycarbonyl, and optionally having 1 to 3 halogen atoms, (iii) a $C_{1-6}$ alkoxy optionally having 1 to 3 halogen atoms, (iv) a $C_{1-6}$ alkylthio optionally having 1 to 3 halogen atoms, (v) a hydroxyl, (vi) a cyano, (vii) a $C_{1-6}$ alkyl-carbonyl, (viii) a $C_{1-6}$ alkyl-carbonyloxy, (ix) a formylamino, (x) an amino, (xi) a mono-$C_{1-6}$ alkylamino, (xii) a di-$C_{1-6}$ alkylamino, (xiii) a carboxyl, (xiv) a $C_{1-6}$ alkoxy-carbonyl, or (xv) a $C_{1-6}$ alkyl-carbonylamino;

(2) a group of the formula:

wherein $R^{10}$ is (i)

in which $R^9$ and $R^{9'}$ are as defined above, (ii) $=NR^9$ in which $R^9$ is as defined above, (iii) O or (iv) S;
(3) $=S(O)q$ wherein q is an integer of 0 to 2; or
(4) $=NR^5$ wherein $R^5$ is (i) a hydrogen, (ii) a $C_{1-16}$ acyclic or cyclic hydrocarbon group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from nitrogen, oxygen and sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl, (iii) —(C=O)—$R^7$ wherein $R^7$ is a hydrogen or a $C_{1-16}$ acyclic or cyclic hydrocarbon group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) 5- or 6-membered cyclic amino optionally having hydroxyl or oxo, (n) —NHCOOR$^6$ wherein $R^6$ is a $C_{1-16}$ acyclic or cyclic hydrocarbon group which may have 1 to 5 substituents selected from the group consisting of (n-1) a halogen, (n-2) a $C_{1-3}$ alkylenedioxy, (n-3) a nitro, (n-4) a cyano, (n-5) a $C_{1-6}$ alkyl optionally having 1 to 3 halogen atoms, (n-6) a $C_{3-6}$ cycloalkyl, (n-7) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (n-8) a $C_{1-6}$ alkylthio optionally having 1 to 3 halogen atoms, (n-9) a hydroxyl, (n-10) an amino, (n-11) a mono-$C_{1-6}$ alkylamino, (n-12) a di-$C_{1-6}$ alkylamino, (n-13) a $C_{1-6}$ alkyl-carbonyl, (n-14) a $C_{1-6}$ alkyl-carbonyloxy, (n-15) a $C_{1-6}$ alkyl-carbonyloxy-$C_{1-3}$ alkyl, (n-16) a carboxyl, (n-17) a $C_{1-6}$ alkoxy-carbonyl, (n-18) a mono-$C_{1-6}$ alkylamino-carbonyl, (n-19) a di-$C_{1-6}$ alkylamino-carbonyl, (n-20) a carbamoyl, (n-21) a mono-$C_{1-6}$ alkyl-carbamoyl, (n-22) a di-$C_{1-6}$ alkyl-carbamoyl, (n-23) a sulfo, (n-24) a $C_{1-6}$ alkylsulfonyl, (n-25) a $C_{6-10}$ aryl, (n-26) a $C_{6-10}$ aryloxy, (n-27) a 5- to 7-membered heterocyclic group having 1 to 4 hetero atoms selected from nitrogen, oxygen and sulfur in addition to carbon atoms, said heterocyclic group being optionally fused with a benzene ring, (n-28) thiocarbamoyl, (n-29) mono-$C_{1-6}$ alkylthio-carbamoyl, (n-30) di-$C_{1-6}$ carbamoyl, (n-31) $C_{6-10}$ aryl-carbamoyl and (n-32alkylthio-) $C_{6-10}$ aryl-thiocarbamoyl, (o) —NHCONHR$^6$ wherein $R^6$ is as defined above, (p) —NHCOR$^6$ wherein $R^6$ is as defined above, (q) —NHSO$_2$R$^6$ wherein $R^6$ is as defined above, (r) a $C_{1-6}$ alkyl-carbonyl, (s) a $C_{1-6}$ alkyl-carbonyloxy, (t) a $C_{1-6}$ alkyl-carbonyloxy-$C_{1-3}$ alkyl, (u) a carboxyl, (v) a $C_{1-6}$ alkoxy-carbonyl, (w) a mono-$C_{1-6}$ alkylamino-carbonyl, (x) a di-$C_{1-6}$ alkylamino-carbonyl, (y) a carbamoyl, (z) a mono-$C_{1-6}$ alkyl-carbamoyl, (aa) a di-$C_{1-6}$ alkyl-carbamoyl, (bb) a sulfo, (cc) a $C_{1-6}$ alkylsulfonyl, (dd) a $C_{6-10}$ aryl, (ee) a $C_{6-10}$ aryloxy, (ff) a 5- to 7-membered heterocyclic group having 1 to 4 hetero atoms selected from nitrogen, oxygen and sulfur in addition to carbon atoms, said heterocyclic group being optionally fused with a benzene ring, (gg) $C_{7-11}$ aralkyloxy-carbonyl, (hh) thiocarbamoyl, (ii) mono-$C_{1-6}$ alkylthio-carbamoyl, (jj) di-$C_{1-6}$ alkylthio-carbamoyl, (kk) $C_{6-10}$ aryl-carbamoyl and (11) $C_{6-10}$ aryl-thiocarbamoyl, (iv) —SO$_2$—R$^7$ wherein $R^7$ is as defined above, (v) —SO—R$^7$ wherein $R^7$ is as defined above, (vi) —(C=O)NR$^8$—R$^7$ wherein $R^7$ is as defined above, $R^8$ is hydrogen or $C_{1-6}$ alkyl or (vii) —(C=O)O—R$^7$ wherein $R^7$ is as defined above;

$Z^1$ is a $C_{1-3}$ alkylene group which may have an oxo or thioxo group;

$Z^2$ is a $C_{1-3}$ alkylene group which may contain oxygen or sulfur within the carbon chain as an ether or thioether and may have a substituent selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from nitrogen, oxygen and sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl;

Ar is (1) a 3- to 14- membered monocyclic or fused polycyclic nonaromatic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{2-6}$ alkenyl optionally having 1 to 3 halogen atoms, (vii) a $C_{2-6}$ alkynyl optionally having 1 to 3 halogen atoms, (viii) a $C_{3-6}$ cycloalkyl, (ix) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (x) a $C_{1-6}$ alkylthio optionally having 1 to 3 halogen atoms, (xi) a hydroxyl, (xii) an amino, (xiii) a mono-$C_{1-6}$ alkylamino, (xiv) a di-$C_{1-6}$ alkylamino, (xv) 5- or 6- membered cyclic amino, (xvi) —NHCOOR$^6$ wherein R$^6$ is as defined above, (xvii) —NHCONHR$^6$ wherein R$^6$ is as defined above, (xviii) —NHCOR$^6$ wherein R$^6$ is as defined above, (xix) —NHSO$_2$R$^6$ wherein R$^6$ is as defined above, (xx) a $C_{1-6}$ alkyl-carbonyl, (xxi) a carboxyl, (xxii) a $C_{1-6}$ alkoxy-carbonyl, (xxiii) a carbamoyl, (xxiv) a mono-$C_{1-6}$ alkyl-carbamoyl, (xxv) a di-$C_{1-6}$ alkyl-carbamoyl, (xxvi) a $C_{6-10}$ aryl-carbamoyl, (xxvii) a sulfo, (xxviii) a $C_{1-6}$ alkylsulfonyl, (xxvix) a $C_{6-10}$ aryl, (xxx) a $C_{6-10}$ aryloxy, (xxxi) $C_{7-16}$ aralkyloxy, (xxxii) thiocarbamoyl, (xxxiii) mono-$C_{1-6}$ alkylthio-carbamoyl, (xxxiv) di-$C_{1-6}$ alkylthio-carbamoyl, (xxxv) $C_{6-10}$ aryl-carbamoyl and (xxxvi) $C_{6-10}$ aryl-thiocarbamoyl, (2) a 6- to 14-membered monocyclic or fused polycyclic aromatic hydrocarbon group, which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{2-6}$ alkenyl optionally having 1 to 3 halogen atoms, (vii) a $C_{2-6}$ alkynyl optionally having 1 to 3 halogen atoms, (viii) a $C_{3-6}$ cycloalkyl, (ix) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (x) a $C_{1-6}$ alkylthio optionally having 1 to 3 halogen atoms, (xi) a hydroxyl, (xii) an amino, (xiii) a mono-$C_{1-6}$ alkylamino, (xiv) a di-$C_{1-6}$ alkylamino, (xv) 5- or 6-membered cyclic amino, (xvi) —NHCOOR$^6$ wherein R$^6$ is as defined above, (xvii) —NHCONHR$^6$ wherein R$^6$ is as defined above, (xviii) —NHCOR$^6$ wherein R$^6$ is as defined above, (xix) —NHSO$_2$R$^6$ wherein R$^6$ is as defined above, (xx) a $C_{1-6}$ alkyl-carbonyl, (xxi) a carboxyl, (xxii) a $C_{1-6}$ alkoxy-carbonyl, (xxiii) a carbamoyl, (xxiv) a mono-$C_{1-6}$ alkyl-carbamoyl, (xxv) a di-$C_{1-6}$ alkyl-carbamoyl, (xxvi) a $C_{6-10}$ aryl-carbamoyl, (xxvii) a sulfo, (xxviii) a $C_{1-6}$ alkylsulfonyl, (xxvix) a $C_{6-10}$ aryl, (xxx) a $C_{6-10}$ aryloxy, (xxxi) $C_{7-16}$ aralkyloxy, (xxxii) thiocarbamoyl, (xxxiii) mono-$C_{1-6}$ alkylthio-carbamoyl, (xxxiv) di-$C_{1-6}$ alkylthio-carbamoyl, (xxxv) $C_{6-10}$ aryl-carbamoyl and (xxxvi) $C_{6-10}$ aryl-thiocarbamoyl, (3) 5- to 10-membered monocyclic nonaromatic heterocyclic group having 1 to 4 hetero atoms selected from the group consisting of a nitrogen, an oxygen and a sulfur in addition to carbon atoms, said heterocyclic group being optionally fused with a benzene ring, which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{2-6}$ alkenyl optionally having 1 to 3 halogen atoms, (vii) a $C_{2-6}$ alkynyl optionally having 1 to 3 halogen atoms, (viii) a $C_{3-6}$ cycloalkyl, (ix) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (x) a $C_{1-6}$ alkylthio optionally having 1 to 3 halogen atoms, (xi) a hydroxyl, (xii) an amino, (xiii) a mono-$C_{1-6}$ alkylamino, (xiv) a di-$C_{1-6}$ alkylamino, (xv) 5- or 6-membered cyclic amino, (xvi) —NHCOOR$^6$ wherein R$^6$ is as defined above, (xvii) —NHCONHR$^6$ wherein R$^6$ is as defined above, (xviii) —NHCOR$^6$ wherein R$^6$ is as defined above, (xix) —NHSO$_2$R$^6$ wherein R$^6$ is as defined above, (xx) a $C_{1-6}$ alkyl-carbonyl, (xxi) a carboxyl, (xxii) a $C_{1-6}$ alkoxy-carbonyl, (xxiii) a carbamoyl, (xxiv) a mono-$C_{1-6}$ alkyl-carbamoyl, (xxv) a di-$C_{1-6}$ alkyl-carbamoyl, (xxvi) a $C_{6-10}$ aryl-carbamoyl, (xxvii) a sulfo, (xxviii) a $C_{1-6}$ alkylsulfonyl, (xxix) a $C_{6-10}$aryl, (xxx) a $C_{6-10}$ aryloxy, (xxxi) $C_{7-16}$ aralkyloxy, (xxxii) thiocarbamoyl, (xxxiii) mono-$C_{1-6}$ alkylthio-carbamoyl, (xxxiv) di-$C_{1-6}$ alkylthio-carbamoyl, (xxxv) $C_{6-10}$ aryl-carbamoyl and (xxxvi) $C_{6-10}$ aryl-thiocarbamoyl; one of R$^1$ and R$^2$ is (1) a hydrogen, (2) a halogen, (3) a hydroxyl, (4) a $C_{1-6}$ alkyl which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from nitrogen, oxygen and sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl, or (5) a $C_{1-6}$alkoxy group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from nitrogen, oxygen and sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl; the other is (1) a halogen, (2) a hydroxyl, (3) a $C_{1-6}$ alkyl which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy;which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$aryl, (z) a $C_{6-10}$ aryloxy, (aa) a 5- to 7-membered heterocyclic group having 1 to 4 hetero atoms selected from nitrogen, oxygen and sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl, or (4) a $C_{1-6}$ alkoxy group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from nitrogen, oxygen and sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl; or $R^1$ and $R^2$ taken together, to form the ring with adjacent —C=C—, are (l) a $C_{1-6}$ alkylene group which may have 1 to 5 Substituents selected from the group consisting of (a) a halogen, (b) a $C_{1-3}$ alkylenedioxy, (c) a nitro, (d) a cyano, (e) a $C_{1-6}$ alkyl optionally which may be substituted with amino, mono- or di-$C_{1-6}$ alkylamino or $C_{1-6}$ alkoxycarbonyl, and having 1 to 3 halogen atoms, (f) a $C_{3-6}$ cycloalkyl, (g) a $C_{1-6}$ alkoxy optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from nitrogen, oxygen and sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl, (2) a $C_{1-6}$ alkylenedioxy group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from nitrogen, oxygen and sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl, or (3) a $C_{1-6}$ alkyleneoxy group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from nitrogen, oxygen and sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl; and ring A is a benzene ring which may have 1 or 2 substituents selected from the group consisting of (1) a hydrogen, (2) a halogen, (3) a $C_{1-16}$ acyclic or cyclic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{3-6}$ cycloalkyl, (vii) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (viii) a $C_{1-6}$ alkylthio optionally having 1 to 3 halogen atoms, (ix) a hydroxyl, (x) an amino, (xi) a mono-$C_1l_6$ alkylamino, (xii) a di-$C_{1-6}$ alkylamino, (xiii) a $C_{1-6}$ alkyl-carbonyl, (xiv) a $C_{1-6}$ alkyl-carbonyloxy, (xv) a $C_{1-6}$ alkyl-carbonyloxy-$C_{1-3}$ alkyl, (xvi) a carboxyl, (xvii) a $C_{1-6}$ alkoxy-carbonyl, (xviii) a mono-$C_{1-6}$ alkylamino-carbonyl, (xix) a di-$C_{1-6}$ alkylamino-carbonyl, (xx) a carbamoyl, (xxi) a mono-$C_{1-6}$ alkyl-carbamoyl, (xxii) a di-$C_{1-6}$ alkyl-carbamoyl, (xxiii) a sulfo, (xxiv) a $C_{1-6}$ alkylsulfonyl, (xxv) a $C_{6-10}$ aryl, (xxvi) a $C_{6-10}$ aryloxy; (xxvii) a 5- to 7-membered heterocyclic group having 1 to 4 hetero atoms selected from nitrogen, oxygen and sulfur in addition to carbon atoms, said heterocyclic group being optionally fused with a benzene ring, (xxviii) thiocarbamoyl, (xxix) mono-$C_{1-6}$ alkylthio-carbamoyl, (xxx) di-$C_{1-6}$ alkylthio-carbamoyl, (xxxi) $C_{6-10}$ aryl-carbamoyl and (xxxii) $C_{6-10}$ aryl-thiocarbamoyl, 3. A compound of the formula:

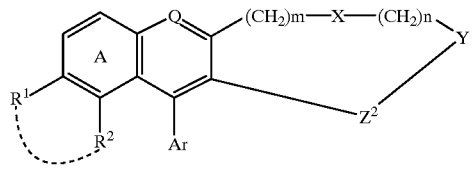

wherein

Q is (1) $CR^4$ wherein $R^4$ is (i) a hydrogen atom, (ii) a halogen atom, (iii) an optionally substituted hydrocarbon group or (iv) an optionally substituted hydroxyl group, or (2) N(O)p wherein p is 0 or 1;

X is C=O or C=S;

Y is (1) $CH_2$, (2) S(O)q wherein q is an integer of 0 to 2, or (3) $NR^5$ wherein $R^5$ is (i) a hydrogen atom, (ii) an optionally substituted hydrocarbon group or (iii) an acyl group;

m and n each represents 0 or 1,

Ar is an optionally substituted carbocyclic group or an optionally substituted heterocyclic group;

one of $R^1$ and $R^2$ is a hydrogen atom, a halogen atom, a hydroxyl group, an optionally substituted lower alkyl group, or an optionally substituted lower alkoxy group;

the other is a halogen atom, a hydroxyl group, an optionally substituted lower alkyl group, or an optionally substituted lower alkoxy group; or $R^1$ and $R^2$ taken together with adjacent —c=c— form a ring; and ring A is a benzene ring which may be substituted in addition to $R^1$ and $R^2$;

4. A compound as described in the above item 3 wherein Q is (A) $CR^4$ wherein $R^4$ is (1) a hydrogen atom, (2) a halogen atom, (3) a $C_{1-16}$ acyclic or cyclic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{3-6}$ cycloalkyl, (vii) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (viii) a $C_{1-6}$ alkylthio optionally having 1 to 3 halogen atoms, (ix) a hydroxyl, (x) an amino, (xi) a mono-$C_{1-6}$ alkylamino, (xii) a di-$C_{1-6}$ alkylamino, (xiii) a $C_{1-6}$ alkyl-carbonyl, (xiv) a $C_{1-6}$ alkyl-carbonyloxy, (xv) a $C_{1-6}$ alkyl-carbonyloxy-$C_{1-3}$ alkyl, (xvi) a carboxyl, (xvii) a $C_{1-6}$ alkoxy-carbonyl, (xviii) a mono-$C_{1-6}$ alkylamino-carbonyl, (xix) a di-$C_{1-6}$ alkylamino-carbonyl, (xx) a carbamoyl, (xxi) a mono-$C_{1-6}$ alkyl-carbamoyl, (xxii) a di-$C_{1-6}$ alkyl-carbamoyl, (xxiii) a sulfo, (xxiv) a $C_{1-6}$ alkylsulfonyl, (xxv) a $C_{6-10}$ aryl, (xxvi) a $C_{6-10}$ aryloxy, (xxvii) a 5- to 7-membered heterocyclic group having 1 to 4 hetero atoms selected from nitrogen, oxygen and sulfur in addition to carbon atoms, said heterocyclic group being optionally fused with a benzene ring, (xxviii) thiocarbamoyl, (xxix) mono-$C_{1-6}$ alkylthio-carbamoyl, (xxx) di-$C_{1-6}$ alkylthio-carbamoyl, (xxxi) $C_{6-10}$ aryl-carbamoyl and (xxxii) $C_{6-10}$ aryl-thiocarbamoyl, or (4) a hydroxyl group which may be substituted with a $C_{1-16}$ acyclic or cyclic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{3-6}$ cycloalkyl, (vii) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (viii) a $C_{1-6}$ alkylthio optionally having 1 to 3 halogen atoms, (ix) a hydroxyl, (x) an amino, (xi) a mono-$C_{1-6}$ alkylamino, (xii) a di-$C_{1-6}$ alkylamino, (xiii) a $C_{1-6}$ alkyl-carbonyl, (xiv) a $C_{1-6}$ alkyl-carbonyloxy, (xv) a $C_{1-6}$ alkyl-carbonyloxy-$C_{1-3}$ alkyl, (xvi) a carboxyl, (xvii) a $C_{1-6}$ alkoxy-carbonyl, (xviii) a mono-$C_{1-6}$ alkylamino-carbonyl, (xix) a di-$C_{1-6}$ alkylamino-carbonyl, (xx) a carbamoyl, (xxi) a mono-$C_{1-6}$ alkyl-carbamoyl, (xxii) a di-$C_{1-6}$ alkyl-carbamoyl, (xxiii) a sulfo, (xxiv) a $C_{1-6}$ alkylsulfonyl, (xxv) a $C_{6-10}$ aryl, (xxvi) a $C_{6-10}$ aryloxy, (xxvii) a 5- to 7-membered heterocyclic group having 1 to 4 hetero atoms selected from nitrogen, oxygen and sulfur in addition to carbon atoms, said heterocyclic group being optionally fused with a benzene ring, (xxviii) thiocarbamoyl, (xxix) mono-$C_{1-6}$ alkylthio-carbamoyl, (xxx) di-$C_{1-6}$ alkylthio-carbamoyl, (xxxi) $C_{6-10}$ arylcarbamoyl and (xxxii) $C_{6-10}$ aryl-thiocarbamoyl;

or (B) N(O)p wherein p is 0 or 1;

Y is (1) $CH_2$, (2) $S(O)q$ wherein q is an integer of 0 to 2, or (3) $NR^5$ wherein $R^5$ is (i) a hydrogen, (ii) a $C_{1-16}$ acyclic or cyclic hydrocarbon group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from nitrogen, oxygen and sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl, (iii) —(C=O)—$R^7$ wherein $R^7$ is a hydrogen or a $C_{1-16}$ acyclic or cyclic hydrocarbon group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) 5- or 6-membered cyclicamino optionally having carboxyl or oxo, (n) —NHCOOR$^6$ wherein $R^6$ is a $C_{1-16}$ acyclic or cyclic hydrocarbon group which may have 1 to 5 substituents selected from the group consisting of (n-1) a halogen, (n-2) a $C_{1-3}$ alkylenedioxy, (n-3) a nitro, (n-4) a cyano, (n-5) a $C_{1-6}$ alkyl optionally having 1 to 3 halogen atoms, (n-6) a $C_{3-6}$ cycloalkyl, (n-7) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (n-8) a $C_{1-6}$ alkylthio optionally having 1 to 3 halogen atoms, (n-9) a hydroxyl, (n-10) an amino, (n-11) a mono-$C_{1-6}$ alkylamino, (n-12) a di-$C_{1-6}$ alkylamino, (n-13) a $C_{1-6}$ alkyl-carbonyl, (n-14) a $C_{1-6}$ alkyl-carbonyloxy, (n-15) a $C_{1-6}$ alkyl-carbonyloxy-$C_{1-3}$ alkyl, (n-16) a carboxyl, (n-17) a $C_{1-6}$ alkoxy-carbonyl, (n-18) a mono-$C_{1-6}$ alkylamino-carbonyl, (n-19) a di-$C_{1-6}$ alkylamino-carbonyl, (n-20) a carbamoyl, (n-21) a mono-$C_{1-6}$ alkyl-carbamoyl, (n-22) a di-$C_{1-6}$ alkyl-carbamoyl, (n-23) a sulfo, (n-24) a $C_{1-6}$ alkylsulfonyl, (n-25) a $C_{6-10}$ aryl, (n-26) a $C_{6-10}$ aryloxy, (n-27) a 5- to 7-membered heterocyclic group having 1 to 4 hetero atoms selected from nitrogen, oxygen and sulfur in addition to carbon atoms, said heterocyclic group being optionally fused with a benzene ring, (n-28) thiocarbamoyl, (n-29) mono-$C_{1-6}$ alkylthio-carbamoyl, (n-30) di-$C_{1-6}$ alkylthio-carbamoyl, (n-31) $C_{6-10}$ arylcarbamoyl and (n-32) $C_{6-10}$ aryl-thiocarbamoyl, (o) —NHCONHR$^6$ wherein $R^6$ is as defined above, (p) —NHCOR$^6$ wherein $R^6$ is as defined above, (q) —NHSO$_2$R$^6$ wherein $R^6$ is as defined above, (r) a $C_{1-6}$ alkyl-carbonyl, (s) a $C_{1-6}$ alkyl-carbonyloxy, (t) a $C_{1-6}$ alkyl-carbonyloxy-$C_{1-3}$ alkyl, (u) a carboxyl, (v) a $C_{1-6}$ alkoxy-carbonyl, (w) a mono-$C_{1-6}$ alkylamino-carbonyl, (x) a di-$C_{1-6}$ alkylamino-carbonyl, (y) a carbamoyl, (z) a mono-$C_{1-6}$ alkyl-carbamoyl, (aa) a di-$C_{1-6}$ alkyl-carbamoyl, $C_{6-10}$ aryl-carbamoyl, (bb) a sulfo, (cc) a $C_{1-6}$ alkylsulfonyl, (dd) a $C_{6-10}$ aryl, (ee) a $C_{6-10}$ aryloxy, (ff) a 5- to 7-membered heterocyclic group having 1 to 4 hetero atoms selected from nitrogen, oxygen and sulfur in addition to carbon atoms, said heterocyclic group being optionally fused with a benzene ring, (gg) $C_{7-11}$ aralkyloxy-carbonyl, (hh) thiocarbamoyl, (ii) mono-$C_{1-6}$ alkylthio-carbamoyl, (jj) di-$C_{1-6}$ alkylthio-carbamoyl, (kk) $C_{6-10}$ aryl-carbamoyl and (11) $C_{6-10}$ aryl-thiocarbamoyl, (iv) —SO$_2$—$R^7$ wherein $R^7$ is as defined above, (v) —SO—$R^7$ wherein $R^7$ is as defined above, (vi) —(C=O)NR$^8$—$R^7$ wherein $R^7$ is as defined above, $R^8$ is hydrogen or $C_{1-6}$ alkyl or (vii) —(C=O)O—$R^7$ wherein $R^7$ is as defined above, 5. A compound as described in the above item 3 wherein Q is $CR^4$ wherein $R^4$ is as defined in the above item 3, 6. A compound as described in the above item 3 wherein X is C=O, 7. A compound as described in the above item 3 wherein Y is $NR^5$ wherein $R^5$ is as described in the above item 3, 8. A compound as described in the above item 3 wherein Y is $CH_2$, 9. A compound as described in the above item 3 wherein Ar is 3- to 14-membered aromatic group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{2-6}$ alkenyl optionally having 1 to 3 halogen atoms, (vii) a $C_{2-6}$ alkynyl optionally having 1 to 3 halogen atoms, (viii) a $C_{3-6}$ cycloalkyl, (ix) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (x) a $C_{1-6}$ alkylthio optionally having 1 to 3 halogen atoms, (xi) a hydroxyl, (xii) an amino, (xiii) a mono-$C_{1-6}$ alkylamino, (xiv) a di-$C_{1-6}$ alkylamino, (xv)

5- or 6-membered cyclic amino, (xvi) —NHCOOR$^6$ wherein R$^6$ is a C$_{1-16}$ acyclic or cyclic hydrocarbon group which may have 1 to 5 substituents selected from the group consisting of (a) a halogen, (b) a C$_{1-3}$ alkylenedioxy, (c) a nitro, (d) a cyano, (e) a C$_{1-6}$ alkyl optionally having 1 to 3 halogen atoms, (f) a C$_{3-6}$ cycloalkyl, (g) a C$_{1-6}$ alkoxy optionally having 1 to 3 halogen atoms, (h) a C$_{1-6}$ alkylthio optionally having 1 to 3 halogen atoms, (i) a hydroxyl, (j) an amino, (k) a mono-C$_{1-6}$ alkylamino, (l) a di-C$_{1-6}$ alkylamino, (m) a C$_{1-6}$ alkyl-carbonyl, (n) a C$_{1-6}$ alkyl-carbonyloxy, (o) a C$_{1-6}$ alkyl-carbonyloxy-C$_{1-3}$ alkyl, (p) a carboxyl, (q) a C$_{1-6}$ alkoxy-carbonyl, (r) a mono-C$_{1-6}$ alkylamino-carbonyl, (s) a di-C$_{1-6}$ alkylamino-carbonyl, (t) a carbamoyl, (u) a mono-C$_{1-6}$ alkyl-carbamoyl, (v) a di-C$_{1-6}$ alkyl-carbamoyl, (w) a sulfo, (x) a C$_{1-6}$ alkylsulfonyl, (y) a C$_{6-10}$ aryl, (z) a C$_{6-10}$ aryloxy, (aa) a 5- to 7-membered heterocyclic group having 1 to 4 hetero atoms selected from the group consisting of a nitrogen, an oxygen and a sulfur in addition to carbon atoms, said heterocyclic group being optionally fused with a benzene ring, (bb) thiocarbamoyl, (cc) mono-C$_{1-6}$ alkylthio-carbamoyl, (dd) di-C$_{1-6}$ alkylthio-carbamoyl, (ee) C$_{6-10}$ aryl-carbamoyl and (ff) C$_{6-10}$ aryl-thiocarbamoyl, (xvii) —NHCONHR$^6$ wherein R$^6$ is as defined above, (xviii) —NHCOR$^6$ wherein R is as defined above, (xix) —NHSO$_2$R$^6$ wherein R$^6$ is as defined above, (xx) a C$_{1-6}$ alkyl-carbonyl, (xxi) a carboxyl, (xxii) a C$_{1-6}$ alkoxy-carbonyl, (xxiii) a carbamoyl, (xxiv) a mono-C$_{1-6}$ alkyl-carbamoyl, (xxv) a di-C$_{1-6}$ alkyl-carbamoyl, (xxvi) a C$_{6-10}$ aryl-carbamoyl, (xxvii) a sulfo, (xxviii) a C$_{1-6}$ alkylsulfonyl, (xxix) a C$_{6-10}$ aryl, (xxx) a C$_{6-10}$ aryloxy, (xxxi) C$_{7-16}$ aralkyloxy, (xxxii) thiocarbamoyl, (xxxiii) mono-C$_{1-6}$ alkylthio-carbamoyl, (xxxiv) di-C$_{1-6}$ alkylthio-carbamoyl, (xxxv) C$_{6-10}$ aryl-carbamoyl and (xxxvi) C$_{6-10}$ aryl-thiocarbamoyl, 10. A compound as described in the above item 4 wherein Ar is a phenyl group which may have 1 to 5 substituents selected from the group consisting of (i) a halogen, (ii) a C$_{1-3}$ alkylenedioxy, (iii) a nitro, (iv) a cyano, (v) a C$_{1-6}$ alkyl optionally having 1 to 3 halogen atoms, (vi) a C$_{2-6}$ alkenyl optionally having 1 to 3 halogen atoms, (vii) a C$_{2-6}$ alkynyl optionally having 1 to 3 halogen atoms, (viii) a C$_{3-6}$ cycloalkyl, (ix) a C$_{1-6}$ alkoxy which may be substituted with amino, mono- or di-C$_{1-6}$ alkylamino or C$_{1-6}$ alkoxycarbonyl, and optionally having 1 to 3 halogen atoms, (x) a C$_{1-6}$ alkylthio optionally having 1 to 3 halogen atoms, (xi) a hydroxyl, (xii) an amino, (xiii) a mono-C$_{1-6}$ alkylamino, (xiv) a di-C$_{1-6}$ alkylamino, (xv) 5- or 6-membered cyclic amino, (xvi) —NHCOOR$^6$ wherein R$^6$ is a C$_{1-16}$ acyclic or cyclic hydrocarbon group which may have 1 to 5 substituents selected from the group consisting of (a) a halogen, (b) a C$_{1-3}$ alkylenedioxy, (c) a nitro, (d) a cyano, (e) a C$_{1-6}$ alkyl optionally having 1 to 3 halogen atoms, (f) a C$_{3-6}$ cycloalkyl, (g) a C$_{1-6}$ alkoxy optionally having 1 to 3 halogen atoms, (h) a C$_{1-6}$ alkylthio optionally having 1 to 3 halogen atoms, (i) a hydroxyl, (j) an amino, (k) a mono-C$_{1-6}$ alkylamino, (l) a di-C$_{1-6}$ alkylamino, (m) a C$_{1-6}$ alkyl-carbonyl, (n) a C$_{1-6}$ alkyl-carbonyloxy, (o) a C$_{1-6}$ alkyl-carbonyloxy-C$_{1-3}$ alkyl, (p) a carboxyl, (q) a C$_{1-6}$ alkoxy-carbonyl, (r) a mono-C$_{1-6}$ alkylamino-carbonyl, (s) a di-C$_{1-6}$ alkylamino-carbonyl, (t) a carbamoyl, (u) a mono-C$_{1-6}$ alkyl-carbamoyl, (v) a di-C$_{1-6}$ alkyl-carbamoyl, (w) a sulfo, (x) a C$_{1-6}$ alkylsulfonyl, (y) a C$_{6-10}$ aryl, (z) a C$_{6-10}$ aryloxy, (aa) a 5- to 7-membered heterocyclic group having 1 to 4 hetero atoms selected from the group consisting of a nitrogen, an oxygen and a sulfur in addition to carbon atoms, said heterocyclic group being optionally fused with a benzene ring, (bb) thiocarbamoyl, (cc) mono-C$_{1-6}$ alkylthio-carbamoyl, (dd) di-C$_{1-6}$ alkylthio-carbamoyl, (ee) C$_{6-10}$ aryl-carbamoyl and (ff) C$_{6-10}$ aryl-thiocarbamoyl, (xvii) —NHCONHR$^6$ wherein R$^6$ is as defined above, (xviii) —NHCOR$^6$ wherein R$^6$ is as defined above, (xix) —NHSO$_2$R$^6$ wherein R$^6$ is as defined above, (xx) a C$_{1-6}$ alkyl-carbonyl, (xxi) a carboxyl, (xxii) a C$_{1-6}$ alkoxy-carbonyl, (xxiii) a carbamoyl, (xxiv) a mono-C$_{1-6}$ alkyl-carbamoyl, (xxv) a di-C$_{1-6}$ alkyl-carbamoyl, (xxvi) a C$_{6-10}$ aryl-carbamoyl, (xxvii) a sulfo, (xxviii) a C$_{1-6}$ alkylsulfonyl, (xxix) a C$_{6-10}$ aryl, (xxx) a C$_{6-10}$ aryloxy, (xxxi) C$_{7-16}$ aralkyloxy, (xxxii) thiocarbamoyl, (xxxiii) mono-C$_{1-6}$ alkylthio-carbamoyl, (xxxiv) di-C$_{1-6}$ alkylthio-carbamoyl, (xxxv) C$_{6-10}$ aryl-carbamoyl and (xxxvi) C$_{6-10}$ aryl-thiocarbamoyl, 11. A compound as described in the above item 4, wherein

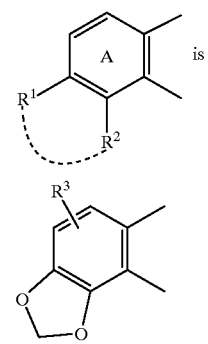

wherein R$^3$ is (1) a hydrogen atom, (2) a halogen atom, (3) a C$_{1-16}$ acyclic or cyclic hydrocarbon group which may have 1 to 5 substituents selected from the group consisting of (a) a halogen, (b) a C$_{1-3}$ alkylenedioxy, (c) a nitro, (d) a cyano, (e) a C$_{1-6}$ alkyl optionally having 1 to 3 halogen atoms, (f) a C$_{3-6}$ cycloalkyl, (g) a C$_{1-6}$ alkoxy which may be substituted with amino, mono- or di-C$_{1-6}$ alkylamino or C$_{1-6}$ alkoxycarbonyl, and optionally having 1 to 3 halogen atoms, (h) a C$_{1-6}$ alkylthio optionally having 1 to 3 halogen atoms, (i) a hydroxyl, (j) an amino, (k) a mono-C$_{1-6}$ alkylamino, (l) a di-C$_{1-6}$ alkylamino, (m) a C$_{1-6}$ alkyl-carbonyl, (n) a C$_{1-6}$ alkyl-carbonyloxy, (o) a C$_{1-6}$ alkyl-carbonyloxy-C$_{1-3}$ alkyl, (p) a carboxyl, (q) a C$_{1-6}$ alkoxy-carbonyl, (r) a mono-C$_{1-6}$ alkylamino-carbonyl, (s) a di-C$_{1-6}$ alkylamino-carbonyl, (t) a carbamoyl, (u) a mono-C$_{1-6}$ alkyl-carbamoyl, (v) a di-C$_{1-6}$ alkyl-carbamoyl, (w) a sulfo, (x) a C$_{1-6}$ alkylsulfonyl, (y) a C$_{6-10}$ aryl, (z) a C$_{6-10}$ aryloxy, (aa) a 5- to 7-membered heterocyclic group having 1 to 3 hetero atoms selected from nitrogen, oxygen and sulfur in addition to carbon atoms, said heterocyclic group being optionally fused with a benzene ring, an optionally substituted hydrocarbon group, (bb) thiocarbamoyl, (cc) mono-C$_{1-6}$ alkylthio-carbamoyl, (dd) di-C$_{1-6}$ alkylthio-carbamoyl, (ee) C$_{6-10}$ aryl-carbamoyl and (ff) C$_{6-10}$ aryl-thiocarbamoyl or (4) a hydroxyl group which may be substituted with a C$_{1-6}$ acyclic or cyclic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{3-6}$ cycloalkyl, (vii) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (viii) a $C_{1-6}$ alkylthio optionally having 1 to 3 halogen atoms, (ix) a hydroxyl, (x) an amino, (xi) a mono-$C_{1-6}$ alkylamino, (xii) a di-$C_{1-6}$ alkylamino, (xiii) a $C_{1-6}$ alkyl-carbonyl, (xiv) a $C_{1-6}$ alkyl-carbonyloxy, (xv) a $C_{1-6}$ alkyl-carbonyloxy-$C_{1-3}$ alkyl, (xvi) a carboxyl, (xvii) a $C_{1-6}$ alkoxy-carbonyl, (xviii) a mono-$C_{1-6}$ alkylamino-carbonyl, (xix) a di-$C_{1-6}$ alkylamino-carbonyl, (xx) a carbamoyl, (xxi) a mono-$C_{1-6}$ alkyl-carbamoyl, (xxii) a di-$C_{1-6}$ alkyl-carbamoyl, (xxiii) a sulfo, (xxiv) a $C_{1-6}$ alkylsulfonyl, (xxv) a $C_{6-10}$aryl, (xxvi) a $C_{6-10}$ aryloxy, (xxvii) a 5- to 7-membered heterocyclic group having 1 to 3 hetero atoms selected from nitrogen, oxygen and sulfur in addition to carbon atoms, said heterocyclic group being optionally fused with a benzene ring, (xxviii) thiocarbamoyl, (xxix) mono-$C_{1-6}$ alkylthio-carbamoyl, (xxv) di-$C_{1-6}$ alkylthio-carbamoyl, (xxvi) $C_{6-10}$ aryl-carbamoyl and (xxvii) $C_{6-10}$ aryl-thiocarbamoyl, 12. A compound as described in the above item 11 wherein $R^3$ is a hydrogen, 13. A compound as described in the above item 3 wherein Q is (1) CR 4 wherein $R^{4'}$ is (i) a $C_{1-6}$ alkyl group which may be substituted with a di-$C_{1-6}$ alkylamino group, (ii) a halogen atom, or (iii) a $C_{1-6}$ alkoxy group, or (2) N;

X is C=O;

Y is $NR^{5'}$ wherein $R^{5'}$ is (i) a hydrogen, (ii) a $C_{1-6}$ alkyl group which may be substituted with (a) a morpholino, (b) a carboxyl, (c) a $C_{1-6}$ alkoxy-carbonyl, or (d) a phenyl which may be substituted with $C_{1-6}$ alkoxy, or (iii) $COR^{7''}$ wherein $R^{7''}$ is (a) a hydrogen, (b) $C_{1-6}$ alkyl which may be substituted with a carboxyl or a benzyloxycarbonyl, or a di-$C_{1-6}$ alkylamino;

m and n each represents 0;

$Z^2$ is (1) C=O, (2) $CH_2$, (3) $(CH_2)_2$, (4) $(CH_2)_3$, or (5) CH—OH;

Ar is (1) a phenyl group which may be substituted with (a) a halogen, (b) a $C_{1-6}$ alkylenedioxy, (c) a $C_{1-6}$ alkoxy which may be substituted with (c-1) a halogen, (c-2) a di-$C_{1-6}$ alkylamino or (c-3) a $C_{1-6}$ alkoxy-carbonyl, (d) a $C_{7-11}$ aralkyloxy, (e) $C_{1-6}$ alkyl which may be substituted with a halogen or (f) hydroxyl, (2) an optionally oxidized pyridyl group, or (3) a pyridinium group which may be substituted with $C_{1-6}$ alkyl;

one of $R^1$ and $R^2$ is (1) a hydrogen, (2) a $C_{1-6}$ alkyl, (3) a $C_{1-6}$ alkoxy which may be substituted with (a) a $C_{1-6}$ alkoxy-carbonyl, (b) a $C_{7-11}$ aralkyl or (c) a carboxyl, or (4) a hydroxyl;

the other is (1) a $C_{1-6}$ alkyl, (2) a $C_{1-6}$ alkoxy which may be substituted with (a) a $C_{1-6}$ alkoxy-carbonyl or (b) a carboxyl, or (3) a hydroxyl; or $R^1$ and $R^2$ taken together with adjacent —c=c— form a $C_{1-6}$ alkylenedioxy group, or a $C_{1-6}$ alkyleneoxy group; or ring A is a benzene ring which may have a $C_{1-6}$ alkoxy group, in addition to $R^1$ and $R^2$, and a $C_{1-6}$ alkoxy group on ring A and a $C_{1-6}$ alkoxy group of $R^1$ may be taken together form a $C_{1-6}$ alkylenedioxy group;

14. A compound as described in the above item 13 wherein

Q is CH or N;

X is C=O;

m and n each represents 0;

$Z^2$ is $CH_2$; and $R^1$ and $R^2$ taken together with adjacent —c=c— form a $C_{1-6}$ alkylenedioxy group, 15. A process for producing a compound of the formula:

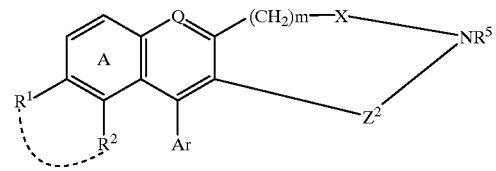

wherein all symbols have the same meanings as defined in the above item 3, or a salt thereof, which comprises subjecting a compound of the formula:

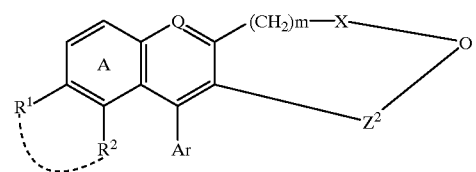

wherein all symbols have the same meaning as defined in the above item 3, or a salt thereof, to lactamization reaction, optionally followed by introducing a substituent $R^5$ into the resulting lactam, 16. A compound of the formula:

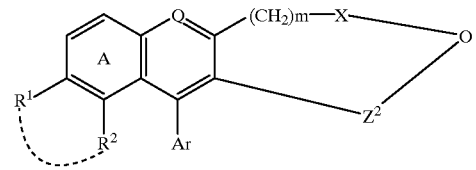

wherein all symbols have the same meaning as defined in the above item 3, or a salt thereof; provided that (1) when both of $R^1$ and $R^2$ are methoxy groups, Q is $CR^4$, X is C=O, $Z^2$ is a methylene, and m is 0, Ar is not any of phenyl, 3,4,5-trimethoxyphenyl, 4,5-dimethoxy-2-methylphenyl and 1,3-benzodioxol-5-yl; that (2) when $R^1$ is a hydroxyl or a methoxy, Q is $CR^4$, X is C=O, $Z^2$ is a methylene, and m is 0, Ar is not 1,3-benzodioxol-5-yl; and that (3) when $R^1$ and $R^2$ taken together represent a methylenedioxy which may be substituted with an oxygen atom, Q is $CR^4$, X is C=O, $Z^2$ is a methylene, and m is 0, Ar is not any of 1,3-benzodioxol-5-yl, 6-bromo-1,3-benzodioxol-5-yl, 7-hydroxyl-1,3-benzodioxol-5-yl, 7-acetoxy-1,3-benzodioxol-5-yl, and 7-methoxy-1,3-benzodioxol-5-yl, 17. A pharmaceutical composition comprising a compound of the above item 1, 18. A cell differentiation inducing factor composition comprising the compound of the above item 1, 19. A composition of the above item 17 which enhances cell differentiation inducing factor, 20. A composition for treating or preventing neuropathy or bone and joint disease which comprises the compound of the above item 1, 21. A bone formation promoting composition comprising the compound of the above item 1, 22. A cartilage disruption inhibitory composition comprising the compound of the above item 1, 23. A method of treating or preventing neuropathy or bone-and-joint disease which comprises administering to a mammal in need thereof an effective amount of a compound of the formula:

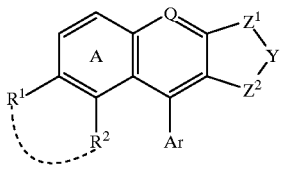

wherein

Q is an optionally substituted carbon atom or N(O)p wherein p is 0 or 1;

Y is an optionally substituted methylene group, S(O)q wherein q is an integer of 0 to 2, or an optionally substituted imino group;

$Z^1$ is a $C_{1-3}$ alkylene group which may have an oxo group or a thioxo group and may contain etherified oxygen or sulfur within the carbon chain;

$Z^2$ is an optionally substituted $C_{1-3}$ alkylene group;

Ar is an optionally substituted carbocyclic group or an optionally substituted heterocyclic group;

one of $R^1$ and $R^2$ is a hydrogen atom, a halogen atom, a hydroxyl group, an optionally substituted lower alkyl group or an optionally substituted lower alkoxy group;

the other is a halogen atom, a hydroxyl group, an optionally substituted lower alkyl group or an optionally substituted lower alkoxy group; or $R^1$ and $R^2$ taken together with adjacent —c═c— form a ring; and ring A is a benzene ring which may have a substituent in addition to $R^1$ and $R^2$; or a salt thereof, 24. Use of a compound of the formula:

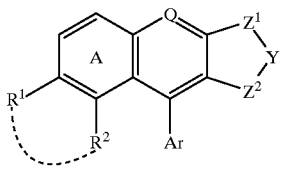

wherein

Q is an optionally substituted carbon atom or N(O)p wherein p is 0 or 1;

Y is an optionally substituted methylene group, S(O)q wherein q is an integer of 0 to 2, or an optionally substituted imino group;

$Z^1$ is a $C_{1-3}$ alkylene group which may have an oxo group or a thioxo group and may contain etherified oxygen or sulfur within the carbon chain;

$Z^2$ is an optionally substituted $C_{1-3}$ alkylene group;

Ar is an optionally substituted carbocyclic group or an optionally substituted heterocyclic group;

one of $R^1$ and $R^2$ is a hydrogen atom, a halogen atom, a hydroxyl group, an optionally substituted lower alkyl group or an optionally substituted lower alkoxy group;

the other is a halogen atom, a hydroxyl group, an optionally substituted lower alkyl group or an optionally substituted lower alkoxy group; or $R^1$ and $R^2$ taken together form a ring; and ring A is a benzene ring which may have a substituent in addition to $R^1$ and $R^2$; or a salt thereof, for the manufacture of a medicament for treating or preventing neuropathy or bone-and-joint disease, and 25. A compound as described in the above item 3, which is 10-(1,3-Benzodioxol-5-yl)-8,9-dihydro-7H- 1,3,-benzodioxolo[4,5-f]isoindol-7-one, 11-(1,3-Benzodioxol-5-yl)-7,8,9,10-tetrahydro-1,3,-benzodioxolo[4,5-g]isoquinolin-7-one, 4-(1,3-Benzodioxol-5-yl)-2,3-dihydro-5-methoxy-1H-benz[f]isoindol-1-one, 8,9-Dihydro-10-(4-trifluoromethylphenyl)-7H-1,3-benzodioxolo[4,5-f]isoindol-7-one, 11-(1,3-Benzodioxol-5-yl)-9,10-dihydro-8H-isoindolo[5,6-f]benz[b]-1,4-dioxan-8-one, 10-(4-Fluorophenyl)-8,9, -dihydro-7H-1,3-benzodioxolo[4,5-f]isoindol-7-one, 10-(1,3-Benzodioxol-5-yl)-8,9-dihydro-6-methyl-7H-1,3-benzodioxolo[4,5-f]isoindol-7-one, 10-(4-Fluorophenyl)-8,9-dihydro-6-methyl-7H-1,3-benzodioxolo[4,5-f]isoindol-7-one, 8,9-Dihydro-6-methyl-10-(4-trifluoromethylphenyl)-7H-1,3-benzodioxolo[4,5-f]isoindol-7-one, 10-(1,3-Benzodixol-5-yl)-8,9-dihydro-6-ethyl-7H-1,3-benzodioxolo[4,5-f]isoindol-7-one, 4-(1,3-Benzodioxol-5-yl)-2,3-dihydro-6-methoxy-1H-benz[f]isoindol-1-one, 2,3-Dihydro-6-methoxy-4-(4-methoxypheny)-1H-benz[f]isoindol-1-one, 2,3-Dihydro-6-methoxy-4-(4-trifluoromethylphenyl)-1H-benz[f]isoindol-1-one, 4-(4-Fluorophenyl)-2,3-dihydro-6-methoxy-9-methyl-1H-benz[f]isoindol-1-one, 4-(4-Methoxyphenyl)-2,3-dihydro-6-methoxy-9-methyl-1H-benz[f]isoindol-1-one, 9-(4-Fluorophenyl)-1,2-dihydro-7-methoxy-3H-pyrrolo[3,4-b]quinolin-3-one, 1,2-Dihydro-7-methoxy-9-(4-methoxyphenyl)-3H-pyrrolo[3,4-b]quinolin-3-one, 3,4-Dihydro-7-methoxy-5-(4-methoxyphenyl)-benzo[b][1,7]naphthyridin-1(2H)-one, or a salt thereof.

DETAILED DESCRIPTION

Referring to the above formulas, the "optionally substituted carbocyclic group or optionally substituted heterocyclic group" as mentioned for Ar may have any number of substituents in substitutable positions (preferably 1 to 5 and more preferably 1 to 3 substituents) and when two or more substitutions are involved, the substituent groups may be same or different and the mutually adjacent substituent groups may be bonded with each other to form a ring.

The ring that may be jointly formed by any two mutually adjacent substituent groups on Ar includes 3- through 10-membered carbocycles (preferably 5- or 6-membered carbocycles) such as, for example, benzene, $C_{3-10}$ cycloalkene (e.g. cyclobutene, cyclopentene, cyclohexene, cycloheptene, cyclooctene, etc.), and $C_{3-10}$ cycloalkanes (e.g. cyclobutane, cyclopentane, cyclohexane, cycloheptane, cyclooctane, etc.). Preferred are 5- to 6-membered carbocycles such as benzene, cyclopentane, and cyclohexane. Among them, benzene ring is particularly preferred.

The above-mentioned "optionally substituted carbocyclic group" and "optionally substituted heterocyclic group" include, for example:

(1) 3- to 14-membered monocyclic or fused polycyclic nonaromatic hydrocarbon groups (preferably 5- or 6-membered carbocyclic groups), for example $C_{3-10}$ cycloalkene (e.g. cyclobutene, cyclopentene, cyclohexene, cycloheptene, cyclooctene, etc.) and $C_{3-10}$ cycloalkane (e.g. cyclobutane, cyclopentane, cyclohexane, cycloheptane, cyclooctane, etc.).

(2) 6- to 14-membered monocyclic or fused polycyclic aromatic hydrocarbon groups, for example $C_{6-14}$ aryl such as phenyl, biphenyl, 1-naphthyl, 2-naphthyl, 2-indenyl, 1-anthryl, 2-anthryl, 3-anthryl, 1-phenanthryl, 2-phenanthryl, 3-phenanthryl, 4-phenanthryl, 9-phenanthryl, etc. Among them, preferred are phenyl, biphenyl, 1-naphthyl and 2-naphthyl, and phenyl is particularly preferred.

(3) 5- to 10-membered monocyclic nonaromatic heterocyclic groups each containing 1 or more (e.g. 1–4, preferably 1–3) hetero atoms of one or two kinds as selected from the group consisting of nitrogen, sulfur, and oxygen in addition to carbon atoms, said heterocyclic group being optionally fused with a benzene ring, preferably 5- or 6-membered nonaromatic heterocyclic groups, more specifically monovalent groups available upon elimination of one optional hydrogen atom each from such rings as tetrahydropyridine, dihydropyridine, tetrahydropyrazine, tetrahydropyrimidine, tetrahydropyridazine, dihydropyran, dihydropyrrole, dihydroimidazole, dihydropyrazole, dihydrothiophene, dihydrofuran, dihydrothiazole, dihydroisothiazole, dihydrooxazole, dihydroisoxazole, piperidine, piperazine, hexahydropyrimidine, hexahydropyridazine, tetrahydropyran, morpholine, pyrrolidine, imidazolidine, pyrazolidine, tetrahydrothiophene, tetrahydrofuran, tetrahydrothiazole, tetrahydroisothiazole, tetrahydrooxazole, and tetrahydroisoxazole rings, preferably from 6-membered nonaromatic heterocyclic rings each containing 1 or 2 nitrogen atoms in addition to carbon (e.g. tetrahydropyridine, tetrahydropyrimidine, tetrahydropyridazine, piperidine, and piperazine rings, more preferably piperazine ring etc.).

(4) 5- to 10-membered monocyclic aromatic heterocyclic groups each containing one or more (for example, 1 to 4, preferably 1 to 3) hetero atoms of one or two kinds as selected from the group consisting of nitrogen, sulfur, and oxygen in addition to carbon atoms, said heterocyclic group being optionally fused with a benzene ring, specifically monovalent groups available upon elimination of any one hydrogen atom each from aromatic heterocyclic rings such as thiophene, benzo[b]thiophene, benzo[b]furan, benzimidazole, benzoxazole, benzothiazole, benzisothiazole, naphtho[2,3-b]thiophene, thianthrene, furan, isoindolidine, xanthrene, phenoxathiin, pyrrole, imidazole, triazole, thiazole, oxazole, pyrazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, isothiazole, phenothiazine, isoxazole, furazan, phenoxazine, isochroman, etc. (preferably pyridine, thiophene, furan, etc., more preferably pyridine) or from the fused rings available on condensation of such rings (preferably said monocyclic heterocyclic rings) with one or more (preferably 1 or 2, more preferably 1) aromatic rings (e.g. the aromatic hydrocarbons mentioned above, preferably benzene ring).

Particularly preferred, among the above items (1) to (4), are aromatic heterocyclic groups such as said "6- to 14-membered monocyclic and fused polycyclic aromatic hydrocarbon groups" and "5- to 10-membered monocyclic aromatic heterocyclic groups each containing one or more (e.g. 1 to 4, preferably 1 to 3) hetero-atoms of one or two kinds as selected from the group consisting of nitrogen, sulfur, and oxygen in addition to carbon atoms, said heterocyclic group being optionally fused with a benzene ring.

The substituent for the "optionally substituted carbocyclic group or optionally substituted heterocyclic group" as mentioned for Ar and $R^6$ includes, for example, (i) halogen (e.g. fluorine, chlorine, bromine, iodine), (ii) lower alkylenedioxy (e.g. $C_{1-3}$ alkylenedioxy such as methylenedioxy, ethylenedioxy, etc.), (iii) nitro, (iv) cyano, (v) lower alkyl that may be halogenated, (vi) lower alkenyl that may be halogenated, (vii) lower alkynyl that may be halogenated, (viii) lower cycloalkyl (e.g. $C_{3-6}$ cycloalkyl such as cyclopropyl, cyclobutyl, cyclopentyl, cyclohexyl, etc.), (ix) lower alkoxy that may be halogenated, (x) lower alkylthio that may be halogenated, (xi) hydroxyl, (xii) amino, (xiii) mono-lower alkylamino (e.g. mono-$C_{1-6}$ alkylamino such as methylamino, ethylamino, propylamino, isopropylamino, butylamino, etc.), (xiv) di-lower alkylamino (e.g. di-$C_{1-6}$ alkylamino such as dimethylamino, diethylamino, dipropylamino, dibutylamino, etc.), (xv) 5- or 6-membered cycloamino (e.g. morpholino, thiomorpholino, piperazin-1-yl, piperidino, pyrrolidin-1-yl, etc.), (xvi) acylamino, (xvii) lower alkylcarbonyl (e.g. $C_{1-6}$ alkyl-carbonyl such as acetyl, propionyl, etc.), (xviii) carboxyl, (xix) lower alkoxycarbonyl (e.g. $C_{1-6}$ alkoxy-carbonyl such as methoxycarbonyl, ethoxycarbonyl, propoxycarbonyl, butoxycarbonyl, etc.), (xx) carbamoyl, (xxi) mono-lower alkylcarbamoyl (e.g. mono-$C_{1-6}$ alkyl-carbamoyl such as methylcarbamoyl, ethylcarbamoyl, etc.), (xxii) di-lower alkylcarbamoyl (e.g. di-$C_{1-6}$ alkyl-carbamoyl such as dimethylcarbamoyl, diethylcarbamoyl, etc.), (xxiii) arylcarbamoyl (e.g. $C_{6-10}$ aryl-carbamoyl such as phenylcarbamoyl, naphthylcarbamoyl, etc.), (xxiv) sulfo, (xxv) lower alkylsulfonyl (e.g. $C_{1-6}$ alkylsulfonyl such as ethylsulfonyl, ethylsulfonyl, etc.), (xxvi) aryl (e.g. $C_{6-10}$ aryl such as phenyl, naphthyl, etc.), (xxvii) aryloxy (e.g. $C_{6-10}$ aryloxy such as phenyloxy, naphthyloxy, etc.), (xxviii) aralkyloxy (e.g. $C_{7-16}$ aralkyloxy such as benzyloxy etc.), (xxix) thiocarbamoyl, (xxx) mono-lower alkylthiocarbamoyl (e.g. mono-$C_{1-6}$ alkylthio-carbamoyl such as methylthiocarbamoyl, ethylthiocarbamoyl, etc.), (xxxi) di-lower alkylthiocarbamoyl (e.g. di-$C_{1-6}$ alkylthio-carbamoyl such as dimethylthiocarbamoyl, diethylthiocarbamoyl, etc.), (xxxii) aryl-carbamoyl (e.g. $C_{6-10}$ aryl-carbamoyl such as phenyl-carbamoyl) and (xxxiii) aryl-thiocarbamoyl (e.g. $C_{6-10}$ aryl-thiocarbamoyl such as phenyl-thiocarbamoyl).

The "lower alkyl that may be halogenated" as mentioned above includes lower alkyl (e.g. $C_{1-6}$ alkyl such as methyl, ethyl, propyl, isopropyl, butyl, isobutyl, sec-butyl, tert-butyl, pentyl, hexyl, etc.) optionally having 1–3 halogen atoms (e.g. fluorine, chlorine, bromine, iodine). Specifically, methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc. can be mentioned.

The "lower alkenyl that may be halogenated" and "lower alkynyl that may be halogenated", both mentioned above, include lower alkenyl (e.g. $C_{2-6}$ alkenyl such as vinyl, propenyl, isopropenyl, 2-buten-1-yl, 4-penten-1-yl, 5-hexen-1-yl, etc.) optionally having 1–3 halogen atoms (e.g. fluorine, chlorine, bromine, iodine) and lower alkynyl (e.g. $C_{26}$ alkynyl such as 2-butyn-1-yl, 4-pentyn-1-yl, 5-hexyn-1-yl, etc.) optionally having 1–3 halogen atoms (e.g. fluorine, chlorine, bromine, iodine), respectively.

The above-mentioned "lower alkoxy that may be halogenated" includes lower alkoxy (e.g. $C_{1-6}$ alkoxy such as methoxy, ethoxy, propoxy, isopropoxy, n-butoxy, isobutoxy, sec-butoxy, tert-butoxy, etc.) optionally having 1–3 halogen atoms (e.g. fluorine, chlorine, bromine, iodine). Specifically, methoxy, difluoromethoxy, trifluoromethoxy, ethoxy, 2,2,2-trifluoroethoxy, n-propoxy, isopropoxy, n-butoxy, 4,4,4-trifluorobutoxy, isobutoxy, sec-butoxy, pentyloxy, hexyloxy, etc. can be mentioned.

The "lower alkoxy" of said "lower alkoxy that may be halogenated" may be substituted by amino, mono- or di-lower alkylamino (e.g. mono- or di-$C_{1-6}$ alkylamino such as methylamino, dimethylamino, ethylamino, dimethylamino, etc.) or lower alkoxycarbonyl (e.g. $C_{1-6}$ alkyl-oxycarbonyl such as methoxycarbonyl, ethoxycarbonyl, etc.).

The above-mentioned "lower alkylthio that may be halogenated" includes lower alkylthio (e.g. $C_{1-6}$ alkylthio such as methylthio, ethylthio, n-propylthio, isopropylthio, n-butylthio, isobutylthio, secbutylthio, tert-butylthio, etc.) optionally having 1–3 halogen atoms (e.g. fluorine, chlorine, bromine, iodine). Specifically, methylthio, difluoromethylthio, trifluoromethylthio, ethylthio, propylthio, isopropylthio, butylthio, 4,4,4-trifluorobutylthio, pentylthio, hexylthio, etc. can be mentioned.

The above-mentioned "acylamino" includes —NHCOOR$^6$, —NHCONHR$^6$, —NHCOR$^6$, and —NHSO$_2$R$^6$ (R$^6$ represents an optionally substituted hydrocarbon group or an optionally substituted heterocyclic group).

The preferred substituent for the "optionally substituted carbocyclic group or optionally substituted heterocyclic group" as mentioned for Ar includes halogen (particularly fluorine and chlorine), lower alkylenedioxy (particularly methylenedioxy), lower alkoxy that may be halogenated (methoxy in particular), and hydroxyl.

Particularly preferred are halogen (F and Cl in particular), lower alkylenedioxy (methylenedioxy in particular), and lower alkoxy (methoxy in particular) that may be halogenated.

Of those substituent groups, lower alkylenedioxy (methylenedioxy in particular) or lower alkoxy (methoxy in particular) that may be halogenated is the most generally preferred.

The "halogen" mentioned for R$^1$, R$^2$, R$^3$ and R$^4$ includes fluorine, chlorine, bromine, and iodine.

The "hydrocarbon" of said "optionally substituted hydrocarbon" as mentioned for R$^3$, R$^4$, R$^5$ and R$^6$ means a group available upon elimination of one hydrogen atom from any of various hydrocarbon compounds, thus including acyclic and cyclic hydrocarbon groups such as alkyl, alkenyl, alkynyl, cycloalkyl, aryl, and aralkyl. Preferred, among them, are $C_{1-16}$ acylic (straight-chain or branched) hydrocarbon and $C_{1-16}$ cyclic hydrocarbon. The more preferable are:

a) alkyl groups [preferably lower alkyl (e.g. $C_{1-6}$ alkyl such as methyl, ethyl, propyl, isopropyl, butyl, isobutyl, sec-butyl, tert-butyl, pentyl, hexyl, etc.)], b) alkenyl groups [preferably lower alkenyl (e.g. $C_{2-6}$ alkenyl such as vinyl, allyl, isopropenyl, butenyl, isobutenyl, sec-butenyl, etc)], c) alkynyl groups [preferably lower alkynyl (e.g. $C_{2-6}$ alkynyl such as propargyl, ethynyl, butynyl, 1-hexynyl, etc.)], d) cycloalkyl groups [preferably lower cycloalkyl (e.g. $C_{3-6}$ cycloalkyl such as cyclopropyl, cyclobutyl, cyclopentyl, and cyclohexyl optionally fused to a benzene ring which, in turn, may have 1–3 lower alkoxy groups (e.g. $C_{1-6}$ alkoxy such as methoxy)], e) aryl groups (e.g. $C_{6-14}$ aryl such as phenyl, biphenyl, 1-naphthyl, 2-naphthyl, 2-indenyl, [2-anthryl], 1-anthryl, 2-anthryl, 3-anthryl, 1-phenanthryl, 2-phenanthryl, 3-phenanthryl, 4-phenanthryl, 9-phenanthryl, etc., preferably phenyl), f) aralkyl groups [preferably lower aralkyl (e.g. $C_{7-16}$ aralkyl such as benzyl, phenethyl, diphenylmethyl, 1-naphthylmethyl, 2-naphthylmethyl, 2-phenylethyl, 2-diphenylethyl, 1-phenylpropyl, 2-phenylpropyl, 3-phenylpropyl, 4-phenylbutyl, 5-phenylpentyl, etc., more preferably benzyl)].

Most preferred are alkyl groups.

The "optionally substituted hydrocarbon" as mentioned for R$^3$, R$^4$, R$^5$, and R$^6$ may have 1 to 5, preferably 1 to 3, substituents in substitutable positions of the hydrocarbon group and where two or more substitutions are involved, the substituent groups may be the same or different.

The "substituent" for said "hydrocarbon that may be substituted" includes (i) halogen (e.g. fluorine, chlorine, bromine, iodine), (ii) lower alkylenedioxy (e.g. $C_{1-3}$ alkylenedioxy such as methylenedioxy, ethylenedioxy, etc.), (iii) nitro, (iv) cyano, (v) lower alkyl that may be halogenated, (vi) lower cycloalkyl (e.g. $C_{3-6}$ cycloalkyl such as cyclopropyl, cyclobutyl, cyclopentyl, cyclohexyl, etc.), (vii) lower alkoxy that may be halogenated, (viii) lower alkylthio that may be halogenated, (ix) hydroxyl, (x) amino, (xi) mono-lower alkylamino (e.g. mono-$C_{1-6}$ alkylamino such as methylamino, ethylamino, etc.), (xii) di-lower alkylamino (e.g. di-$C_{1-6}$ alkylamino such as dimethylamino, diethylamino, etc.), (xiii) lower alkyl-carbonyl (e.g. $C_{1-6}$ alkyl-carbonyl such as acetyl, ethylcarbonyl, etc.), (xiv) lower alkyl-carbonyloxy (e.g. $C_{1-6}$ alkyl-carbonyloxy such as acetoxy, ethylcarbonyloxy, etc.), (xv) lower alkyl-carbonyloxy-$C_{1-3}$ alkyl (e.g. $C_{1-6}$ alkyl-carbonyloxy-$C_{1-3}$ alkyl such as acetoxymethyl, ethylcarbonyloxymethyl, isopropylcarbonyloxymethyl, etc.), (xvi) carboxyl, (xvii) lower alkoxy-carbonyl (e.g. $C_{1-6}$ alkyl-oxycarbonyl such as methoxycarbonyl, ethoxycarbonyl, propoxycarbonyl, butoxycarbonyl, etc.), (xviii) mono-lower alkylamino-carbonyl (e.g. mono-$C_{1-6}$ alkylamino-carbonyl such as methylaminocarbonyl, ethyl-aminocarbonyl, etc.), (xix) di-lower alkylamino-carbonyl (di-$C_{1-6}$ alkylamino-carbonyl such as dimethylaminocarbonyl, diethylaminocarbonyl, etc.), (xx) carbamoyl, (xxi) mono-lower alkyl-carbamoyl (e.g. mono-$C_{1-6}$ alkyl-carbamoyl such as methylcarbamoyl, ethylcarbamoyl, etc.), (xxii) di-lower alkyl-carbamoyl (e.g. di-$C_{1-6}$ alkyl-carbamoyl such as dimethylcarbamoyl, diethylcarbamoyl, etc.), (xxiii) sulfo, (xxiv) lower alkylsulfonyl (e.g. $C_{1-6}$ alkanesulfonyl such as methanesulfonyl, ethanesulfonyl, etc.), (xxv) aryl (e.g. $C_{6-10}$ aryl such as phenyl, naphthyl, etc.), (xxvi) aryloxy (e.g. $C_{6-10}$ aryloxy such as phenyloxy, naphthyloxy, etc.), (xxvii) 5- to 7-membered heterocyclic group each containing 1–4 heteroatoms selected from among nitrogen, oxygen, and sulfur in addition to carbon, said heterocyclic group being optionally fused with a benzene ring, (xxix) thiocarbamoyl, (xxx) mono-lower alkylthiocarbamoyl (e.g. mono-$C_{1-6}$ alkylthiocarbamoyl such as methylthiocarbamoyl, ethylthiocarbamoyl, etc.), (xxxi) di-lower alkylthiocarbamoyl (e.g. di-$C_{1-6}$ alkylthio-carbamoyl such as dimethylthiocarbamoyl, diethylthiocarbamoyl, etc.), (xxxii)

aryl-carbamoyl (e.g. $C_{6-10}$ aryl-carbamoyl such as phenyl-carbamoyl) and (xxxiii) aryl-thiocarbamoyl (e.g. $C_{6-10}$ aryl-thiocarbamoyl such as phenyl-thiocarbamoyl).

The above-mentioned "lower alkyl that may be halogenated", "lower alkoxy that may be halogenated", and "lower alkylthio that may be halogenated" have the same meaning of "lower alkyl that may be halogenated", "lower alkoxy that may be halogenated", and "lower alkylthio that may be halogenated" as mentioned above for the "substituent" of said "optionally substituted carbocyclic group or optionally substituted heterocyclic group".

The above-mentioned "aryl (preferably phenyl)" and "aryloxy (preferably phenyloxy)" may have substituent similar to those mentioned for the "substituent" for said "carbocyclic group that may be substituted or "heterocyclic group that may be substituted".

The above-mentioned "5- to 7-membered heterocyclic group or said heterocyclic group being optionally fused with a benzene ring" includes 5- to 7-membered (preferably 5- or 6-membered) heterocyclic groups containing 1 to 3, preferably 1 or 2, hetero-atoms of preferably 1 or 2 kinds as selected from the group consisting of nitrogen, oxygen, and sulfur in addition to carbon. The specific examples of such groups includes 1-, 2- or 3-pyrrolidinyl, 2- or 4-imidazolidinyl, 2-, 3-, or 4-pyrazolidinyl, 3-, 4-, or 5-pyrazolyl, 2-, 4-, or 5-imidazolyl, piperidino, 2-, 3-, or 4-piperidyl, 1- or 2-piperazinyl, morpholino, 2- or 3-morpholinyl, 2- or 3-thienyl, 2-, 3-, or 4-pyridyl, 2- or 3-furyl, pyrazinyl, 2-, 4-, or 5-pyrimidinyl, 2- or 3-pyrrolyl, 2-, 4-, or 5-oxazolyl, 2-, 4-, or 5-thiazolyl, 3-pyridazinyl, 3-, 4-, or 5-isothiazolyl, 3-, 4- or 5-isoxazolyl, etc. These groups may respectively be fused to a benzene ring in any position. Furthermore, this "5- to 7-membered heterocyclic group or said heterocyclic group being optionally fused with a benzene ring" may have 1 to 3 substituents in any substitutable positions.

The substituent of the above "5- to 7-membered heterocyclic group or said heterocyclic group being optionally fused with a benzene ring" is the same substituent of the "optionally substituted carbocyclic group that may be substituted or heterocyclic group" as mentioned for Ar.

Preferred, among such substituent groups, are (i) halogen (e.g. fluorine, chlorine, bromine, iodine), (ii) lower alkylenedioxy (e.g. $C_{1-3}$ alkylenedioxy such as methylenedioxy, ethylenedioxy, etc.), (iii) nitro, (iv) cyano, (v) lower alkyl that may be halogenated, (vi) lower cycloalkyl (e.g. $C_{3-6}$ cycloalkyl such as cyclopropyl, cyclobutyl, cyclopentyl, cyclohexyl, etc.), (vii) lower alkoxy that may be halogenated, (viii) lower alkylthio that may be halogenated, (ix) hydroxyl, (x) amino, (xi) mono-lower alkylamino (e.g. mono-$C_{1-6}$ alkylamino such as methylamino, ethylamino, propylamino, isopropylamino, butylamino, etc.), (xii) di-lower alkylamino (e.g. di-$C_{1-6}$ alkylamino such as dimethylamino, diethylamino, dipropylamino, dibutylamino, etc.), (xiii) 5- or 6-membered cycloamino (e.g. morpholino, piperazin-1-yl, piperidino, pyrrolidin-1-yl, etc.), (xiv) lower alkylcarbonyl (e.g. $C_{1-6}$ alkyl-carbonyl such as acetyl, propionyl, etc.), (xv) carboxyl, (xvi) lower alkoxycarbonyl (e.g. $C_{1-6}$ alkoxy-carbonyl such as methoxycarbonyl, ethoxycarbonyl, propoxycarbonyl, butoxycarbonyl, etc.), (xvii) carbamoyl, (xviii) mono-lower alkylcarbamoyl (e.g. mono-$C_{1-6}$ alkyl-carbamoyl such as methylcarbamoyl, ethylcarbamoyl, etc.), (xix) di-lower alkylcarbamoyl (e.g. di-$C_{1-6}$ alkyl-carbamoyl such as dimethylcarbamoyl, diethylcarbamoyl, etc.), (xx) arylcarbamoyl (e.g. $C_{6-10}$ aryl-carbamoyl such as phenylcarbamoyl, naphthylcarbamoyl, etc.), (xxi) sulfo, (xxii) lower alkanesulfonyl (e.g. $C_{1-6}$ alkanesulfonyl such as methanesulfonyl, ethanesulfonyl, etc.), (xxiii) aryl (e.g. $C_{6-10}$ aryl such as phenyl, naphthyl, etc.), (xxiv) aryloxy (e.g. $C_{6-10}$ aryloxy such as phenyloxy, naphthyloxy, etc.), (xxv) thiocarbamoyl, (xxvi) mono-$C_{1-6}$ alkylthio-carbamoyl, (xxvii) di-$C_{1-6}$ alkylthio-carbamoyl, (xxviii) $C_{6-10}$ aryl-carbamoyl and (xxix) $C_{6-10}$ aryl-thiocarbamoyl, among others.

The above-mentioned "lower alkyl that may be halogenated", "lower alkoxy that may be halogenated", and "lower alkylthio that may be halogenated" have the same meaning of "lower alkyl that may be halogenated", "lower alkoxy that may be substituted", and "lower alkylthio that may be substituted" as mentioned above for the "substituent" of said "carbocyclic group or optionally substituted heterocyclic group" as mentioned for Ar.

The "optionally substituted carbon atom" for Q includes a group of the formula $CR^4$ ($R^4$ is as defined above).

Q is preferably $CR^{4'}$ wherein $R^{4'}$ is a hydrogen atom or a $C_{1-6}$ alkyl group; or $N(O)p$ wherein p is as defined above.

Ring A may have substituent groups, such as those mentioned for $R^3$ ($R^3$ is as defined above), in addition to $R^1$ and $R^2$.

The "optionally substituted methylene" as mentioned for Y includes (1) groups of the formula

wherein $R^9$ and $R^{9'}$ may be the same or different and each represents (i) hydrogen, (ii) lower alkyl that may be halogenated, (iii) lower alkoxy that may be halogenated, (iv) lower alkylthio that may be halogenated, (v) hydroxyl, (vi) cyano, (vii) alkylcarbonyl (e.g. $C_{1-6}$ alkyl-carbonyl such as acetyl, propionyl, etc.), (viii) lower alkylcarbonyloxy (e.g. $C_{1-6}$ alkyl-carbonyloxy such as acetyloxy, propionyloxy, etc.), (ix) formylamino, (x) amino, (xi) mono-lower alkylamino (e.g. mono-$C_{1-6}$ alkylamino such as methylamino, ethylamino, propylamino, isopropylamino, butylamino, etc.), (xii) di-lower alkylamino (e.g. di-$C_{1-6}$ alkylamino such as dimethylamino, diethylamino, dipropylamino, dibutylamino, etc.), (xiii) carboxyl, (xiv) lower alkoxy-carbonyl (e.g. $C_{1-6}$ alkyloxy-carbonyl such as methoxycarbonyl, ethoxycarbonyl, propoxycarbonyl, butoxycarbonyl, etc.), or (xv) lower alkyl-carbonylamino (e.g. $C_{1-6}$ alkyl-carbonylamino such as acetylamino, propionylamino, etc.) wherein the "lower alkyl that may be halogenated", "lower alkoxy that may be halogenated", and "lower alkylthio that may be halogenated" include the same meaning of "lower alkyl that may be halogenated", "lower alkoxy that may be halogenated", and "lower alkylthio that may be halogenated" as mentioned for the "substituent" for the "optionally substituted carbocyclic group or optionally substituted heterocyclic group" as mentioned for Ar. $R^9$ and $R^{9'}$ are the same or different and each preferably represents hydrogen, hydroxyl, cyano, $C_{1-6}$ alkoxy, amino, or mono-$C_{1-6}$ alkylamino, more preferably represents hydrogen, hydroxyl, amino, or mono-$C_{1-6}$ alkylamino, and most preferably represents hydrogen and (2) groups of the formula >C=R$^{10}$ wherein R$^{10}$ represents (i)

wherein R$^9$ and R$^{9'}$ are as defined above, (ii) =NR$^9$ wherein R$^9$ is as defined above, (iii) O or (iv) S.

The "imino that may be substituted" as mentioned for Y includes NR$^5$ (wherein R$^5$ is as defined above).

The "heterocyclic group" of the "optionally substituted heterocyclic group" as mentioned for R$^6$ preferably includes 5- to 10-membered (monocyclic or bicyclic) heterocyclic groups each containing 1 or more (e.g. 1 to 4, preferably 1 to 3, and more preferably 1 or 2) hetero-atoms of preferably one or two kinds as selected from the group consisting of nitrogen, oxygen, and sulfur in addition to carbon, for example non-aromatic heterocyclic groups such as 1-, 2-, or 3-pyrrolidinyl, 2- or 4-imidazolidinyl, 2-, 3-, or 4-pyrazolidinyl, piperidino, 2-, 3-, or 4-piperidyl, 1-or 2-piperazinyl, morpholinyl, thiomorpholinyl, 3- or 4-azepinyl, etc. (particularly saturated 5- through 7-membered cycloamino groups (e.g. 1- or 2-piperazinyl) are preferred) and aromatic heterocyclic groups such as 2- or 3-thienyl, 2-, 3-, or 4-pyridyl, 2- or 3-furyl, 4- or 8-quinolyl, 4-isoquinolyl, pyrazinyl, 2-pyrimidinyl, 3-pyrrolyl, 2-imidazolyl, 3-pyridazinyl, 3-isothiazolyl, 3-isoxazolyl, 1-indolyl, 2-isoindolyl, etc. Among them, the aromatic heterocyclic groups and saturated 5- to 7-membered cycloamino groups are preferred. The more preferred are 5- or 6-membered aromatic heterocyclic groups each containing 1 to 3 hetero-atoms of preferably one or two kinds as selected from among nitrogen, oxygen, and sulfur in addition to carbon (e.g. 2- or 3-thienyl, 2- or 4-pyridyl, etc.) and saturated 5- to 7-membered cycloamino groups.

The "substituent" of said "optionally substituted heterocyclic" includes the same as the "substituent" for the "optionally substituted hydrocarbon group" of R$^3$, R$^4$, R$^5$, and R$^6$.

The "acyl" as mentioned for R$^5$ includes —(C=O)—R$^7$, —SO$_2$—R$^7$, —SO—R$^7$, —(C=O)NR$^8$—R$^7$, —(C=O)O—R$^7$, —(C=S)O—R$^7$, and —(C=S)NR$^8$—R$^7$ [wherein R$^7$ is hydrogen or optionally substituted hydrocarbon and R$^8$ is hydrogen or lower alkyl (e.g. C$_{1-6}$ alkyl such as methyl, ethyl, propyl, isopropyl, butyl, isobutyl, sec-butyl, tert-butyl, pentyl, hexyl, etc. and preferably C$_{1-3}$ alkyl such as methyl, ethyl, propyl, isopropyl, etc.)].

Among those groups, —(C=O)—R$^7$, —SO$_2$—R$^7$, —SO—R$^7$, —(C=O)NR$^8$—R$^7$, and —(C=O)O—R$^7$ (R$^7$ and R$^8$ are as defined above) are preferred and —(C=O)—R$^7$ (R$^7$ is as defined above) is more preferred.

The "hydrocarbon" of the "optionally substituted hydrocarbon" as mentioned above for R$^7$ is a group available upon elimination of one hydrogen atom from a hydrocarbon compound and includes acylic (straight-chain or branched) and cyclic hydrocarbon groups such as alkyl, alkenyl, alkynyl, cycloalkyl, aryl, and aralkyl. The specific list of such groups includes the same groups as those mentioned for the "hydrocarbon" of the "optionally substituted hydrocarbon" as mentioned for R$^3$, R$^4$, and R$^5$. Among those groups, C$_{1-16}$ acyclic or cyclic hydrocarbon groups are preferred and lower alkyl groups are particularly preferred.

The preferred substituent that may be present on the "hydrocarbon group" for R$^7$ includes (i) halogen (e.g. fluorine, chlorine, bromine, iodine), (ii) lower alkylenedioxy (e.g. C$_{1-3}$ alkylenedioxy such as methylenedioxy, ethylenedioxy, etc.), (iii) nitro, (iv) cyano, (v) lower alkyl that may be halogenated, (vi) lower cycloalkyl (e.g. C$_{3-6}$ cycloalkyl such as cyclobutyl, cyclopentyl, cyclohexyl, etc.), (vii) lower alkoxy that may be halogenated, lower alkylthio that may be halogenated, (ix) hydroxyl, (x) amino, (xi) mono-lower alkylamino (e.g. C$_{1-6}$ alkylamino such as methylamino, ethylamino, propylamino, isopropylamino, butylamino, etc.), (xii) di-lower alkylamino (e.g. di-C$_{1-6}$ alkylamino such as dimethylamino, diethylamino, dipropylamino, dibutylamino, etc.), (xiii) 5- or 6-membered cycloamino (e.g. morpholino, piperazin-1-yl, piperidino, pyrrolidin-1-yl, 2-pyrrolidon-1-yl, 2-pyridon-1-yl, etc.) optionally having hydroxyl or oxo, (xiv) acylamino, (xv) lower alkyl-carbonyl (e.g. C$_{1-6}$ alkyl-carbonyl such as acetyl, propionyl, etc.), (xvi) lower alky-carbonyloxy (e.g. C$_{1-6}$ alkyl-carbonyloxy such as methylcarbonyloxy, ethylcarbonyloxy, etc.), (xvii) lower alkyl-carbonyloxy-C$_{1-3}$ alkyl (e.g. C$_{1-6}$ alkyl-carbonyloxy-C$_{1-3}$ alkyl such as methylcarbonyloxymethyl, ethylcarbonyloxymethyl, etc.), (xviii) carboxyl, (xix) lower alkoxy-carbonyl (e.g. C$_{1-6}$ alkyl-oxycarbonyl such as methoxycarbonyl, ethoxycarbonyl, propoxycarbonyl, butoxycarbonyl, etc.), (xx) mono-lower alkylamino-carbonyl (e.g. mono-C$_{1-6}$ alkylamino-carbonyl such as methylamino-carbonyl, ethylamino-carbonyl, etc.), (xxi) di-lower alkylamino-carbonyl (e.g. di-C$_{1-6}$ alkylamino-carbonyl such as dimethylamino-carbonyl, diethylamino-carbonyl, etc.), (xxii) carbamoyl, (xxiii) mono-lower alkyl-carbamoyl (e.g. mono-C$_{1-6}$ alkyl-carbamoyl such as methylcarbamoyl, ethylcarbamoyl, etc.), (xxiv) di-lower alkylcarbamoyl (e.g. di-C$_{1-6}$ alkyl-carbamoyl such as dimethylcarbamoyl, diethylcarbamoyl, etc.), (xxv) arylcarbamoyl (e.g. C$_{6-10}$ aryl-carbamoyl such as phenylcarbamoyl, naphthylcarbamoyl, etc.), (xxvi) sulfo, (xxvii) lower alkyl-sulfonyl (e.g. C$_{1-6}$ alkylsulfonyl such as methylsulfonyl, ethylsulfonyl, etc.), (xxviii) aryl (e.g. C$_{6-10}$ aryl such as phenyl, naphthyl, etc.), (xxix) aryloxy (e.g. C$_{6-10}$ aryloxy such as phenyloxy, naphthyloxy, etc.), (xxx) 5- to 7-membered heterocyclic group having 1 to 3 hetero atoms selected from nitrogen, oxygen and sulfur in addition to carbon atoms, said heterocyclic group being optionally fused with a benzene ring, (xxxi) lower aralkyloxy-carbonyl (e.g. C$_{7-11}$ aralkyloxy-carbonyl such as benzyloxycarbonyl etc.), (xxxii) thiocarbamoyl, (xxxiii) mono-lower alkylthio-carbamoyl (e.g. mono-C$_{1-6}$ alkylthio-carbamoyl such as methylthiocarbamoyl, ethylthiocarbamoyl, etc.), (xxxiv) di-lower alkylthio-carbamoyl (e.g. di-C$_{1-6}$ alkylthio-carbamoyl such as dimethylthiocarbamoyl, diethylthiocarbamoyl, etc.) and (xxxv) arylthiocarbamoyl (e.g. C$_{6-10}$ aryl-thiocarbamoyl such as phenylthiocarbamoyl etc.).

Preferred, among them, are halogen, di-lower alkylamino, carboxyl, and lower alkoxycarbonyl.

More preferred are di-lower alkylamino and carboxyl.

The above-mentioned "lower alkyl that may be halogenated", "lower alkoxy that may be halogenated", "lower alkylthio that may be halogenated", and "acylamino" are the same meaning as those mentioned for the "substituent" the "optionally substituted hydrocarbon group or optionally substituted heterocyclic group" as mentioned for Ar.

The "lower alkyl", of the "optionally substituted lower alkyl" as mentioned for R$^1$ and R$^2$ includes straight-chain or branched lower(C$_{1-6}$)alkyl (e.g. methyl, ethyl, propyl, isopropyl, butyl, isobutyl, sec-butyl, tert-butyl, pentyl, hexyl, etc.).

The "lower alkoxy" of the "optionally substituted lower alkoxy" as mentioned for R$^1$ and R$^2$ includes straight-chain or branched lower(C$_{1-6}$)alkyloxy (e.g. methoxy, ethoxy, propoxy, isopropoxy, butoxy, isobutoxy, sec-butoxy, tert-butoxy, pentyloxy, isopentyloxy, neopentyloxy, hexyloxy, etc.).

The "substituent" of the above "optionally substituted lower alkyl" and "optionally substituted lower alkoxy are the same meaning as those mentioned for the "substituent" of the "optionally substituted hydrocarbon group" as mentioned for $R^3$ $R^4$, and $R^5$.

Referring to various combinations of $R^1$ and $R^2$, the combination of any of hydrogen, halogen, hydroxyl, optionally substituted lower alkyl, and optionally substituted lower alkoxy for $R^1$ and any of hydrogen, halogen, hydroxyl, optionally substituted lower alkyl, and optionally substituted lower alkoxy for $R^2$ are preferred and the combination of methoxy for $R^1$ and hydrogen for $R^2$ is generally useful.

Another preferable combinations of $R^1$ and $R^2$ are
one of $R^1$ and $R^2$ is (1) a hydrogen, (2) a $C_{1-6}$ alkyl, (3) a $C_{1-6}$ alkoxy which may be substituted with (a) a $C_{1-6}$ alkoxy-carbonyl, (b) a $C_{7-11}$ aralkyl or (c) a carboxyl, or (4) a hydroxyl;
the other is (1) a $C_{1-6}$ alkyl, (2) a $C_{1-6}$ alkoxy which may be substituted with (a) a $C_{1-6}$ alkoxy-carbonyl or (b) a carboxyl, or (3) a hydroxyl.

Where $R^1$ and $R^2$ taken together form a ring with adjacent —C=C—, the preferred includes lower alkylene (e.g. $C_{1-6}$ alkylene such as methylene, ethylene, propylene, trimethylene, tetramethylene, etc.), lower alkylenedioxy (e.g. $C_{1-6}$ alkylenedioxy such as methylenedioxy, ethylenedioxy, etc.) or lower alkyleneoxy (e.g. $C_{1-6}$ alkyleneoxy, such as methyleneoxy, ethyleneoxy, etc.). Particularly preferred is lower alkylenedioxy (e.g. $C_{1-6}$ alkylenedioxy such as methylenedioxy, ethylenedioxy, etc.), or lower alkyleneoxy (e.g. $C_{1-6}$ alkyleneoxy, such as methyleneoxy, ethyleneoxy, etc.), especially lower alkylenedioxy, with methylenedioxy being particularly preferred.

The "substituent" of the ring formed by $R^1$ and $R^2$, taken together, are the same "substituent" the "optionally substituted hydrocarbon group" as mentioned for $R^3$, $R^4$, and $R^5$.

$R^1$ and $R^3$ may taken together form a ring with adjacent —C=C—.

The preferred includes lower alkylenedioxy (e.g. $C_{1-6}$ alkylenedioxy such as methylenedioxy, ethylenedioxy, propylenedioxy, trimethylenedioxy, tetramethylenedioxy, etc.).

The "substituent" of the ring formed by $R^1$ and $R^3$, taken together, are the same "substituent" of the "optionally substituted hydrocarbon group" as mentioned for $R^3$, $^4$and $R^5$.

The "optionally substituted hydroxyl" for $R^3$ and $R^4$ is either a hydroxyl group or a hydroxyl group having a group as said "optionally substituted hydrocarbon group" instead of its hydrogen atom. The "optionally substituted hydroxyl" is preferably a hydroxyl group or a hydroxyl group having said optionally substituted lower alkyl. Said "lower alkyl" includes straight-chain or branched lower($C_{1-6}$)alkyl (e.g. methyl, ethyl, propyl, isopropyl, butyl, isobutyl, sec-butyl, tert-butyl, pentyl, hexyl, etc.) and the substituent of the "lower alkyl" includes the same groups as those mentioned for the substituent of the "optionally substituted hydrocarbon group" as defined for $R^3$, $R^4$ and $R^5$.

Preferably, $R^3$ is $C_{1-6}$ alkoxy.

The "$C_{1-3}$ alkylene" of the "$C_{1-3}$ alkylene which may have an oxo or thioxo" as mentioned for $Z^1$ is —$CH_2$—, —$(CH_2)_2$—, or —$(CH_2)_3$— and may contain oxygen or sulfur within the carbon chain as an ether or thioether as it is the case with —$CH_2$—O—$CH_2$—, —$CH_2$—O—$CH_2$—$CH_2$—, —$CH_2$—S—$CH_2$—, and —$CH_2$—S—$CH_2$—$CH_2$— and the sulfur may be in the sulfoxide form or in the sulfone form.

More specifically, the "oxo- or thioxo-$C_{1-3}$ alkylene" includes groups of the following formula.

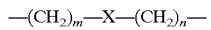

wherein X is C=O or C=S; m and n each is 0 or 1.

In the above formula, X preferably is C=O and m and n each is preferably equal to 0.

The "$C_{1-3}$ alkylene" of the "optionally substituted $C_{1-3}$ alkylene" as mentioned for $Z^2$ includes —$CH_2$—, —$(CH_2)_2$— or —$(CH_2)_3$— and may contain etherified oxygen or sulfur within the carbon chain as it is the case with —$CH_2$—O—$CH_2$—, —$CH_2$—O—$CH_2$—$CH_2$—, —$CH_2$—S—$CH_2$—, or —$CH_2$—S—$CH_2$—$CH_2$— and the sulfur may be in the sulfoxide form or in the sulfone form.

The "substituent" of said "optionally substituted $C_{1-3}$ alkylene" includes the same groups as those mentioned for the substituent of the "optionally substituted hydrocarbon group" mentioned for $R^3$, $R^4$, and $R^5$.

The "$C_{1-3}$ alkylene" of the "optionally substituted $C_{1-3}$ alkylene substituted" as mentioned for $Z^2$ may have an oxo or thioxo bond in a chemically feasible position.

Preferably $Z^2$ is (1) C=O, (2) $CH_2$, (3) $(CH_2)_2$, (4) $(CH_2)_3$ or (5) CH—OH.

Also preferably $Z^2$ is —$(CH_2)_p$— (where p represents an integer of 1 to 3). More preferably $Z^2$ is —$CH_2$—.

Among species of compound [I], the compounds in which Q is $CR^4$ (where $R^4$ is as defined above) are preferred.

Preferably, $R^4$ is hydrogen, halogen, optionally substituted hydrocarbon, or optionally substituted hydroxyl, more preferably, hydrogen, halogen, optionally substituted alkyl or hydroxyl optionally substituted by lower alkyl. The more preferred are hydrogen, halogen, lower alkyl, and hydroxyl optionally having lower alkyl as a substituent. Hydrogen is the most useful.

More preferably, Q is (1) $CR^4$ wherein $R^{4'}$ is (i) a $C_{1-6}$ alkyl which may be substituted with a di-$C_{1-6}$ alkylamino, (ii) a halogen, or (iii) a $C_{1-6}$ alkoxy, or (2) N.

Q is also preferably (1) $CR^4$ wherein $R^4$ is hydrogen, halogen, optionally substituted hydrocarbon, or optionally substituted hydroxyl, or (2) N(O)p wherein p is 0 or 1.

Q is also preferably CH or N.

X is preferably C=O.

Y is preferably $CH_2$ or $NR^5$ (where $R^5$ is as defined above) and more preferably $NR^5$ (where $R^5$ is as defined above).

Y is also preferably, $NR^{5'}$ wherein $R^{5'}$ is (i) hydrogen, (ii) $C_{1-6}$ alkyl which may be substituted with (a) morpholino, (b) carboxyl, (C) $C_{1-6}$ alkoxy-carbonyl, or (d) phenyl which may be substituted with $C_{1-6}$ alkoxy, or (iii) $COR^{7"}$ wherein $R^{7"}$ is (a) hydrogen, (b) $C_{1-6}$ alkyl which may be substituted with carboxyl or benzyloxycarbonyl, or (c) di-$C_{1-6}$ alkylamino.

$R^5$ is preferably hydrogen, alkyl that may be substituted, or acyl of the formula —(C=O)—$R^7$ (where $R^7$ is as defined above), with hydrogen being particularly preferred.

More preferred $R^5$ is (i) hydrogen, (ii) $C_{1-6}$ alkyl which may be substituted with (a) morpholino, (b) carboxyl, (c) $C_{1-6}$ alkoxy-carbonyl, or (d) phenyl which may be substituted with C16 alkoxy, or (iii) $COR^{7"}$ wherein $R^{7"}$ is (a) hydrogen, (b) $C_{1-6}$ alkyl which may be substituted with carboxyl or benzyloxycarbonyl, or (c) di-$C_{1-6}$ alkylamino.

Ar is preferably optionally substituted 3- to 14-membered aromatic group, preferably, optionally substituted aryl and more preferably optionally substituted phenyl.

The above-mentioned "optionally substituted 3- to 14-membered aromatic group", "optionally substituted aryl" and "optionally substituted phenyl" include 3- to 14-membered aromatic group, aryl, or phenyl optionally substituted with, for example, (i) halogen (e.g. fluorine, chlorine, bromine, iodine), (ii) lower alkylenedioxy (e.g. $C_{1-3}$ alkylenedioxy such as methylenedioxy, ethylenedioxy, etc.), (iii) nitro, (iv) cyano, (v) lower alkyl that may be halogenated, (vi) lower alkenyl that may be halogenated, (vii) lower alkynyl that may be halogenated, (viii) lower cycloalkyl (e.g. $C_{3-6}$ cycloalkyl such as cyclopropyl, cyclobutyl, cyclopentyl, cyclohexyl, etc.), (ix) lower alkoxy that may be halogenated, (x) lower alkylthio that may be halogenated, (xi) hydroxyl, (xii) amino, (xiii) mono-lower alkylamino (e.g. mono-$C_{1-6}$ alkylamino such as methylamino, ethylamino, propylamino, isopropylamino, butylamino, etc.), (xiv) di-lower alkylamino (e.g. di-$C_{1-6}$ alkylamino such as dimethylamino, diethylamino, dipropylamino, dibutylamino, etc.), (xv) 5- or 6-membered cycloamino (e.g. morpholino, thiomorpholino, piperazin-1-yl, piperidino, pyrrolidin-1-yl, etc.), (xvi) acylamino, (xvii) lower alkylcarbonyl (e.g. $C_{1-6}$ alkyl-carbonyl such as acetyl, propionyl, etc.), (xviii) carboxyl, (xix) lower alkoxy-carbonyl (e.g. $C_{1-6}$ alkyl-oxycarbonyl such as methoxycarbonyl, ethoxycarbonyl, propoxycarbonyl, butoxycarbonyl, etc.), (xx) carbamoyl, (xxi) mono-lower alkylcarbamoyl (e.g. mono-$C_{1-6}$ alkyl-carbamoyl such as methylcarbamoyl, ethylcarbamoyl, etc.), (xxii) di-lower alkylcarbamoyl (e.g. di-$C_{1-6}$ alkyl-carbamoyl such as dimethylcarbamoyl, diethylcarbamoyl, etc.), (xxiii) aryl-carbamoyl (e.g. $C_{6-10}$ aryl-carbamoyl such as phenylcarbamoyl, naphthylcarbamoyl, etc.), (xxiv) sulfo, (xxv) lower alkylsulfonyl (e.g. $C_{1-6}$ alkylsulfonyl such as methylsulfonyl, ethylsulfonyl, etc.), (xxvi) aryl (e.g. $C_{6-10}$ aryl such as phenyl, naphthyl, etc.), (xxvii) aryloxy (e.g. $C_{6-10}$ aryloxy such as phenyloxy, naphthyloxy, etc.), (xxix) thiocarbamoyl, (xxx) mono-lower alkylthiocarbamoyl (e.g. mono-$C_{1-6}$ alkylthio-carbamoyl such as methylthiocarbamoyl, ethylthiocarbamoyl, etc.), (xxxi) di-lower alkylthiocarbamoyl (e.g. di-$C_{1-6}$ alkylthio-carbamoyl such as dimethylthiocarbamoyl, diethylthiocarbamoyl, etc.), (xxxii) aryl-carbamoyl (e.g. $C_{6-10}$ aryl-carbamoyl such as phenyl-carbamoyl) and (xxxiii) aryl-thiocarbamoyl (e.g. $C_{6-10}$ aryl-thiocarbamoyl such as phenyl-thiocarbamoyl). The above-mentioned "lower alkyl that may be substituted", "lower alkoxy that may be halogenated", "lower alkylthio that may be halogenated", and "acylamino" are the same as those respectively mentioned for the "substituent" of the "optionally substituted hydrocarbon group or optionally substituted heterocyclic group" as mentioned for Ar). Preferred is phenyl substituted with halogen (fluorine or chlorine in particular), lower alkylenedioxy (methylenedioxy in particular), lower alkoxy (methoxy in particular) that may be halogenated, or hydroxyl.

To be more specific, said "phenyl that may be substituted" includes groups of the following formulas.

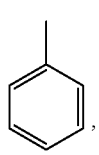
(A1)

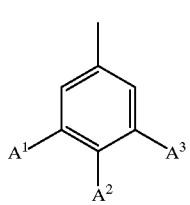
(A2)

[wherein $A^1$, $A^2$, and $A^3$ are the same or different and each represents halogen (e.g. fluorine, chlorine, bromine, iodine), lower alkoxy that may be halogenated (e.g. methoxy, difluoromethoxy, trifluoromethoxy, ethoxy, 2,2,2-trifluoroethoxy, n-propoxy, isopropoxy, n-butoxy, 4,4,4-trifluorobutoxy, isobutoxy, sec-butoxy, pentyloxy, hexyloxy, etc.), or hydroxyl; or either $A^1$ and $A^2$ or $A^2$ and $A^3$, taken together, represent lower alkylenedioxy (e.g. $C_{1-3}$ alkylenedioxy such as methylenedioxy, ethylenedioxy, etc.]

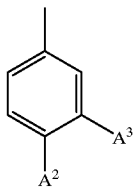
(A3)

[wherein $A^2$ and $A^3$ are as defined above] or

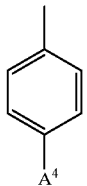
(A4)

[wherein $A^4$ is halogen (e.g. fluorine, chlorine, bromine, iodine), lower alkoxy that may be halogenated (e.g. methoxy, difluoromethoxy, trifluoromethoxy, ethoxy, 2,2,2-trifluoroethoxy, n-propoxy, isopropoxy, n-butoxy, 4,4,4-trifluorobutoxy, isobutoxy, sec-butoxy, pentyloxy, hexyloxy, etc.), or hydroxyl]

More preferred are groups of the formula

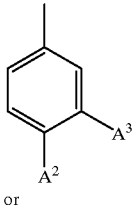
(A3)

or

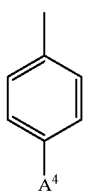
(A4)

[wherein the all symbols have the same meanings as defined above].

Most useful is

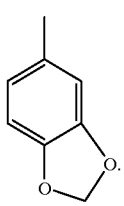

Ar is also preferably optionally substituted pyridyl group or optionally substituted pyridinium.

Substituents of the above-mentioned "optionally substituted pyridyl group" and "optionally substituted pyridinium" are the same as the substituents of "optionally substituted 3- to 14-membered aromatic group" for Ar, as mentioned above.

Preferable example of Ar is (1) a phenyl group which may be substituted with (a) a halogen, (b) a $C_{1-6}$ alkylenedioxy, (c) a $C_{1-6}$ alkoxy which may be substituted with (c-1) a halogen (c-2) a di-$C_{1-6}$ alkylamino, or (c-3) a $C_{1-6}$ alkoxycarbonyl, (d) a $C_{7-11}$ aralkyloxy, (e) $C_{1-6}$ alkyl which may be substituted with a halogen, or (f) hydroxyl, (2) an optionally oxidized pyridyl group, or (3) a pyridinium group which may be substituted with $C_{1-6}$ alkyl Preferably, $R^1$ and $R^2$ each is hydrogen, halogen, hydroxyl, or lower alkoxy, or, taken together, represent lower alkylenedioxy.

Preferably, $R^3$ is hydrogen, halogen, lower alkyl, or hydroxyl optionally having lower alkyl as a substituent.

Each of m and n is equal to 0.

In the above formula [I], ring A as represented by the formula

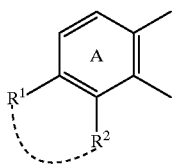

wherein all symbols have the same meanings as defined above is preferably a ring of the formula

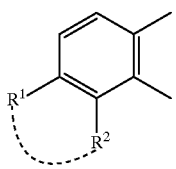

wherein all have the same meanings as defined above or a ring of the formula

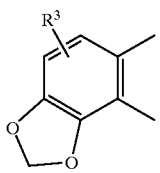

wherein $R^3$ represents hydrogen, halogen, optionally substituted hydrocarbon group (preferably, lower alkyl), or hydroxyl optionally having lower alkyl as a substituent.

Particularly preferred is the ring of the formula

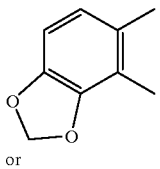

or

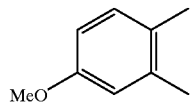

Moreover, in formula [I], the ring represented by the formula

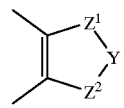

wherein all symbols have the same meanings as defined above, is preferably a ring of the formula

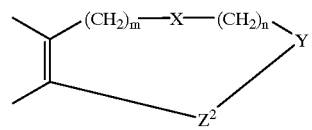

wherein all symbols have the same meanings as defined above.

More preferred is a ring of the following formula.

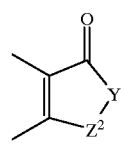

wherein Y and $Z^2$ are as defined above.

Particularly preferred is a ring of the following formula.

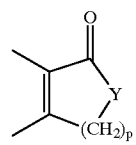

wherein p is an integer of 1 to 3; Y is as defined above.

The preferred compounds; among species of compound [I], are compounds of the following formula.

[II]

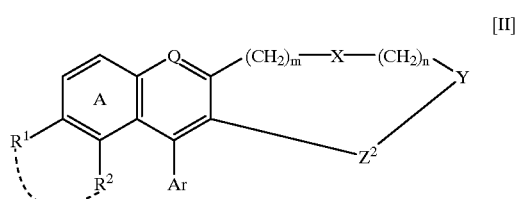

wherein all symbols have the same meanings as defined above.

More preferred are the compounds of the following formulas.

[IV]

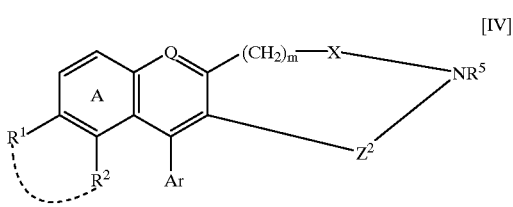

wherein all symbols have the same meanings as defined above.

[V]

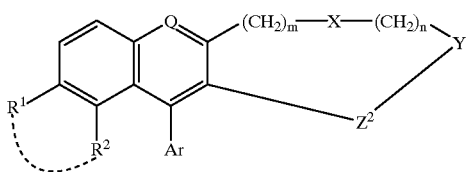

wherein all symbols have the same meanings as defined above.

[VII]

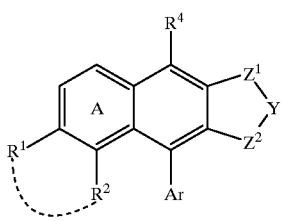

wherein all symbols have the same meanings as defined above.

[XIII]

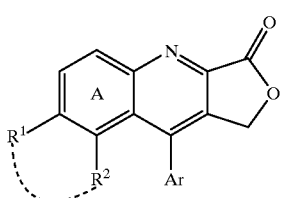

wherein all symbols have the same meanings as defined above.

[XVI]

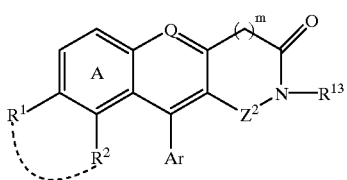

wherein $R^{13}$ is hydrogen or optionally substituted lower alkyl; the other symbols have the same meanings as defined. The above "optionally substituted alkyl" has the same meaning as defined in $R^1$ and $R^2$.

[XX]

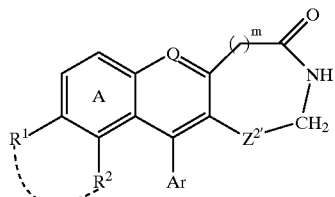

wherein $Z^{2'}$ is optionally substituted $C_{1-2}$ alkylene; the other symbols have the same meanings as defined above. The "optionally substituted $C_{1-2}$ alkylene" have the same substituents as defined in $Z^2$.

[XXIII]

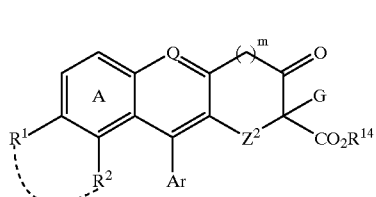

wherein $R^{14}$ is lower alkyl (e.g. $C_{1-6}$ alkyl such as methyl, ethyl, propyl, etc.); G is hydrogen or the same group as the substituent of the substituted methylene mentioned above for Y; the other symbols have the same meanings as defined above.

Still more preferred are compounds of the following formula:

[VI]

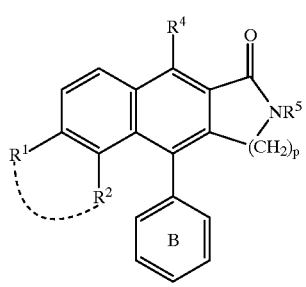

wherein ring B is a benzene ring that may be substituted wherein the substituent for this "benzene ring that may be substituted" has the same meaning as those mentioned for the "substituent" of the "optionally substituted hydrocarbon group or optionally substituted heterocyclic group" as mentioned for Ar); the other symbols have the same meanings as defined above.

As the preferred species of compound [II],
Q is (1) $CR^{4'}$ wherein $R^{4'}$ is (i) a $C_{1-6}$ alkyl group which may be substituted with a di-$C_{1-6}$ alkylamino group, (ii) a halogen atom, or (iii) a $C_{1-6}$ alkoxy group, or (2) N;
X is C=O;
Y is $NR^{5'}$ wherein $R^{5'}$ is (i) a hydrogen, (ii) a $C_{1-6}$ alkyl group which may be substituted with (a) a morpholino, (b) a carboxyl, (c) a $C_{1-6}$ alkoxy-carbonyl, or (d) a phenyl which may be substituted with $C_{1-6}$ alkoxy, or (iii) $COR^{7'}$ wherein $R^{7'}$ is (a) a hydrogen, (b) $C_{1-6}$ alkyl which may be substituted with a carboxyl or a benzyloxycarbonyl, or a di-$C_{1-6}$ alkylamino;
m and n each represents 0;

$Z^2$ is (1) C=O, (2) $CH_2$, (3) $(CH_2)_2$, (4) $(CH_2)_3$, or (5) CH—OH;

Ar is (1) a phenyl group which may be substituted with (a) a halogen, (b) a $C_{1-6}$ alkylenedioxy, (c) a $C_{1-6}$ alkoxy which may be substituted with (c-1) a halogen or (c-2) a di-$C_{1-6}$ alkylamino, or (c-3) a $C_{1-6}$ alkoxy-carbonyl, (d) a $C_{7-11}$ aralkyloxy, (e) $C_{1-6}$ alkyl which may be substituted with a halogen, or (f) hydroxyl, (2) an optionally oxidized pyridyl group, or (i) a pyridinium group which may be substituted with $C_{1-6}$ alkyl;

one of $R^1$ and $R^2$ is (1) a hydrogen, (2) a $C_{1-6}$ alkyl, (3) a $C_{1-6}$ alkoxy which may be substituted with (a) a $C_{1-6}$ alkoxy-carbonyl, (b) a $C_{7-11}$ aralkyl or (c) a carboxyl, or (4) a hydroxyl.

the other is (1) a $C_{1-6}$ alkyl, (2) a $C_{1-6}$ alkoxy which may be substituted with (a) a $C_{1-6}$ alkoxy-carbonyl or (b) a carboxyl, or (3) a hydroxyl;

$R^1$ and $R^2$ taken together with adjacent —c=c— form a $C_{1-6}$ alkylenedioxy group, or a $C_{1-6}$ alkyleneoxy group; or ring A is a benzene ring which may have a $C_{1-6}$ alkoxy group, in addition to $R^1$ and $R^2$; and a $C_{1-6}$ alkoxy group or ring A and a $C_{1-6}$ alkoxy group of $R^1$ may be taken together form $C_{1-6}$ alkylenedioxy group.

More preferably,
Q is CH or N;
X is C=O;
m and n each represents 0;
$Z^2$ is $CH_2$; and
$R^1$ and $R^2$ taken together form a $C_{1-6}$ alkylenedioxy group.

As the preferred species of compound [I], the following compounds can be specifically mentioned.

10-(1,3-Benzodioxol-5-yl)-8,9-dihydro-7H-1,3,-benzodioxolo[4,5-f]isoindol-7-one,
11-(1,3-Benzodioxol-5-yl)-7,8,9,10-tetrahydro-1,3,-benzodioxolo[4,5-g]isoquinolin-7-one,
4-(1,3-Benzodioxol-5-yl)-2,3-dihydro-5-methoxy-1H-benz[f]isoindol-1-one,
8,9-Dihydro-10-(4-trifluoromethylphenyl)-7H-1,3-benzodioxolo[4,5-f]isoindol-7-one,
11-(1,3-Benzodioxol-5-yl)-9,10-dihydro-8H-isoindolo[5,6-f]benz[b]-1,4-dioxan-8-one,
10-(4-Fluorophenyl)-8,9, -dihydro-7H-1,3-benzodioxolo[4,5-f]isoindol-7-one,
10-(1,3-Benzodioxol-5-yl)-8,9-dihydro-6-methyl-7H-1,3-benzodioxolo[4,5-f]isoindol-7-one,
10-(4-Fluorophenyl)-8,9-dihydro-6-methyl-7H-1,3-benzodioxolo[4,5-f]isoindol-7-one,
8,9-Dihydro-6-methyl-10-(4-trifluoromethylphenyl)-7H-1,3-benzodioxolo[4,5-f]isoindol-7-one,
10-(1,3-Benzodixol-5-yl)-8,9-dihydro-6-ethyl-7H-1,3-benzodioxolo[4,5-f]isoindol-7-one,
4-(1,3-Benzodioxol-5-yl)-2,3-dihydro-6-methoxy-1H-benz[f]isoindol-1-one,
2,3-Dihydro-6-methoxy-4-(4-methoxypheny)-1H-benz[f]isoindol-1-one,
2,3-Dihydro-6-methoxy-4-(4-trifluoromethylphenyl)-1H-benz[f]isoindol-1-one,
4-(4-Fluorophenyl)-2,3-dihydro-6-methoxy-9-methyl-1H-benz[f]isoindol-1-one,
4-(4-Methoxyphenyl)-2,3-dihydro-6-methoxy-9-methyl-1H-benz[f]isoindol-1-one,
9-(4-Fluorophenyl)-1,2-dihydro-7-methoxy-3H-pyrrolo[3,4-b]quinolin-3-one,
1,2-Dihydro-7-methoxy-9-(4-methoxyphenyl)-3H-pyrrolo[3,4-b]quinolin-3-one,
3,4-Dihydro-7-methoxy-5-(4-methoxyphenyl)-benzo[b][1,7]naphthyridin-1(2H)-one.

The preferred, among the above-mentioned compounds of formula [III], are the compounds in which Q is CH or N; X is C=O;

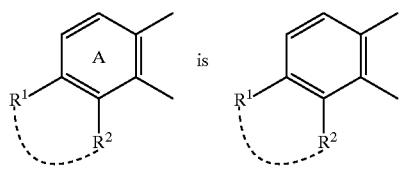

wherein $R^1$ is hydrogen and $R^2$ is methyl, or $R^1$ and $R^2$ jointly form methylenedioxy; Ar is phenyl that may be substituted with hydroxyl, halogen (e.g. fluorine, chlorine, bromine, etc.), lower alkoxy (e.g. $C_{1-6}$ alkoxy such as methoxy, ethoxy, propoxy, isopropoxy, butoxy, isobutoxy, sec-butoxy, tert-butoxy, pentyloxy, isopentyloxy, neopentyloxy, and hexyloxy), and/or methylenedioxy; $Z^2$ is $CH_2$, and m is equal to 0 (exclusive of Helioxanthin mentioned above. Compound [III], inclusive of its salt, like compound [I] and its salt, has cell differentiation inducing factor activity or enhancing activity of the cell differentiation inducing factor.

A variety of synthetic processes may be used for the production of compound [I] of the invention (hereinafter referred to briefly as compound [I]) and its salt. Some representative reactions of compound [I] are presented below in Schemes 1–5.

In the explanation of the following processes, starting materials and reaction products way form a salt thereof which does not inhibit the reaction.

Referring to compound [I] wherein Q is $N(O)_p$ (where p is equal to 0 or 1), the compound in which p is equal to 1 or a salt thereof can be provided by subjecting the corresponding compound in which p is equal to 0 or a salt thereof or an intermediate thereof in a suitable production stage to a known chemical oxidation reaction [cf. Chemistry of the Heterocyclic N-Oxide, 22–60 (1971), Academic Press, London & New York or G. Jones (ed.), Quinolines Part 1, John Wiley & Sons, Chapter 1, pp. 61–62 (1977)] or an analogous reaction.

The compound of formula [I] wherein Q represents carbon that may be substituted, namely compound [VII], can be synthesized typically by the process shown below in Schema 1.

Schema 1

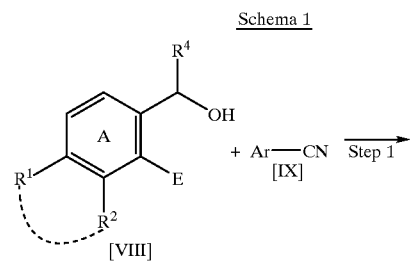

-continued

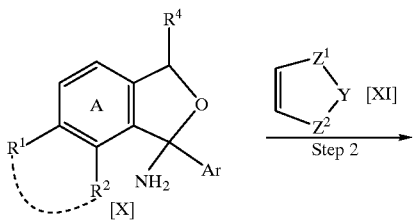

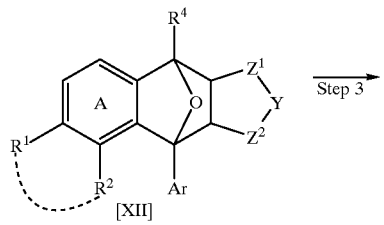

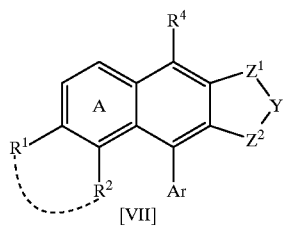

Referring to compounds [VII]–[XII] in the above Schema 1, E represents hydrogen or halogen and the other symbols have the same meanings as defined above.

Compound [I] in which Q is N can be produced using an anthranil derivative of the following formula:

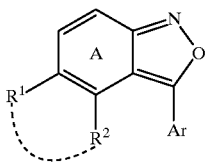

wherein all symbols have the same meanings as defined above, instead of compound [X] in the above Schema 1 in a manner similar to that described the per se known technology (E. C. Taylor et al., Journal of Organic Chemistry, 32, 1899–1900, 1967).

Moreover, compound [I] can also be produced by subjecting compound of the following formula:

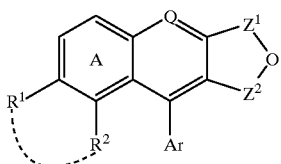

wherein all symbols have the same meanings as defined above, to the reactions illustrated below in Schema 3–5.

Compound [I'] in which Q is a carbon atom that may be substituted can be produced using a compound of the formula:

wherein the respective symbols have the same meanings as defined above, instead of compound [XI] in Schema 1.

Compound [XI] and compound [XI'] can be purchased from commercial sources or synthesized by using the per se known procedures for the synthesis of olefins, ketones, esters, amides, acid anhydrides, and imides [e.g. S. R. Sandler and W. Karo, Organic Functional Group Preparations I, 2nd ed., Academic Press, Chapter 2, pp. 39–81, Chapter 8, pp. 206–235, Chapter 10, pp. 289–315, and Chapter 11, pp. 316–358 (1983) and S. R. Sandler and W. Karo, Organic Functional Group Preparations III, 2nd ed., Academic Press, Chapter 2, pp. 87–128 and Chapter 7, pp. 281–313 (1989)] in a suitable combination.

When the compound of formula [I'] is an aryl-naphthalenelignan compound, it can also be produced by any of the per se known synthetic processes such as the processes described in R. S. Ward, Chemical Society Reviews, 11, 75–125 (1982), R. S. Ward, Synthesis, 719–730 (1985), D. A. Whiting, Natural Product Reports, 2, 191–211 (1985) and 4, 499–525 (1985), R. Stevenson et al., Journal of Natural Products, 52 (2), 367–375 (1989), and other literature.

Compound [I'] in which Q is N, $Z^1$ is C=O, and $Z^2$ is methylene, namely compound [XIII], can be produced by, for example, the process illustrated below in Schema 2.

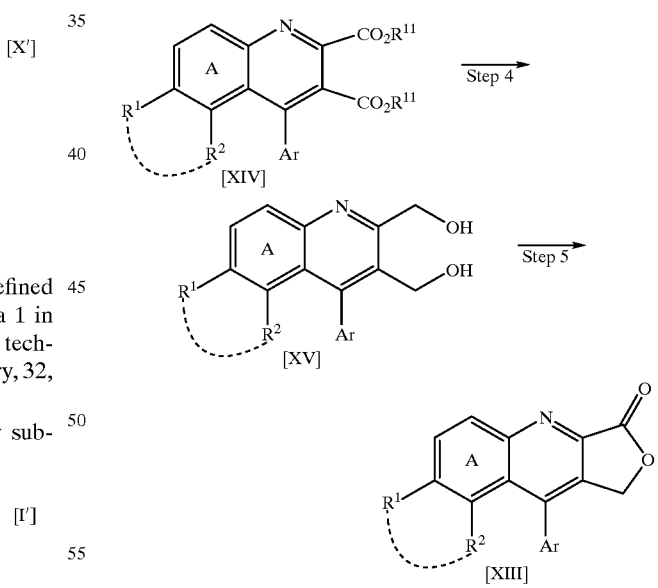

Referring to compounds [XIII]–[XV] in the above Schema 2, $R^{11}$ is lower alkyl (e.g. $C_{1-6}$ alkyl such as methyl, ethyl, propyl, isopropyl, butyl, isobutyl, sec-butyl, tert-butyl, pentyl, hexyl, etc.; the other symbols have the same meanings as defined above.

Compound [II] wherein Y is $NR^{13}$, wherein $R^{13}$ is hydrogen or optionally substituted lower alkyl, and n=0, that is compound [XVI], can be produced by, for example, the process illustrated below in Schema 3.

Schema 3

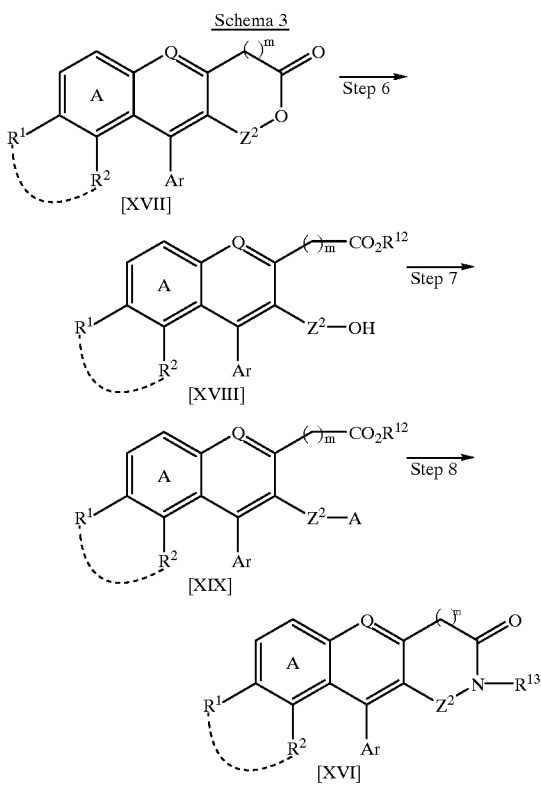

Referring to compounds [XVI]–[XIX] in the above Schema 3, $R^{12}$ is lower alkyl; $R^{13}$ is hydrogen or optionally substituted lower alkyl; A is a leaving group.

The "lower alkyl" as mentioned for $R^{12}$ includes $C_{1-6}$ alkyl such as methyl, ethyl, propyl, isopropyl, butyl, isobutyl, sec-butyl, tert-butyl, pentyl, hexyl, etc.

The "lower alkyl" of the "optionally substituted lower alkyl" as mentioned for $R^{13}$ includes $C_{1-6}$ alkyl such as methyl, ethyl, propyl, isopropyl, butyl, isobutyl, sec-butyl, tert-butyl, pentyl, hexyl, etc. and the "substituent" for this "optionally substituted lower alkyl" includes the same groups as those mentioned for the "substituent" of the "optionally substituted hydrocarbon group" as mentioned for $R^3$, $R^4$, $R^5$, and $R^6$.

The compound of formula [II] wherein Y is NH, $Z^2$ is $-Z^{2'}-CH_2-$, wherein $Z^{2'}$ is optionally substituted $C_{1-2}$ alkylene, and n=0, that is compound [XX], can be produced by, for example, the process illustrated below in Schema 4.

Schema 4

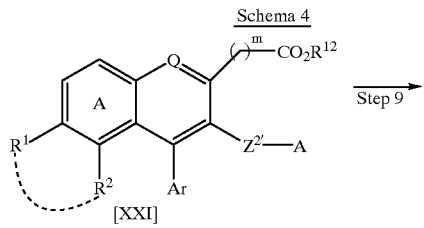

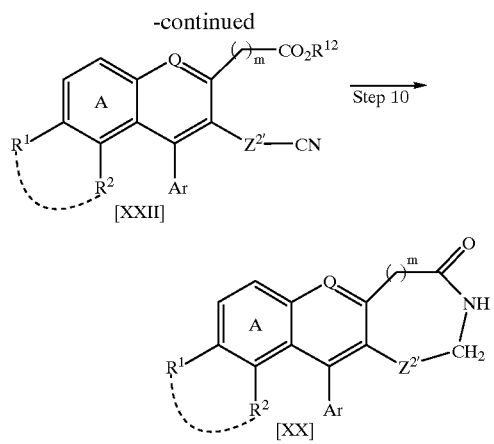

Referring to compounds [XX]–[XXII] in the above Schema 4, all symbols have the same meanings as defined above.

The "$C_{1-2}$ alkylene" of the "optionally substituted $C_{1-2}$ alkylene" as mentioned for $Z^{2'}$ above is methylene or ethylene, and the "substituent" for this "optionally substituted $C_{1-2}$ alkylene" includes the same groups as those mentioned for the "substituent" of the "optionally substituted hydrocarbon group" as mentioned for $R^3$, $R^4$, $R^5$, and $R^6$.

The compound of formula [II] wherein Y is substituted methylene and n=0, that is compound [XXIII], wherein $R^{14}$ is lower alkyl (e.g. $C_{1-6}$ alkyl such as methyl, ethyl, propyl, isopropyl, butyl, isobutyl, sec-butyl, tert-butyl, pentyl, hexyl, etc.); G is hydrogen or the same group as the substituent of the substituted methylene mentioned above for Y; the other symbols have the same meanings as defined above, can be produced by, for example, the process illustrated below in Schema 5.

Schema 5

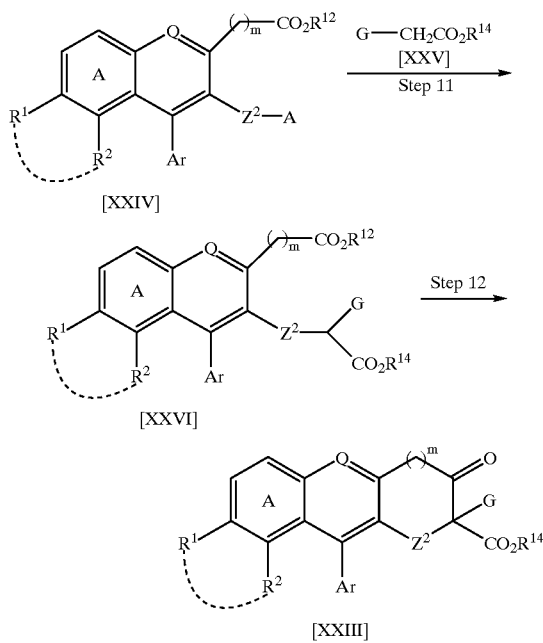

Referring to compounds [XXIII]–[XXVI] in the above Schema 5, all symbols have the same meanings as defined above.

In this connection, the group $CO_2R^{14}$ may be eliminated by subjecting compound [XXIII] to decarboxylation reaction, and when G is a carboxylic acid derivative, G can also be eliminated by this decarboxylation reaction.

The compound [I] in which Y is NR', wherein R' is optionally substituted $C_{1-3}$ alkyl or optionally substituted $C_{1-3}$ alkanoyl, can also be produced by subjecting the compound of general formula [I] wherein Y is NH or an intermediate thereof in a suitable production stage to a per se known alkylation or acylation reaction.

The reactions involved in the above production Schemes 1 to 5 are now described in further detail.

Steps 1 to 3 can be carried out by the procedure reported by J. G. Smith et al. (Journal of Organic Chemistry, 53, 2942–2953, 1988).

In step 4, compound [XIV] is reduced to compound [XV]. This reaction can be carried out by, for example, a per se known method [S. R. Sandler and W. Karo, Organic Functional Group Preparations I, 2nd ed., Academic Press (1983), Chapter 4 (pp. 111–114). If this reaction involves reduction of the quinoline ring, the reduced quinoline ring can be reoxidized by a per se known method (M. Antini et al., Heterocycles, 38, 103–111 (1994)].

The starting compound [XIV] for this reaction can be produced by, for example, a per se known method (G. Jones (ed.), Quinolines Part 1, John Wiley & Sons (1977), Chapter 2 (pp. 93–318)].

Step 5 can be carried out in a per se known manner [M. Antini et al., Heterocycles, 3, 103–111 (1994)].

Step 6 can be carried out by subjecting compound [XVII] to alkaline hydrolysis and treating the resulting hydroxycarboxylate with a lower alkyl halide.

The base that can be used for this alkaline hydrolysis includes but is not limited to inorganic bases (e.g. lithium hydroxide, sodium hydroxide, potassium hydroxide, sodium carbonate, potassium carbonate, sodium hydrogen carbonate, potassium hydrogen carbonate, cesium carbonate, etc.). The amount of the base is generally equimolar through about 10 molar equivalents and preferably equimolar—about 3 molar equivalents with respect to compound [XVIII].

The lower alkyl halide may for example be methyl iodide, ethyl iodide, or ethyl bromide. The proportion of the lower alkyl halide is generally equimolar to about 100 molar equivalents and preferably 20–100 molar equivalents with respect to compound [XVIII].

This reaction can be carried out with advantage in a solvent. For this reaction, a solvent that does not interfere with the reaction is employed. Thus, the solvent can be selected from among hydrocarbons (e.g. pentane, hexane, cyclohexane, benzene, etc.), lower alkanols (e.g. methanol, ethanol, propanol, etc.), ethers (e.g. diethyl ether, tetrahydrofuran, dioxane, etc.), amides (e.g. N,N-dimethylformamide, hexamethylphosphoric triamide, etc.), and ureas (e.g. 1,3-dimethyl-3,4,5,6-tetrahydro-2(1H)-pyrimidine etc.). Those solvents can be used each alone or, where necessary, as a mixture comprising two or more species in a suitable ratio, or even in admixture with water. The proportion of the solvent is generally 1 to 100 milliliters and preferably 5 to 20 mL per gram of compound [XVIII]. The reaction temperature is generally –20° C. through the boiling point of the solvent used and preferably 25° C. to 100° C. The reaction time is 10 minutes to 24 hours and preferably 20 minutes to 2 hours for each of the alkaline hydrolysis and the lower alkyl halide treatment.

In Step 7, the hydroxyl group of compound [XVIII] is converted to a leaving group. The leaving group represented by A in compound [XIX] includes (1) halogen (e.g. chlorine, bromine, iodine, fluorine), (2) lower alkanesulfonyloxy that may be substituted by 1 to 3 halogen atoms (e.g. $C_{1-6}$ alkylsulfonyloxy optionally substituted by 1 to 3 halogen atoms (e.g. chlorine, bromine, fluorine, etc.) such as methylsulfonyloxy, ethylsulfonyloxy, butylsulfonyloxy, trifluoromethylsulfonyloxy, etc.), and (3) lower arylsulfonyloxy that may be substituted by 1 to 3 halogen atoms (e.g. $C_{6-10}$ arylsulfonyloxy optionally substituted by 1 to 3 halogen atoms (e.g. chlorine, bromine, fluorine, etc.) such as benzenesulfonyloxy, p-toluenesulfonyloxy, p-bromobenzenesulfonyloxy, mesitylenesulfonyloxy, etc.).

This reaction can be carried out in a per se known manner (S. R. Sandler and W. Karo, Organic Functional Group Preparations 1 (2nd ed.), Academic Press (1983), Chapter 6 (pp. 148–179) and Chapter 21 (pp. 630–633).

In step 8, compound [XIX] is reacted with ammonia or a monoalkylamine of the formula $H_2NR^{13}$ (where $R^{13}$ is as defined above).

Ammonia as mentioned just above may be either aqueous ammonia, ammonia gas, or liquid ammonia.

The proportion of ammonia or monoalkylamine is generally equimolar through about 100 molar equivalents and preferably 2 to 10 molar equivalents with respect to compound [XIX].

This reaction can be carried out with advantage in a solvent which does not inhibit the reaction. Thus, the solvent that can be used includes hydrocarbons (e.g. pentane, hexane, cyclohexane, benzene, etc.), lower alkanols (e.g. methanol, ethanol, propanol, etc.), ethers (e.g. diethyl ether, tetrahydrofuran, dioxane, etc.), amides (e.g. N,N-dimethylformamide, hexamethylphosphoric triamide, etc.), and ureas (e.g. 1,3-dimethyl-3,4,5,6-tetrahydro-2(1H)-pyrimidine etc.). Those solvents can be used each alone or, where necessary, as a mixture of suitable proportions of two or more species or even in admixture with water. The proportion of the solvent is generally 1 to 100 mL and preferably 5 to 20 mL per gram of compound [XIX]. The reaction temperature is generally –20° C. through the boiling point of the solvent used and preferably 25° C. to 100° C.

The reaction time is generally 30 minutes to 24 hours and preferably 30 minutes to 12 hours.

In Step 9, compound [XXI] is reacted with a cyanide.

The starting compound [XXI] can be synthesized typically by the same procedure as shown for the production of compound [XIX] in Schema 3.

The cyanide that can be used includes the sodium salt, potassium salt, copper salt, silver salt, etc. and the proportion of the cyanide is generally equimolar through about 100 molar equivalents and preferably 2 to 10 molar equivalents with respect to compound [XXI].

This reaction can be carried out with advantage in a solvent which does not inhibit the reaction. Thus, the solvent that can be used includes hydrocarbons (e.g. pentane, hexane, cyclohexane, benzene, etc.), lower alkanols (e.g. methanol, ethanol, propanol, etc.), ethers (e.g. diethyl ether, tetrahydrofuran, dioxane, etc.), amides (e.g. N,N-dimethylformamide, hexamethylphosphoric triamide, etc.), and ureas (e.g. 1,3-dimethyl-3,4,5,6-tetrahydro-2(1H)-pyrimidine etc.). Those solvents can be used each alone or, where necessary, as a mixture of suitable proportions of two or more species or even in admixture with water. The proportion of the solvent is generally 1 to 100 milliliters and preferably 5 to 20 mL per gram of compound [XXI].

The reaction temperature is generally –20° C. through the boiling point of the solvent used and preferably 25° C. to 100° C. The reaction time is generally 30 minutes to 24 hours and preferably 1 to 12 hours.

In Step 10, the nitrile group of compound [XXII] is reduced. This reduction reaction can be carried out by a per se known method [e.g. S. R. Sandler and W. Karo, Organic Functional Group Preparations I" 2nd ed., Academic Press (1983), Chapter 13 (pp. 403–405)].

In Step 11, compound [XXIV] is condensed with compound [XXV] in the presence of a base.

The relative proportions of the starting compounds [XXIV] and [XXV] for this reaction are dependent on the species of compounds, reaction conditions, etc. However, compound [XXV] is used in a proportion of generally 1 to 10 molar equivalents or preferably 1 to 2 molar equivalents for each mole of compound [XXIV].

The base that can be used includes alkyllithium reagents (e.g. methyllithium, n-butyllithium, s-butyllithium, t-butyllithium, etc., preferably n-butyllithium), inorganic bases (e.g. sodium hydroxide, potassium hydroxide, sodium carbonate, potassium carbonate, sodium hydrogen carbonate, potassium hydrogen carbonate, cesium carbonate, sodium hydride, sodium metal, etc.), and organic bases (e.g. sodium methoxide, sodium ethoxide, triethylamine, pyridine, diethylisopropylamine, etc.). The proportion of the base is generally equimolar through about 10 molar equivalents and preferably equimolar to 2 molar equivalents with respect to compound [XXV].

This reaction can be conducted with advantage in a solvent selected from among, for example, lower alkanols (e.g. methanol, ethanol, propanol, isopropyl alcohol, etc.), hydrocarbons (e.g. pentane, hexane, cyclohexane, benzene, etc.), ethers (e.g. diethyl ether, tetrahydrofuran, dioxane, etc.), amides (e.g. N,N-dimethylformamide, hexamethylphosphoric triamide, etc.), halogenated hydrocarbons (e.g. dichloromethane, chloroform, etc.), sulfoxides (e.g. dimethyl sulfoxide etc.), and ureas (e.g. 1,3-dimethyl-3,4,5,6-tetrahydro-2(1H)-pirimidine etc.). Those solvents can be used each alone or, where necessary, as a mixture of suitable proportions of two or more species or even in admixture with water. The proportion of the solvent is generally 0.1 to 100 mL and preferably 5 to 20 mL per gram of compound [XXV].

The reaction temperature is generally −20° C. through the boiling point of the solvent used and preferably −5° C. through the boiling point. The reaction time is generally 100 minutes to 24 hours and preferably 30 minutes to 5 hours.

In Step 12, compound [XXVI] is treated with a base to subject cyclization reaction.

The base that can be used includes alkyllithium reagents (e.g. methyllithium, n-butyllithium, s-butyllithium, t-butyllithium, etc., preferably n-butyllithium), lithium dialkylamides (e.g. lithium diisopropylamide, lithium hexamethyldisilazide, etc.), inorganic bases (e.g. sodium hydroxide, potassium hydroxide, sodium carbonate, potassium carbonate, sodium hydrogen carbonate, potassium hydrogen carbonate, cesium carbonate, sodium hydride, sodium metal, etc.), and organic bases (e.g. sodium methoxide, sodium ethoxide, triethylamine, pyridine, diethylisopropylamine, etc.). The proportion of the base is generally equimolar through about 10 molar equivalents and preferably equimolar to 2 molar equivalents with respect to compound [XXVI].

This reaction can be conducted with advantage in a solvent selected from among, for example, lower alkanols (e.g. methanol, ethanol, propanol, isopropyl alcohol, etc.), hydrocarbons (e.g. pentane, hexane, cyclohexane, benzene, etc.), ethers (e.g. diethyl ether, tetrahydrofuran, dioxane, etc.), amides (e.g. N,N-dimethylformamide, hexamethylphosphoric triamide, etc.), halogenated hydrocarbons (e.g. dichloromethane, chloroform, etc.), sulfoxides (e.g. dimethyl sulfoxide etc.), and ureas (e.g. 1,3-dimethyl-3,4,5,6-tetrahydro-2(1H)-pirimidine etc.). Those solvents can be used each alone or, where necessary, as a mixture of suitable proportions of two or more species or even in admixture with water. The proportion of the solvent is generally 0.1 to 100 mL and preferably 5 to 20 mL per gram of compound [XXV].

The reaction temperature is generally −20° C. through the boiling point of the solvent used and preferably −5° C. through the boiling point. The reaction time is generally 10 minutes to 24 hours and preferably 30 minutes to 5 hours.

As shown in Scheme 5, compound [XXIII] may be subjected to decarboxylation. This decarboxylation can be carried out by a per se known procedure for hydrolysis of an ester (e.g. S. Patai (ed.), The Chemistry of Carboxylic Acids and Esters, Chapter 12 (pp. 589–622).

The compound of general formula [I] wherein $Z^1$ is C═O, $Z^2$ is methylene, both of m and n are equal to 0, and Y is $NR^{13}$ wherein $R^{13}$ is as defined above, can also be produced by partial reduction of the compound in which each of $Z^1$ and $Z^2$ is C═O, both of m and n are equal to 0, and Y is $NR^{13}$, wherein $R^{13}$ is as defined above.

This partial reduction can be carried out by, for example, electrolytic reduction (e.g. the technique described in L. C. Craig, Journal of the American Chemical Society, 55, 295–298, 1933), catalytic reduction (e.g. the method described in A. Dunet et al., Bulletin de la Societe Chimique de France, 17, 877–881, 1950), reduction with a metal hydride (e.g. the method described in E. Tagmann et al., Helvetica Chimica Acta, 37, 185–190, 1954), or reduction with zinc (e.g. the method described in J. H. Brewster and A. M. Fusco, Journal of Organic Chemistry, 28, 501–503, 1963).

The compound of general formula [I] wherein Y is alkylated or acylated nitrogen can also be produced by applying N-alkylation or N-acylation, in the per se known manner, to the compound of formula [I] wherein Y is NH or an intermediate thereof in a suitable production stage.

In the production of the respective objective compounds by the processes shown in Schema 1 through Schema 5, where any substituent group on ring A, $R^4$, Ar, Y, $Z^1$, $Z^2$, $Z^{2'}$, or G in [VII] through [XXV] contains a functional group such as hydroxyl, amino, mono-$C_{1-6}$ alkylamino, ketone, carboxyl, or tetrazolyl, the functional group may be protected beforehand. As to the kinds of protective groups and methods for protection and deprotection that can be used, those groups and methods which are known per se can be successfully employed [T. W. Green and P. G. M. Wuts, Protective Groups in Organic Synthesis, 2nd ed., John Wiley & Sons, Inc., 1991].

The compound [I] or salt thus produced can be isolated and purified by the per se known procedure (e.g. redistribution, concentration, solvent extraction, fractional distillation, crystallization, recrystallization, chromatography, etc.).

The salt of compound [I] according to the present invention is preferably a pharmacologically acceptable salt. Thus, for example, salts with inorganic bases, salts with organic bases, salts with inorganic acids, salts with organic acids, and salts with basic or acidic amino acids can be mentioned. The preferred salts with inorganic bases are salts with alkali metals (e.g. sodium salt, potassium salt, etc.), salts with alkaline earth metals (e.g. calcium salt, magnesium salt, etc.), aluminum salt, and ammonium salts. The preferred salts with organic bases are salts with trimethylamine, triethylamine, pyridine, picoline, ethanolamine, diethanolamine, triethanolamine, dicyclohexylamine, N,N'-dibenzylethylenediamine, etc.

The preferred salts with inorganic acids are salts with hydrochloric acid, hydrobromic acid, nitric acid, sulfuric acid, phosphoric acid, etc.

The preferred salts with organic acids are salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

The preferred salts with basic amino acids are salts with arginine, lysine, ornithine, etc.

The preferred salts with acidic amino acids are salts with aspartic acid, glutamic acid, etc. When the objective compound produced is a free compound, it can be converted to a salt by the conventional procedure and when the objective compound obtained is in the form of a salt, it can be converted to the free compound.

The compound [I] or salt of the present invention may be a hydrated compound or anhydrous.

The compound [I] or salt of the invention can be isolated and purified by the per se known procedures such as solvent extraction, pH adjustment, redistribution, crystallization, recrystallization, chromatography, etc. While the starting compounds or salts for the compound [I] of the invention can also be isolated and purified by the same known procedures as above, the respective reaction mixtures containing them may be used as reactants for the next reactions.

In the event the compound [I] or salt of the present invention includes optical isomers, stereoisomers, position isomers or rotamers, those isomers also fall within the scope of the invention and can respectively be isolated by the per se known synthetic and/or fractionation techniques. For example, when the compound of the invention exists as optical isomers, the respective isomers falling within the scope of the invention can be separately provided.

Thus, optical isomers can be produced by per se known techniques. Thus, the desired optical isomer can be provided by using an optically active synthetic intermediate or subjecting the racemic end product to routine optical resolution.

Optical resolution can be achieved by the per se known alternative procedures such as fractional recrystallization, chromatography on a chiral column, and the diastereomer method, all described briefly below.

(1) Fractional Recrystallization

This method comprises treating the racemic substrate with an optically active compound to give the corresponding salt, separating it by fractional recrystallization, and where necessary, neutralizing the same to recover the free optical isomer.

(2) Chiral Column Chromatography

This is a method in which the racemic substrate or a salt thereof is fractionated on a chiral column. Taking liquid chromatography as an example, the mixture of optical isomers is run on a chiral column, such as ENANTIO-OVM (Tosoh Corporation), and elution is carried out with water, a buffer (e.g. phosphate buffer), or an organic solvent (e.g. ethanol, methanol, acetonitrile, etc.), or a mixture thereof, to thereby separate the desired optical isomer. Resolution by gas chromatography can be carried out using CP-Chirasil-DeXCB (G. L. Science), for instance, as a chiral column.

(3) Diastereomer Method

This method comprises reacting the racemic substrate with an optically active reagent chemically to prepare a mixture of diastereomers, subjecting it to the routine fractionation treatment (e.g. fractional recrystallization, chromatography, etc.) to give the respective isomers, and cleaving the moiety corresponding to the optically active reagent off through chemical reaction such as hydrolysis. For example, when the compound of the invention contains a hydroxyl group or a primary or secondary amino group, diastereomers of its ester or amide can be obtained by subjecting said compound and an optically active organic acid (e.g. MTPA [α-methoxy-α-(trifluoromethyl) phenylacetic acid], (–)-menthoxyacetic acid, or the like) to condensation reaction. On the other hand, when the compound of the invention contains a carboxyl function, diastereomers of its amide or ester can be obtained by subjecting the compound and an optically active amine or alcohol to condensation reaction. The isolated diastereomers can be converted to optical isomers of the substrate compound by acid hydrolysis or alkaline hydrolysis.

The cell differentiation inducing factor relevant to the present invention includes a variety of factors which induce characteristic transductions in the process of differentiation from undifferentiated precursors of the osteoblasts, neurons, and other cells which are in charge of maintenance of vital functions in specific tissues, such as bone morphogenetic protein, neurotrophic factor, factors belonging to the TGF-β superfamily, such as transforming growth factor (TGF)-β and activins, factors belonging to the FGF superfamily, such as basic fibroblast growth factor (bFGF) and acidic fibroblast growth factor (aFGF), factors belonging to the neuropoietic cytokine family, such as leukemia inhibitory factor (LIF; also known as cholinergic differentiation factor, CDF), ciliary neurotrophic factor (CNTF), etc., interleukin (IL; this abbreviation applies hereinafter)-1; IL-2, IL-3, IL-5, IL-6 IL-7, IL-9, and IL-11, tumor necrosis factor —α(TNF-α) interferon-γ (INF-γ), etc. Preferred are bone morphogenetic protein and neurotrophic factor.

The bone morphogenetic protein includes factors of the BMP family, such as BMP-2, -4, -5, -6, -7, -8, -9, -10, -11, -12, etc., all of which are proteins which accelerate osteogenesis and chondrogenesis. Particularly preferred are BMP-2, -4, -6, and -7. BMP that can be used includes various homodimers of the respective factors mentioned above or heterodimers of all possible combinations of the factors.

The neurotrophic factor includes nerve growth factor (NGF), brain-derived neurotrophic factor (BDNF), neurotrophin-3 (NT-3), etc. Preferred are factors of the NGF family.

The compound [I] or salt of the present invention can be safely administered as it is or in the form of a pharmaceutical composition prepared by using a pharmacologically acceptable carrier. The composition includes a variety of dosage forms such as tablets (e.g. dragees, film-coated tablets, etc.), powders, granules, capsules (inclusive of soft capsules), syrup, emulsion, suspension, injection (e.g. subcutaneous, intradermal, intramuscular and other injections), suppositories, and controlled-release dosage forms as prepared by the established pharmaceutical procedures, and such dosage forms can be administered either orally or otherwise (e.g. topically, rectally, or intravenously). The proportion of compound [I] or its salt in a dosage form of the invention may range from 0.1 to 100 weight %. The dosage depends on the recipient's characteristics, route of administration, diagnosis, and other factors. When the composition is used as a cell differentiation factor agent or agonist in an adult patient (b. wt. 60 kg), for instance, the oral dose of about 0.1 to 500 mg, preferably about 1 to 100 mg, or more preferably about 5 to 100 mg, as the active ingredient, can be administered once daily or in a few divided doses daily.

The injection can be prepared and used in the per se known manner. Thus, compound [I] or salt of the invention can be used independently or in combination with one or more other substances having cell differentiation factor activity, such as BMP and neurotrophic factor. The aqueous vehicle for such an injection includes physiological saline, isotonic solution, etc. and, where necessary, the vehicle can be used together with a suspending agent such as those mentioned hereinafter. The oily medium for an injection includes sesame oil, soybean oil, and other oils and these oils may be used together with a solubilizer such as those also mentioned hereinafter. The prepared injection is generally dispensed and sealed in suitable ampules.

The pharmacologically acceptable carrier that can be used in the production of the pharmaceutical composition of the invention includes various organic and inorganic pharmaceutical carriers which are conventionally used in pharmaceutical production. Thus, the excipient, lubricant, binder, disintegrator, etc. can be used for solid dosage forms and the solvent, solubilizer, suspending agent, isotonizing agent, buffer, local anesthetic, etc. can be used for liquid dosage forms. Where necessary, such other additives as the antiseptic, antioxidant, colorant, sweetener, adsorbent, wetting agent, etc. can also be used. The excipient includes but is not limited to lactose, sucrose, D-mannitol, starches such as corn starch, crystalline cellulose, and light silicic anhydride. The lubricant includes but is not limited to magnesium stearate, calcium stearate, talc, and colloidal silica.

The binder includes but is not limited to crystalline cellulose, sucrose, D-mannitol, dextrin, hydroxypropylcellulose, hydroxypropylmethylcellulose, polyvinylpyrrolidone, starch, cane sugar, gelatin, methylcellulose, and carboxymethylcellulose sodium.

The disintegrator includes but is not limited to starch, carboxymethylcellulose, carboxymethylcellulose calcium, croscarmellose sodium, carboxymethylstarch sodium, and L-hydroxypropylcellulose.

The solvent includes but is not limited to water for injection, alcohol, propylene glycol, macrogols, sesame oil, and corn oil.

The solubilizer includes but is not limited to polyethylene glycol, propylene glycol, D-mannitol, benzyl benzoate, ethanol, trisaminomethane, cholesterol, triethanolamine, sodium carbonate, and sodium citrate.

The suspending agent includes but is not limited to surfactants such as stearyltriethanolamine, sodium lauryl sulfate, lauryl aminopropionate, lecithin, benzalkonium chloride, benzethonium chloride, glycerol monostearate, etc., and hydrophilic macromolecular substances such as polyvinyl alcohol, polyvinylpyrrolidone, carboxymethylcellulose sodium, methylcellulose, hydroxymethylcellulose, hydroxyethylcellulose, hydroxypropylcellulose, etc.

The isotonizing agent includes but is not limited to glucose, D-sorbitol, sodium chloride, glycerin, and D-mannitol.

The buffer includes various buffer solutions such as phosphate, acetate, carbonate, citrate, and other buffers.

The local anesthetic includes but is not limited to benzyl alcohol.

The antiseptic includes but is not limited to p-hydroxybenzoic esters, chlorobutanol, benzyl alcohol, phenethyl alcohol, dehydroacetic acid, and sorbic acid.

The antioxidant includes but is not limited to sulfites and ascorbic acid.

The pharmaceutical composition of the invention, which comprises compound [I] or a pharmacologically acceptable salt thereof, has satisfactory cell differentiation inducing factor activity or its enhancing activity and, as such, can be successfully used either as it is or in combination with other active substances having cell differentiation inducing factor activity (e.g. BMP and neurotrophic factor) in the treatment or prevention of various nerve diseases [e.g. neurodegenerative lesions in cerebrovascular dementia, senile dementia, or Alzheimer's disease, amyotrophic lateral sclerosis (Lou Gehrig's disease), diabetic peripheral neuropathy, etc.] or bone-and-joint diseases [e.g. bone fracture, osteoporosis, osteoarthritis, rheumatoid arthritis, etc.]. Specifically, as a therapeutic and prophylactic drug for bone-and-joint diseases, the pharmaceutical composition of the invention can be used as a bone formation accelerator, a cartilage disruption inhibitor, a bone fracture healing accelerator, or a bone remodeling accelerator, for instance.

Furthermore, the physiological roles of BMP and neurotrophic factor remaining to be fully elucidated, there may be other diseases in which argumentation of BMP activity or neurotrophic factor activity should lead to improvements in morbidity. The enhancing activity of cell differentiation factor of the present invention may be useful for the treatment or prevention of such diseases associated with BMP and/or neurotrophic factor.

The enhancing activity of cell differentiation inducing factor of the present invention can be indicated in the above-mentioned diseases not only in man but also in other mammalian animals (e.g. the mouse, rat, rabbit, dog, cat, cattle, swine, etc.).

The pharmaceutical composition of the invention, which comprises compound [I] or a salt thereof, has a high toxicological threshold and a low risk for adverse reactions.

Because it has high activity to promote bone formation, the compound of the present invention can be incorporated in a bone remodeling matrix as a bone morphogenesis accelerator for bone repairing or in bone grafting. For example, the compound of the invention can be applied as attached to or incorporated in an artificial bone of a metal, ceramic material, or polymer material. The artificial bone is preferably provided with a porous surface so that, when it is implanted in the missing part of the host, the cell differentiation factor agonist of the invention will be released into the tissue. The compound of the invention can be attached to or incorporated in such a prosthesis by dispersing it in a suitable dispersion medium, binder or diluent (e.g. collagen, physiological saline, citric acid solution, acetic acid solution, hydroxyapartite, fibrin, or a mixture of them), coating or impregnating the prosthesis with the dispersion, and drying it. Such an artificial bone is implanted in the missing part of the host and securely immobilized there. The cementing agent for an artificial bone can be prepared by mixing the compound of the present invention with a physiologically acceptable dispersion medium, binder, or diluent and optionally with other ingredients useful for bone remodeling (e.g. calcium). The artificial bone cement can also be used in such a manner that, in lieu of being applied to or incorporated in a prosthesis, it is filled in the gap between the implant and the missing part of the host. The non-oral composition mentioned above can be put to use after osteoinductive proteins such as factors of the BMP family, have been deposited thereon or incorporated therein.

MODE OF WORKING THE INVENTION

The present invention is now described in further detail by way of the following reference examples, working examples, formulation examples, and test examples but all of these examples are merely illustrative and should by no means be construed as defining the scope of the invention. Thus, many changes and modifications may be made by those skilled in the art without departing from the spirit of the invention.

In the column chromatographic procedures in the following reference and working examples, all elutions (eluents are shown in brackets) were carried out under thin-layer chromatographic (TLC) monitoring.

The TLC monitoring was carried out using Kieselgel $60F_{250}$ (70–230 mesh, Merck) for TLC plates, the column chromatographic solvents as developers, and a UV detector in combination with phosphomolybdate color reaction for detection. As the silica gel for column chromatography, Kieselgel 60 (70–230 mesh, Merck) was used. The NMR spectra represent proton NMR ($^1$H-NMR) spectra, which were measured with Gemini 200 (Varian) using tetramethylsilane either as internal standard or as external standard and expressed in δ (ppm). The infrared absorption spectra were recorded with IR-810 spectrophotometer (Nippon Bunko Kogyo). The melting points were determined with the Yanagimoto micro-melting point meter MP-500D and the uncorrected values were tabulated. The term "room temperature" as used in the following reference and working examples means 0°–30° C. and, in most cases, about 15°–25° C. In the drying procedures, anhydrous magnesium sulfate or anhydrous sodium sulfate was used. All percents (%) are by weight unless otherwise indicated.

In the chemical formulas included in the following reference and working examples, Me stands for methyl, Ms for methanesulfonyl, Et for ethyl, and Ac for acetyl.

The other symbols or abbreviations used in the text have the following meanings.

s: singlet d: doublet dd: double doublet t: triplet m: multiplet br: broad

J: coupling constant

Hz: Hertz

THF: tetrahydrofuran

DMF: N,N-dimethylformamide

DME: Dimethoxyethane $CDC_3$: deuterochloroform

NMR: proton nuclear magnetic resonance

REFERENCE EXAMPLE 1

10-(3,4-Dihydroxyphenyl)-furo[3',4':6,7[naphtho]1,2-d]-1,3-dioxol-7(9H)-one

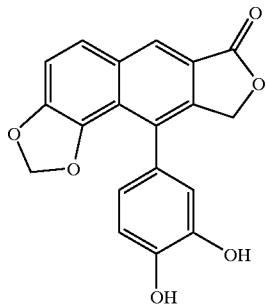

Boron trichloride (1M dichloromethane solution: 15 ml) was added dropwise to a dichloromethane solution (50 ml) of Helioxanthin (1.0 g) and stirred for 3 days at room temperature. To the solution was added methanol to stop the reaction and the reaction mixture was concentrated under reduced pressure. The residue was purified by column chromatography (silica gel 50 g, eluent:ethyl acetate-hexane=2:1) and triturated with methanol. Thus, the entitled compound (120 mg) was obtained as powder.

m.p.:288° C. (decomp.); NMR(DMSO-$d_6$)δ: 5.21(1H,d, J=15 Hz), 5.33(1H,d,J=15 Hz), 6.00(1H,s), 6.01(1H,s), 6.68 (1H,dd,J=2 Hz,8 Hz), 6.77(1H,d,J=2 Hz), 6.79(1H,d,8 Hz), 7.51(1H,d,J=9 Hz), 7.94(1H,d,J=9 Hz), 8.55(1H,s), 8.97 (1H,s), 9.09(1H,s), IR(KBr): 3510, 3230, 1715, 1625, 1450, 1275, 1245, 1075, 1060, 1030 cm$^{-1}$; Elemental Analysis for $C_{19}H_{12}O_6$·0.3$H_2O$; Calcd.: C:66.79%, H:3.72%; Found: C:66.98%, H:4.04%

REFERENCE EXAMPLE 2

10-(3,4-Dimethoxyphenyl)-furo[3',4':6,7]naphtho[1,2-d]-1,3-dioxol-7(9H)-one

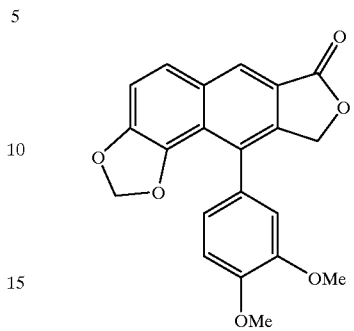

To a DMF (2 ml) solution of 10-(3,4-dihydrophenyl)-furo [3', 4':6,7]naphtho[1,2-d]-1,3-dioxol-7(9H)-one (120 mg) as obtained in Reference Example 1 was added sodium hydride (60% oily:36 mg) under ice cooling, then methyl iodide(67 μl) was added thereto after bubbling was stopped. The mixture was stirred for one hour at room temperature, and water was added thereto, then 1N hydrochloric acid was added thereto until the pH of the mixture became about 1. Then, the mixture was extracted with ethyl acetate. The extract was washed with saturated sodium chloride solution and dried with magnesium sulfate, then concentrated under reduced pressure. The residue was purified by column chromatography(silica gel 10 g, eluent:dichloromethane-ether=95:5). After recrystallized from THF-hexane, 53 mg of the entitled compound was obtained.

m.p.:221–223° C.; NMR(CDCl$_3$)δ: 3.88(3H,s), 3.98(3H, s); 5.16(1H,d,J=15 Hz), 5.29(1H,d,J=15 Hz), 5.94(2H,s), 6.86(1H,d,J=1.7 Hz), 6.92(1H,dd,J=1.7 Hz,8 Hz), 6.97(1H, d,J=8 Hz), 7.33(1H,d,J=9 Hz), 7.73(1H,d,J=9 Hz), 8.44(1H, s); IR(KBr): 1750, 1510, 1455, 1260, 1245, 1130, 1065, 1025 cm$^{-1}$; Elemental Analysis for $C_{21}H_{16}O_6$ Calcd.: C:69.23%, H:4.43%; Found: C:69.21%, H:4.53%

REFERENCE EXAMPLE 3

5,6-Dihydroxy-4-(3,4-dihydroxyphenyl)-naphtho[2,3-c]fran-1(3H)-one

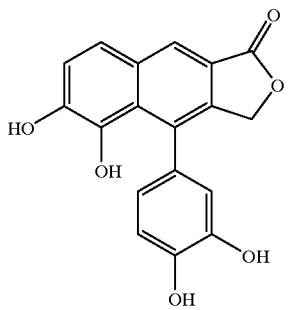

8,9-Dihydro-10-(2-oxo-1,3-benzodioxol-5-yl)-furo[1,2-d]-1,3-dioxol-2,7(9H)-dione(300 mg) was synthesized by the ordinary method as described in T. L. Holmaes and R. Stevenson, Journal of the Chemical Society(C),2091–2094, 1971. To the methanol (2 ml) solution of 8,9-dihydro-10-(2-oxo-1,3-benzodioxol-5-yl)-furo[1,2-d]-1,3-dioxol-2,7 (9H)-dione (300 mg), was added 6N hydrochloric acid (10 ml), and the mixture was refluxed overnight. The reaction mixture was concentrated under reduced pressure, then the mixture was extracted with ethyl acetate. The extract was dried with magnesium sulfate and concentrated under reduced pressure. The residue was purified by column chromatography (silica gel 10 g, eluent:ethyl acetate). Precipitation from chloroform-ethyl acetate gave the entitled compound (172 mg).

m.p.:160–165° C.; NMR(DMSO-$d_6$)δ: 5.03(1H,d,J=15 Hz), 5.17(1H,d,J=15 Hz), 6.59(1H,dd.J=2 Hz,8 Hz), 6.67 (1H,d,J=2 Hz), 6.75(1H,J=8 Hz), 7.29(1H,d,J=9 Hz), 7.62 (1H,d,J=9 Hz), 8.05(1H,s), 8.34(12H,s), 8.86(1H,s), 8,87 (1H,s), 9.90(1H,s), IR(KBr): 3460, 3380, 1720, 1615, 1270, 1230, 1200, 1155cm-$^{-1}$;

REFERENCE EXAMPLE 4

5,6-Dimethoxy-4-(3,4-dimethoxyphenyl)-naphtho[2,3-c]fran-1 (3H)-one

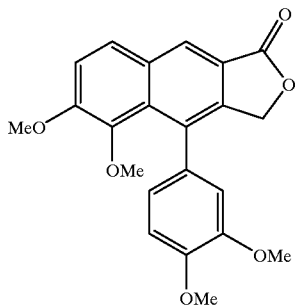

To a DMF (6 ml) solution of 5,6-dihydroxy-4-(3,4-dihydroxyphenyl)-naphtho[2,3-c]fran-1(3H)-one (300 mg) as obtained in Reference Example 3, was added sodium hydride (60% oily: 185 mg) under ice cooling, then methyl iodide (290 μl) was added after bubbling was stopped. The mixture was stirred for one hour at room temperature, and water was added thereto, then 1N hydrochloric acid was added until the pH of the mixture became about 3. Then the mixture was extracted with ethyl acetate. The extract was washed with saturated sodium chloride solution and dried with magnesium sulfate, then concentrated under reduced pressure. The residue was purified by column chromatography(silica gel 10 g, eluent:dichloromethane-ether=95:5). After recrystallized from THF-hexane, 37 mg of the entitled compound was obtained m.p.:207–209° C.; NMR(DMSO-$d_6$)δ: 3.27(3H,s), 3.87 (3H,s), 3.97(3H,s), 4.01(3H,s), 5.06(1H,d,J=15 Hz), 5.17 (1H,d,J=15 Hz), 6.86(1H,d.J=1.6 Hz), 6.87(1H,dd,J=1.6 Hz,9 Hz), 6.94(1H,d,J=9 Hz), 7.43(1H,d,J=9 Hz), 7.89(1H, d,J=9 Hz), 8.44(1H,s), IR(KBr): 1750, 1510, 1270, 1240, 1225, 1130, 1070, 1020 cm$^{-1}$; Elemental Analysis for $C_{22}H_{20}O_6$ Calcd.: C:69.46%,H:5.30%; Found: C:69.14%, H:5.31%

REFERENCE EXAMPLE 5

10-(2-Naphthyl)-furo[3',4':6,7]naphtho[1,2-d]-1,3-dioxol-7(9H)-one

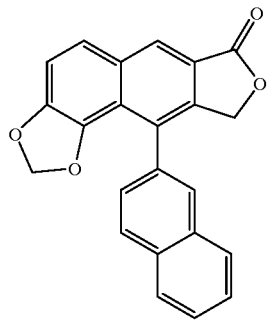

To a benzene solution (200 ml) of helio alcohol (4.0 g)was dropwise added n-BuLi (1.6M-hexane solution:36 ml) at room temperature. The mixture was stirred for 2 hours at room temperature, then 2-cyanonaphthalene (3.9 g:1.1 equivalent) was dropwise added thereto. The mixture was stirred over night at room temperature, then water was added thereto, and the mixture was extracted with ether. The extract was washed with water and dried with magnesium sulfate, then concentrated under reduced pressure. The residue (orange, oily substance) was dissolved in toluene (250 ml), then maleic anhydride (7.7 g) and p-toluene sulfonic acid (catalitic amount) were added thereto. The mixture was heated under reflux for 20 hours, then precipitates were removed by suction and the obtained filtrate was concentrated under reduced pressure. To the residue was added concentrated hydrochloric acid and heated under reflux for one hour. The mixture was cooled to room temperature, and the resultant yellow-brown precipitates were collected by suction. The precipitates were washed with water and recrystallized from tetrahydrofran and acid anhydride (about 3.4 g) were obtained. To the DME (80 ml) solution of $NaBH_4$ was gradually added the acid anhydride. The mixture was stirred for 30 minutes at 0° C., then the reaction mixture was added to diluted hydrochloric acid under ice cooling. The reaction mixture was extracted with ethyl acetate. The extract was washed with water and dried with magnesium sulfate, then concentrated under reduced pressure. The obtained residue was purified by column chromatography (eluent:chloroform) and the entitled compound (1.5 g) was obtained. For elemental analysis and other analysis, some of the entitled compound was recrystallized from THF.

m.p.:224–226° C.; NMR(CDC$^{13}$)δ: 5.13(1H, d, J=15.2 Hz), 5.29(1H, d, J=15.2 Hz), 5.85(1H, d, J=1.4 Hz), 5.85 (1H, d, J=1.4 Hz), 7.334(1H, d, J=8.8 Hz), 7.43(1H, dd, J=8.2 Hz, J=1.8 Hz), 7.57(2H, m), 7.75(1H, d, J=8.8 Hz), 7.8–8.0(4H, m), 8.48(1H, s) Elemental Analysis for $C_{23}H_{14}O_4$ Calcd.: C:77.96%, H:3.98%; Found: C:77.57%, H:4.10%

Reference Example 6

10-(3,4,5-Trimethoxyphenyl)furo[3'4':6,7]naphtho[1,2-d]-1,3-dioxol-7(9H)-one

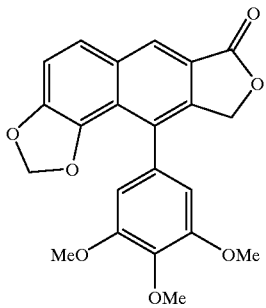

The entitled compound was obtained in a manner similar to that described in Reference Example 5.

m.p.:213–215° C.; NMR(CDCl$_3$)δ: 3.85(6H, s), 3.96(3H, s), 5.25(2H, s), 5.95(2H, s), 6.56(2H, s), 7.33(1H, d, J=8.0 Hz), 7.73(1H, d, J=8.0 Hz), 8.44(1H, s) Elemental Analysis for C$_{22}$H$_{18}$O$_7$ Calcd: C:67.00%, H:4.60%; Found: C:66.57%, H:4.57%

REFERENCE EXAMPLE 7

10-(4-Methoxyphenyl)-furo[3',4':6,7]naphtho[1,2-d]-1,3-dioxol-7(9H)-one

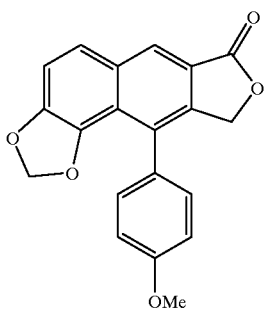

The entitled compound was obtained in a manner similar to that described in Reference Example 5.

m.p.:217–219° C.; NMR(CDCl$_3$)δ: 3.90(3H, s), 5.20(2H, s), 5.93(2H, s), 6.99(1H, d, J=8.8 Hz), 7.28(1H, d, J=8.8 Hz), 7.32(1H, d, J=8.6 Hz), 7.72(1H, d, J=8.6 Hz), 8.43(1H, s) Elemental Analysis for C$_{20}$H$_{14}$O$_5$.0.5H$_2$O Calcd.:C:70.58%, H:4.34%; Found:C:70.52%, H:4.38%

REFERENCE EXAMPLE 8

10-(4-Fluorophenyl)-furo[3',4':6,7]naphtho[1,2-d]-1,3-dioxol-7(9H)-one

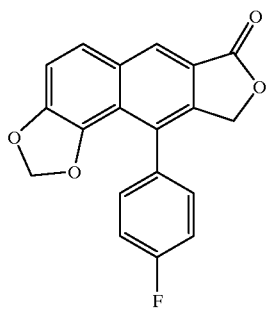

The entitled compound was obtained in a manner similar to that described in Reference Example 5.

m.p.:215–218° C.; NMR(CDCl$_3$)δ: 5.18(2H, s), 5.92(2H, s), 7.15(2H, m), 7.33(3H, m), 7.73(1H, d, J=8.8 Hz), 8.45 (1H, s) Elemental Analysis for C$_{19}$H$_{11}$O$_4$F Calcd.: C:70.81%, H:3.44%; Found: C:70.57%, H:3.65%

REFERENCE EXAMPLE 9

10-Phenyl-furo[3',4':6,7]naphtho[1,2-d]-1,3-dioxol-7(9H)-one

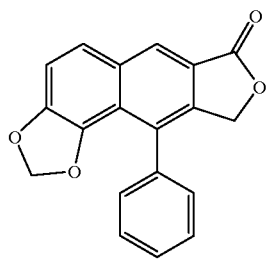

The entitled compound was obtained in a manner similar to that described in Reference Example 5.

m.p.:202–204° C.; NMR(CDCl$_3$)δ: 5.19(2H, s), 5.91(2H, s), 7.32(1H, d, J=8.4 Hz), 7.37(2H, m), 7.44(3H, m), 7.72 (1H, d, J=8.4 Hz), 8.45(1H, s) Elemental Analysis for C$_{19}$H$_{12}$O$_4$ Calcd.: C:74.99%, H:3.97%; Found: C:74.47%, H:3.95%

REFERENCE EXAMPLE 10

10-(4-Chlorophenyl)-furo[3',4':6,7]naphtho[1,2-d]-1,3-dioxol-7(9H)-one

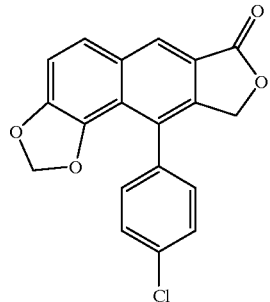

The entitled compound was obtained in a manner similar to that described in Reference Example 5.

m.p.:225–227° C.; NMR(CDCl$_3$)δ: 5.18(2H, s), 5.93(2H, S), 7.33(3H, m), 7.44(2H, d, J=8.4 Hz), 7.73(1H, d, J=8.4 Hz), 8.45(1H, s) Elemental Analysis for C$_{19}$H$_{11}$O$_4$Cl.0.2H$_2$O Calcd.: C:66.66%, H:3.36%; Found: C:66.59%, H:3.14%

REFERENCE EXAMPLE 11

10-(4-Methylphenyl)-furo[3',4':6,7]naphtho[1,2-d]-1,3-dioxol-7(9H)-one

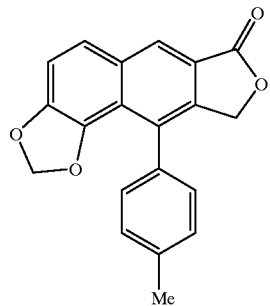

The entitled compound was obtained in a manner similar to that described in Reference Example 5.

m.p.:208–210° C.; NMR(CDCl$_3$)δ: 1.45(3H, s), 5.19(2H, s), 7.25(4H, s), 7.32(1H, d, J=8.4 Hz), 7.72(1H, d, J=8.4 Hz), 8.43(1H, s) Elemental Analysis for C$_{20}$H$_{14}$O$_4$ Calcd.: C:75.46%, H:4.43%; Found: C:75.17%, H:4.52%

REFERENCE EXAMPLE 12

10-(1,3-Benzodioxol-5-yl)-1,3-dioxolo[4,5-f]furo[3,4-b]quinolin-7(9H)-one

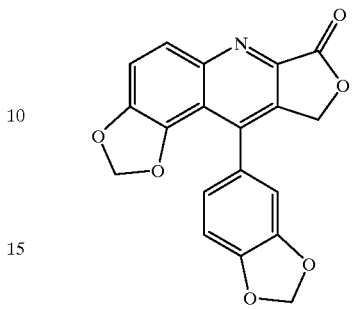

To a suspension of and lithium aluminum Hydride (LAH) (2.0 g) in THF (50 ml) was gradually added diethyl 8-(1,3-benzodioxol-5-yl)-1,3-dioxolo[4,5-f]quinoline-7,8-dicarboxylate (2.4 g) which was synthesized by the ordinally method described in E. A. Fehnel, Journal of organic Chemistry, vol.31, 2899–2092, 1966 or W. Ried, et al., Chemische Berichte, vol.85,204–216, at 0° C. The mixture was stirred for 1 hour at room temperature. To the reaction mixture was added water to stop the reaction, then the insoluble solid was filtered off with Celite. The filtrate was extracted with ethyl acetate and the extract was washed with water and dried with magnesium sulfate. The solvent was removed by distillation and the obtained residue was dissolved in ethanol (100 ml), and 10% Pd—C (2.5 g) was added thereto. The mixture was stirred overnight at room temperature. The catalyst was filtered off, and the solvent was removed by distillation. The obtained residue was dissolved in chloroform (300 ml) and manganese dioxide (20 g) was added thereto, then the mixture was stirred for 3 hours at room temperature. The manganese dioxide was filtered off with Celite and the filtrate was concentrated under reduced pressure. The obtained crude crystals were washed with diisopropyl ether and the entitled compound (0.9 g) was obtained. For elemental analysis, some of the entitle compound was recrystallized from THF.

m.p.:272–274° C.; NMR(CDCl$_3$)δ: 5.30(1H, d, J=15.6 Hz), 5.41(1H, d, J=15.6 Hz), 6.05(2H, d, J=4.4 Hz), 6.10 (2H, d, J=4.2 Hz), 6.86(2H, m), 6.95(1H, d, J=8.4 Hz), 7.57(1H, d, J=9.2 Hz), 8.11(1H, d, J=9.2 Hz) Elemental Analysis for C$_{19}$H$_{11}$NO$_6$ Calcd.: C:65.33%, H:3.17%, N:4.01%; Found: C:64.91%, H:3.07%, N:4.18%

REFERENCE EXAMPLE 13

4-(1,3-Benzodioxol-5-yl)-5-methoxynaphtho[2,3-c]fran-1(3H)-one

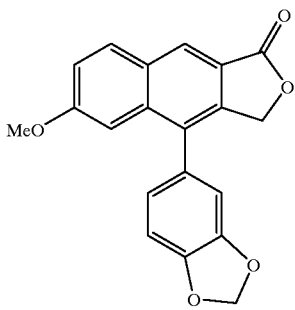

By using 3-methoxybenzyl alcohol, the entitled compound was obtained in a manner similar to that described in Reference Example 5.

m.p.:216–219° C.; NMR(CDCl$_3$)δ: 3.57(3H, s), 5.09(1H, d, J=15.0 Hz), 5.18(1H, d, J=15.0 Hz), 6.05(2H, d, J=4.0 Hz), 6.69(1H, d, J=7.6 Hz), 6.73(1H, s), 6.88(1H, d, J=7.6 Hz), 6.93(1H, d, J=8.0 Hz), 7.50(1H, t, J=8.0 Hz), 7.67(1H, d, J=8.4 Hz), 8.44(1H, s) Elemental Analysis for C$_{20}$H$_{14}$O$_5$ Calcd.: C:71.85%, H:4.22%; Found: C:71.45%, H:4.18%

REFERENCE EXAMPLE 14

Methyl 9-(1,3-Benzodixol-5-yl)-8-methanesulfonyloxymethylnaphtho[1,2-d]-1,3-benzodioxole-7-carboxylate acid

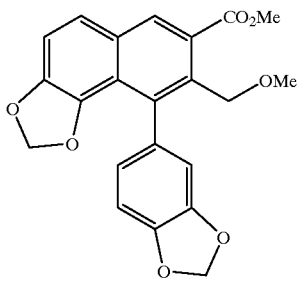

To a DMF (10 ml) solution of Helioxanthin (1 g) was added 1N sodium hydroxide solution (2.9 ml), the mixture was stirred at 60° C., for 30 minutes. The solvent was removed by distillation under reduced pressure, the residue was dissolved in DMF (10 ml). To the mixture was added methyl iodide (5 ml), the mixture was stirred at 60° C. for 1 hour. The solvent was removed by distillation under reduced pressure and to the residue was added water. The mixture was extracted with ethyl acetate. The extract was washed with saturated sodium chloride solution and dried with magnesium sulfate, then concentrated under reduced pressure. The obtained residue was dissolved in THF (10 ml), triethylamine (0.80 ml) was added thereto. To the mixture was dropwise added methanesulfonylchloride (0.22 ml) under ice cooling and stirred for 30 minutes. Water was added to the reaction mixture and the mixture was extracted with ethyl acetate. The extract was washed with saturated sodium chloride solution and dried with magnesium sulfate, then concentrated under reduced pressure to give the entitled compound (1.25 g). The crude compound as obtained was used for the following reactions without further purification.

NMR(CDCl$_3$)δ: 3.00(3H,s), 3.91(3H,s), 5.24(1H,d,J=10Hz), 5.34(1H,d,J=10Hz), 5.91(1H,d,J=1.2 Hz), 5.94(1H,d,J=1.2 Hz), 6.09(1H,d,J=0.8 Hz), 6.13(1H,d,J=0.8 Hz), 6.73(1H,dd,J=1.6 Hz,8 Hz), 6.86(1H,d,J=1.6 Hz), 6.98(1H,d,J=8 Hz), 7.49(1H,d,J=9 Hz), 7.81(1H,d,J=9 Hz), 8.54(1H, s)

REFERENCE EXAMPLE 15

Methyl 9-(1,3-Benzodioxol-5-yl)-8-cyanomethyl-naphtho[1,2-d]-1,3-benzoxole-7-carboxylate

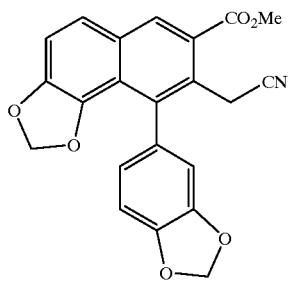

To a DMF (10 ml) solution of methyl 9-(1,3-benzodixol-5-yl)-8-methanesulfonyloxymethyl-naphtho(1,2-d]-1,3-benzodioxole-7-carboxylate (1.25 g) as obtained in Reference Example 14 was added sodium cyanide (0.28 g) and stirred for 6 hours at room temperature. To the reaction mixture was added water and resultant precipitates were collected by suction. The obtained precipitates were washed with water and dissolved in ethyl acetate. The obtained ethyl acetate solution was washed with saturated sodium chloride solution and dried with magnesium sulfate, then concentrated under reduced pressure. The obtained residue was triturated with ethyl acetate and purified by column chromatography (silica gel 10 g, eluent:dichloromethane). Then the residue was recrystallized from chloroform (3.5 ml)-hexane (12 ml) to give the entitled compound (0.23 g).

m.p.:200–202° C.; NMR(CDCl$_3$)δ: 3.91(1H,d,J=16 Hz), 4.00(3H,s), 4.01(1H,d,J=16 Hz), 5.84(1H,d,J=1.4 Hz), 5.87 (1H,d,J=1.4 Hz), 6.05(1H,d,J=1.4 Hz), 6.09(1H,d,J=1.4 Hz), 6.75(1H,dd,J=1.6 Hz,8 Hz), 6.76(1H,d,J=1.6 Hz), 6.90(1H, d,J=8 Hz), 7.26(1H,d,J=9 Hz), 7.57(1H,d,J=9 Hz), 8.60(1H, s), IR(KBr):2240, 1705, 1450, 1435, 1265, 1225, 1085 cm$^{-1}$; Elemental Analysis for C$_{22}$H$_{15}$NO$_6$.0.2H$_2$O Calcd.: C:67.24%, H:3.95%, N:3.56%; Found: C:67.23%, H:3.92%, N:3.59%

REFERENCE EXAMPLE 16

N-(3-Phenyl-2-propin-1-yl)-3-(6-bromobenzo[d]-1,3-benzodioxol-5-yl)-2-propenoylamide

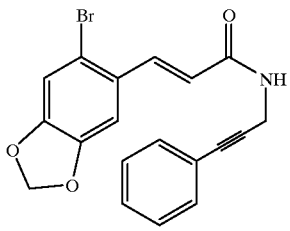

To a thionyl chloride (2 ml) was added 3-(6-bromobenzo[d]-1,3-benzodioxol-5-yl)-2-propenoic acid (461 mg) which was synthesized from 6-bromopiperonal mentioned in D. Brown and R. Stevenson, Journal of Chemical Society, vol. 30, 1759–1763, 1965 by using the known Wittig-Horner reaction, and heated under reflux for 2 hours. The reaction mixture was concentrated under reduced pressure to give a corresponding crude compound of acid chloride. Sodium hydrogen carbonate (429 mg) was dissolved in water (5 ml), and dichloromethane(3 ml) solution of N-(3-phenyl)-3-propin-2-yl amine.hydrochloride (285 mg) described in LeRoy H. Klemm et al, Journal of Chemical Society, vol. 41, 2571–2570, 1976, was added thereto under ice cooling. After bubbling was stopped dichloromethane (3 ml) solution of above-mentioned acid chloride was dropwise added, and the mixture was stirred at room temperature for 1 hour. The product were extracted with dichloromethane and the extract was dried with magnesium sulfate, then concentrated under reduced pressure. The obtained crude crystals were recrystallized from ethyl acetate (20 ml)—hexane (5 ml) to give the entitled compound (483 mg).

NMR(CDCl$_3$)δ: 4.25(2H,m), 5.87(1H,brs), 6.02(2H,s), 6.23(1H,d,J=16 Hz), 7.04(1H,s), 7.06(1H,s), 7.25–7.50 (5H, m), 7.94(1H,d,J=16 Hz)

REFERENCE EXAMPLE 17

Ethyl 3-{9-(1,3-Benzodioxol-5-yl)-7-methoxycarbonyl-naphto[1,2-d]-1,3-benzodioxol-8-yl}-2-cyanopropionate

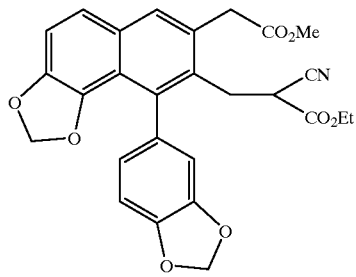

THF (1 ml) solution of ethyl cyanoacetate (23 μl) was added sodium hydride (60% oily:11 mg) and stirred for 5 minutes under ice cooling. To the reaction mixture was added methyl 9-(1,3-benzodioxol-5-yl)-8-methanesulfonyloxymethyl-naphtho[1,2-d]-1,3-benzodioxole-7-carbonxylate (0.1 g) as obtained in Reference Example 14 and stirred for 2 hours, at room temperature. 1N hydrochloric acid was added thereto and the mixture was extracted with ethyl acetate. The extract was washed with saturated sodium chloride solution and dried with magnesium sulfate, then concentrated under reduced pressure. The obtained residue was purified with column chromatography (silica gel 10 g, eluent:ethyl acetate-dichloromethane-hexane=1:1:8) to give the entitled compound (12 mg).

NMR(CDCl$_3$)δ: 1.25(3H,t,J=7 Hz), 3.45–4.00(3H,m), 4.18(2H,quartet,J=7 Hz), 5.81(1H,d,J=1.4 Hz), 5.83(1H,d, J=1.4 Hz), 6.06(1H,d,J=1.6 Hz), 6.08(1H,d,J=1.6 Hz), 6.60–6.70(1H,m), 6.80–6.95(2H,m), 7.23(1H,d,J=9 Hz), 7.54(1H,d,J=8 Hz), 8.58(1H,s)

REFERENCE EXAMPLE 18

Methyl 9-(1,3-Benzodioxol-5-yl)-8-methanesulfonyloxymethyl-1,3-dioxolo[4,5-f]quinoline-7-carboxylate

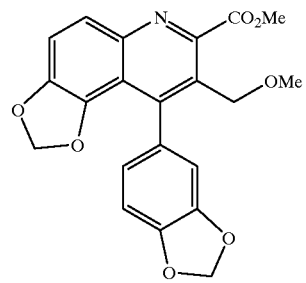

The entitled compound was obtained from 10-(1,3-benzodioxol-5-yl)-1,3-dioxolo[4,5-f]furo-[3,4-b]quinolin-7(9H)-one in a manner similar to that described in Reference Example 14.

NMR(CDCl$_3$)δ: 2.97(3H,s), 4.07(3H,s), 5.36(1H,d,J= 10Hz), 5.42(1H,d,J=10Hz), 5.93(1H,d,J=1.6 Hz), 5.96(1H, d,J=1.6 Hz), 6.07(1H,d,J=2 Hz), 6.10(1H,d,J=2 Hz), 6.75–6.95(3H,m), 7.49(1H,d,J=9 Hz), 7.90(1H,d,J=9 Hz).

REFERENCE EXAMPLE 19

Dimethyl 6-Methoxy-9-(4-methoxyphenyl)-naphtho[1,2-d]-1,3-dioxole-7,8-dicarboxylate (a) Dimethyl 6-Hydroxy-9-(4-methoxyphenyl)-naphtho[1,2-d]-1,3-dioxol-7,8-dicarboxylate

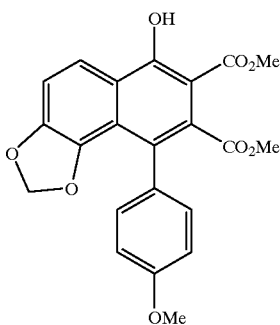

To a solution of benzene (200 ml) solution of helio alcohol (4.0 g, 26.3 mmol) was dropwise added 1.6M n-butyl lithium (1.6M-hexane solution:37 ml, 59 mmol) at room temperature and stirred for 1.5 hours at room temperature. Then, a benzene solution (50 ml) of p-methoxybenzonitrile (3.86 g, 29.0 mmol) was dropwise added thereto at room temperature and stirred for 2 hours at room temperature. To the reaction mixture was added water and extracted with ether. The extract was washed with water, saturated sodium chloride solution and dried with magnesium sulfate, then the solvent was distilled off. To the residue was added toluene (200 ml), acetylenedicarbonic acid dimethylester (16.8 g, 118 mmol), and p-toluenesulfonic acid-mono hydrate (1 g, 5 mmol), and then heated under reflux for 12 hours. To the reaction mixture was added sodium hydrogencarbonate solution and the mixture was extracted with ethyl acetate. The extract was washed with water, saturated sodium chloride solution and, dried with magnesium sulfate, then the solvent was distilled off to give the entitled compound (3.28 g, 30%) as a colorless crystals.

m.p.:200–201° C. (ether); NMR(CDCl$_3$)δ: 3.51(3H, s), 3.86(3H, s), 3.92(3H, s), 5.81(2H, s), 6.87(2H, d, J=9 Hz), 7.00–7.30(3H, m), 8.14(1H, d, J=9 Hz), IR(KBr): 2948, 2896, 1739, 1652, 1521, 1444, 1332, 1290, 1224 cm$^{-1}$; Elemental Analysis for $C_{22}H_{18}$, $N_8$ Calcd.: C:64.39%, H:4.42%; Found: C:64.27%, H:4.55%.

(b) Dimethyl 6-Methoxy-9-(4-methoxyphenyl)-naphtho[1.2-d]-1,3-dioxole-7,8-dicarboxylate

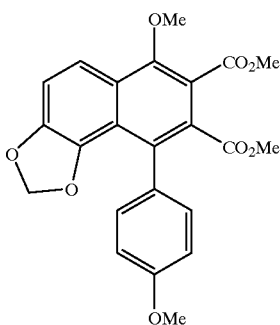

To an acetone (200 ml) solution of dimethyl 6-hydroxy-9-(4-methoxyphenyl)-naphtho[1,2-d]-1,3-dioxole-7,8-dicarbonic acid (3.0 g, 7.31 mmol) was added methyl iodide (1.5 ml, 24 mmol) and potassium carbonate (5.0 g, 36 mmol), and then heated under reflux for 2 hours. The solvent was distilled off and water was added to the residue and the mixture was extracted with ether. The extract was washed with water, saturated sodium chloride solution and dried with magnesium sulfate, then the solvent was distilled off to give the entitled compound (2.92 g, 94%) as colorless crystals.

m.p.:166–167° C. (ether); NMR(CDCl$_3$)δ: 3.51(3H, s), 3.86(3H, s), 3.92(3H, s), 4.06(3H, s), 5.83(2H, s), 6.88(2H, d, J=9 Hz), 7.15-7.30(3H, m), 7.88(1H, d, J=9 Hz). IR(KBr): 2950, 1842, 1744, 1708, 1629, 1612, 1521, 1438, 1345, 1270 cm$^{-1}$; Elemental Analysis for $C_{23}H_{20}O_8$ Calcd.: C:65.09%, H:4.75%; Found: C:65.04%, H:4.88%.

REFERENCE EXAMPLE 20

Dimethyl 9-(1,3-Benzodioxol-5-yl)-6-(2-N,N-dimethylaminoethoxy)-naphthofl,[1,2-d]-1,3-dioxole-7,8-dicarboxylate (a) Dimethyl 9-(1,3-Benzodioxol-5-yl)-6-hydroxy-naphtho[1,2-d]-1,3-dioxole-7,8-dicarboxylate

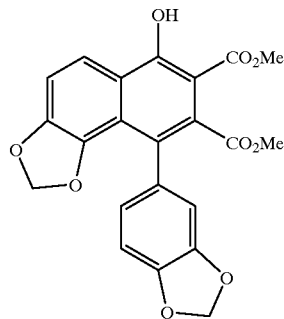

The entitled compound was obtained in a manner similar to that described in Reference Example 19(a).

m.p.:222–223° C. (THF-ether); NMR(CDCl3)δ: 3.57(3H, s), 3.92(3H, s), 5.85(1H, d, J=1.4 Hz), 5.87(1H, d, J=1.4 Hz), 6.00(1H, d, J=1.4 Hz), 6.03(1H, d, J=1.4 Hz), 6.60–6.703H, m), 7.25(1H, d, J=9 Hz), 8.14(1H, d, J=9 Hz), 12.60(1H, s), IR(KBr): 3001, 2952, 2895, 1729, 1654, 1448, 1226 cm$^{-1}$; Elemental Analysis for $C_{22}H_{16}O_9$ Calcd.: C:62.27%, H:3.80%; Found: C:62.05%, H:3.76%.

(b) Dimethyl 9-(1,3-Benzodioxol-5-yl)-6-[2-(N,N-dimethylamino)ethoxy]-naphtho[1,2-d]-1,3-dioxole-7,8-dicarboxylate

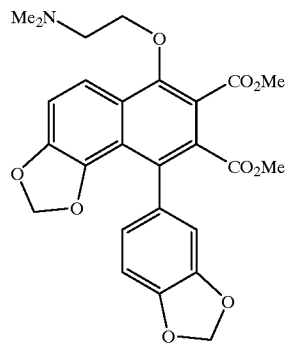

The entitled compound was obtained in a manner similar to that described in Reference Example 19(b).

m.p.:129–130° C. (THF-ether); NMR(CDCl$_3$)δ: 2.39(6H, s), 2.82(2H, t, J=5 Hz), 3.57(3H, s), 3.91(3H, s), 4.24(2H, t, J=5 Hz), 5.87(1H, brs), 5.89(1H, brs), 6.01(1H, brs), 6.03

(1H, brs), 6.68–6.75(3H, m), 7.28(1H, d, J=9 Hz), 7.97(1H, d, J=9 Hz), IR(KBr): 2950, 2898, 2779, 1720, 1710, 1629, 1488, 1442, 1344, 1235 cm$^{-1}$; Elemental Analysis for $C_{26}H_{25}NO_9$ Calcd.: C:63.03%, H:5.09%, N:2.83%; Found: C:62.79%, H:5.07%, N:2.82%.

REFERENCE EXAMPLE 21

Dimethyl 9-(1,3-Benzodioxol-5-yl)-7,8-dimethyl-6-(1-hexyloxy)-naphtho[1,2-d]-1,3-dioxole-7,8-dicarboxylate

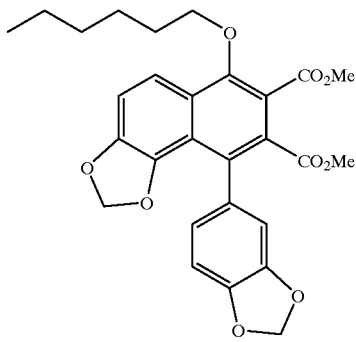

The entitled compound was obtained in a manner similar to that described in Reference Example 19(b).

m.p.:110–111° C. (ethyl acetate-isopropyl ether); NMR (CDCl$_3$)δ: 0.93(3H, t, J=6.6 Hz), 1.30–1.60(6H, m), 1.89 (2H, m), 3.57(3H, s), 3.91(3H, s), 4.11(2H, t, J=7 Hz), 5.86(1H, d, J=1.4 Hz), 5.89(1H, d, J=1.4 Hz), 6.00(1H, d, J=1.4 Hz), 6.03(1H, d, J=1.4 Hz), 6.70-6.85(3H, m), 7.26 (1H, d, J=9 Hz), 7.88(1H, d, J=9 Hz). IR(KBr): 2950, 1716, 1629, 1490, 1442, 1276, 1222 cm$^{-1}$; Elemental Analysis for $C_{28}H_{28}O_9$ Calcd.: C:66.13%, H:5.55%; Found: C:65.91%, H:5.53%.

REFERENCE EXAMPLE 22

Dimethyl 9-(1,3-Benzodioxol-5-yl)-6-methoxy-naphtho[1,2-d]-1,3-dioxole-7,8-dicarboxylate

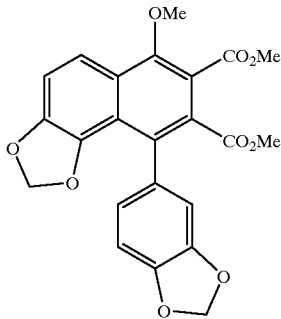

The entitled compound was obtained in a manner similar to that described in Reference Example 19(b).

m.p.:170–171° C. (THF-ether); NMR(CDCl$_3$)δ: 3.58(3H, s), 3.93(3H, s), 4.06(3H, s), 5.87(1H, brs), 5.90(1H, brs), 6.01(1H, brs), 6.04(1H, brs), 6.70–6.85(3H, m), 7.29(1H, d, J=9 Hz), 7.88(1H, d, J=9 Hz), IR(KBr): 2949, 2891, 1739, 1442, 1218 cm$^{-1}$; Elemental Analysis for $C_{23}H_{18}O_9$ Calcd.: C:63.02%, H:4.14%; Found: C:62.83%, H:4.09%.

REFERENCE EXAMPLE 23

Dimethyl 9-(1,3-Benzodioxol-5-yl)-6-(2-propyl)-naphtho[1,2-d]1,3-dioxole-7,8-dicarboxylate

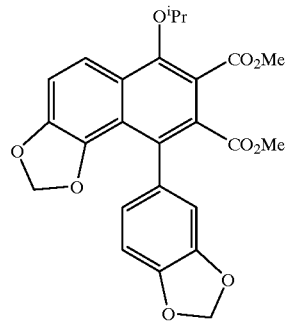

The entitled compound was obtained in a manner similar to that described in Reference Example 19(b).

m.p.:155–156° C. (THF-ether); NMR(CDCl$_3$)δ: 1.35(6H, dd, J=1.6 Hz,6 Hz), 3.57(3H, s), 3.91(3H, s), 4.41(1H, septet, J=6 Hz), 5.85(1H, d, J=1.4 Hz), 5.88(1H, d, J=1.4 Hz), 6.00(1H, d, J=1.4 Hz), 6.03(1H, d, J=1.4 Hz), 6.70–6.85(3H, m), 7.24(1H, d, J=9 Hz), 7.93(1H, d, J=9 Hz), IR(KBr): 2980, 2880, 1745, 1727, 1625, 1488, 1438, 1214 cm$^{-1}$; Elemental Analysis for $C_{25}H_{22}O_9$ Calcd.: C:64.38%, H:4.75%; Found: C:64.16%, H:4.69%.

REFERENCE EXAMPLE 24

Dimethyl 9-(4-Fluorophenyl)-6-methoxy-naphtho[1,2-d]-1,3-dioxole-7,8-dicarboxylate (a) Dimethyl 9-(4-Fluorophenyl)-6-hydroxy-naphtho[1,2-d]-1,3-dioxole-7,8-dicarboxylate

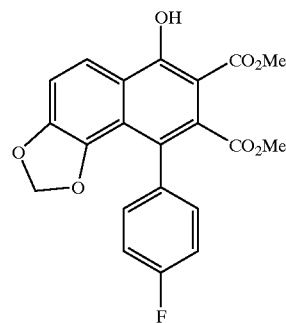

The entitled compound was obtained in a manner similar to that described in Reference Example 19(a).

m.p.:223–224 (THF-ether); NMR(CDCl$_3$)δ: 3.51(3H, s), 3.92(3H, s), 5.81(2H, s), 6.95–7.10(2H, m), 7.15–7.30(3H, m), 8.65(1H, d, J=9 Hz), IR(KBr): 2950, 2900, 1733, 1650, 1520, 1455, 1386, 1226 cm$^{-1}$; Elemental Analysis for $C_{21}H_{15}O_7F$ .0.2$H_2O$ Calcd.: C:62.75%, H:3.85%; Found: C:62.75%, H:3.93%.

(b) Dimethyl 9-(4-Fluorophenyl)-6-methoxy-naphtho[1,2-d]-1,3-dioxole-7,8-dicarboxylate

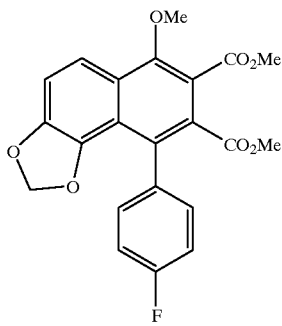

The entitled compound was obtained in a manner similar to that described in Reference Example 19(b).

m.p.:154–155 (THF-ether); NMR(CDCl$_3$)δ: 3.52(3H, s), 3.93(3H, s), 4.07(3H, s), 5.83(2H, s), 6.95–7.10(2H, m), 7.15–7.30(3H, m), 7.89(1H, d, J=9 Hz), IR(KBr): 2960, 2890, 1745, 1735, 1640, 1521, 1455, 1371, 1226 cm$^{-1}$; Elemental Analysis for C$_{22}$H$_{17}$O$_7$F Calcd.: C:64.08%, H:4.16%; Found: C:63.80%, H:4.14%.

REFERENCE EXAMPLE 25

(a) 6-Methyl-4-(4-methylphenyl)-naphtho[2,3-c]furan-1,3-dione

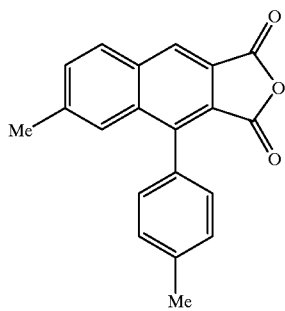

WSC (1-ethyl-3-(3-dimethylaminopropyl)carbodiiimide hydrochloride) (9.0 g) at −10° C. and stirred at room temperature for overnight. The solvent was distilled off under reduced pressure and water was added thereto, then the mixture was extracted with chloroform. The extract was washed with water and dried with magnesium sulfate, then concentrated under reduced pressure. The obtained crude crystal was washed with isopropyl ether to give the entitled compound (6.0 g).

NMR(CDCl$_3$)δ: 2.51 (6H, s), 7.30 (2H, d, J=8 Hz), 7.40 (2H, d, J=8 Hz), 7.6–7.7 (2H, m), 8.06 (1H, d, J=9 Hz), 8.49 (1H, s), IR(KBr):3028, 2922, 1835, 1772 cm$^{-1}$.

(b) 6-Methyl-4-(4-methylphenyl)-naphtho[2,3-c]furan-1(3H)-one

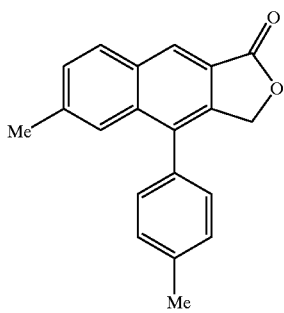

To a suspension of sodium boron hydride (2.0 g) in DME (100 ml) was gradually added 6-methyl-4-(4-methylphenyl)-naphtho[2,3-c]furan-1,3-dione (6.0 g) under ice cooling and stirred for 30 minutes. The reaction mixture was added to the diluted hydrochloric acid under ice cooling and the mixture was extracted with ethyl acetate. The extract was washed with water and dried with magnesium sulfate, then concentrated under reduced pressure. The obtained residue was purified with silica gel column chromatography (eluent:hexane-ethyl acetate=3:1), recrystallized from THF to give the entitled compound (0.7 g) as colorless crystals.

m.p.:175–176° C. (THF); NMR(CDCl$_3$)δ: 2.47 (3H, s), 2.49 (3H, s), 5.25 (2H, s), 7.27 (2H, d, J=8 Hz), 7.38 (2H, d, J=8 Hz), 7.44 (1H, dd, J=1.6 Hz,9 Hz), 7.58 (1H, d, J=1.6 Hz), 7.99 (1H, d, J=8 Hz), 8.46 (1H, s), IR(KBr): 3026, 2922, 1768, 1629, 1515 cm$^{-1}$; Elemental Analysis for C$_{20}$H$_{16}$O$_2$·0.4H$_2$O Calcd.: C:81.28%, H:5.73%; Found: C:81.12%, H:5.63%.

(c) Methyl 3-(4-Methanesulfonyloxymethyl)-6-methyl-4-(4-methylphenyl)naphthalene-2-carboxylate

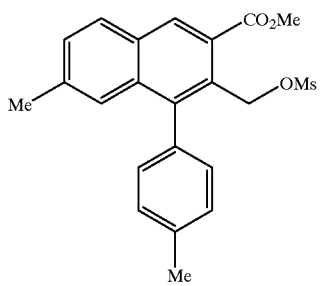

The entitled compound was obtained in a manner similar to that described in Reference Example 14.

NMR(CDCl$_3$)δ: 2.40 (3H, s), 2.49 (3H, s), 2.90 (3H, s), 3.99(3H, s), 5.48 (2H, s), 7.15–7.60(5H, m), 7.86 (2H, d, J=8 Hz), 8.52 (1H, s).

REFERENCE EXAMPLE 26

11-(1,3-Benzodioxol-5-yl)-9,10-dihydro-7H-1,3-benzodioxolo[5,4-e][2]benzopyran-7-one (a) Methyl 2-{9-(1,3-Benzodioxol-5-yl)-7-methoxycarbonylnaphtho[1,2-d]-1,3-benzodioxol-8-yl} acetate

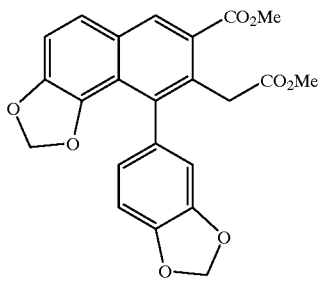

To an acetic acid (50 ml) solution of methyl 9-(1,3-benzodioxol-5-yl)-8-cyanomethylnaphtho[1,2-d]-1,3-benzodioxol-7-carboxylate (3.0 g) was added concentrated hydrochloric acid (25 ml), and then heated under reflux for 6 hours. The mixture was cooled to room temperature and water was added thereto. The resultant precipitates were collected by suction and dissolved in THF (30 ml), and then an ether solution of diazomethane was added thereto under ice cooling. The reaction mixture was concentrated under reduced pressure and the obtained residue was purified with column chromatography (silica gel 50 g, eluent:ethyl acetate-hexane=1:3) to give the entitled compound (328 mg). NMR(CDCl$_3$)δ: 3.66(3H,s), 3.85(1H,d,J=17 Hz), 3.90 (1H,d,J=17 Hz), 3.91(3H,s), 5.82(1H,brs), 5.82(1H,brs), 6.02(1H,d,J=1.4 Hz), 6.05(1H,d,J=1.4 Hz), 6.69(1H,dd,J= 1.4 Hz,8 Hz), 6.73(1H,d,J=1.4 Hz), 6.82(1H,d,J=8 Hz), 7.21(1H,d,J=9 Hz), 7.54(1H,d,J=9 Hz), 8.55(1H,s).

(b) 9-(1,3-Benzodioxol-5-yl)-8-(2-hydroxyethyl)-7-hydroxymethylnaphtho[1,2-d]-1,3-dioxole

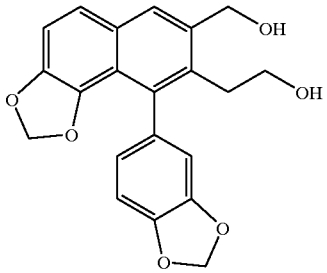

To a suspension of lithium aluminum hydride (LAH) (36 mg) in THF (1 ml) was added THF (2 ml) solution of methyl 3-{9-(1,3-benzodioxol-5-yl)-7-methoxycarbonylnaphtho[1,2-d]-1,3-benzodioxol-8-yl} acetate (208 mg) dropwise thereto under ice cooling and stirred at room temperature for 1 hour. To the mixture was added saturated sodium sulfate solution under ice cooling to stop the reaction. The reaction mixture was diluted with ethyl acetate, and washed with 1 n hydrochloric acid and saturated sodium chloride solution and dried with magnesium sulfate, then concentrated under reduced pressure. The obtained residue was purified with column chromatography (silica gel 20 g, eluent:ethyl acetate-hexane=2:1) to give the entitled compound (35 mg).

NMR(CDCl$_3$)δ: 2.89(2H,t,J=6 Hz), 3.57(2H,t,J=6 Hz), 4.74(2H,s), 5.74(2H,s), 6.00(1H,brs), 6.03(1H,brs), 6.64 (1H,dd,J=0.9 Hz,8 Hz), 6.70(1H,d,J=0.9 Hz), 6.80(1H,d,J=8 Hz), 7.10(1H,d,J=9 Hz), 7.34(1H,d,J=9 Hz), 7.72(1H,s).

(c) 11-(1,3-Benzodioxol-5-yl)-9,10-dihydro-7H-1,3-benzodioxolo[5,4-e][2]benzopyran-7-one

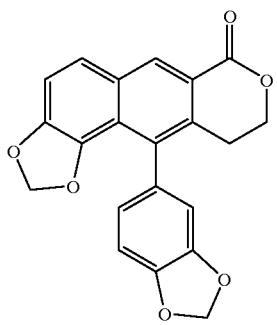

To a chloroform (3 ml) solution of 9-(1,3-benzodioxol-5-yl)-8-(2-hydroxyethyl)-7-hydroxymethylnaphtho[1,2-d]-1,3-dioxole (36 mg) was added manganese dioxide (360 mg) and stirred for 4 hours, at room temperature. The manganese dioxide was filtered off and the filtrate was concentrated under reduced pressure. The obtained residue was crystallized from ethyl acetate to give the entitled compound (16 mg).

m.p.:263–266° C.; NMR(CDCl$_3$)δ: 2.80–2.90(2H,m), 4.45(2H,t,J=6 Hz), 5.87(1H,d,J=1.4 Hz), 5.89(1H,d,J=1.4 Hz), 6.04(1H,d,J=1.5 Hz), 6.07(1H,d,J=1.5 Hz), 6.70(1H, dd,J=1.6 Hz,8 Hz), 6.74(1H,d,J=1.6 Hz), 6.88(1H,d,J=8 Hz), 7.23(1H,d,J=9 Hz), 7.62(1H,d,J=9 Hz), 8.69(1H,s). Elemental Analysis for C$_{21}$H$_{14}$O$_6$ Calcd.: C.:69.61%, H:3.89%; Found: C:69.46%, H:3.77%

REFERENCE EXAMPLE 27

Methyl 8-(3-Aminopropyl)-9-(1,3-benzodioxol-5-yl)-naphtho[1,2-d]-1,3-dioxole-7-carboxylate (a) Methyl 9-(1,3-Benzodioxol-5-yl)-8-(2-methanesulfonyloxyethyl)-naphtho[1,2-d]-1,3-benzodioxole-7-carboxylate

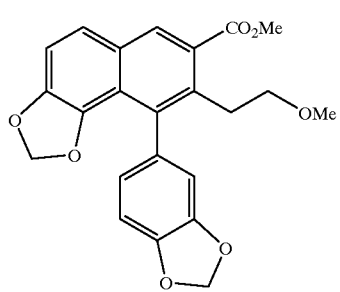

The entitled compound was obtained from 11-(1,3-benzodioxol-5-yl)-9,10-dihydro-7H-1,3-benzodioxolo[5,4-e][2]benzopyran-7-one as in a manner similar to that described in Reference Example 14.

NMR(CDCl$_3$)δ: 2.91(3H,s), 3.20–3.45(2H,m), 3.96(3H, s), 4.29(2H,t,J=8 Hz), 5.80(1H,d,J=1Hz), 5.82(1H,d,J= 1Hz), 6.04(1H,d,J=1.2 Hz), 6.06(1H,d,J=1.2 Hz), 6.65–6.75 (2H,m), 6.86(1H,d,J=8 Hz), 7.21(1H,d,J=9 Hz), 7.51(1H,d, J=9 Hz), 8.45(1H,s).

(b) Methyl 9-(1,3-Benzodioxol-5-yl)-8-(2-cyanoethyl)-naphtho[1,2-d]-1,3-benzodioxole-7-carboxylate

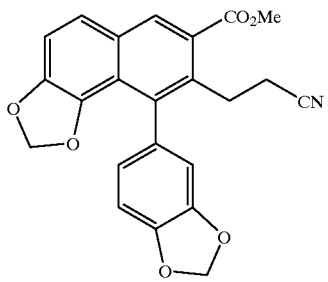

The entitled compound was obtained from methyl 9-(1,3-benzodioxol-5-yl)-8-(2-methanesulfonyloxyethyl)-naphtho[1,2-d]-1,3-benzodioxole-7-carboxylate as in a manner similar to that described in Reference Example 15.

NMR(CDCl$_3$)δ: 2.50–2.60(2H,m), 3.10–3.35(2H,m), 3.97(3H,s), 5.81(1H,d,J=1Hz), 5.82(1H,d,J=1Hz), 6.06(1H,d,J=1.2 Hz), 6.08(1H,d,J=1.2 Hz), 6.65–6.75(2H,m), 6.87 (1H,d,J=9 Hz), 7.21(1H,d,J=9 Hz), 7.52(1H,d,J=9 Hz), 8.49 (1H,s).

(c) Methyl 8-(3-Aminopropyl)-9-(1,3-benzodioxol- 5-yl)-naphtho[1,2-d]-1,3-dioxole-7-carboxylate

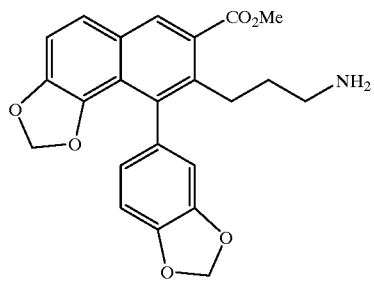

To a DMF (1 ml) solution of methyl 9-(1,3-benzodioxol-5-yl)-8-(2-cyanoethyl)-naphtho[1,2-d]-1,3-benzodioxole-7-carboxylate (21 mg) was added Raney nickel (about 200 mg) and stirred for 6 hours under hydrogen atmosphere. The catalyst was filtered off and the reaction mixture was concentrated under reduced pressure, and the obtained residue was purified with column chromatography (silica gel 1 g, eluent:dichloromethane-methanol concentrated NH$_4$OH= 15:1:0.1) to give the entitled compound (11 mg).

NMR(CDCl$_3$)δ: 1.45–1.70(2H,m), 2.50–2.70(2H,m), 2.75–2.95(2H,m), 3.94(3H,s), 5.79(1H,d,J=1.4 Hz), 5.80 (1H,d,J=1.4 Hz), 6.03(1H,d,J=1.6 Hz), 6.06(1H,d,J=1.6 Hz), 6.69(1H,dd,J=1.6 Hz,8 Hz), 6.73(1H,d,J=1.6 Hz), 6.84(1H,d,J=8 Hz), 7.17(1H,d,J=9 Hz), 7.48(1H,d,J=9 Hz), 8.47(1H,s).

REFERENCE EXAMPLE 28

Methyl 8-Cyanomethyl-9-(4-fluorophenyl)-6-methylnaphtho[1,2-d]-1,3-dioxole-7-carboxylate (a) Dimethyl 9-(4-Fluorophenyl)-6-methylnaphtho[1,2-d]-1,3-dioxole-7,8-dicarboxylate

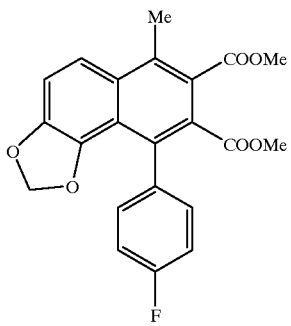

To a THF (200 ml) solution of 1-(1,3-benzodioxol-5-yl)-ethanol (8.2 g) was dropwise added butyl lithium 1.6M (hexane solution, 68.7 ml) at 0° C. The mixture was stirred for 1.5 hours and THF (30 ml) solution of p-fluorobenzonitrile (6.9 g) was dropwise added thereto and stirred for 1 hour at 0° C. To the reaction mixture was added water and the mixture was extracted with diethyl ether and dried with magnesium sulfate, then the solvent was distilled off under reduced pressure. The obtained residue was dissolved in toluene (200 ml), then dimethyl fumarate (14.4 g) and trichloroacetic acid (2.45 g) were added therein, and heated under reflux for 3 hours. After cooling, the solvent was distilled off under reduced pressure, and concentrated hydrochloric acid (75 ml) was added thereto. The reaction mixture was heated under reflux for 1 hour, separated crystals were collected and washed with, methanol and ether to give the entitled compound (2.0 g).

m.p.:160–162° C. (AcOEt-isopropyl ether); NMR (CDCl$_3$)δ: 2.74(3H,s), 3.50(3H,s), 3.90(3H,s), 5.82(2H,s), 6.92–7.33(5H,m), 7.76(1H,d,J=9 Hz) Elemental Analysis for C$_{22}$H$_{17}$FO$_6$ Calcd.: C:66.67%, H:3.95%, N:4.79%; Found: C:66.63%, H:4.25%, N:4.53%.

(b) 9-(4-Fluorophenyl)-8-hydroxymethyl-6-methylnaphtho [1,2-d]-1,3-dioxole-7-methanol

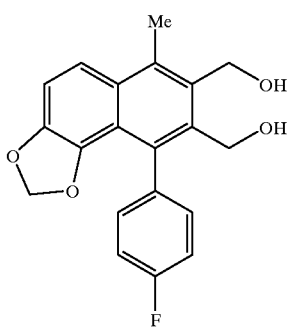

To a suspension of Lithium aluminum hydride (0.32 g) in THF (30 ml) was dropwise added a THF (30 ml) solution of dimethyl 9-(4-fluorophenyl)-6-methylnaphtho[1,2-d]-1,3-dioxole-7,8-dicarboxylate (1.67 g). After 1.5 hours, a saturated sodium sulfate solution was added thereto and insoluble materials were filtered off. The filtrate was concentrated under reduced pressure, and the residue was recrystallized from ethyl acetate-isopropyl ether to give the entitled compound (1.3 g) as colorless crystals.

m.p.:170–172° C.; NMR(CDCl$_3$)δ: 2.43(1H,brs), 2.80 (3H,s), 2.96(1H,brs), 4.62(2H,s), 5.01(2H,s), 5.73(2H,s), 7.01–7.27(5H,m), 7.72(1H,d,J=9 Hz), IR(KBr) : 3275 cm⁻¹; Elemental Analysis for C₂₀H₁₇FO₄ Calcd.: C:70.58%, H:5.03%; Found: C:70.36%, H:4.78%.

(c) 10-(4-Fluorophenyl)-6-methylfuro[3',4':6,7]-naphtho[1,2-d]-1,3-dioxole-7(9H)-one

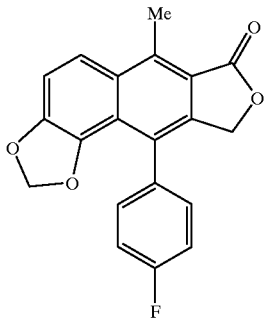

To a chloroform (40 ml) solution of 9-(4-fluorophenyl)-8-hydroxymethyl-6-methylnaphtho[1,2-d]-1,3-dioxole-7-methanol (880 mg) was added manganese dioxide (8.8 g) and stirred for 60 hours at room temperature. The insoluble substances were filtered off and the filtrate was concentrated under reduced pressure. The residue was purified with silica gel column chromatography (ethyl acetate-hexane ) to give the entitled compound (93 mg) as a pale-yellow crystals.

m.p.:197–199° C. (AcOEt-isopropyl ether); NMR (CDCl₃)δ: 3.13(3H,s), 5.06(2H,s), 5.89(2H,s), 7.08–7.38 (5H,m), 7.93(1H,d,J=9 Hz). Elemental Analysis for C₂₀H₁₃FO₄·0.25 H₂O Calcd.: C:70.48%, H:3.99%; Found: C:70.76%, H:3.71%.

(d) Methyl 9-(4-Fluorophenyl)-8-methanesulfonyloxymethyl-6-methylnaphtho[1,2-d]-1,3-dioxole-7-carboxylate

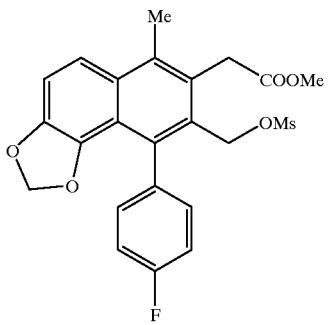

The entitled compound was obtained in a manner similar to that described in Reference Example 14.

NMR(CDCl₃)δ: 2.66(3H,s), 2.82(3H,s), 4.01(3H,s), 5.78 (2H,s), 7.00–7.40(5H,m), 7.76(1H,d,J=9 Hz).

(e) Methyl 8-Cyanomethyl-9-(p-fluorophenyl)-6-methylnaphtho[1,2-d]-1,3-dioxol-7-carboxylate

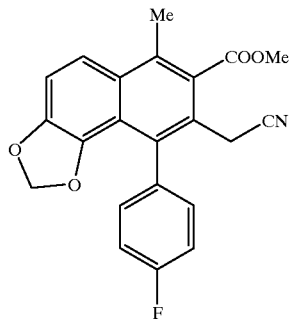

The entitled compound was obtained in a manner similar to that described in Reference Example 15.

NMR(CDCl₃)δ: 2.67(3H,s), 3.50(2H,s), 4.04(3H,s), 5.77 (2H,s), 7.09–7.35(5H,m), 7.71(1H,d,J=9 Hz), IR(KBr) : 2249, 1732 cm⁻¹

REFERENCE EXAMPLE 29

8-Cyanomethyl-9-(4-fluorophenyl)-naphtho[1,2-d]-1,3-dioxole-7-carboxylic acid (a) Dimethyl 9-(p-Fluorophenyl)-naphtho[1,2-d]-1,3-dioxole-7,8-dicarboxylate

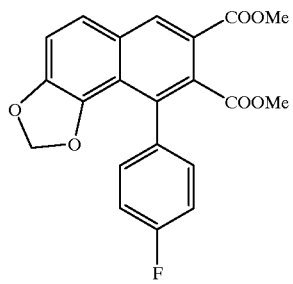

The entitled compound was obtained in a manner similar to that described in Reference Example 28(a).

m.p.:172–174° C. (AcOEt-hexane); NMR(CDCl₃)δ: 3.59 (3H,s), 3.94(3H,s), 5.85(2H,s), 6.98–7.12(2H,m), 7.24–7.35 (2H,m), 7.29(1H,d,J=9 Hz), 7.61(1H,d,J=9 Hz), 8.56(1H,s), IR(KBr): 1741, 1720, 1455, 1272, 1261, 1216, 1160, 1077 cm⁻¹; Elemental Analysis for C₂₁H₁₅FO₆ Calcd.: C:65.97%, H:3.95%; Found: C:65.96%, H:3.84%.

(b) 9-(4-Fluorophenyl)-8-hydroxymethylnaphtho[1,2-d]-1,3-dioxole-7-methanol

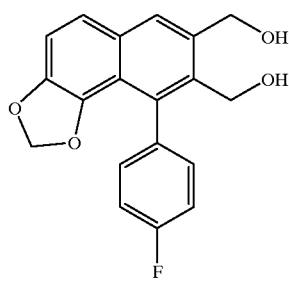

The entitled compound was obtained in a manner similar to that described in Reference Example 28(b).

m.p.:206–208° C. (THF); NMR(CDCl₃)δ: 2.70–3.00(2H, m), 4.57(2H,brs), 4.93(2H,brs), 5.76(2H,s), 7.04–7.34(5H, m), 7.45(1H,d,J=9 Hz), 7.81(1H,s), IR(KBr): 3332, 1453, 1324, 1295, 1046, 1000 cm⁻¹; Elemental Analysis for $C_{19}H_{15}FO_4$ Calcd.: C:69.93%, H:4.63%; Found: C:69.83%, H:4.61%.

(c) 8-(tert-Butyldiphenylsilyloxymethyl)-9-(4-fluorophenyl)-naphtho[1,2-d]-1,3-dioxole-7-methanol

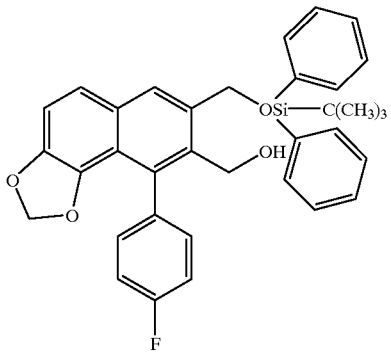

To a DMF (20 ml) solution of 9-(4-Fluorophenyl)-8-hydroxymethylnaphtho[1,2-d]-1,3-dioxole-7-methanol (2.28 g) were added imidazole (0.95 g) and tert-butylcholorodiphenylsilane (2.31 g) and stirred for 1 hour at room temperature. To the reaction mixture was added water and resultant precipitates were collected by suction. The obtained precipitates were dissolved in ethyl acetate and washed with 1N hydrochloric acid, saturated sodium chloride solution, saturated sodium hydrogencarbonate solution, and saturated sodium chloride solution successively. The ethyl acetate solution was dried with magnesium sulfate and then concentrated under reduced pressure. The obtained residue was purified with silica gel column chromatography (eluent:ethyl acetate-hexane=1:9) to give the entitled compound (1.48 g, 83%) as colorless powder.

NMR(CDCl₃)δ: 1.06(9H,s), 3.45(1H,t,J=7 Hz), 4.52(2H, d,J=7 Hz), 4.94(2H,brs), 5.77(2H,s), 7.00–7.55(13H,m), 7.70–7.80(4H,m), IR(KBr): 3516, 1504, 1448, 1322, 1068, 1048 1039 cm⁻¹.

(d) 7-(tert-Butyldiphenylsilyloxymethyl)-9-(p-fluorophenyl)-naphtho[1,2-d]-1,3-dioxole-8-acetonitrile

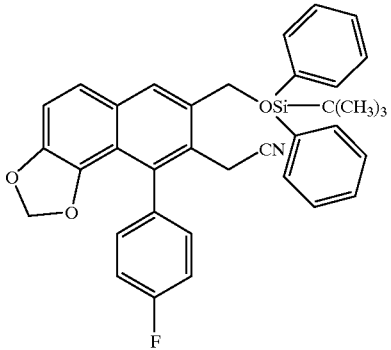

To a THF(30 ml) solution of 8-(tert-Butyldiphenylsilyloxymethyl)-9-(4-fluorophenyl)-naphtho[1,2-d]-1,3-dioxole-7-methanol (3.0 g) were added triethylamine (1.48 ml) and methanesulfonylchloride (0.49 ml) and stirred for 30 minutes under ice cooling. To the reaction mixture was added water and the mixture was extracted with ethyl acetate. The extract was washed with saturated sodium chloride solution and dried with magnesium sulfate, then concentrated under reduced pressure. The obtained residue was dissolved in DMF (30 ml) and sodium cytnide (0.52 g) was added thereto and stirred overnight. To the reaction mixture was added water and the mixture was extracted with ethyl acetate. The extract was washed with saturated sodium chloride solution and dried with magnesium sulfate, then concentrated under reduced pressure. The obtained crude crystals were recrystallized from diisopropyl ether to give the entitled compound (2.54 g) as colorless crystals.

m.p.:147–149° C.; NMR(CDCl₃)δ: 1.08(9H,s), 3.69(2H, brs), 4.96(2H,brs), 5.77(2H,s), 7.10–7.55(12H,m), 7.57(1H, s), 7.65–7.75(4H,m), IR(KBr): 2248, 1455, 1220, 1112, 1073 cm⁻¹; Elemental Analysis for $C_{36}H_{32}FNO_3Si$ Calcd.: C:75.36%, H:5.62%, N:2.44%; Found: C:75.13%, H:5.57%, N:2.43%.

(e) 9-(4-Fluorophenyl)-7-hydroxymethylnaphtho[1,2-d]-1, 3-dioxole-8-acetonitrile

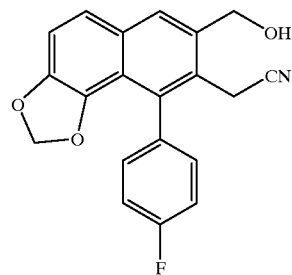

To a THF (10 ml) solution of 7-(tert-butyldiphenylsilyloxymethyl)-9-(4-fluorophenyl)naphtho [1,2-d]-1,3-dioxole-8-acetonitrile (1.0 g) was added tetrabutylammoniumfluoride (1 N THF solution) (2.3 ml) and stirred for 30 minutes at room temperature. The solvent was distilled off under reduced pressure, and water was added to the residue. Separated solid was collected and washed with methanol to give a crude crystals (481 mg) of the entitled compound. Some of the crude crystals were recrystallized from ethyl acetate-hexane for analysis.

m.p.:190–193° C.; NMR(CDCl₃)δ: 3.69(2H,s), 4.96(2H, s), 5.77(2H,s), 7.10–7.34(5H,m), 7.45(1H,d,J=8.4 Hz), 7.82 (1H,s). IR(KBr): 3554, 2252, 1505, 1459, 1326, 1266, 1222, 1077 cm⁻¹; Elemental Analysis for $C_{20}H_{14}FNO_3 \cdot 0.1H_2O$ Calcd.: C:71.25%, H:4.25%, N:4.15%; Found: C:71.09%, H:4.22%, N:3.98%.

(f) 8-Cyanomethyl-9-(4-fluorophenyl)-naphtho[1,2-d]-1,3-dioxole-7-carboxylic acid

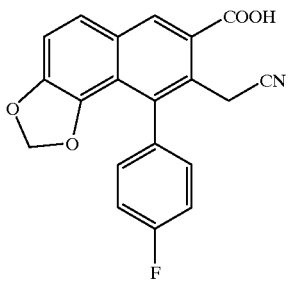

To a mixture of acetone (5 ml) and water (2 ml) was dissolved 9-(4-fluorophenyl)-7-hydroxymethylnaphtho[1,2-d]-1,3-dioxole-8-acetonitrile (200 mg), and potassium permanganate (400 mg) was gradually added thereto. The mixture was stirred for 1 hour at room temperature and potassium permanganate (200 mg) was gradually added thereto. The insoluble substances were filtered off and 1N hydrochloric acid was added to the filtrate. The resultant precipitates were collected by suction and recrystallized from methanol to give the entitled compound (23 mg) as colorless crystals.

m.p.:230–233° C.; NMR(CDCl$_3$)δ: 3.98(2H,s), 5.79(2H, s), 7.10–7.35(5H,m), 7.58(1H,d,J=8 Hz), 8.69(1H,s). IR(KBr): 2997, 2240, 1681, 1451, 1274, 1230, 1097 cm$^{-1}$;

REFERENCE EXAMPLE 30

Methyl 9-(1,3-Benzodioxol-5-yl)-8-cyanomethyl-6-methylnaphtho[1,2-d]-1,3-dioxole-7-carboxylate (a) Dimethyl 9-(1,3-Benzodioxol-5-yl)-6-methylnaphtho[1,2-d]-1,3-dioxole-7,8-dicarboxylate

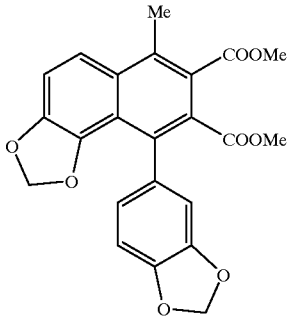

The entitled compound was obtained in a manner similar to that described in Reference Example 28(a).

m.p.:157–158° C. (MeOH); NMR(CDCl$_3$)δ: 2.73(3H,s), 3.56(3H,), 3.90(3H,s), 5.85(1H,d,J=1.4 Hz), 5.89(1H,d,J=1.4 Hz), 6.00(1H,d,J=1.4 Hz), 6.04(1H,d,J=1.4 Hz), 6.72 (1H,dd,J=1.6 Hz,8 Hz), 6.79(1H,d,J=8 Hz), 6.80(1H,d,J=1.6 Hz), 7.29(1H,d,J=9 Hz), 7.74(1H,d,J=9 Hz). IR(KBr): 1726, 1488, 1438, 1235, 1205, 1035 cm$^{-1}$; Elemental Analysis for C$_{23}$H$_{18}$O$_8$ Calcd.: C:65.40%, H:4.30%; Found: C:65.21%, H:4.20%.

(b) 9-(1,3-Benzodioxol-5-yl)-8-hydroxymethyl-6-amethylnaphtho[1,2-d]-1,3-dioxole-7-methanol

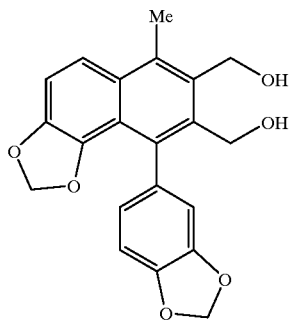

The entitled compound was obtained in a manner similar to that described in Reference Example 28(b).

m.p.:215–217° C. (THF); NMR(CDCl$_3$)δ: 1.70–2.00(2H, m), 2.80(2H,s), 4.69(2H,brs), 5.01(2H,brs), 5.78(1H,d,J=1.4 Hz), 5.80(1H,d,J=1.4 Hz), 6.02(1H,d,J=1.4 Hz), 6.06(1H,d, J=1.4 Hz), 6.69(1H,dd,J=1.6 Hz,8 Hz), 6.74(1H,d,J=1.6 Hz), 6.84(1H,d,J=8 Hz), 7.21(1H,d,J=9 Hz), 7.72(1H,d,J=9 Hz).

IR(KBr): 3298, 1492, 1434, 1291, 1070, 1039, 998 cm$^{-1}$; Elemental Analysis for C$_{21}$H$_{18}$O$_6$ Calcd.: C:68.85%, H:4.95%; Found: C:68.49%, H:4.93%.

(c) 9-(1,3-Benzodioxol-5-yl)-8-(tert-butyldiphenylsilyloxymethyl)-6-methylnaphtho[1,2-d]-1,3-dioxole-7-methanol

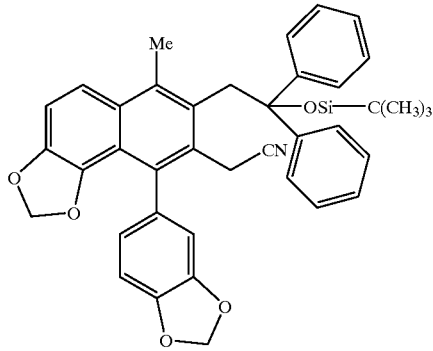

The entitled compound was obtained in a manner similar to that described in Reference Example 29(c).

NMR(CDCl$_3$)δ: 1.05(9H,s), 2.32(3H,s), 3.14(1H,brs), 4.53(2H,m), 5.05(2H,s), 5.77(1H,d,J=1.4 Hz), 5.79(1H,d,J=1.4 Hz), 6.00(1H,d,J=1.4 Hz), 6.05(1H,d,J=1.4 Hz), 6.74–6.88(3H,m), 7.18(1H,d,J=9 Hz), 7.28–7.52(6H,m), 7.59(1H,d,J=9 Hz), 7.68–7.80(4H,m), IR(KBr): 3340, 1488, 1436, 1230, 1072, 1041 cm$^{-1}$.

(d) 9-(1,3-Benzodioxol-5-yl)-7-(tert-butyldiphenylsilyloxymethyl)-6-methylnaphtho[1,2-d]-30 1,3-dioxole-8-acetonitrile

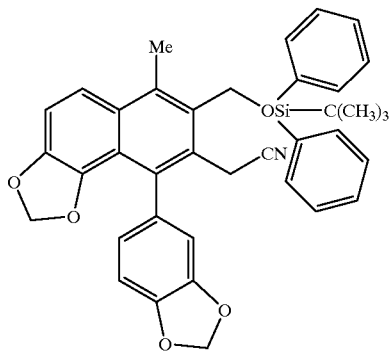

The entitled compound was obtained in a manner similar to that described in Reference Example 29(d).

m.p.:191–193° C. (AcOEt); NMR(CDCl$_3$)δ: 1.04(9H,s), 2.42(3H,s), 3.58(1H,d,J=16 Hz), 3.70(1H,d,J=16 Hz), 5.02 (2H,s), 5.78(1H,d,J=1.4 Hz), 5.80(1H,d,J=1.4 Hz), 6.04(1H, d,J=1.4 Hz), 6.07(1H,d,J=1.4 Hz), 6.68-6.80(2H,m), 6.88 (1H,d,J=8 Hz), 7.20(1H,d,J=9 Hz), 7.28-7.52(6H,m), 7.62 (1H,d,J=9 Hz), 7.64–7.70(4H,m). IR(KBr): 2246, 1488, 1436, 1068, 1039 cm$^{-1}$; Elemental Analysis for C$_{38}$H$_{35}$FNO$_5$Si Calcd.: C:75.29%, H:5.83%, N:2.25%; Found: C:75.26%, H:5.79%, N:2.32%.

(e) 9-(1,3-Benzodioxol-5-yl)-7-hydroxymethyl-6-methylnaphtho[1,2-d]-1,3-dioxole-8-acetonitrile

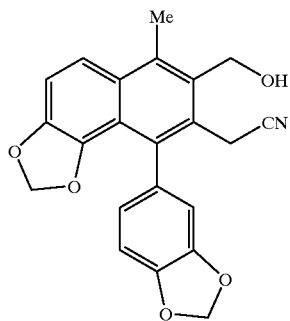

The entitled compound was obtained in a manner similar to that described in Reference Example 29(e).

NMR(CDCl$_3$)δ: 1.70(1H,m), 2.79(3H,s), 3.72(1H,d,J=17 Hz), 3.81(1H,d,J=17 Hz), 5.04(2H,m), 5.79(1H,d,J=1.4 Hz), 5.82(1H,d,J=1.4 Hz), 6.05(1H,d,J=1.4 Hz), 6.08(1H,d,J=1.4 Hz), 6.70–6.80(2H,m), 6.89(1H,d,J=8 Hz), 7.24(1H,d,J=9 Hz), 7.72(1H,d,J=9 Hz), IR(KBr): 3280, 2249, 1489, 1437, 1229, 1067, 1040 cm$^{-1}$.

(f) Methyl 9-(1,3-Benzodioxol-5-yl)-8-cyanomethyl-6-methylnaphtho[1,2-d]-1,3-dioxole-7-carboxylate

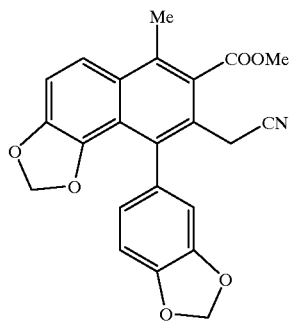

9-(1,3-Benzodioxol-5-yl)-7-hydroxymethyl-6-methylnaphtho[1,2-d]-1,3-dioxol-8-acetonitrile (180 mg) was dissolved in a mixture of acetone (5 ml) and water (1.5 ml) and 1N sodium hydroxide solution (0.48 ml) was added thereto under ice cooling. To the mixture potassium permanganate (400 mg) was added gradually and stirred for 2 hours under ice cooling, then stirred 1 hour at room temperature. The insoluble substance was filtered off, and 1N hydrochloric acid was added-to the filtrate and the mixture was extracted with ethyl acetate. To the extract was added diazomethane (ether solution) and washed with 1N hydrochloric acid, saturated sodium chloride solution, saturated sodium hydrogen carbonate solution, and saturated sodium chloride solution successively, and dried with magnesium sulfate, then concentrated under reduced pressure. The obtained residue was purified with silica gel column chromatography (eluent:ethyl acetate-hexane=1:2) to give the entitled compound (12 mg). NMR(CDCl$_3$)δ: 2.66(3H,s), 3.56(2H,s), 4.04(3H,s), 5.04(2H,m), 5.81(1H,d,J=1.4 Hz), 5.83(1H,d,J=1.4 Hz), 6.04(1H,d,J=1.4 Hz), 6.07(1H,d,J=1.4 Hz), 6.70–6.80(2H,m), 6.88(1H,d,J=8 Hz), 7.26(1H,d,J=9 Hz), 7.78(1H,d,J=9 Hz), IR(KBr): 2251, 1728, 1489, 1439, 1260, 1244, 1040 cm$^{-1}$.

REFERENCE EXAMPLE 31

Methyl 8-Cyanomethyl-9-(4-fluorophenyl)-6-methylnaphtho[1,2-d]-1,3-dioxole-7-carboxylate
(a) Dimethyl 9-(4-Fluorophenyl)-6-methylnaphtho[1,2-d]-1,3-dioxole-7,8-dicarboxylate

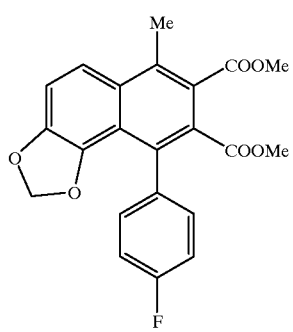

The entitled compound was obtained in a manner similar to that described in Reference Example 28(a).
m.p.:160–162° C. (AcOEt-isopropyl ether); NMR (CDCl$_3$)δ: 2.74(3H,s), 3.50(3H,s), 3.90(3H,s), 5.82(2H,s), 6.92–7.33(5H,m), 7.76(1H,d,J=9 Hz). Elemental analysis for $C_{22}H_{17}FO_6$ Calcd.: C:66.67%, H:3.95%; Found: C:65.63%, H:4.25%.

(b) 9-(4-Fluorophenyl)-8-hydroxymethyl-6-methylnaphtho[1,2-d]-1,3-dioxole-7-methanol

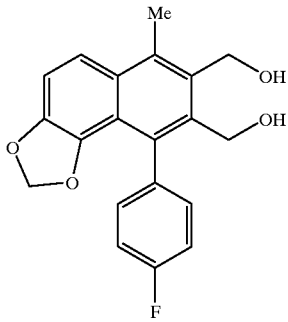

The entitled compound was obtained in a manner similar to that described in Reference Example 28(b).

m.p.:170–172° C. (AcOEt-isopropyl ether); NMR (CDCl$_3$)δ: 2.43(1H,brs), 2.80(3H,s), 2.96(1H,brs), 4.62(2H,s), 5.01(2H,s), 5.73(2H,s), 7.01–7.27(5H,m), 7.72(1H,d,J=9 Hz). IR(KBr): 3275 cm$^{-1}$; Elemental analysis for $C_{20}H_{17}FO_4$ Calcd.: C:70.58%, H:5.03%; Found: C:70.36%, H:4.78%.

(c) 10-(4-Fluorophenyl)-6-methylfuro[3',4':6,7]naphtho[1,2-d]-1,3-dioxol-7(9H)-one

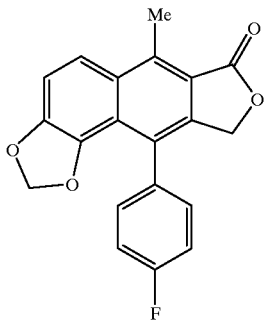

The entitled compound was obtained in a manner similar to that described in Reference Example 26(c).

m.p.:197–199° C. (AcOEt-isopropyl ether); NMR (CDCl$_3$)δ: 3.13(3H,s), 5.06(2H,s), 5.89(2H,s), 7.08–7.38 (5H,m), 7.93(1H,d,J=9 Hz). Elemental analysis for $C_{20}H_{13}FO_4 \cdot 0.25H_2O$ Calcd.: C:70.48%, H:3.99%; Found: C:70.76%, H:3.71%.

(d) Methyl 9-(4-Fluorophenyl)-8-methanesulfonyloxymethyl-6-methylnaphtho[1,2-d]-1,3-dioxole-7-carboxylate

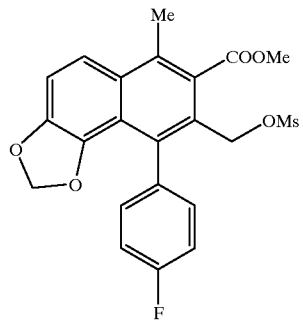

The entitled compound was obtained in a manner similar to that described in Reference Example 14.

NMR(CDCl$_3$)δ: 2.66(3H,s), 2.82(3H,s), 4.01(3H,s), 5.78 (2H,s), 7.00–7.40(5H,m), 7.76(1H,d,J=9 Hz).

(e) Methyl 8-Cyanomethyl-9-(4-fluorophenyl)-6-methylnaphtho[1,2-d]-1,3-dioxole-7-carboxylate

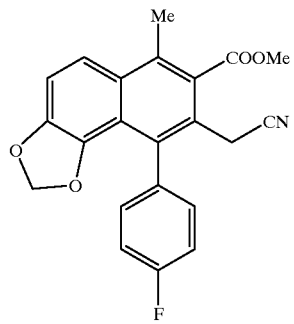

The entitled compound was obtained in a manner similar to that described in Reference Example 15.

NMR(CDCl$_3$)δ: 2.67(3H,s), 3.50(2H,s), 4.04(3H,s), 5.77 (2H,s), 7.09–7.35(5H,m), 7.71(1H,d,J=9 Hz), IR(KBr): 2249, 1732 cm$^{-1}$.

REFERENCE EXAMPLE 32

Methyl 8-Cyanomethyl-9-(4-methoxyphenyl)naphtho[1,2-d]-1,3-dioxole-7-carboxylate (a) Dimethyl 9-(4-Methoxyphenyl)naphtho[1,2-d]-1,3-dioxole-7,8-dicarboxylate

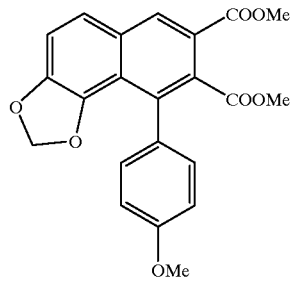

The entitled compound was obtained in a manner similar to that described in Reference Example 28(a).

m.p.:219–221° C.; NMR(CDCl$_3$)δ: 3.60(3H,s), 3.87(3H,s), 3.94(3H,s), 5.85(2H,s), 6.90(2H,d,J=9z), 7.20–7.31(3H,m), 7.60(1H,d,J=9 Hz), 8.54(1H,s), IR(KBr) :1723, 1454, 1271 cm$^{-1}$;

(b) 8-Hydroxymethyl-9-(4-methoxyphenyl)naphtho[1,2-d]-1,3-dioxole-7-methanol

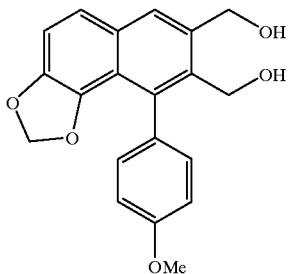

The entitled compound was obtained in a manner similar to that described in Reference Example 28(b).

m.p.:181–183° C. (AcOEt-isopropyl ether); NMR (CDCl$_3$)δ: 2.82(2H,brs), 3.89(3H,s), 4.60(2H,s), 4.93(2H,s), 5.77(2H,s), 6.95(2H,d,J=9 Hz), 7.15–7.27(3H,m), 7.44(1H, d,J=8 Hz), 7.80(1H,s). IR(KBr): 3348, 2926, 1451, 1244 cm$^{-1}$;

(c) 10-(4-Methoxyphenyl)furo[3',4':6,7]naphtho[1,2-d]-1,3-dioxol-7(9H)-one

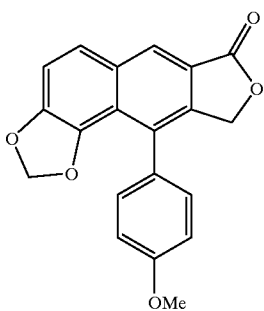

The entitled compound was obtained in a manner similar to that described in Reference Example 26(c).

m.p.:216–218° C. (CHCl$_3$); NMR(CDCl$_3$)δ: 3.90(3H,s), 5.20(2H,s), 5.93(2H,s), 6.95–7.10(2H,m), 7.24–7.35(3H,m), 7.71(1H,d,J=9 Hz), 8.43(1H,s). Elemental analysis for C$_{20}$H$_{14}$O$_5$ Calcd.: C:71.85%, H:4.22%; Found: C:71.66%, H:4.11%.

(d) Methyl .8-Methanesulfonyloxymethyl-9-(4-methoxyphenyl)naphtho[1,2-d]-1,3-dioxole-7-carboxylate

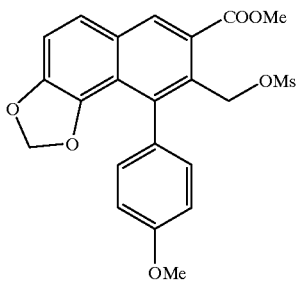

The entitled compound was obtained in a manner similar to that described in Reference Example 14.

NMR(CDCl$_3$)δ: 2.89(3H,s), 3.89(3H,s), 3.97(3H,s), 5.43 (2H,s), 5.81(2H,s), 6.95(2H,d,J=9 Hz), 7.18–7.30(3H,m), 7.55(1H,d,J=8 Hz), 8.49(1H,s).

(e) Methyl 8-Cyanomethyl-9-(4-methoxyphenyl)naphtho[1,2-d]-1,3-dioxole-7-carboxylate

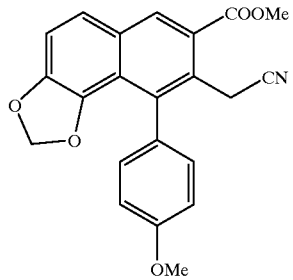

The entitled compound was obtained in a manner similar to that described in Reference Example 15.

m.p.:163–166° C. (CHCl$_3$); NMR(CDCl$_3$)δ: 3.91(3H,s), 3.93(2H,s), 4.01(3H,s), 5.81(2H,s), 6.99(2H,d,J=8 Hz), 7.13–7.30(3H,m), 7.57(1H,d,J=9 Hz), 8.60(1H,s).

REFERENCE EXAMPLE 33

Methyl 8-Cyanomethyl-9-(4-trifluoromethylphenyl) naphtho[1,2-d]-1,3-dioxole-7-carboxylate (a) Dimethyl 9-(4-trifluoromethylphenyl)naphtho[1,2-d]-1,3-dioxole-7,8-dicarboxylate

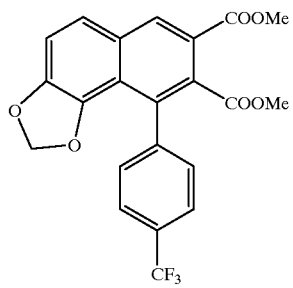

The entitled compound was obtained in a manner similar to that described in Reference Example 28(a).

m.p.:163–166° C. (CHCl$_3$); NMR(CDCl$_3$)δ: 3.56(3H,s), 3.94(3H,s), 5.83(2H,s), 7.30(1H,d,J=9 Hz), 7.46(2H,d,J=8 Hz), 7.60–7.65(3H,m), 8.58(1H,s), IR(KBr): 1732, 1456, 1325, 1271 cm$^{-1}$;

(b) 8-Hydroxymethyl-9-(4-trifluoromethylphenyl)naphtho[1,2-d]-1,3-dioxole-7-methanol The entitled compound was obtained in a manner similar to that described in Reference Example 28(b).

m.p.:196–198° C. (AcOEt-isopropyl ether); NMR (CDCl$_3$)δ: 2.80–3.00(2H,brs), 4.52(2H,s), 4.94(2H,s), 5.74 (2H,s), 7.21(1H,d,J=8 Hz), 7.40–7.50(3H,m), 7.67(2H,d,J=8

Hz), 7.84(1H,s), IR(KBr): 3310, 1453, 1323 cm⁻¹; Elemental analysis for C₂₀H₁₅F₃O₄ Calcd.: C:63.83%, H:4.02%; Found C:63.92%, H:4.01%.

(c) 10-(4-Trifluoromethylphenyl)furo[3',4':6,7]naphtho[1,2-d]-1,3-dioxol-7(9H)-one

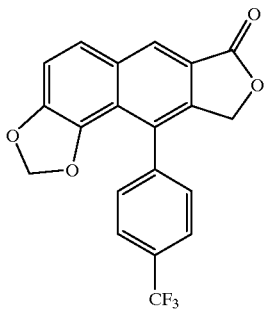

The entitled compound was obtained in a manner similar to that described in Reference Example 26(c).

m.p.:235–237° C. (CHCl₃); NMR(CDCl₃)δ: 5.17(2H,s), 5.92(2H,s), 7.35(1H,d,J=9 Hz), 7.46–7.54(2H,m), 7.70–7.78 (3H,m), 8.49(1H,s), IR(KBr): 1755, 1464, 1327, 1073 cm⁻¹ Elemental analysis for C₂₀H₁₁F₃O₄ Calcd.: C:64.52%, H:2.98%; Found: C:64.35%, H:2.95%.

(d) Methyl 8-Methanesulfonyloxymethyl-9-(4-trifluoromethylphenyl)naphtho(1,2-d]-1,3-dioxole-7-carboxylate

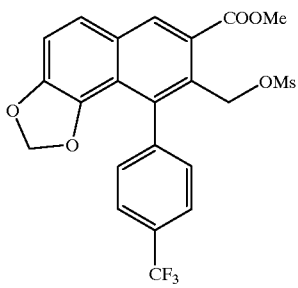

The entitled compound was obtained in a manner similar to that described in Reference Example 14.

NMR(CDCl₃)δ: 2.89(3H,s), 4.00(3H,s), 4.85(2H,s), 5.77 (2H,s), 7.20–7.80(6H,m), 8.51(1H,s).

(e) Methyl 8-Cyanomethyl-9-(4-trifluoromethylphenyl) naphtho(1,2-d]-1,3-dioxole-7-carboxylate

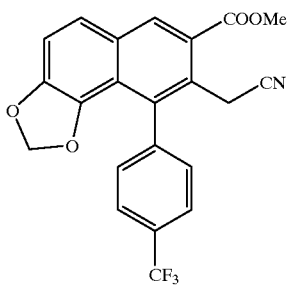

The entitled compound was obtained in a manner similar to that described in Reference Example 15.

m.p.:180–181° C. (CHCl₃); NMR(CDCl₃)δ: 3.88(2H,s), 4.02(3H,s), 5.79(2H,s), 7.28(1H,d,J=9 Hz), 7.46(2H,d,J=8 Hz), 7.61(1H,d,J=9 Hz), 7.74(2H,d,J=8 Hz), 8.65(1H,s). Elemental analysis for C₂₂H₁₄F₃O₄.0.2H₂O Calcd.: C:63.37%, H:3.48%; Found: C:63.43%, H:3.47%.

EXAMPLE 1

10-(1,3-Benzodioxol-5-yl)-8,9-dihydro-7H-1,3-benzodioxolo[4,5-f]isoindol-7-one

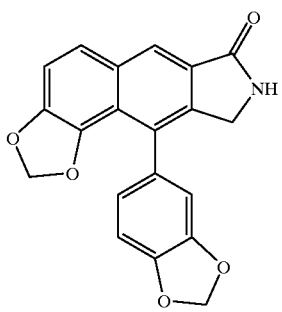

Methyl 9-(1,3-benzodioxol-5-yl)-8-methanesulfonyloxymethyl-naphtho[1,2-d]-1,3-benzodioxole-7-methylcarboxylate (150 mg), which was obtained in Reference Example 14, was dissolved in a mixture of THF (6 ml) and methanol (3 ml) and concentrated NH₄OH (1 ml) was added thereto. The mixture was stirred overnight at room temperature, and the reaction mixture was concentrated under reduced pressure. The obtained residue was dissolved in ethyl acetate. The obtained ethyl acetate solution was washed with saturated sodium chloride solution and dried with magnesium sulfate, then concentrated under reduced pressure. The obtained residue was purified with column chromatography (silica gel 5 g, eluent:dichloromethane-methanol=95:5) and recrystallized from THF to give the entitled compound (55 mg).

m.p.:252–254° C.; NMR(DMSO-d₆)δ: 4.20(2H,brs), 5.95 (1H,brs), 5.96(1H,brs), 6.07(1H,brs), 6.11(1H,brs), 6.86 (1H,dd,J=1.5 Hz,8 Hz), 6.95(1H,d,J=,8 Hz), 7.00(1H,d,J= 1.5 Hz), 7.42(1H,d,J=9 Hz), 7.84(1H,d,J=9 Hz), 8.29(1H,s), 8.60(1H,brs), IR(KBr): 1695, 1630, 1590, 1435, 1270, 1230, 1035 cm⁻¹; Elemental Analysis for C₂₀OH₁₃NO₅.0.5H₂O Calcd.: C:67.41%, H:3.96%, N:3.93%; Found: C:67.72%, H:3.82%, N:3.84%

EXAMPLE 2

10-(1,3-Benzodioxol-5-yl)-8,9-dihydro-8-methyl-7H-1,3-benzodioxolo[4,5-f]isoindol-7-one.

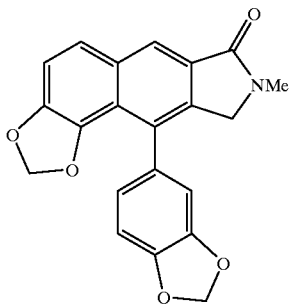

Methyl 9-(1,3-benzodioxol-5-yl)-8-methanesulfonyloxymethyl-naphtho[1,2-d]-1,3-benzodioxol-7-carboxylate (150 mg), which was obtained in Reference Example 14 was dissolved in THF (6 ml) and methylamine (40% methanol solution: 1 ml) was added thereto. The mixture was stirred for 3 days at room temperature and the reaction mixture was concentrated under reduced pressure. To the obtained residue was added water and extracted with ethyl acetate. The obtained extract was washed with saturated sodium chloride solution and dried magnesium sulfate, then concentrated under reduced pressure. The obtained residue was purified with column chromatography (silica gel 5 g, eluent:dichloromethane-ether= 4:1) and recrystallized from ethyl acetate-hexane to give the entitled compound (67 mg).

m.p.:234–236° C.; NMR(CDCl$_3$)δ: 3.18(3H,s), 4.21(1H,d,J=17 Hz), 4.30(1H,d,J=17 Hz), 5.91(1H,d,J=1.4 Hz), 5.93 (1H,d,J=1.4 Hz), 6.05(1H,d,J=1.4 Hz), 6.08(1H,d,J=1.4 Hz), 6.79–6.92(3H,m), 7.26(1H,d,J=9 Hz), 7.66(1H,d,J=9 Hz), 8.30(1H,s), IR(KBr): 1685, 1485, 1435, 1270, 1230, 1065, 1025 cm$^{-1}$; Elemental Analysis for C$_{21}$H$_{15}$NO$_5$.0.2H$_2$O Calcd.: C:69.11%, H:4.25%, N:3.84%; Found: C:69.09%, H:4.31%, N:3.90%

EXAMPLE 3

10-(1,3-Benzodioxol-5-yl)-8,9-dihydro-8-(2-morpholinoethyl)-7H-1,3-benzodioxolo[4,5-f]isoindol-7-one hydrochloride

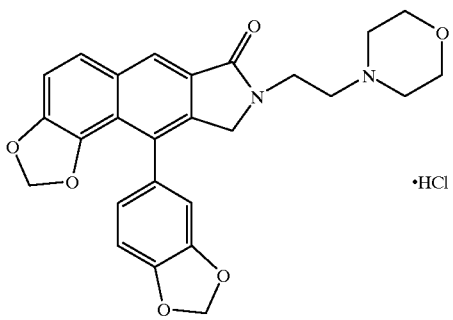

Methyl 9-(1,3-benzodioxol-5-yl)-8-methanesulfonyloxymethyl-naphtho[1,2-d]-1,3-benzodioxol-7-carboxylate (150 mg), which was obtained in Reference Example 14, was dissolved in THF (6 ml) and 2-(morpholino)-ethylamine (69 μl) was added thereto. The mixture was stirred for over night at room temperature, then 2-(morpholino)-ethylamine (69 μl) was added thereto and stirred for 8 hours. The reaction mixture was concentrated under reduced pressure. To the obtained residue was added water and extracted with ethyl acetate. The obtained extract was washed with saturated sodium chloride solution and dried with magnesium sulfate, then concentrated under reduced pressure. The obtained residue was purified with column chromatography (silica gel 5 g, eluent:dichloromethane-methanol=95:5) to give a free amine of the entitled compound. The free amine of the entitled compound was dissolved in a mixture of methanol (1 ml) and dichloromethane (1 ml) and 4N hydrogen chloride-ethyl acetate was added thereto. The reaction mixture was concentrated under reduced pressure. The obtained residue was recrystallized from methanol to give the entitled compound (115 mg).

m.p.:260° C. (decomp.); NMR(DMSO-d$_6$)δ: 3.00–3.80 (8H,m), 3.85–4.05(4H,rm), 4.43 (2H,s), 5.96(1H,s), 5.97 (1H,s), 6.08(1H,s), 6.15(1H,s), 6.88(1H,dd,J=1.4 Hz,8 Hz), 7.00(1H,d,J=8 Hz), 7.01(1H,d,J=1.4 Hz), 7.46(1H,d,J=9 Hz), 7.87(1H,d,J=9 Hz), 8.35(1H,s), 9.95(1H,brs), IR(KBr): 3430, 1685, 1675, 1630, 1485, 1455, 1435, 1270, 1235, 1060 cm$^{-1}$; Elemental Analysis for C$_{26}$H$_{24}$N$_3$O$_6$HCl.0.5H$_2$O Calcd.: C:61.72%, H:5.18%, N:5.54%; Found: C:61.58%, H:5.42%, N:5.45%

EXAMPLE 4

10-(1,3-Benzodioxol-5-yl)-8,9-dihydro-8-ethyl-7H-1,3-benzodioxolo[4,5-f]isoindol-7-one

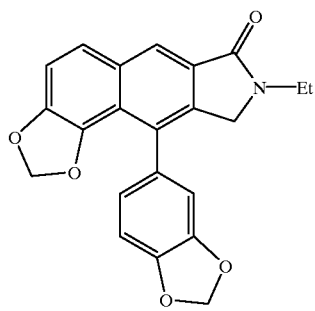

10-(1,3-Benzodioxol-5-yl)-8,9-dihydro-7H-1,3-benzodioxolo[4,5-f]isoindol-7-one (200 mg), which was obtained in Example 1 was dissolved in DMF (5 ml) and sodium hydride (34.5 mg) was added thereto under ice cooling. The mixture was stirred for 5 minutes at room temperature and ethyl iodide (0.14 ml) was added thereto and stirred overnight. The reaction mixture was concentrated under reduced pressure. To the obtained residue was added water and the resultant precipitates were collected by suction and dissolved in ethyl acetate. The obtained ethyl acetate solution was washed with saturated sodium chloride solution and dried with magnesium sulfate, then concentrated under reduced pressure. The obtained residue was purified with column chromatography (silica gel 5 g, eluent:ethyl acetate-hexane=4:1) and recrystallized from ethyl acetate/diisopropyl ether to give the entitled compound (113 mg).

m.p.:210–212° C.; NMR(CDCl₃)δ: 1,25(3H,t,J=7 Hz), 3.86(2H,d,J=7 Hz), 4.21(1H,d,J=17 Hz), 4.30(1H,d,J=17 Hz), 5.91(1H,d,J=1.4 Hz), 5.93(1H,d,J=1.4 Hz), 6.05(1H,d, J=1.4 Hz), 6.08(1H,d,J=1.4 Hz), 6.79–6.86(2H,m), 6.91(1H, dd,J=1Hz,8 Hz), 7.26(1H,d,J=9 Hz), 7.66(1H,d,J=9 Hz), 8.30(1H,s) Elemental Analysis for $C_{22}H_{17}NO_5 \cdot 0.2H_2O$ Calcd.: C:70.39%, H:4.56%, N:3.73%; Found: C:70.07%, H:4.65%, M:3.66%

EXAMPLE 5

10-(1,3-Benzodioxol-5-yl)-B,9-dihydro-8-(isopropyl)-7H-1,3-benzoxolo[4,5-f]isoindol-7-one

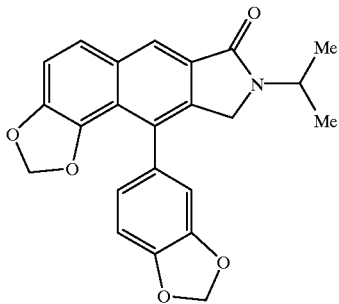

10-(1,3-Benzodioxol-5-yl)-8,9-dihydro-7H-1,3-benzodioxolo[4,5-f]isoindol-7-one (200 mg), which was obtained in Example 1 was dissolved in DMF (5 ml) and sodium hydride (34.5 mg) was added thereto under ice cooling. The mixture was stirred for 5 minutes at room temperature and isopropyl iodide (0.17 ml) was added thereto and stirred overnight, then stirred for 3 hours at 60° C. The reaction mixture was concentrated under reduced pressure. To the obtained residue was added water and the resultant precipitates were collected by suction and dissolved in dichloromethane. The obtained dichloromethane solution was dried with magnesium sulfate and concentrated under reduced pressure. The obtained residue was purified with column chromatography (silica gel 5 g, eluent:ethyl acetate-hexane=4:1) and recrystallized from ethyl acetate-diisopropyl ether to give the entitled compound (27 mg).

m.p.:218–220° C.; NMR(CDCl₃)δ: 1.26(6H,d,J=7 Hz), 4.14(1H,d,J=17 Hz), 4.22(1H,d,J=17 Hz), 4,71(1H,m), 5.91 (1H,d,J=1.4 Hz), 5.92(1H,d,J=1.4 Hz), 6.07(1H,d,J=1.4 Hz), 6.09(1H,d,J=1.4 Hz), 6.80–6.87(2H,m), 6.92(1H,dd,J= 1Hz,7 Hz,), 7.26(1H,d,J=9 Hz), 7.66(1H,d,J=9 Hz), 8.30 (1H,s) Elemental Analysis for $C_{23}H_1 gNO5–0.2H_2O$ Calcd.: C:70.29%, H:4.98%, N:3.56%; Found: C:70.28%, H:5.16%, N:3.43%

EXAMPLE 6

Ethyl 10-(1,3-Benzodioxol-5-yl)-8,9-dihydro-7H-1,3-benzodioxolo[4,5-f]isoindol-7-one-8-acetate

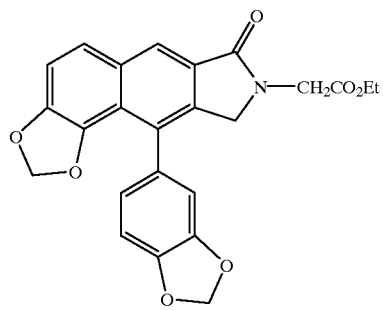

10-(1,3-Benzodioxol-5-yl)-8,9-dihydro-7H-1,3-benzodioxolo[4,5-f]isoindol-7-one (400 mg), which was obtained in Example 1 was dissolved in DMF (10 ml) and added sodium hydride (50.6 mg) under ice cooling. The mixture was stirred at room temperature and ethyl bromoacetate (0.14 ml) was added thereto and stirred overnight. To the mixture was added ethyl bromoacetate (0.07 ml) and stirred for 2 hours at 60° C. The reaction mixture was concentrated under reduced pressure. To the obtained residue was added water and the resultant precipitates were collected by suction and dissolved in dichloromethane. The obtained dichloromethane solution was dried with magnesium sulfate and concentrated under reduced pressure. The obtained residue was purified with column chromatography (silica gel 5 g, eluent:dichloromethane-ether=9:1) to give the entitled compound (318 mg).

m.p.:80–85° C.; NMR(CDCl₃)δ: 1,28(3H,t,J=7 Hz), 4.20 (2H,d,J=7 Hz), 4.35(1H,d,J=17 Hz), 4.38(2H,s), 4.43(1H,d, J=17 Hz), 5.92(1H,d,J=1.4 Hz), 5.93(1H,d,J=1.4 Hz), 6.04 (1H,d,J=1.4 Hz), 6.07(1H,d,J=1.4 Hz), 6.75–6.86(2H,m), 6.89(1H,dd,J=1Hz, 8 Hz), 7.27(1H,d,J=9 Hz), 7.67(1H,d, J=9 Hz), 8.34(1H,s) Elemental Analysis for $C_{24}H_{19}NO_7 \cdot 0.5H_2O$ Calcd.: C:65.16%, H:4.56%, N:3.17%; Found: C:65.34%, H:4.46%, N:3.19%

EXAMPLE 7

10-(1,3-Benzodioxol-5-yl)-8,9-dihydro-7H-1,3-benzodioxolo[4,5-f]isoindol-7-one-8-acetic acid

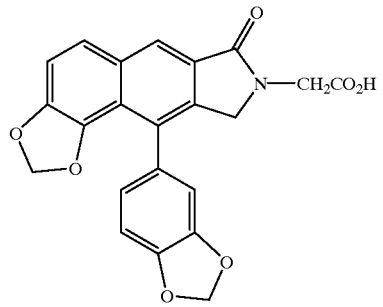

Ethyl 10-(1,3-benzodioxol-5-yl)-8,9-dihydro-7H-1,3-benzodioxolo[4,5-f]isoindol-7-one-8-acetate (260 mg), which was obtained in Example 6, was dissolved in a mixture of THF (3 ml) and methanol (3 ml) and 1N sodium hydroxide solution (1.2 ml) was added thereto. The mixture was stirred for 3 hours at room temperature and the reaction mixture was concentrated under reduced pressure. To the obtained residue was added 1N hydrochloric acid and the resultant precipitates were collected by suction and dissolved in dichloromethane. The obtained dichloromethane solution was dried with magnesium sulfate and concentrated under reduced pressure. The obtained residue was recrystallized from methanol to give the entitled compound (201 mg).

m.p.:160–161° C.; NMR(DMSO-$d_6$)δ: 4.27(2H,brs), 4.35 (1H,s), 5.96(1H,d,J=1.4 Hz), 5.98(1H,d,J=1.4 Hz), 6.06(1H, d,J=1.4 Hz), 6.13(1H,d,J=1.4 Hz), 6.86(1H,dd,J=1.6 Hz,8 Hz), 6.97(1H,d,J=8 Hz), 7.00(1H,d,J=1.6 Hz), 7.44(1H,d,J=9 Hz), 7.87(1H,d,J=9 Hz), 8.34(1H,s) Elemental Analysis for $C_{22}H_{15}NO_7 \cdot H_2O$ Calcd.: C:62.41%, H:4.05%, N:3.31%; Found: C:62.14%, H:4.23%, N:3.20%

EXAMPLE 8

8-Acetyl-5-bromo-10-phenyl-8,9-dihydro-7H-1,3-benzodioxolo[4,5-f]isoindol-7-one

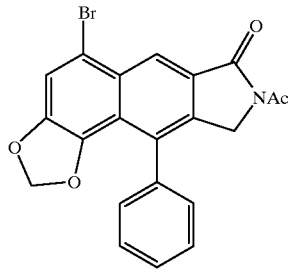

N-(3-Phenyl-2-propin-1-yl)-3-(6-bromobenzo[d]-1,3-benzodioxol-5-yl)-2-propenoylamide (0.50 g), which was obtained in Reference Example 16, was dissolved in acetic anhydride (200 ml) and heated under reflux for 4 hours. The solvent was distilled off under reduced pressure and the obtained residue was dissolved in p-cymene (25 ml). To the mixture was added 10% palladium-carbon (0.25 g) and heated under reflux for 10 hours. The catalyst was filtered off and the filtrate was concentrated under reduced pressure. The obtained residue was washed with water and purified with column chromatography (silica gel 40 g, eluent:dichloromethane) to give the entitled compound (0.16 g).

NMR(CDCl$_3$)δ:2.71(3H,s), 4.64(2H,s), 5.89(2H,s), 7.20–7.35(2H,m), 7.40–7.64(3H,m), 7.64(1H,s), 8.89(1H,s)

EXAMPLE 9

8-Acetyl-10-phenyl-8,9-dihydro-7H-1,3-benzodioxolo[4,5-f]isoindol-7-one

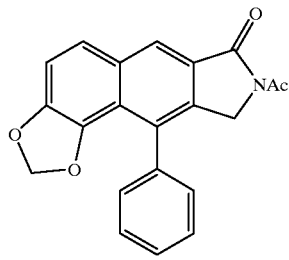

8-Acetyl-5-bromo-10-phenyl-8,9-dihydro-7H-1,3-benzodioxolo[4,5-f]isoindol-7-one (156 mg), which was obtained in Example 8 was dissolved in DMF (60 ml) and sodium acetate (182 mg) and 10% palladium-carbon (80 mg) was added thereto, then the mixture was stirred for 2 hours under hydrogen atmosphere. The catalysts were filtered off and the filtrate was concentrated under reduced pressure and the obtained residue was triturated with DMF. The obtained powder was washed with water and methanol to give the entitled compound (83 mg).

m.p.:335° C. (decomp.); NMR(DMSO-$d_6$)δ: 2.70(3H,s), 4.65(2H,s), 5.89(2H,s), 7.30(1H,d,J=,8 Hz), 7.30–7.40(2H, m), 7.40–7.50(3H,m), 7.72(1H,d,J=8 Hz), 8.44(1H,brs), IR(KBr): 1725, 1685, 1335, 1315, 1295, 1280, 1265 cm$^{-1}$; Elemental Analysis for $C_{21}H_{15}NO_4 \cdot 0.2H_2O$ Calcd.: C:75.28%, H:4.45%, N:4.01%; Found: C:75.12%, H:4.45%, N:4.17%

EXAMPLE 10

10-Phenyl-8,9-dihydro-7H-1,3-benzodioxolo[4,5-f] isoindol-7-one

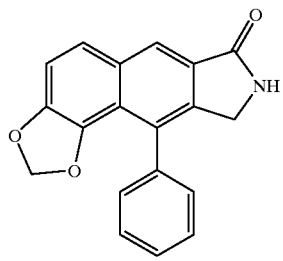

To an ethanol (60 ml) solution of 8-acetyl-10-phenyl-8, 9-dihydro-7H-1,3-benzodioxolo[4,5-f]isoindol-7-one (60 mg), which was obtained in Example 9, was added concentrated hydrochloric acid (1 ml) and the mixture was heated under reflux for 2 hours. The reaction mixture was concentrated under reduced pressure and the obtained residue was dissolved in ethyl acetate. The ethyl acetate solution was washed with saturated sodium chloride solution and dried with magnesium sulfate, then concentrated under reduced pressure. The obtained residue was purified with column chromatography (silica gellg, eluent:dichloromethane-methanol=95:5) and recrystallized from ethanol to give the entitled compound (32 mg).

m.p.:290–292° C.; NMR(DMSO-d$_6$)δ: 4.17(2H,s), 5.91 (2H,s), 7.43(5H,s), 7.45(1H,d,J=,8 Hz), 7.87(1H,d,J=8 Hz), 8.33(1H,brs), 8.62(1H,brs), IR(KBr): 1695, 1630, 1455, 1290, 1265cm$^{-1}$; Elemental Analysis for C$_{19}$H$_{13}$NO$_3$ Calcd.: C:75.24%, H:4.32%, N:4.62%; Found: C:75.21%, H:4.31%, N:4.63%

EXAMPLE 11

11-(1,3-Benzodioxol-5-yl)-7,8,9,10-tetrahydro-1,3-benzodioxolo[4,5-g]isoquinolin-7-one

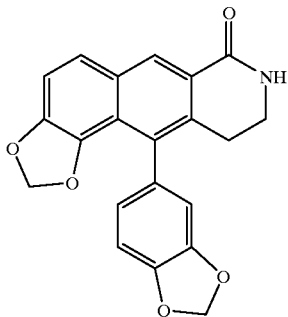

To the DMF (2 ml) solution of Methyl 9-(1,3-benzodioxol-5-yl)-8-cyanomethyl-naphtho[1,2-d]-1,3-dioxole-7-carboxylate (10 mg), which was obtained in Reference Example 15 was added Raney nickel (about 100 mg) and stirred for 6 days under hydrogen atmosphere. The solvent was filtered off and the reaction mixture was concentrated under reduced pressure. The obtained residue was purified with column chromatography (silica gel 1 g, eluent:dichloromethane-methanol=95:5) and recrystallized from chloroform to give the entitled compound (40 mg).

m.p.:256–258° C.; NMR(CDCl$_3$)δ: 2.82(2H,t,J=6 Hz), 3.40–3.50(2H,m), 5.84(2H,brs), 6.03(1H,d,J=1.4 Hz), 6.12 (1H,m) 6.68(1H,dd,J=1.4 Hz,8 Hz), 6.75(1H,d,J=1.4 Hz), 6.87(1H,d,J=8 Hz), 7.19(1H,d,J=,9 Hz), 7.60(1H,d,J=9 Hz), 8.63(1H,brs), IR(KBr): 1660, 1625, 1480, 1455, 1285, 1230, 1075 cm$^{-1}$ Elemental Analysis for C$_{21}$H$_{15}$NO$_5$·0.2H$_2$O Calcd.: C:69.11, H:4.25, N:3.84; Found: C:69.06, H:4.19, N:3.77

EXAMPLE 12

10-(1,3-Benzodioxol-5-yl)-8,9-dihydro-7H-cyclopenta[6.7]naphtho[1,2-d]-1,3-dioxol-7-one

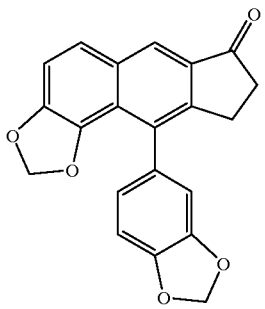

Ethyl 3-{9-(1,3-Benzodioxol-5-yl)-7-methoxycarbonyl-naphtho[1,2-d]-1,3-benzodioxol-8-yl}-2-cyano propionate (407 mg), which was obtained in Reference Example 17, was dissolved in a mixture of THF (5 ml), and methanol (5 ml) and 1N sodium hydroxide solution (3.5 ml) was added thereto and stirred for 2 hours at room temperature. The reaction mixture was concentrated under reduced pressure and washed with ethyl acetate. 1N hydrochloric acid was added to the water layer to adjust the pH to about 2, and the mixture was extracted with ethyl acetate. The extract was dried with magnesium sulfate and concentrated under reduced pressure. The obtained residue was dissolved in acetic acid (4 ml) and heated under reflux overnight. The reaction mixture was concentrated under reduced pressure. The obtained residue was purified with column chromatography (silica gel 50 g, eluent:ethyl acetate-hexane=1:4) and recrystallized from ethyl acetate to give the entitled compound (25 mg).

m.p.:235–237° C.; NMR(CDCl$_3$)δ: 2.65–2.75(2H,m), 2.90–3.15(2H,m), 5.91(1H,d,J=1.4 Hz), 5.92(1H,d,J=1.4 Hz), 6.05(1H,d.J=1.4 Hz), 6.07(1H,d,J=1.4 Hz), 6.75–6.85 (2H,m), 6.89(1H,d,J=8 Hz), 7.24(1H,d,J=9 Hz), 7.67(1H,d, J=9 Hz), 8.29(1H,s) Elemental Analysis for C$_{21}$H$_{14}$O$_5$ Calcd.: C:72.83%, H:4.07%; Found: C:72.51%, H:4.00

EXAMPLE 13

10-(1,3-Benzodioxol-5-yl)-8,9-dihydro-7H-1,3-dioxolo[4,5-f]pyrrolo[3,4-b]quinolin-7-one

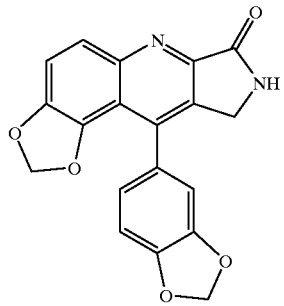

The entitled compound was obtained from methyl 9-(1,3-benzodioxol-5-yl)-8-methanesulfonyloxymethyl-1,3-dioxolo[4,5-f]quinoline-7-carboxylate, which was obtained in Reference Example 18, in a manner similar to that described in Example 1.

m.p.:310° C. (decomp.); NMR(CDCl$_3$)δ: 4.36(1H,d J=17 Hz), 4.45(1H,d,J=17 Hz), 5.99(1H,brs), 6.01(1H,brs), 6.74 (1H,m), 6.80–6.88(2H,m), 7.50(1H,d,J=9 Hz), 8.09(1H,d, J=9 Hz) Elemental Analysis for C$_{19}$H$_{12}$N$_2$O$_5$·0.5H$_2$O Calcd.: C:64.19%, H:3.63%, N:7.88%; Found: C:64.04%, H:3.77%, N:7.87%

EXAMPLE 14

10-(4-Methoxyphenyl)-7H-1,3-benzodioxolo[4,5-f]isoindol-7,9(8H)-dione

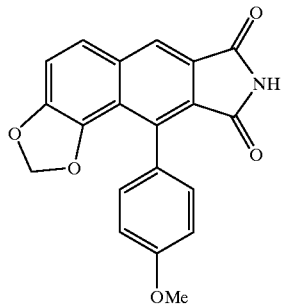

To a benzene (200 ml) solution of helio alcohol (4.0 g) was added dropwise n-BuLi (1.6M hexane solution:36 ml) at room temperature. The mixture was stirred for 2 hours at room temperature and benzene (50 ml) solution of p-methoxybenzonitrile (3.9 g:1.1equivalent) was dropwise added thereto. The mixture was stirred overnight at room temperature and water was added thereto, then extracted with ether. The organic layer was washed with water and dried with magnesium sulfate, then concentrated under reduced pressure. The obtained residue (orange, oily substance) was dissolved in toluene.(250 ml) and maleimide (6.0 g) and p-toluenesulfonic acid monohydrate (catalysis equivalent) were added thereto. The mixture was heated under reflux for 20 hours and the separated solid was filtered off. The filtrate was concentrated under reduced pressure. To the obtained residue was added concentrated hydrochloric acid and heated under reflux for 1 hour. The mixture was cooled to the room temperature and the resultant yellow-brown solid was collected by suction. The yellow-brown solid was washed with water and recrystallized from THF to give the entitled compound (7.2 g).

m.p.:311–313° C.; NMR(CDCl$_3$)δ: 3.89(3H,s), 5.90(2H, s), 6.95(2H,d,J=8.8 Hz), 7.30(2H, d, J=8.8 Hz), 7.34(1H, d, J=8.4 Hz), 7.67(1H, d, J=8.4 Hz), 8.23(1H, s), 10.42(1H, brs) Elemental Analysis for $C_{20}H_{13}NO_5$ Calcd.: C:69.16%, H:3.77%, N:4.03%; Found: C:69.07%, H:4.15%, N:4.00%

EXAMPLE 15

10-(3,4,5-Trimethoxyphenyl)-7H-1,3-benzodioxolo[4,5-f]isoindol-7,9(8H)-dione

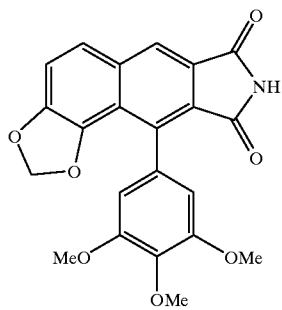

The entitled compound was obtained in a manner similar to that described in Example 14.

m.p.:318–322° C.; NMR(CDCl$_3$)δ: 3.84(6H, s), 3.97(3H, s), 5.92(2H, s), 6.59(2H, s), 7.38(1H, d, J=8.4 Hz), 7.70(1H, d, J=8.4 Hz), 7.72(1H, brs), 8.30(1H, s) Elemental Analysis for $C_{22}H_{17}NO_7$ Calcd.: C:64.86%, H:4.21%, N:3.44%; Found: C:64.25%, H:4.21%, N:3.24%

EXAMPLE 16

10-(1,3-Benzodioxol-5-yl)-7H-1,3-benzodioxolo[4,5-f]isoindol-7,9(8H)-dione

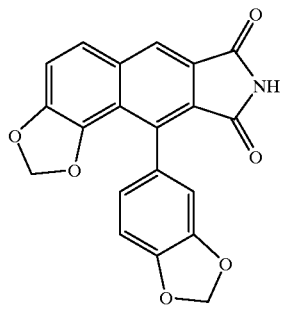

The entitled compound was obtained in a manner similar to that described in Example 14.

m.p.:320° C. (decomp.)(THF); NMR(DMSO-d$_6$)δ: 5.97 (1H,brs), 5.99(1H,brs), 6.10(1H,brs), 6.06(1H,d,J=1.4 Hz), 6.81(1H,dd,J=1.5 Hz,8Hz), 6.92(1H,d,J=8 Hz), 6.95(1H,d, J=1.5 Hz), 7.57(1H,d,J=9 Hz), 7.93(1H,d,J=9 Hz), 8.41(1H, s). IR(KBr): 1745, 1705, 1440, 1285, 1225 cm$^{-1}$; Elemental Analysis for $C_{20}H_{11}O_6$ Calcd.: C:66.49%, H:3.07%, N:3.88%; Found: C:66.71%, H:3.20%, N:3.72%.

EXAMPLE 17

4-(1,3-Benzodioxol-5-yl)-5-methoxy-1H-benz[f]isoindol-1,3(2H)-dione

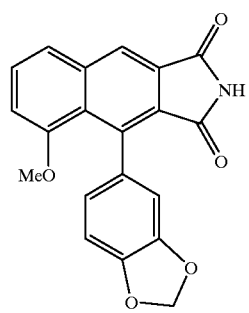

The entitled compound was obtained in a manner similar to that described in Example 14.

m.p.:291–293° C. (THF); NMR(DMSO-d$_6$)δ: 3.48(3H,s), 6.06(1H,brs), 6.10(1H,brs), 6.64(1H,dd,J=1.4 Hz,8 Hz), 6.82(1H,d,J=1.4 Hz), 6.89(1H,d,J=8 Hz), 7.14(1H,d,J=8 Hz), 7.68(1H,t,J=8 Hz), 7.85(1H,d,J=8 Hz), 8.40(1H,s), IR(KBr): 1756, 1714, 1538, 1505, 1472 cm$^{-1}$; Elemental Analysis for $C_{20}H_{13}NO_5 \cdot 0.4H_2O$ Calcd.: C:67.76%, H:3.92%, N:3.95%; Found C:67.83%, H:4.07%, N:3.94%.

EXAMPLE 18

4-(1,3-Benzodioxol-5-yl)-5,6-dimethoxy-1H-benz[f]isoindol-1,3(2H)-dione

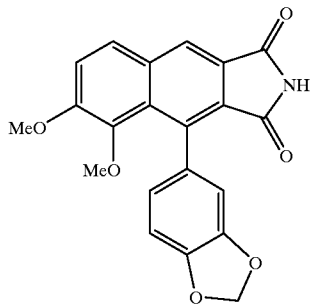

The entitled compound was obtained in a manner similar to that described in Example 14.

m.p.:274–276° C. (THF); NMR(DMSO-$d_6$)δ: 3.19(3H,s), 3.94(3H,s), 6.05(1H,brs), 6.09(1H,brs), 6.61(1H,brs), 6.71(1H,dd,J=1.6 Hz,8 Hz), 6.85(1H,d,J=1.6 Hz), 6.89(1H,d,J=8 Hz), 7.72(1H,d,J=9 Hz), 8.08(1H,d,J=9 Hz), 8.39(1H,s), IR(KBr): 1760, 1710, 1515, 1275, 1225, 1060 cm$^{-1}$; Elemental Analysis for $C_{21}H_{15}NO_6$ Calcd.: C:66.84%, H:4.01%, N:3.71%; Found: C:67.14%, H:3.72%, N:3.82%

EXAMPLE 19

5,6-Dimethoxy-4-(4-methoxyphenyl)-1H-benz[f]isoindol-1,3(2H)-dione

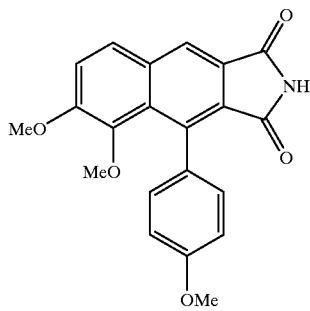

The entitled compound was obtained in a manner similar to that described in Example 14.

m.p.:288–290° C. (THF); NMR(DMSO-$d_6$)δ: 3.08(3H,s), 3.83(3H,s), 3.93(3H,s), 6.92(1H,d,J=9 Hz), 7.20(1H,d,J=9 Hz), 7.73(1H,d,J=9 Hz), 8.10(1H,d,J=9 Hz), 8.40(1H,s), 11.24(1H,brs). IR(KBr): 1762, 1714, 1520, 1280, 1245, 1066 cm$^{-1}$; Elemental Analysis for $C_{21}H_{17}NO_5$ Calcd.: C:69.41%, H:4.72%, N:3.85%; Found: C:69.32%, H:4.92%, N:3.82%.

EXAMPLE 20

10-(4-Trifluoromethylphenyl)-7H-1,3-benzodioxolo[4,5-f]isoindol-7,9(8H)-dione

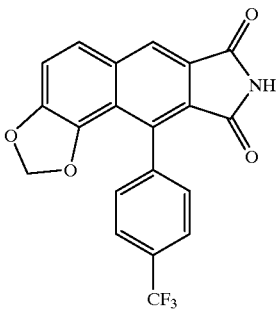

The entitled compound was obtained in a manner similar to that described in Example 14.

m.p.:304–306° C. (AcOEt); NMR(CDCl$_3$)δ: 5.89(2H,s), 7.39(1H,d,J=8 Hz), 7.50(2H,d,J=8 Hz), 7.70(2H,d,J=8 Hz), 7.72(1H,d,J=8 Hz), 7.82(1H,brs), 8.34(1H,s), IR(KBr): 1762, 1722, 1328, 1291, 1160, 1126, 1068 cm$^{-1}$; Elemental Analysis for $C_{20}H_{10}NO_4F_3 \cdot 0.2H_2O$ Calcd.: C:61.77%, H:2.70%, N:3.60%; Found: C:61.73%, H:2.92%, N:3.49%.

EXAMPLE 21

10-(4-Benzyloxyphenyl)-7H-1,3-benzodioxolo[4,5-f]isoindol-7,9(8H)-dione

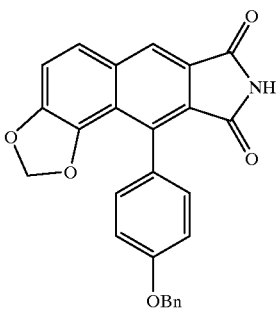

The entitled compound was obtained in a manner similar to that described in Example 14.

m.p.:265–267° C. (THF); NMR(CDCl$_3$)δ: 5.14(2H,s), 5.90 (2H,s), 7.06(2H,d,J=8 Hz), 7.30–7.50(8H,m), 7.68(1H,d,J=8Hz), 7.88(1H,brs), 8.27(1H,s). IR(KBr): 3288, 3261, 3093, 2927, 1733, 1714, 1506 cm$^{-1}$; Elemental Analysis for $C_{26}H_{27}NO_5$ Calcd.: C:73.75%, H:4.05%, N:3.31%; Found: C:73.23%, H:4.12%, N:3.08%.

EXAMPLE 22

10-(4-Pyridyl)-7H-1,3-benzodioxolo[4,5-f]isoindole-7,9(8H)-dione

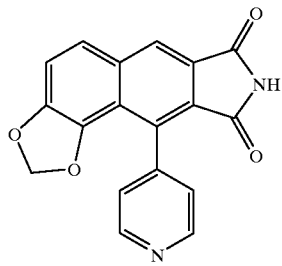

The entitled compound was obtained in a manner similar to that described in Example 14.

m.p.:299–302° C. (THF); NMR(CDCl$_3$-one drop DMSO-d$_6$)δ: 5.89(2H,s), 7.34(2H,d,J=6 Hz), 7.42(1H,d,J=6 Hz), 7.72(1H,d,J=6 Hz), 8.31(1H,s), 8.67(2H,d,J=6 Hz), 10.77 (1H,brs). IR(KBr): 2900, 1756, 1714 cm$^{-1}$; Elemental Analysis for C$_{18}$H$_{10}$N$_2$O$_4$.0.3H$_2$O Calcd.: C:66.67%, H:3.32%, N:8.64%; Found: C:66.79%, H:3.05%, N:8.54%.

EXAMPLE 23

10-(3-Pyridyl)-7H-1,3-benzodioxolo[4,5-f]isoindol-7,9(8H)-dione

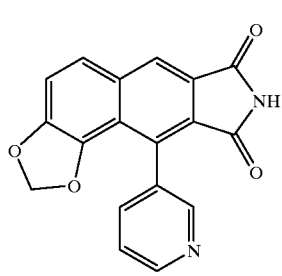

The entitled compound was obtained in a manner similar to that described in Example 14.

m.p.:323–325° C. (THF); NMR(DMSO-d$_6$)δ: 5.96(2H,s), 7.44(1H,m), 7.61(1H,d,J=8 Hz), 7.85(1H,m), 7.98(1H,d,J=8 Hz), 8.50(1H,s), 8.61(2H,m), 11.40(1H,brs), IR(KBr): 2949, 1718 cm$^{-1}$; Elemental Analysis for C$_{18}$H$_{10}$N$_2$O$_4$.0.3H$_2$O Calcd.: C:66.67%, H:3.32%, N:8.64%; Found: C:66.40%, H:3.08%, N:8.42%.

EXAMPLE 24

10-(4-Benzyloxy-3-methoxyphenyl)-7H-1,3-benzoxolo[4,5-f]isoindol-7,9(8H)-dione

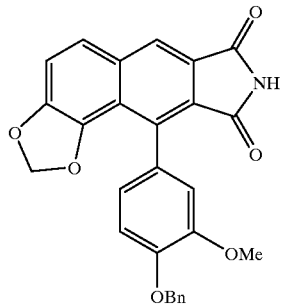

The entitled compound was obtained in a manner similar to that described in Example 14.

m.p.:282–284° C. (THF); NMR(DMSO-d$_6$)δ: 3.72(3H,s), 5.13(2H,s), 5.97(2H,d,J=3 Hz), 6.90(1H,dd,J=2 Hz,8 Hz), 7.04(2H,m), 7.40–7.60(6H,m), 7.93(1H,d,J=9 Hz), 8.41(1H, s), 11.31(1H,brs), IR(KBr): 3168, 3068, 2783, 1760, 1714 cm$^{-1}$; Elemental Analysis for C$_{27}$H$_{19}$NO$_6$ Calcd.: C:71.52%, H:4.22%, N:3.09%; Found: C:71.75%, H:4.45%, N:3.00%.

EXAMPLE 25

11-(1,3-Benzodioxol-5-yl)-8H-isoindolo[5,6-f]benz[b]-1,4-dioxan-8,10(9H)-dione

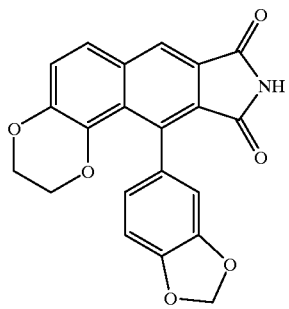

The entitled compound was obtained in a manner similar to that described in Example 14.

m.p.:346–349° C. (THF); NMR(DMSO-d$_6$)δ: 3.90(2H, m), 4.21(2H,m), 6.06(2H,d,J=7 Hz), 6.67(1H,d,J=6 Hz), 6.86(2H,m), 7.36(1H,d,J=8 Hz), 7.79(1H,d,J=8 Hz), 8.33 (1H,s), 11.22(1H,brs), IR(KBr): 3176, 3072, 2765, 1751, 1704, 1606, 1585 cm$^{-1}$; Elemental Analysis for C$_{21}$H$_{13}$NO$_6$ Calcd.: C:67.20%, H:3.49%, N:3.73%; Found: C:66.67%, H:3.82%, N:3.44%.

EXAMPLE 26

10-(4-Bromophenyl)-7H-1,3-benzodioxolo[4,5-f]isoindol-7,9(8H)-dione

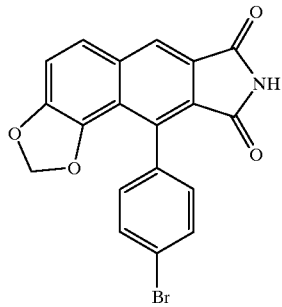

The entitled compound was obtained in a manner similar to that described in Example 14.

m.p.:324–327° C. (THF); NMR(CDCl$_3$-one drop DMSO-d$_6$)δ: 5.92 (2H,s), 7.28(2H,d,J=9 Hz), 7.37(1H,d,J9=Hz), 7.55(2H,d,J=9 Hz), 7.71(1H,d,J=9 Hz), 8.28(1H,s), 10.72 (1H,brs). IR(KBr): 3170, 3064, 2885, 2759, 1751, 1718 cm$^{-1}$; Elemental Analysis for C$_{19}$H$_{10}$BrNO$_4$ Calcd.: C:57.60%, H:2.54%, N:3.54%; Found: C:57.63%, H:2.84%, N:3.39%.

EXAMPLE 27

10-(4-Fluorophenyl)-7H-1,3-benzodioxolo[4,5-f]isoindol-7,9(8H)-dione

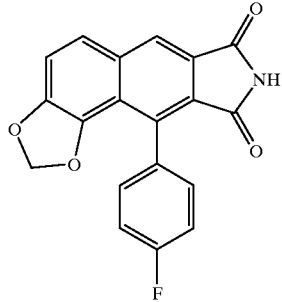

The entitled compound was obtained in a manner similar to that described in Example 14.

m.p.:269–271° C. (THF); NMR(CDCl$_3$)δ: 5.90(2H,s), 7.10–7.30(5H,m), 7.37(1H,d,J=8 Hz), 7.70(1H,d,J=8 Hz), 8.30(1H,s). IR(KBr): 3182, 3074, 1760, 1716, 1540, 1509, 1287 cm$^{-1}$;

EXAMPLE 28

10-(1,3-Benzodioxol-5-yl)-6-methyl-7H-1,3-benzodioxolo[4,5-f]isoindol-7,9(8H)-dione

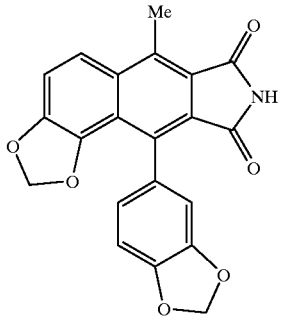

The entitled compound was obtained in a manner similar to that described in Example 14.

m.p.:310–313° C. (ethanol); NMR(DMSO-d$_6$)δ: 2.99(3H, s), 5.99–6.20(4H,m), 6.65–7.00(3H,m), 7.53(1H,d,J=9 Hz), 7.93(1H,d,J=9 Hz). IR(KBr):3172, 3062, 1753, 1710, 1625, 1550, 1492, 1360, 1284 cm$^{-1}$; Elemental Analysis for C$_{21}$H$_{13}$NO$_6$.0.2H$_2$O Calcd.: C:66.56%, H:3.45%, N:3.69%; Found: C:66.48%, H:3.72%, N:3.69%.

EXAMPLE 29

10-(4-Fluorophenyl)-6-methyl-7H-1,3-benzodioxolo[4,5-f]isoindol-7,9(8H)-dione

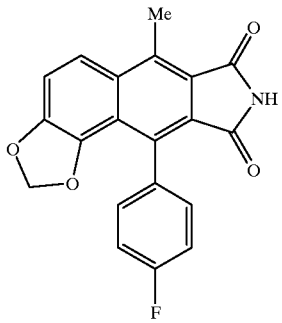

The entitled compound was obtained in a manner similar to that described in Example 14.

m.p.:302–304° C. (THF); NMR(DMSO-d$_6$)δ: 3.00(3H,s), 5.91(2H,s), 7.10–7.40(5H,m), 7.55(1H,d,J=9 Hz), 7.95(1H, d,J=9 Hz). IR(KBr): 3170, 3060, 1749, 1714, 1625, 1513, 1362, 1274 cm$^{-1}$; Elemental Analysis for C$_{20}$H$_{12}$NO$_4$F Calcd.: C:68.77%, H:3.46%, N:4.01%; Found: C:68.55%, H:3.59%, N:4.09%.

EXAMPLE 30

6-Methyl-10-(4-trifluoromethylphenyl)-7H-1,3-benzodioxolo[4,5-f]isoindol-7,9(8H)-dione

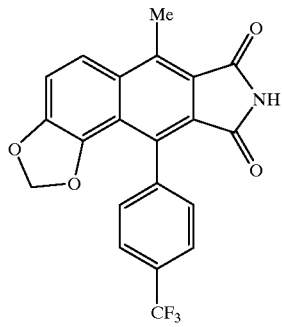

The entitled compound was obtained in a manner similar to that described in Example 14.

m.p.:315–317° C. (THF-ether); NMR(CDCl$_3$)δ: 3.12(3H, s), 5.86(2H,s), 7.30–7.55(4H,m), 7.60–7.75(3H,m), 7.92 (1H,d,J=9 Hz), IR(KBr): 3190, 3050, 1753, 1714, 1620, 1550, 1457, 1363, 1330, 1277 cm$^{-1}$; Elemental Analysis for C$_{21}$H$_{12}$NO$_4$F$_3$.0.3H$_2$O Calcd.: C:62.32%, H:3.14%, N:3.46%; Found: C:62.33%, H:3.07%, N:3.87%.

EXAMPLE 31

10-(4-Methoxyphenyl)-6-methyl-7H-1,3-benzodioxolo[4,5-f]isoindol-7,9(8H)-dione

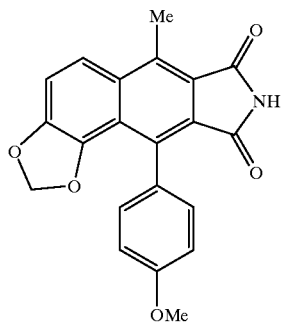

The entitled compound was obtained in a manner similar to that described in Example 14.

m.p.:311–313° C. (THF-ether); NMR(CDCl$_3$)δ: 3.09(3H, s), 3.90(3H,s), 5.88(2H,s), 6.96(2H,d,J=9 Hz), 7.20–7.35 (2H,m), 7.36(1H,d,J=9 Hz), 7.66(1H,brs), 7.89(1H,d,J=9 Hz), IR(KBr): 3167, 3064, 1753, 1710, 1623, 1548, 1511, 1450, 1360, 1277 cm$^{-1}$; Elemental Analysis for C$_{21}$H$_{15}$NO$_5$.0.1H$_2$O Calcd.: C:69.46%, H:4.22%, N:3.86%; Found: C:69.40%, H:4.44%, N:4.02%.

EXAMPLE 32

10-(1,3-Benzodioxol-5-yl)-6-ethyl-7H-1,3-benzodioxolo[4,5-f]isoindol-7,9(8H)-dione

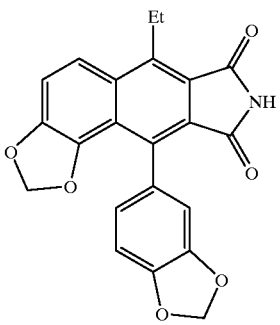

The entitled compound was obtained in a manner similar to that described in Example 14.

m.p.:253–254° C. (THF-ether); NMR(CDCl$_3$)δ: 1.39 (3H,t J=7 Hz), 3.65(2H,q,J=7 Hz), 5.91(1H,d,J=1.4 Hz), 5.93(1H,d,J=1.4 Hz), 6.04(1H,d,J=1.4 Hz), 6.07(1H,d,J=1.4 Hz), 6.75–6.90(3H,m), 7.37(1H,d,J=9 Hz), 7.75(1H,brs), 7.93(1H,d,J=9 Hz). IR(KBr): 3172, 3064, 2974, 1754, 1708, 1625, 1550, 1502, 1401, 1280 cm$^{-1}$;

EXAMPLE 33

10-(1,3-Benzodioxol-5-yl)-6-[2-(N,N-dimethylamino)ethyl]-7H-1,3-benzodioxolo[4,5-f]isoindol-7,9(8H)-dione

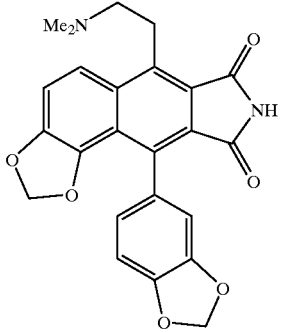

The entitled compound was obtained in a manner similar to that described in Example 14.

NMR(CDCl$_3$)δ: 2.52(2H,m), 2.65–2.85(2H,m),3.80–3.95 (2H,m), 5.85–6.10(4H,m), 6.50–6.95(3H,m), 7.05(1H,brs), 7.38(1H,d,J=9 Hz), 8.00(1H,d,J=9Ha)

EXAMPLE 34

10-(4-Methylphenyl)-7H-1,3-benzodioxolo[4,5-f]isoindol-7,9(8H)-dione

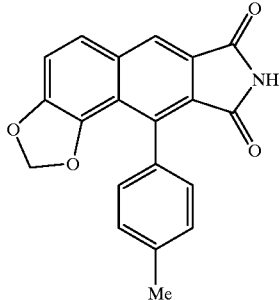

The entitled compound was obtained in a manner similar to that described in Example 14.

m.p.:297–299° C. (THF-ethanol); NMR(CDCl$_3$)δ: 2.46 (3H,s), 5.90(2H,s), 7.26(4H,brs), 7.35(1H,d,J=9 Hz), 7.68 (1H,d,J=9 Hz), 7.86(1H,brs), 8.28(1H,s). IR(KBr): 3230, 3064, 1760, 1713, 1544, 1455, 1287 cm$^{-1}$; Elemental Analysis for $C_{20}H_{13}NO_4 \cdot 0.2H_2O$ Calcd.: C:71.72%, H:4.03%, N:4.18%; Found: C:71.67%, H:3.94%, N:4.17%.

EXAMPLE 35

10-(3-Methylphenyl)-7H-1,3-benzodioxolo[4,5-f]isoindol-7,9(8H)-dione

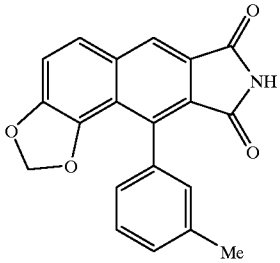

The entitled compound was obtained in a manner similar to that described in Example 14.

m.p.:261–264° C. (THF); NMR(CDCl$_3$)δ: 2.42(3H,s), 5.90(2H,s), 7.19(2H,m), 7.31(2H,m), 7.36(1H,d,J=BHz), 7.69(1H,d,J=BHz), 7.87(1H,brs), 8.29(1H,s). IR(KBr): 3190, 3064, 1756, 1716, 1629, 1538 cm$^{-1}$ Elemental Analysis for $C_{20}H_{13}NO_4 \cdot 0.2H_2O$ Calcd.: C:71.72%, H:4.03%, N:4.18%; Found: C:71.47%, H:4.19%, N:4.03%.

EXAMPLE 36

10-(2-Methylphenyl)-7H-1,3-benzodioxolo[4,5-f]isoindol-7,9(BH)-dione

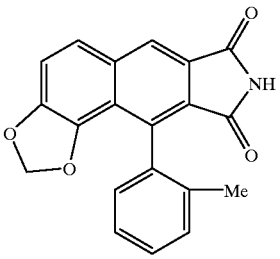

The entitled compound was obtained in a manner similar to that described in Example 14.

m.p.:275–278° C. (THF); NMR(CDCl$_3$)δ: 2.06(3H,s), 5.88(2H,s), 7.20–7.40(5H,m), 7.70(1H,d,J=8 Hz), 7.81(1H, brs), 8.31(1H,s), IR(KBr): 3176, 3062, 2767, 1760, 1718, 1627 cm$^{-1}$; Elemental Analysis for $C_{20}H_{13}NO_4$ Calcd.: C:72.50%, H:3.95%, N:4.23%; Found: C:72.21%, H:4.14%, N:4.08%.

EXAMPLE 37

4-(1,3-Benzodioxol-5-yl)-6-methoxy-1H-benz[f]isoindol-1,3(2H)-dione

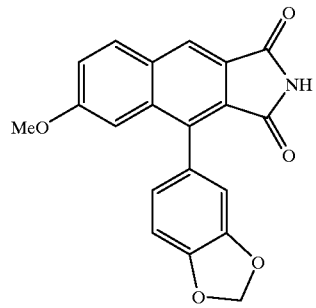

To a THF (50 ml) solution of 2-bromo-5-methoxybenzaldehyde (10 g) was added dropwise a THF (30 ml) solution of the Grignard reagent prepared from 5-Bromo-1,3-benzodioxole (11.2 g) and Mg (1.6 g). The mixture was stirred for 1 hour at room temperature and ammonium chloride solution was added therein, then extracted with ethyl acetate. The extract was washed with water and dried with magnesium sulfate, then concentrated. The residue was purified with silica gel column (Hex/EA= 3/1) to give (2-bromo-5-methoxyphenyl)(1,3-benzodioxol-5-yl)methanol as an oily substance (15 g). (2-bromo-5-methoxyphenyl)(1,3-benzodioxol-5-yl)methanol was dissolved in ether (300 ml) and n-BuLi(1.6M/Hex: 64 ml) was added dropwise at –78° C. The reaction mixture was stirred for 5 minutes at –78° C., then stirred for 1 hour at 0° C. To the mixture was added DMF (30 ml) and stirred for 1 hour at room temperature. To the reaction mixture was added water and extracted with ether. The extract was washed with water and dried with magnesium sulfate then concentrated under reduced pressure. The obtained residue was dissolved in toluene (250 ml) and maleimide (6 g) and p-toluenesulfonic acid monohydrate (1.0 g) were added thereto. The reaction mixture was refluxed for 20 hours and the separated solid was filtered off. The filtrate was concentrated under reduced pressure. To the obtained residue was added concentrated hydrochloric acid and heated under reflux for 1 hour. The mixture was cooled to room temperature and the resultant yellow-brown solid was collected by suction and washed with water, then recrystalized with THF to give the entitled compound (5.4 g).

m.p.:307–310° C. (THF); NMR(CDCl$_3$-one drop DMSO-d$_6$)δ: 3.84(3H,s), 6.30(2H,s), 6.92(2H,m), 7.04(1H,m), 7.23 (1H,d,J=9 Hz), 7.36(1H,d,J=9 Hz), 7.46(1H,d,J=8 Hz), 8.32 (1H,s), 10.57(1H,brs). IR(KBr): 3070, 2900, 2744, 1756, 1713 cm$^{-1}$; Elemental Analysis for C$_{20}$H$_{13}$NO$_5$ Calcd.: C:69.16%, H:3.77%, N:4.03%; Found: C:68.88%, H:3.82%, N:3.95%.

EXAMPLE 38

6-Methoxy-4-(4-methoxyphenyl)-1H-benz[f]isoindol-1,3(2H)-dione

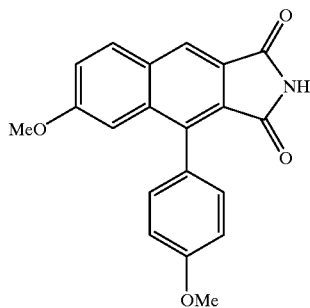

The entitled compound was obtained in a manner similar to that described in Example 37.

m.p.:290–292° C. (THF); NMR(CDCl$_3$-one drop DMSO-d$_6$)δ: 3.76(3H,s), 3.92(3H,s), 7.07(2H,d,J=9 Hz), 7.14(1H, d,J=2 Hz), 7.35(3H,m), 7.98(1H,d,J=9 Hz), 8.25(1H,s), 10.23(1H,brs). IR(KBr): 3170, 3066, 2949, 2785, 1760, 1724, 1616, 1515 cm$^{-1}$; Elemental Analysis for C$_{20}$H$_{15}$NO$_4$ Calcd.: C:72.06%, H:4.54%, N:4.20%; Found: C:71.79%, H:4.48%, N:4.19%.

EXAMPLE 39

6-Methoxy-4-(4-methylphenyl)-1H-benz[f]isoindol-1,3(2H)-dione

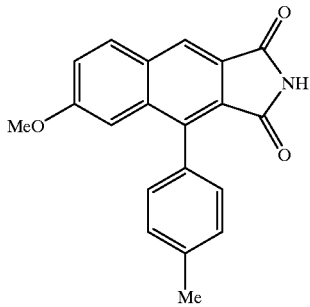

The entitled compound was obtained in a manner similar to that described in Example 37.

m.p.:298–301° C. (THF); NMR(CDCl$_3$)δ: 2.49(3H,s), 3.76(3H,s), 7.13(1H,d,J=2 Hz), 7.33(5H,m), 7.83(1H,brs), 7.99(1H,d,J=9 Hz), 8.30(1H,s). IR(KBr): 3167, 3064, 2773, 1760, 1714, 1616 cm$^{-1}$; Elemental Analysis for C$_{20}$H$_{15}$NO$_3$ Calcd.: C:75.70%, H:4.76%, N:4.41%; Found C:75.36%, H:4.88%, N:4.32%.

EXAMPLE 40

6-Methoxy-4-(4-trifluoromethylphenyl)-1H-benz[f]isoindol-1,3(2H)-dione

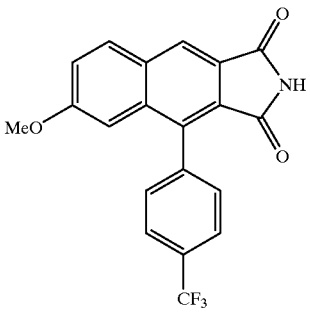

The entitled compound was obtained in a manner similar to that described in Example 37.

NMR(CDCl$_3$)δ: 3.76(3H,s), 6.96(1H,d,J=2 Hz), 7.37(1H, d,J=2 Hz,9 Hz), 7.55(2H,d,J=8 Hz), 7.83(2H,d,J=8 Hz), 7.85(1H,brs), 8.03(1H,d,J=9 Hz), 8.36(1H,s)

EXAMPLE 41

6-Methoxy-4-(4-trifluoromethoxyphenyl)-1H-benz[f]isoindol-1,3(2H)-dione

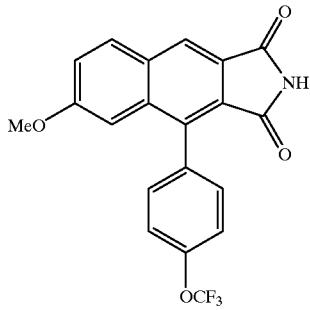

The entitled compound was obtained in a manner similar to that described in Example 37.

m.p.:282–284° C. (THF); NMR(CDCl$_3$)δ: 3.77 (3H,s), 7.02(1H,d,J=2 Hz), 7.36(1H,dd,J=2 Hz,9 Hz), 7.44(4H,m), 7.80(1H,bs), 8.02(1H,d,J=9 Hz), 8.34(1H,s). IR(KBr):3174, 3068, 2775, 1762, 1733, 1616 cm$^{-1}$; Elemental Analysis for $C_{20}H_{12}F_3NO_4$ Calcd.: C:62.02%, H:3.12%, N:3.62%; Found: C:62.18%, H:3.23%, N:3.69%.

EXAMPLE 42

6-Benzyloxy-4-(4-methoxyphenyl)-1H-benz[f]isoindol-1,3(2H)-dione

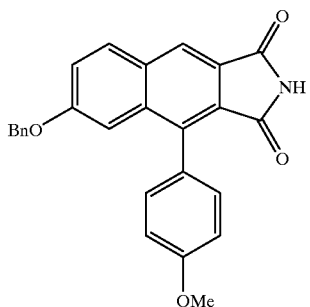

The entitled compound was obtained in a manner similar to that described in Example 37.

m.p.:208–210° C. (THF); NMR(CDCl$_3$)δ: 3.94(3H,s), 5.02(2H,s), 7.06(2H,d,J=9 Hz), 7.34(9H,m), 7.76(1H,brs), 7.99(1H,d,J=9 Hz), 8.28(1H,s). IR(KBr): 3066, 2836, 1766, 1714, 1616, 1515 cm$^{-1}$; Elemental Analysis for $C_{26}H_{19}NO_4$ Calcd.: C:76.27%, H:4.68%, N:3.42%; Found: C:75.64%, H:4.68%, N:3.47%.

EXAMPLE 43

4-(4-Fluorophenyl)-6-methoxy-1H-benz[f]isoindol-1,3(2H)-dione

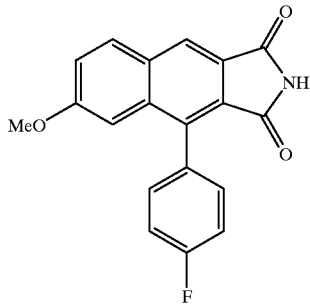

The entitled compound was obtained in a manner similar to that described in Example 37.

m.p.:281–284° C. (THF); NMR(CDCl$_3$)δ: 3.77(3H,s), 7.05(1H, d, J=2 Hz), 7.20–7.40 (5H, m), 7.85 (1H, brs), 8.01 (1H, d, J=9 Hz), 8.32 (1H, s). IR(KBr): 3178, 3072, 1762, 1718, 1610, 1508 cm$^{-1}$; Elemental Analysis for $C_{19}H_{12}FNO_3 \cdot 0.2H_2O$ Calcd.: C:70.24%, H:3.85%, N:4.31%; Found: C:70.25%, H:3.90%, N:4.26%.

EXAMPLE 44

4-(4-Fluorophenyl)-6-methoxy-9-methyl-1H-benz[f]isoindol-1,3(2H)-dione

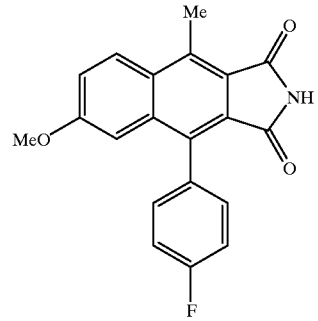

The entitled compound was obtained in a manner similar to that described in Example 37.

m.p.:311–314° C. (THF); NMR(CDCl$_3$)δ: 3.11 (3H, s), 3.75 (3H, s), 7.00 (1H, d, J=3 Hz), 7.22 (2H, t, J=9 Hz), 7.34 (3H, m), 8.21 (1H, d, J=9 Hz), 9.59 (1H, brs). IR(KBr): 3184, 3062, 2966, 1756, 1714, 1602 cm$^{-1}$; Elemental Analysis for $C_{20}H_{14}FNO_3$ 0.2H$_2$O Calcd.: C:70.87%, H:4.28%, N:4.13%; Found: C:70.64%, H:4.33%, N:4.06%

EXAMPLE 45

6-Methoxy-4-(4-methoxyphenyl)-9-methyl-1H-benz[f]isoindol-1,3(2H)-dione

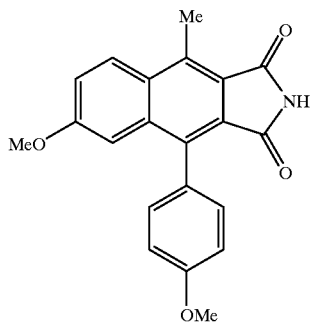

The entitled compound was obtained in a manner similar to that described in Example 37.

m.p.:282–284° C. (THF); NMR(CDCl$_3$)δ: 3.11 (3H, s), 3.75 (3H, s), 3.92 (3H, s), 7.06 (2H, d, J=9 Hz), 7.12 (1H, d, J=3 Hz), 7.32 (3H, m), 7.59 (1H, brs), 8.20 (1H, d, J=9 Hz). IR(KBr): 3165, 3055, 2839, 1747, 1710, 1616 cm$^{-1}$; Elemental Analysis for C$_{21}$H$_{17}$NO$_4$ Calcd.: C:72.61%, H:4.93%, N:4.03%; Found: C:72.40%, H:4.92%, N:4.06%.

EXAMPLE 46

6-Methoxy-10-(4-methoxyphenyl)-7H-1,3-benzodioxolo[4,5-f]isoindol-7,9(8H)-dione

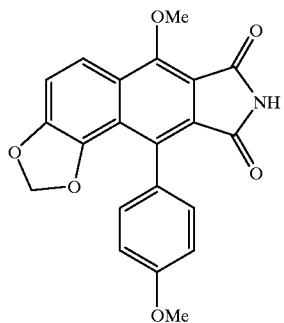

To an ethanol (100ml) solution of dimethyl 6-methoxy-9-(4-methoxyphenyl)-naphtho[1,2-d]-1,3-dioxole-7,8-dicarboxylate (2.33 g, 5.04 mmol) was added 4N sodium hydroxide solution (10 ml) and heated under reflux for 2 hours. Ethanol was distilled off under reduced pressure. Concentrated hydrochloric acid was added to the residue to adjust the pH of the mixture to about 1 and extracted with THF-ethyl acetate(1:1) twice. The organic layer was washed with saturated sodium chloride solution and dried with magnesium sulfate, then the solvent was distilled off under reduced pressure. The obtained residue was heated for 10 minutes at 150° C. to give crude crystals of 6-methoxy-10-(4-methoxyphenyl)-furo[3',4':6,7]naphtho[1,2-d]-1,3-dioxol-7,9-dione.

The obtained crude crystals of 6-methoxy-10-(4-methoxyphenyl)-furo[3',4':6,7]naphtho[1,2-d]-1,3-dioxol-7,9-dione (1.79 g) was dissolved in THF (30 ml) and 25% NH$_4$OH (3 ml) was added thereto and stirred for 2 minutes at room temperature. The solvent was distilled off and the residue was heated for 10 minutes at 200° C. The above procedure was repeated 8 times and water was added thereto, then extracted with THF-ethyl acetate (1:1) twice. The organic layer was washed with saturated sodium chloride solution and dried with magnesium sulfate. The solvent was removed by distillation under reduced pressure to give the entitled compound(1.48 g, 83 g) as yellow crystals.

m.p.:265–266° C. (ethanol ether); NMR(CDCl$_3$)δ: 3.89 (3H, s), 4.37(3H, s), 5.88(2H, s), 6.96(2H, d, J=8 Hz), 7.20–7.30(3H, m), 7.81(1H, brs), 8.12(1H, d, J=9 Hz), IR(KBr): 3217, 3074, 1745, 1708, 1542, 1450, 1335, 1276 cm$^{-1}$; Elemental Analysis for C$_{21}$H$_{15}$NO$_6$.0.2H$_2$O Calcd.: C:66.21%, H:4.07%, N:3.68%; Found: C:66.36%, H:4.04%, N:3.73%.

EXAMPLE 47

10-(1,3-Benzodioxol-5-yl)-6-(2-N,N-dimethylaminoethoxy)-7H-1,3-benzodioxolo[4,5-f]isoindol-7,9(8H)-dione

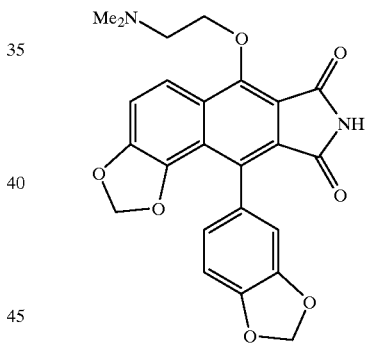

The entitled compound was obtained in a manner similar to that described in Example 46.

m.p.:223–225° C. (THF-ether); NMR(CDCl$_3$)δ: 2.42(6H, s), 2.91(2H, t, J=5 Hz), 4.70(2H, t, J=5 Hz), 5.89(1H, brs), 5.91(1H, brs), 6.02(1H, d, J=1.4 Hz), 6.06(1H, d, J=1.4 Hz), 6.70–6.80(2H, m), 6.86(1H, d, J=8 Hz), 7.29(1H, d, J=9 Hz), 8.19(1H, d, J=9 Hz), IR(KBr): 2900, 1747, 1712, 1544, 1490, 1369, 1266, 1228 cm$^{-1}$; Elemental Analysis for C$_{24}$H$_{20}$N$_2$O$_7$.0.5H$_2$O Calcd.: C:63.02%, H:4.63%, N:6.12%; Found: C:63.03%, H:4.46%, N:6.00%.

EXAMPLE 48

10-(1,3-Benzodioxol-5-yl)-6-(1-hexyloxy)-7H-1,3-benzodioxolo[4,5-f]isoindol-7,9(8H)-dione

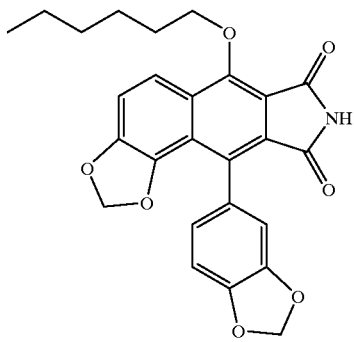

The entitled compound was obtained in a manner similar to that described in Example 46.

m.p.:222–223° C. (ethyl acetate-isopropyl ether); NMR (CDCl$_3$)δ: 0.92(3H, brt), 1.30–2.10(8H, m), 4.59(2H, t, J=7 Hz), 5.92(1H, brs), 5.93(1H, brs), 6.04(1H, brs), 6.07(1H, brs), 6.70–6.90(3H, m), 7.30(1H, d, J=9 Hz), 8.15(1H, d, J=9 Hz). IR(KBr): 3174, 3064, 2925, 1754, 1718, 1627, 1540, 1344 cm$^{-1}$; Elemental Analysis for C$_{26}$H$_{23}$NO$_7$.0.2H$_2$O Calcd.: C:67.15%, H:5.07%, N:3.01%; Found: C:67.22%, H:5.04%, N:3.14%.

EXAMPLE 49

10-(1,3-Benzodioxol-5-yl)-6-methoxy-7H-1,3-benzodioxolo[4,5-f]isoindol-7,9(8H)-dione

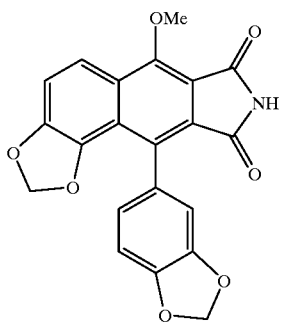

The entitled compound was obtained in a manner similar to that described in Example 46.

m.p.:263–265° C. (ethyl acetate ether); NMR(CDCl$_3$)δ: 4.37(3H, s), 5.90–5.93(2H, m), 6.00–6.08(2H, m), 6.75–6.90(3H, m), 7.31(1H, d, J=9 Hz), 8.12(1H, d, J=9 Hz), IR(KBr): 3200, 1750, 1716, 1630, 1445, 1359 cm$^{-1}$; Elemental Analysis for C$_{21}$H$_{13}$NO$_7$.0.2H$_2$O Calcd.: C:63.87%, H:3.42%, N:3.55%; Found: C:63.41%, H:3.43%, N:3.54%.

EXAMPLE 50

10-(1,3-Benzodioxol-5-yl)-6-(2-propyloxy)-7H-1,3-benzodioxolo[4,5-f]isoindol-7,9(8H)-dione

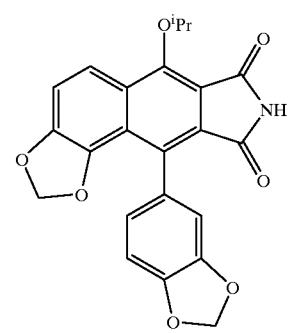

The entitled compound was obtained in a manner similar to that described in Example 46.

m.p.:259–260° C. (THF-ether); NMR(CDCl$_3$)δ: 1.45(6H, d, J=6 Hz), 5,27(1H, septet, J=6 Hz), 5.91(1H, d, J=1.4 Hz), 5.93(1H, d, J=1.4 Hz), 6.03(1H, d, J=1.4 Hz), 6.07(1H, d, J=1.4 Hz), 6.70–6.90(3H, m), 7.29(1H, d, J=9 Hz), 7.85(1H, brs), 8.17(1H, d, J=9 Hz). IR(KBr): 3207, 3068, 2979, 1754, 1710, 1625, 1544, 1461, 1371, 1228 cm$^{-1}$; Elemental Analysis for C$_{23}$H$_{17}$NO$_7$.0.5H$_2$O Calcd.: C:65.03%, H:4.18%, N:3.30%; Found: C:64.91%, H:4.39%, N:3.15%.

EXAMPLE 51

10-(4-Fluorophenyl)-6-methoxy-7H-1,3-benzodioxolo[4,5-f]isoindol-7,9(8H)-dione

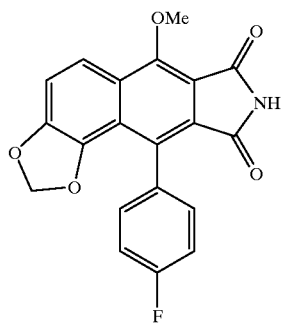

The entitled compound was obtained in a manner similar to that described in Example 46.

m.p.:274–276° C. (THF-ether); NMR(CDCl$_3$)δ: 4.39(3H, s), 5.88(2H, s), 7.05–7.20(3H, m), 7.25–7.35(2H, m), 7.64 (1H, brs), 8.14(1H, d, J=9 Hz), IR(KBr): 3213, 3068, 1753, 1716, 1621, 1544, 1513, 1442, 1361, 1281 cm$^{-1}$; Elemental Analysis for C$_{20}$H$_{12}$NO$_5$F Calcd.: C:65.11%, H:3.39%, N:3.80%; Found: C:64.90%, H:3.45%, N:3.68%.

EXAMPLE 52

10-Cyclohexyl-7H-1,3-benzodioxolo[4,5-f]isoindol-7,9(8H)-dione

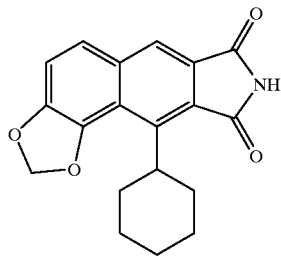

The entitled compound was obtained in a manner similar to that described in Example 14.

m.p.:305–308° C. (THF); NMR(CDCl$_3$)δ: 1.4–2.0 (8H, m), 2.45 (2H⁻, m), 4.25 (1H, m), 6.25 (2H, s), 7.35 (1H, d, J=8 Hz), 7.62 (1H, d, J=8 Hz), 7.96 (1H, brs), 8.14 (1H, s), IR(KBr): 3193, 2935, 2854, 1756, 1714 cm$^{-1}$; Elemental Analysis for $C_{19}H_{14}NO_4.0.2H_2O$ Calcd.: C:70.45%, H:4.48%, N:4.32%; Found: C:70.58%, H:4.83%, N:4.20%.

EXAMPLE 53

8,9-Dihydro-10-(4-methoxyphenyl)-7H-1,3-benzodioxolo[4,5-f]isoindol-7-one

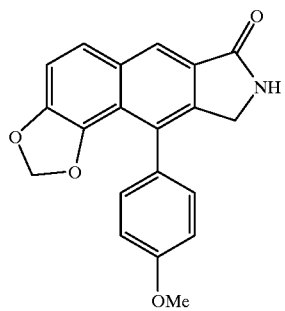

8,9-Dihydro-10-(4-methoxyphenyl)-7H-1,3-benzodioxolo[4,5-f]isoindol-7,9(8H)-dione (200 mg) was dissolved in acetic acid (10 ml) and zinc powder (1.5 g) was added thereto, then heated under reflux for 3 hours. The insoluble solid was filtered off and the solvent was distilled off. The obtained residue was dissolved in ethyl acetate, and the solution was washed with water and sodium hydrogen carbonate solution, then dried with magnesium sulfate. The mixture was concentrated under reduced pressure and the obtained residue was recrystallized from THF to give the entitled compound (107 mg).

m.p.:266–269° C.; NMR(CDCl$_3$)δ: 3.90(3H, s), 4.30(2H, s), 5.88(2H, s), 6.62(1H, brs), 6.98(2H, d, J=8.6 Hz), 7.27 (1H, d, J=8.4 Hz), 7.28(2H, d, J=8.6 Hz), 7.68(1H, d, J=8.4 Hz), 8.34(1H, s). IR(KBr): 3290, 2898, 1710, 1662, 1635, 1508, 1463 cm$^{-1}$; Elemental Analysis for $C_{20}H_{15}NO_4$ Calcd.: C:72.06%, H:4.54%, N:4.20%; Found: C:71.40%, H:4.73%, N:4.14%

EXAMPLE 54

8,9-Dihydro-10-(3,4,5-trimethoxyphenyl)-7H-1,3-benzodioxolo[4,5-f]isoindol-7-one

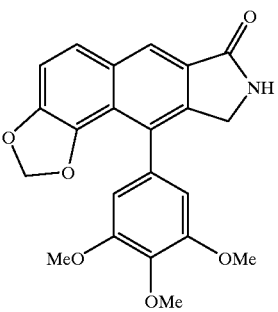

The entitled compound was obtained in a manner similar to that described in Example 53.

m.p.:263–265° C.; NMR(CDCl$_3$)δ: 3.85(6H, s), 3.96(3H, s), 4.36(2H, s), 5.92(2H, s), 6.58(2H, s), 6.62(1H, brs), 7.29(1H, d, J=8.8 Hz), 7.69(1H, d, J=8.8 Hz), 8.36(1H, s). IR(KBr): 3163, 3062, 2775, 1756, 1714, 1627, 1583 cm$^{-1}$; Elemental Analysis for $C_{22}H_{19}NO_6$ ; Calcd.: C:67.17%, H:4.87%, N:3.56%; Found: C:66.72%, H:5.05%, N:3.29%

EXAMPLE 55

4-(1,3-Benzodioxol-5-yl)-2,3-dihydro-5-methoxy-1H-benz[f]isoindol-1-one

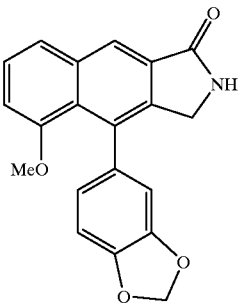

The entitled compound was obtained in a manner similar to that described in Example 53.

m.p.:295–298° C. (THF); NMR(DMSO-d$_6$)δ: 3.49(3H,s), 4.10(2H,brs), 6.07(1H,brs), 6.08(1H,brs), 6.71(1H,dd,J=1.5 Hz,8 Hz), 6.85(1H,d,J=1.5 Hz), 6.94(1H,d,J=8 Hz), 7.01 (1H,d,J=8 Hz), 7.49(1H,t,J=8 Hz), 7.75(1H,d,J=8 Hz), 8.27 (1H,s), 8.66(1H,brs). IR(KBr): 1697, 1490, 1465, 1237, 1039 cm$^{-1}$; Elemental Analysis for $C_{20}H_{15}NO_4.0.2H_2O$ Calcd.: C:71.29%, H:4.61%, N:4.16%; Found: C:71.09%, H:4.84%, N:4.20%.

EXAMPLE 56

4-(1,3-Benzodioxol-5-yl)-2,3-dihydro-5,6-dimethoxy-1H-benz[f]isoindol-1-one

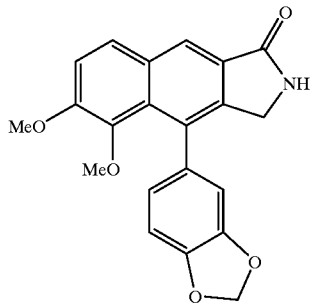

The entitled compound was obtained in a manner similar to that described in Example 53.

m.p.:255–256° C. (MeOH); NMR(CDCl$_3$)δ: 3.32(3H,s), 3.99(3H,s), 4.17(1H,d,J=14 Hz), 4.27(1H,d,J=14 Hz), 6.02 (1H,d,J=1.4 Hz), 6.03(1H,d,J=1.4 Hz), 6.14(1H,brs), 6.78 (1H,dd,J=1.6 Hz,8 Hz), 6.80(1H,d,J=1.6 Hz), 6.88(1H,d,J=8 Hz), 7.39(1H,d,J=9 Hz), 7.85(1H,d,J=9 Hz), 8.35(1H,s). IR(KBr): 1695, 1485, 1265, 1230, 1085, 1030 cm$^{-1}$; Elemental Analysis for $C_{21}H_{17}NO_5 \cdot 0.2H_2O$ Calcd.: C:68.73%, H:4.78%, N:3.82%; Found: C:68.84%, H:4.84%, N:3.85%.

EXAMPLE 57

2,3-Dihydro-5,6-dimethoxy-4-(4-methoxyphenyl)-1H-benz[f]isoindol-1-one

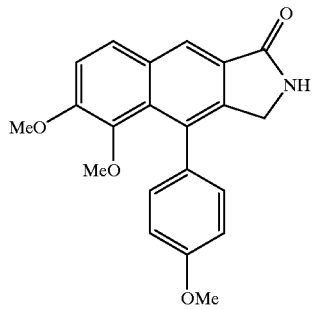

The entitled compound was obtained in a manner similar to that described in Example 53.

m.p.:258–260° C. (THF); NMR(DMSO-d$_6$)δ: 3.10(3H,s), 3.82(3H,s), 3.91(3H,s), 4.02(2H,brs), 6.97(1H,d,J=9 Hz), 7.25(1H,d,J=9 Hz), 7.56(1H,d,J=9 Hz), 8.00(1H,d,J=9 Hz), 8.26(1H,s), 8.53(1H,brs). IR(KBr): 1697, 1515, 1508, 1457, 1272, 1249, 1093 cm$^{-1}$; Elemental Analysis for $C_{21}H_{19}NO_4 \cdot 0.2H_2O$ Calcd.: C:71.46%, H:5.54%, N:3.97%; Found: C:71.52%, H:5.46%, N:3.95%.

EXAMPLE 58

8,9-Dihydro-10-(4-trifluoromethylphenyl)-7H-1,3-benzodioxolo[4,5-f]isoindol-7-one

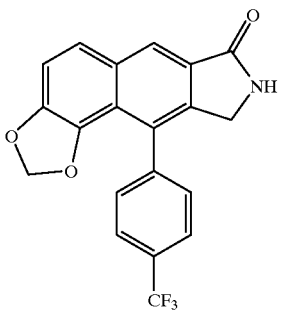

The entitled compound was obtained in a manner similar to that described in Example 53.

m.p.:315–317° C. (THF); NMR(DMSO-d$_6$)δ: 4.21(2H, brs), 5.94(2H,s), 7.47(1H,d,J=9 Hz), 7.69(2H,d,J=8 Hz), 7.80(2H,d,J=8 Hz), 7.91(1H,d,J=9 Hz), 8.39(1H,s), 8.64 (1H,brs), IR(KBr): 1698, 1324, 1274, 1162, 1124, 1110, 1079, 1070 cm$^{-1}$; Elemental Analysis for $C_{20}H_{12}NO_3F_3$ Calcd.: C:64.69%, H:3.26%, N:3.77%; Found: C:64.81%, H:3.50%, N:3.74%.

EXAMPLE 59

10-(4-Benzyloxyphenyl)-8,9-dihydro-7H-1,3-benzodioxolo[4,5-f]isoindol-7-one

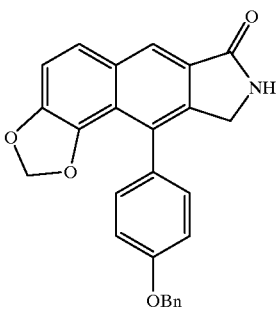

The entitled compound was obtained in a manner similar to that described in Example 53.

m.p.:257–260° C. (THF); NMR(CDCl$_3$-one drop DMSO-d$_6$)δ: 4.27 (2H, s), 5.14 (2H, s), 5.89 (2H, s), 7.05 (2H, d, J=9 Hz), 7.3–7.5 (9H, m), 7.68 (1H, d, J=9 Hz), 8.30 (1H, s), IR(KBr): 3290, 2883, 1708, 1662, 1635 cm$^{-1}$; Elemental Analysis for $C_{26}H_{19}NO_4 \cdot 0.3H_2O$ Calcd.: C:75.17%, H:4.77%, N:3.37%; Found: C:74.98%, H:4.75%, N:3.28%.

EXAMPLE 60

8,9-Dihydro-10-(4-pyridyl)-7H-1,3-benzodioxolo[4,5-f]isoindol-7-one

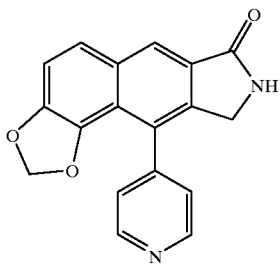

The entitled compound was obtained in a manner similar to that described in Example 53.

m.p.:316–319° C. (THF-MeOH); NMR(CDCl$_3$)δ: 4.30 (2H, s), 5.89 (2H, s), 6.58 (1H, b), 7.32 (3H, m), 7.72 (1H, d, J=9 Hz), 8.41 (1H, s), 8.71 (2H, d, J=6 Hz), IR(KBr): 3082, 2904, 1683, 1635 cm$^{-1}$; Elemental Analysis for C$_{18}$H$_{12}$N$_2$O$_3$ Calcd.: C:71.05%, H:3.97%, N:9.21%; Found: C:70.76%, H:4.17%, N:8.97%.

EXAMPLE 61

8,9-Dihydro-10-(3-pyridyl)-7H-1,3-benzodioxolo[4,5-f]isoindol-7-one

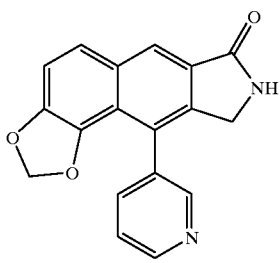

The entitled compound was obtained in a manner similar to that described in Example 53.

m.p.:257–260° C. (THF); NMR(CDCl$_3$-one drop DMSO-d$_6$)δ: 4.27 (2H, s), 5.14 (2H, s), 5.89 (2H, s), 7.05 (2H, d, J=9 Hz), 7.3–7.5 (9H, m), 7.68 (1H, d, J=9 Hz), 8.30 (1H, s), IR(KBr): 3290, 2883, 1708, 1662, 1635 cm$^{-1}$; Elemental Analysis for C$_{26}$H$_{19}$NO$_4$.0.3H$_2$O Calcd.: C:75.17%, H:4.77%, N:3.37%; Found: C:74.98%, H:4.75%, N:3.28%.

EXAMPLE 62

10-(4-Benzyloxy-3-methoxyphenyl)-8,9-dihydro-7H-1,3-benzodioxolo[4,5-f]isoindol-7-one

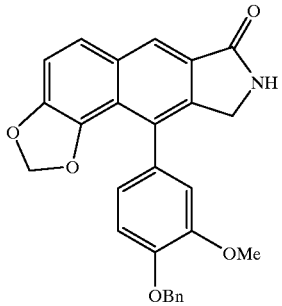

The entitled compound was obtained in a manner similar to that described in Example 53.

m.p.:236–239° C. (THF); NMR(CDCl$_3$)δ: 3.87 (3H, s), 4.25 (1H, d, J=17 Hz), 4.38 (1H, d, J=17 Hz), 5.23 (2H, s), 5.88 (2H, s), 6.65 (1H, brs), 6.88 (2H, m), 6.98 (1H, d, J=8 Hz), 7.3–7.5 (6H, m), 7.68 (1H, d, J=8 Hz), 8.35 (1H, s). IR(KBr): 3176, 3064, 2893, 1695, 1635, 1515 cm$^{-1}$; Elemental Analysis for C$_{27}$H$_{21}$NO$_5$.0.2H$_2$O Calcd.: C:73.19%, H:4.87%, N:3.16%; Found C:72.92%, H:5.13%, N:3.11%.

EXAMPLE 63

11-(1,3-Benzodioxol-5-yl)-9,10-dihydro-8H-isoindolo[5,6-f]benz[b]-1,4-dioxan-8-one

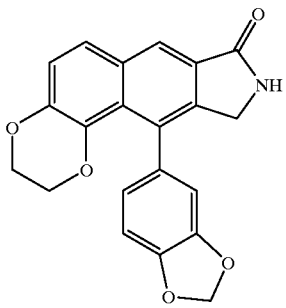

The entitled compound was obtained in a manner similar to that described in Example 53.

m.p.:312–315° C. (THF); NMR(CDCl$_3$)δ: 3.97 (2H, m), 4.22 (4H, m), 6.03 (2H, d, J=4 Hz), 6.66 (1H, b), 6.74 (2H, m), 6.85 (1H, d, J=8 Hz), 7.16 (1H, d, J=9 Hz), 7.57 (1H, d, J=9 Hz), 8.28 (1H, s), IR(KBr): 3195, 3078, 2879, 1695, 1616 cm$^{-1}$; Elemental Analysis for C$_{21}$H$_{15}$NO$_5$.0.2H$_2$O Calcd.: C:69.11%, H:4.25%, N:3.84%; Found: C:69.10%, H:4.20%, N:3.72%.

EXAMPLE 64

10-(4-Bromophenyl)-8,9-dihydro-7H-1,3-benzodioxolo[4,5-f]isoindol-7-one

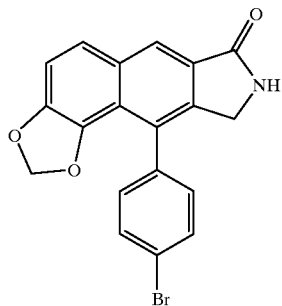

The entitled compound was obtained in a manner similar to that described in Example 53.

m.p.:273–274° C. (THF); NMR(CDCl$_3$)δ: 4.28 (2H, s), 5.89 (2H, s), 6.54 (1H, b), 7.24 (2H, d, J=8 Hz), 7.28 (1H, d, J=9 Hz), 7.57 (2H, d, J=8 Hz), 7.69 (1H, d, J=9 Hz), 8.37 (1H, b). IR(KBr): 3203, 3085, 2908, 1700, 1635 cm$^{-1}$; Elemental Analysis for C$_{19}$H$_{12}$BrNO$_3$ Calcd.: C:59.71%, H:3.16%, N:3.66%; Found C:59.77%, H:3.44%, N:3.47%.

Example 65

10-(4-Fluorophenyl)-8,9-dihydro-7H-1,3-benzodioxolo[4,5-f]isoindol-7-one

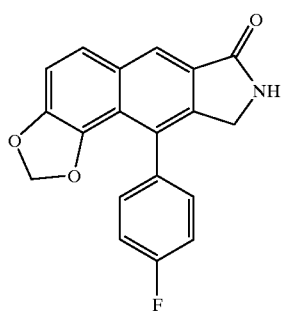

The entitled compound was obtained in a manner similar to that described in Example 53.

m.p.:294–297° C. (THF-ethanol); NMR(CDCl$_3$)δ: 4.28 (2H, s), 5.88(2H, s), 6.83(1H, brs), 7.05–7.20(5H, m), 7.68(1H, d, J=9 Hz), 8.36(1H, s). IR(KBr): 3199, 3085, 2904, 1693, 1637, 1508, 1461, 1272 cm$^{-1}$; Elemental Analysis for C$_{19}$H$_{12}$NO$_3$·0.2H$_2$O Calcd.: C:70.24%, H:3.85%, N:4.31%; Found: C:70.53%, H:3.72%, N:4.31%.

EXAMPLE 66

10-(1,3-Benzodioxol-5-yl)-8,9-dihydro-6-methyl-7H-1,3-benzodioxolo[4,5-f]isoindol-7-one

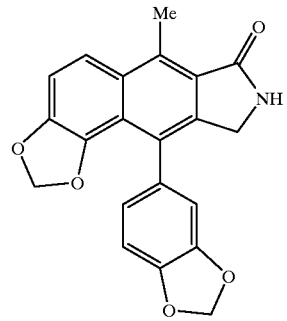

The entitled compound was obtained in a manner similar to that described in Example 53.

m.p.:292–293° C. (ethanol); NMR(CDCl$_3$)δ: 3.16(3H, s), 4.15(1H, d, J=16 Hz), 4.25(1H, d, J=16 Hz), 5.89(1H, d, J=1.4 Hz), 5.91(1H, d, J=1.4 Hz), 6.03(1H, d, J=1.4 Hz), 6.06(1H, d, J=1.4 Hz), 6.70–6.95(4H, m), 7.28(1H, d, J=9 Hz), 7.87(1H, d, J=9 Hz). IR(KBr): 3184, 3078, 2889, 1689, 1633, 1490, 1438, 1378, 1237 cm$^{-1}$; Elemental Analysis for C$_{21}$H$_{15}$NO$_5$ Calcd.: C:69.80%, H:4.18%, N:3.88%; Found: C:69.41%, H:4.31%, N:3.85%.

Example 67

10-(4-Fluorophenyl)-8,9-dihydro-6-methyl-7H-1,3-benzodioxolo[4,5-f]isoindol-7-one

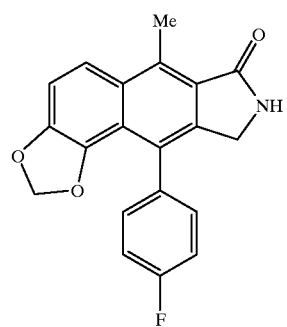

The entitled compound was obtained in a manner similar to that described in Example 53.

m.p.:293–295° C. (THF-ethanol); NMR(CDCl$_3$)δ: 3.17 (3H, s), 4.16(2H, s), 5.85(2H, s), 6.44(1H, brs), 7.00–7.40 (5H, m), 7.89(1H, d, J=9 Hz). IR(KBr): 3186, 3080, 2891, 1683, 1634, 1508, 1459, 1291, 1218 cm$^{-1}$; Elemental Analysis for C$_{20}$H$_{14}$NO$_3$F Calcd.: C:71.64%, H:4.21%, N:4.18%; Found: C:71.36%, H:4.07%, N:4.40%.

EXAMPLE 68

8,9-Dihydro-6-methyl-10-(4-trifluoromethylphenyl)-7H-1,3-benzodioxolo[4,5-f]isoindol-7-one

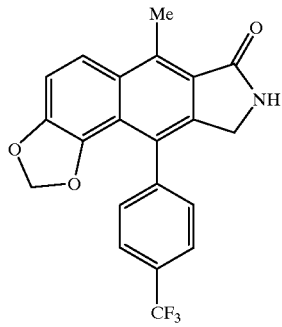

The entitled compound was obtained in a manner similar to that described in Example 53.

m.p.:303–305° C. (ethyl acetate-isopropyl ether); NMR (CDCl$_3$)δ: 3.18(3H, s), 4.15(2H, s), 5.85(2H, s), 6.48(1H, brs), 7.31(1H, d, J=9 Hz), 7.46(2H, d, J=8 Hz), 7.69(2H, d, J=8 Hz), 7.91(1H, d, J=9 Hz). IR(KBr): 3210, 3090, 1691, 1620, 1470, 1328, 1295 cm$^{-1}$; Elemental Analysis for C$_{21}$H$_{14}$NO$_3$F$_3$ Calcd.: C:65.46%, H:3.66%, N:3.63%; Found: C:65.37%, H:3.65%, N:3.69%.

EXAMPLE 69

8,9-Dihydro-10-(4-methoxyphenyl)-6-methyl-7H-1,3-benzodioxolo[4,5-f]isoindol-7-one

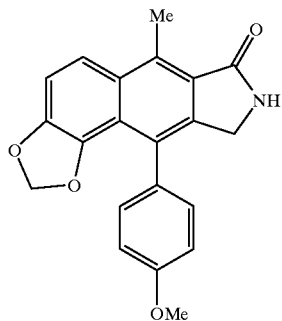

The entitled compound was obtained in a manner similar to that described in Example 53.

m.p.:295–296° C. (THF-ether); NMR(CDCl$_3$)δ: 3.16(3H, s), 3.89(3H, s), 4.17(2H, s), 5.86(2H, s), 6.37(1H, brs), 6.96(2H, d, J=9 Hz), 7.20–7.35(3H, m), 7.88(1H, d, J=9 Hz). IR (KBr): 3201, 3082, 2871, 1687, 1633, 1511, 1461, 1378, 1243 cm$^{-1}$; Elemental Analysis for C$_{21}$H$_{17}$NO$_4$ Calcd.: C:72.61% , H:4.93% , N:4.03%; Found: C:72.34%, H:4.81%, N:4.11%.

EXAMPLE 70

10-(1,3-Benzodioxol-5-yl)-6-ethyl-8,9-dihydro-7H-1,3-benzodioxolo[4,5-f]isoindol-7-one

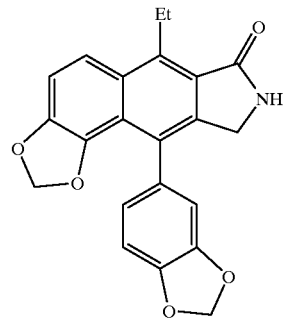

The entitled compound was obtained in a manner similar to that described in Example 53.

m.p.:296–298° C. (THF-ether); NMR(CDCl$_3$)δ: 1.38(3H, t, J=7 Hz), 3.77(2H, q, J=7 Hz), 4.15(1H, d, J=17 Hz), 4.25(1H, d, J=17 Hz), 5.88(1H, m), 5.86(1H, m), 6.03(1H, d, J=1.4 Hz), 6.05(1H, d, J=1.4 Hz), 6.64(1H, brs), 6.70–6.90(3H, m), 7.28(1H, d, J=9 Hz), 7.92(1H, d, J=9 Hz). IR(KBr): 3197, 2887, 1685, 1631, 1614, 1457, 1236 cm$^{-1}$; Elemental Analysis for C$_{22}$H$_{17}$NO$_5$ Calcd.: C:70.39%, H:4.56%, N:3.73%; Found: C:70.02%, H:4.61%, N:3.76%.

EXAMPLE 71

10-(1,3-Benzodioxol-5-yl)-8,9-dihydro-6-(2-N,N-dimethylaminoethyl)-7H-1,3-benzodioxolo[4,5-f]isoindol-7-one

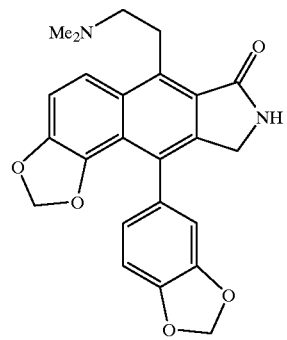

The entitled compound was obtained in a manner similar to that described in Example 53.

m.p.:226–228° C. (THF-ether); NMR(CDCl$_3$)δ: 2.47(6H, s), 2.71(2H, m), 3.97(2H, m), 4.14(1H, d, J=16 Hz), 4.24 (1H, d, J=16 Hz), 5.85–5.95(2H, m), 6.03(1H, d, J=1.4 Hz), 6.06(1H, d, J=1.4 Hz), 6.25(1H, brs), 6.70–6.90(3H, m), 7.30(1H, d, J=9 Hz), 7.96(1H, d, J=9 Hz). IR(KBr): 3210, 2850, 1685, 1629, 1492, 1455, 1374, 1239 cm$^{-1}$; Elemental Analysis for C$_{24}$H$_{22}$N$_2$O$_5$.0.4H$_2$O Calcd.: C:67.44%, H:5.42%, N:6.65%; Found: C:67.63%, H:5.37%, N:6.72%.

EXAMPLE 72

8,9-Dihydro-10-(4-methylphenyl)-7H-1,3-benzodioxolo[4,5-f]isoindol-7-one

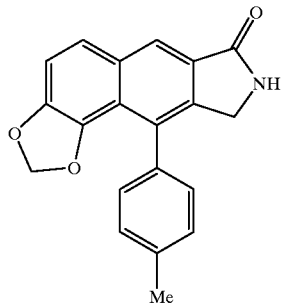

The entitled compound was obtained in a manner similar to that described in Example 53.

m.p.:284–286 (THF); NMR(CDCl$_3$)δ: 2.45(3H, s), 4.28 (2H, s), 5.88(2H, s), 7.06(1H, brs), 7.15–7.35(5H, m), 7.67(1H, d, J=9 Hz), 8.34(1H, s). IR(KBr): 3192, 3080, 2887, 1697, 1637, 1457, 1274 cm$^{-1}$; Elemental Analysis for C$_{20}$H$_{15}$NO$_3$.0.3H$_2$O Calcd.: C:74.43%, H:4.87%, N:4.34%; Found: C:74.30%, H:4.58%, N:4.31%.

EXAMPLE 73

8,9-Dihydro-10-(3-methylphenyl)-7H-1,3-benzodioxolo[4,5-f]isoindol-7-one

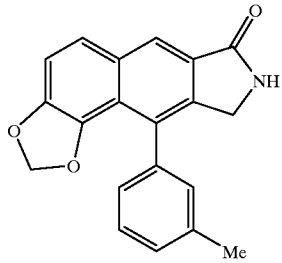

The entitled compound was obtained in a manner similar to that described in Example 53.

m.p.:244–246° C. (THF); NMR(CDCl$_3$)δ: 2.41 (3H, s), 4.30 (2H, s), 5.88 (2H, s), 6.92 (1H, brs), 7.2–7.4 (5H, m), 7.68 (1H, d, J=9Hz), 8.35 (1H, s); IR(KBr): 3210, 3091, 2893, 1683, 1637, 1457 cm$^{-1}$; Elemental Analysis for C$_{20}$H$_{15}$NO$_3$ Calcd.: C:75.70%, H:4.76%, N:4.41%; Found: C:75.25%, H:4.93%, N:4.30%.

EXAMPLE 74

8,9-Dihydro-10-(2-methylphenyl)-7H-1,3-benzodioxolo[4,5-f]isoindol-7-one

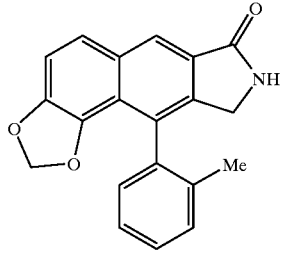

The entitled compound was obtained in a manner similar to that described in Example 53.

m.p.:252–255° C. (THF); NMR(CDCl$_3$)δ: 4.04 (1H, d, J–17 Hz), 4.29 (1H, d, J=17 Hz), 5.84 (2H, s), 6.78 (1H, brs), 7.2–7.4 (6H, m), 7.90 (1H, d, J=8 Hz), 8.36 (1H, s); IR(KBr): 3222, 3060, 2881, 1695, 1635, 1461 cm$^{-1}$; Elemental Analysis for C$_{20}$H$_{15}$NO$_3$ Calcd.: C:75.70%, H:4.76%, N:4.41%; Found: C:75.10%, H:4.85%, N:4.38%.

EXAMPLE 75

4-(1,3-Benzodioxol-5-yl)-2,3-dihydro-6-methoxy-1H-benz[f]isoindol-1-one

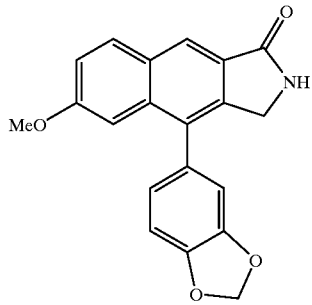

The entitled compound was obtained in a manner similar to that described in Example 53.

m.p.:259–262° C. (CHCl$_3$); NMR(CDCl$_3$)δ: 3.85 (3H, s), 4.33 (2H, s), 6.24 (2H, s), 6.54 (1H, brs), 6.9–7.1 (3H, m), 7.20 (1H, d, J=9 Hz), 7.31 (1H, d, J=9 Hz), 7.45 (1H, m), 8.43 (1H, s); IR(KBr): 3419, 3055, 2902, 1704, 1683 cm$^{-1}$; Elemental Analysis for C$_{20}$H$_{15}$NO$_4$.0.2H$_2$O Calcd.: C:71.29%, H:4.61%, N:4.16%; Found: C:71.27%, H:4.66%, N:4.28%.

EXAMPLE 76

2,3-Dihydro-6-methoxy-4-(4-methoxyphenyl)-1H-benz[f]isoindol-1-one

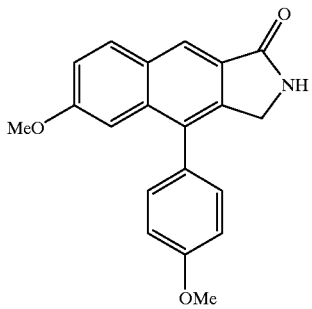

The entitled compound was obtained in a manner similar to that described in Example 53.

m.p.:290–292° C. (THF); NMR(CDCl$_3$-one drop DMSO-d$_6$)δ: 3.76 (3H, s), 3.92 (3H, s), 7.07 (2H, d, J=9 Hz), 7.14 (1H, d, J=2 Hz), 7.35 (3H, m), 7.98 (1H, d, J=9 Hz), 8.25 (1H, s), 10.23 (1H, brs); IR(KBr): 3170, 3066, 2949, 2785, 1760, 1724, 1616, 1515 cm$^{-1}$; Elemental Analysis for C$_{20}$H$_{15}$NO$_4$ Calcd.: C:72.06%, H:4.54%, N:4.20%; Found: C:71.79%, H:4.48%, N:4.19%.

EXAMPLE 77

2,3-Dihydro-6-methoxy-4-(4-methylphenyl)-1H-benz[f]isoindol-1-one

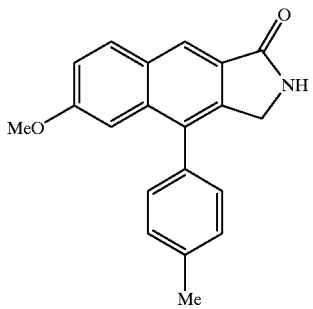

The entitled compound was obtained in a manner similar to that described in Example 53.

m.p.:298–301° C. (THF); NMR(CDCl$_3$)δ: 2.49 (3H, s), 3.76 (3H, s), 7.13 (1H, d, J=2 Hz), 7.33 (5H, m), 7.83 (1H, brs), 7.99 (1H, d, J=9 Hz), 8.30 (1H, s); IR(KBr): 3167, 3064, 2773, 1760, 1714, 1616 cm$^{-1}$; Elemental Analysis for C$_{20}$H$_{15}$NO$_3$ Calcd.: C:75.70%, H:4.76%, N:4.41%; Found: C:75.36%, H:4.88%, N:4.32%.

EXAMPLE 78

2,3-Dihydro-6-methoxy-4-(4-trifluoromethylphenyl)-1H-benz[f]isoindol-1-one

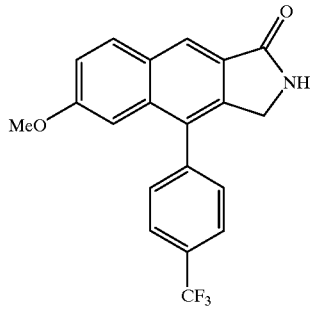

The entitled compound was obtained in a manner similar to that described in Example 53.

m.p.:219–221° C. (THF); NMR(CDCl$_3$)δ: 3.76 (3H, s), 4.32 (2H, s), 6.90 (1H, d, J=3 Hz), 7.25 (1H, dd, J=3 Hz,9 Hz), 7.49 (1H, brs), 7.55 (2H, d, J=8 Hz), 7.83 (2H, d, J=8 Hz), 7.99 (1H, d, J=9 Hz), 8.39 (1H, s). IR(KBr): 3184, 3070, 2889, 1695, 1623 cm$^{-1}$; Elemental Analysis for C$_{20}$H$_{14}$F$_3$NO$_2$ Calcd.: C:67.23%, H:3.95%, N:3.92%; Found: C:67.25%, H:3.94%, N:3.98%.

EXAMPLE 79

2,3-Dihydro-6-methoxy-4-(4-trifluoromethoxyphenyl)-1H-benz[f]isoindol-1-one

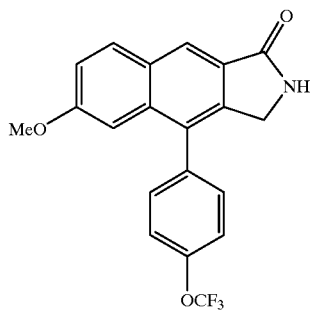

The entitled compound was obtained in a manner similar to that described in Example 53.

m.p.:277–280° C. (THF); NMR(CDCl$_3$)δ: 3.77 (3H, s), 4.33 (2H, s), 6.93 (1H, d, J=2 Hz), 7.24 (1H, dd, J=2 Hz,9 Hz), 7.39 (1H, brs), 7.43 (4H, m), 7.98 (1H, d, J=9 Hz), 8.37 (1H, s); IR(KBr): 3184, 3078, 2898, 1695, 1635, 1506 cm$^{-1}$; Elemental Analysis for C$_{20}$H$_{14}$F$_3$NO$_3$ Calcd.: C:64.34%, H:3.78%, N:3.75%; Found: C:64.37%, H:3.80%, N:3.81%.

EXAMPLE 80

6-Benzyloxy-2,3-dihydro-4-(4-methoxyphenyl)-1H-benz[f]isoindol-1-one

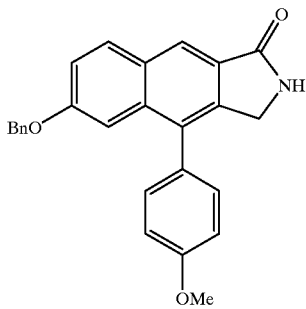

The entitled compound was obtained in a manner similar to that described in Example 53.

m.p.:213–216° C. (THF); NMR(CDCl$_3$)δ: 3.93 (3H, s), 4.32 (2H, s), 5.01 (2H, s), 7.08 (3H, m), 7.20–7.30 (9H, m), 7.97 (1H, d, J=9 Hz), 8.33 (1H, s), IR(KBr): 2837, 1695 cm$^{-1}$;

EXAMPLE 81

4-(4-Fluorophenyl)-2,3-dihydro-6-methoxy-1H-benz[f]isoindol-1-one

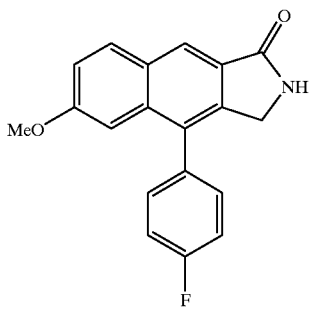

The entitled compound was obtained in a manner similar to that described in Example 53.

m.p.:282–284° C. (THF); NMR(CDCl$_3$)δ: 3.76 (3H, s), 4.32 (2H, s), 6.78 (1H, brs), 6.95 (1H, d, J=2 Hz), 7.26 (2H, m), 7.37 (3H, m), 7.98 (1H, d, J=9 Hz), 8.37 (1H, s); IR(KBr): 3184, 3068, 1695, 1623, 1506 cm$^{-1}$; Elemental Analysis for C$_{19}$H$_{14}$FNO$_2$ Calcd.: C:74.26%, H:4.59%, N:4.56%; Found: C:73.61%, H:4.90%, N:4.37%.

EXAMPLE 82

4-(4-Fluorophenyl)-2,3-dihydro-6-methoxy-9-methyl-1H-benz[f]isoindol-1-one

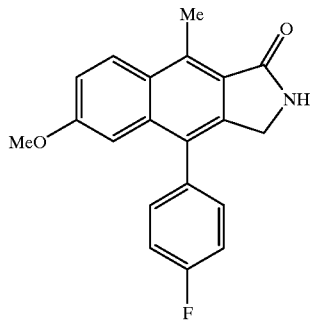

The entitled compound was obtained in a manner similar to that described in Example 53.

m.p.:236–238° C. (THF); NMR(CDCl$_3$)δ: 3.17 (3H, s), 3.75 (3H, s), 4.21 (2H, s), 6.61 (1H, brs), 6.91 (1H, d, J=3 Hz), 7.2–7.4 (5H, m), 8.20 (1H, d, J=9 Hz); IR(KBr): 3184, 3070, 2900, 1695, 1623 cm$^{-1}$; Elemental Analysis for C$_{20}$H$_{16}$FNO$_2$ Calcd.: C:74.75%, H:5.02%, N:4.36%; Found: C:74.61%, H:5.09%, N:4.36%.

EXAMPLE 83

2,3-Dihydro-6-methoxy-4-(4-methoxyphenyl)-9-methyl-1H-benz[f]isoindol-1-one

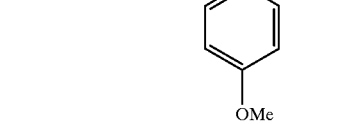

The entitled compound was obtained in a manner similar to that described in Example 53.

m.p.:235–237° C. (THF); NMR(CDCl$_3$)δ: 3.17 (3H, s), 3.76 (3H, s), 3.91 (3H, s) 4.22 (2H, s), 6.24 (1H, brs), 7.00 (1H, d, J=3 Hz), 7.06 (2H, d, J=9 Hz), 7.27 (3H, m), 8.19 (1H, d, J=9 Hz). IR(KBr): 3228, 2933, 2885, 1673, 1621 cm$^{-1}$; Elemental Analysis for C$_{21}$H$_{19}$NO$_3$ Calcd.: C:75.66%, H:5.74%, N:4.20%; Found: C:75.52%, H:5.74%, N:4.22%.

EXAMPLE 84

8,9-Dihydro-6-methoxy-10-(4-methoxyphenyl)-7H-1,3-benzodioxolo[4,5-f]isoindol-7-one

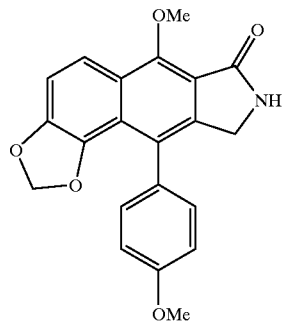

The entitled compound was obtained in a manner similar to that described in Example 53.

m.p.:274–276° C. (THF-ether); NMR(CDCl$_3$)δ: 3.89(3H, s), 4.22(2H, s), 4.31(3H, s), 5.87(2H, s), 6.70(1H, brs), 6.96(2H, d, J=9 Hz), 7.10–7.30(3H, m), 8.10(1H, d, J=9 Hz); IR (KBr): 3210, 1685, 1612, 1513, 1457, 1369, 1290, 1245 cm$^{-1}$; Elemental Analysis for C$_{21}$H$_{17}$NO$_5$ Calcd.: C:69.41%, H:4.72%, N:3.85%; Found: C:69.17%, H:4.62%, N:3.81%.

EXAMPLE 85

10-(1,3-Benzodioxol-5-yl)-6-(2-N,N-dimethylaminoethoxy)-8,9-dihydro-7H-1,3-benzodioxolo[4,5-f]isoindol-7-one

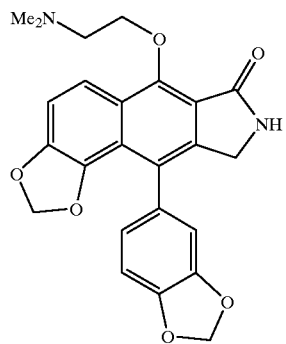

The entitled compound was obtained in a manner similar to that described in Example 53.

m.p.:200–202° C. (ethyl acetate ether); NMR(CDCl$_3$)δ: 2.43(6H, s), 2.90(2H, brs), 4.22(2H, brs), 4.61(2H, brs), 5.89(1H, brs), 5.90(1H, brs), 6.03(1H, brs), 6.05(1H, brs), 6.75–6.90(3H, m), 7.23(1H, d, J=9 Hz), 8.20(1H, d, J=9 Hz); IR (KBr): 3190, 3090, 2900,;1691, 1630, 1460, 1240 cm$^{-1}$; Elemental Analysis for C$_{24}$H$_{22}$N$_2$O$_6$.0.5H$_2$O Calcd.: C:63.02%, H:4.63%, N:6.12%; Found: C:63.03%, H:4.46%, N:6.00%.

EXAMPLE 86

10-(1,3-Benzodioxol-5-yl)-6-(1-hexyloxy)-8,9-dihydro-7H-1,3-benzodioxolo[4,5-f]isoindol-7-one

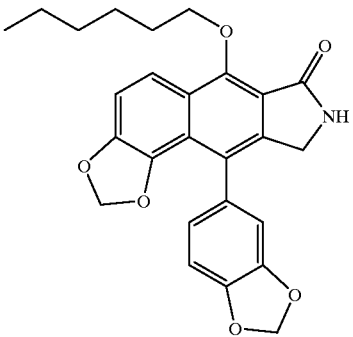

The entitled compound was obtained in a manner similar to that described in Example 53.

m.p.:182–183° C. (ethyl acetate ether); NMR(CDCl$_3$)δ: 0.91(3H, t, J=7 Hz), 1.30–1.70(6H, m), 1.94(2H, m), 4.16 (1H, d, J=17 Hz), 4.26(1H, d, J=17 Hz), 4.52(2H, t, J=7 Hz), 5.89(1H, d, J=1.4 Hz), 5.90(1H, d, J=1.4 Hz), 6.03(1H, d, J=1.4 Hz), 6.05(1H, d, J=1.4 Hz), 6.35(1H, brs), 6.70–6.90 (3H, m), 7.22(1H, d, J=9 Hz), 8.13(1H, d, J=9 Hz); IR (KBr): 3199, 3072, 2927, 1700, 1631, 1615, 1461, 1440, 1237 cm$^{-1}$; Elemental Analysis for C$_{26}$H$_{25}$NO$_6$.0.2H$_2$O Calcd.: C:69.23%, H:5.68%, N:3.11%; Found: C:69.34%, H:5.49%, N:3.20%.

EXAMPLE 87

10-(1,3-Benzodioxol-5-yl)-8,9-dihydro-6-methoxy-7H-1,3-benzodioxolo[4,5-f]isoindol-7-one

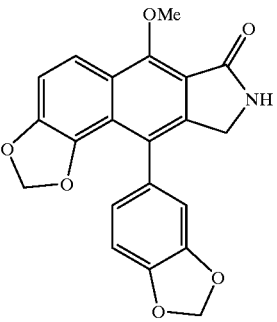

The entitled compound was obtained in a manner similar to that described in Example 53.

m.p.:262–264° C. (THF-ether); NMR(CDCl$_3$)δ: 4.10–4.39(2H, m), 4.31(3H, s), 5.90(1H, d, J=1.8 Hz), 5.92(1H, d, J=1.8 Hz), 6.03(1H, d, J=1.2 Hz), 6.06(1H, d, J=1.2 Hz), 6.70(1H, brs), 6.70–6.90(3H, m), 7.23(1H, d, J=9 Hz), 8.10(1H, d, J=9 Hz); IR (KBr): 3194, 3085, 2875, 1685, 1629, 1442, 1367, 1239 cm$^{-1}$; Elemental Analysis for C$_{21}$H$_{15}$NO$_6$.0.2H$_2$O Calcd.: C:66.21%, H:4.07%, N:3.68%; Found: C:65.95%, H:4.17%, N:3.56%.

EXAMPLE 88

10-(1,3-Benzodioxol-5-yl)-8,9-dihydro-6-(2-propoxy)-7H-1,3-benzodioxolo[4,5-f]isoindol-7-one

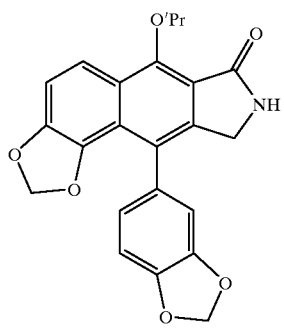

The entitled compound was obtained in a manner similar to that described in Example 53.

m.p.:283–285° C. (THF-ether); NMR(CDCl$_3$)δ: 1.41(6H, d, J=6 Hz), 4.16(1H, d, J=17 Hz), 4.26(1H, J=17 Hz), 5.26(1H, septet, J=6 Hz), 5.89(1H, d, J=1.4 Hz), 5.90(1H, d, J=1.4 Hz), 6.03(1H, d, J=1.4 Hz), 6.05(1H, d, J=1.4 Hz), 6.49(1H, brs), 6.75–6.90(.3H, m), 7.20(1H, d, J=9 Hz), 8.15(1H, d, J=9 Hz); IR(KBr): 3197, 3100, 1693, 1627, 1533, 1496, 1380, 1239 cm$^{-1}$; Elemental Analysis for C$_{23}$H$_{19}$NO$_6$.0.2H$_2$O Calcd.: C:67.54%, H:4.78%, N:3.42%; Found: C:67.43%, H:4.83%, N:3.35%.

EXAMPLE 89

10-(4-Fluorophenyl)-8,9-dihydro-6-methoxy-7H-1,3-benzodioxolo[4,5-f]isoindol-7-one

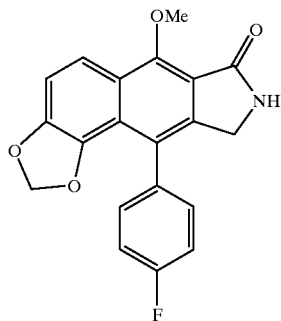

The entitled compound was obtained in a manner similar to that described in Example 53.

m.p.:308–310° C. (THF-ether); NMR(CDCl$_3$)δ: 4.19(2H, s), 4.33(3H, s), 5.87(2H, s), 6.13(1H, brs), 7.05–7.35(5H, m), 8.12(1H, d, J=9 Hz); IR (KBr):3197, 3084, 1689, 1627, 1617, 1508, 1444, 1372, 1291 cm$^{-1}$; Elemental Analysis for C$_{20}$H$_{14}$NO$_4$ Calcd.: C:68.37%, H:4.02%, N:3.99%; Found: C:67.98%, H:4.31%, N:3.75%.

EXAMPLE 90

10-(Cyclohexyl)-8,9-dihydro-6-methoxy-7H-1,3-benzodioxolo[4,5-f]isoindol-7-one

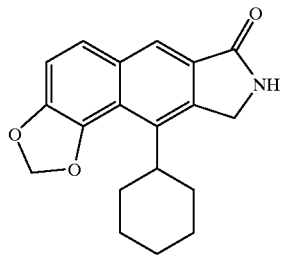

The entitled compound was obtained in a manner similar to that described in Example 53.

m.p.:244–246° C. (THF); NMR(CDCl$_3$)δ: 1.20–1.90 (10H, m), 4.20 (1H, m), 4.75 (2H, s), 6.16 (2H, s), 7.05 (1H, brs), 7.25 (1H, d, J=9 Hz), 7.61 (1H, d, J=9 Hz), 8.20 (1H, s); IR(KBr): 3184, 3084, 2927, 2858, 1724, 1683, 1644 cm$^{-1}$; Elemental Analysis for C$_{19}$H$_{19}$NO$_3$ Calcd.: C:69.71%, H:6.47%, N:4.28%; Found:° C.:69.80%, H:6.11%, N:3.93%.

EXAMPLE 91

10-(1,3-Benzodioxol-5-yl)-8,9-dihydro-9-hydroxy-7H-1,3-benzodioxolo[4,5-f]isoindol-7-one

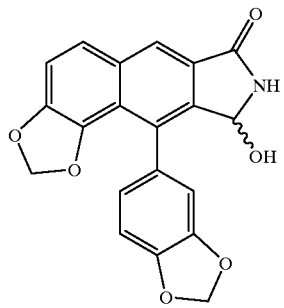

To a suspension of 10-(1,3-benzodioxol-5-yl)-8,9-dihydro-7H-1,3-benzodioxolo[4,5-f]isoindol-7,9(8H)-dione (1.00 g) in DMF (100 ml) and methanol (50 ml) was added NaBH$_4$ (0.31 g), then stirred for 2 hours. To the reaction mixture was added water and the mixture was extracted with ethyl acetate. The extract was washed with saturated sodium chloride solution and dried with magnesium sulfate, then concentrated under reduced pressure. The obtained residue was purified with column chromatography (silica gel 100 g, eluent:ethyl acetate) and recrystallized from THF to give the entitled compound (21 mg) as colorless crystals.

m.p.:227–232° C. (AcOEt); Elemental Analysis for C$_{20}$H$_{13}$NO$_6$.0.7H$_2$O NMR(DMSO-d$_6$)δ: 5.75–6.15(6H,m), 6.80–7.05(3H,m), 7.43(1H,d,J=9 Hz), 7.83(1H,d,J=9 Hz), 8.22(1H,s), 8.95(1H,brs); IR(KBr): 3215, 1675, 1490, 1293, 1234, 1060, 1041 cm$^{-1}$; Calcd.: C:63.90%, H:3.86%, N:3.73%; Found: C:63.99%, H:3.76%, N:3.57%.

EXAMPLE 92

2,3-Dihydro-6-methyl-4-(4-methylphenyl)-1H-1,3-benzodioxolo[4,5-f]isoindol-1-one

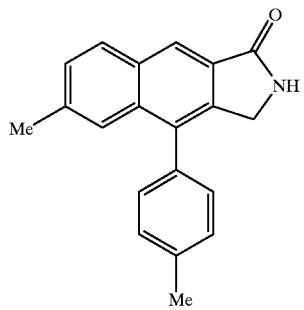

The entitled compound was obtained in a manner similar to that described in Example 1.

m.p.:297–298° C. (THF); NMR(CDCl$_3$)δ: 2.45 (3H, s), 2.49 (3H, s), 4.34 (2H, s), 6.64 (1H, brs), 7.27 (2H, d, J=8 Hz), 7.36 (2H, d, J=8 Hz), 7.39 (1H, m), 7.52 (1H, m), 7.97 (1H, d, J=8 Hz), 8.38 (1H, s); IR(KBr): 3190, 3082, 2902, 1708, 1633 cm$^{-1}$; Elemental Analysis for C$_{20}$H$_{17}$NO.0.1H$_2$O Calcd.: C:83.05%, H:6.03%, N:4.84%; Found: C:82.94, H:5.88%, N:4.88%.

EXAMPLE 93

10-(4-Cyanophenyl)-8,9-dihydro-7H-1,3-benzodioxolo[4,5-f]isoindol-7-one

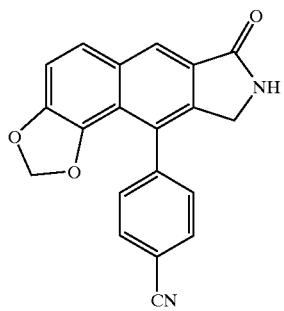

To a DMF (2ml) solution of 10-(4-Bromophenyl)-8,9-dihydro-7H-1,3-benzodioxolo[4,5-f]isoindol-7-one (150 mg) was added CuCN (60 mg) and heated under reflux for 9 hours. To the reaction mixture was added water and extracted with ethyl acetate. The extract was washed with water and dried with magnesium sulfate, then concentrated to give the entitled compound (64 mg).

m.p.:306–308° C. (THF); NMR(CDCl$_3$)δ: 4.23 (2H, s), 5.89 (2H, s), 7.31 (1H, d, J=9 Hz), 7.52 (2H, d, J=8 Hz), 7.71 (1H, d, J=9 Hz), 7.76 (2H, d, J=8 Hz), 7.85 (1H, brs), 8.36 (1H, S); IR(KBr): 3261, 2893, 2225, 1706, 1634 cm$^{-1}$; Elemental Analysis for C$_{20}$H$_{12}$N$_2$O$_3$.0.3H$_2$O Calcd.: C:71.85%, H:3.82%, N:8.38%; Found: C:71.93%, H:3.95%, N:8.08%.

EXAMPLE 94

11-(1,3-Benzodioxol-5-yl)-8-pivaloyloxymethyl-7,8,9,10-tetrahydro-1,3-benzodioxolo[4,5-g]isoquinolon-7-one

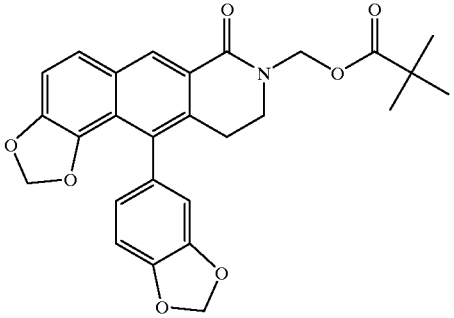

The entitled compound was obtained in a manner similar to that described in Example 4.

m.p.:173–175° C. (AcOEt-hexane); NMR(CDCl$_3$)δ: 1.20 (9H,s), 2.82(2H,t,J=7 Hz), 3.61(2H,t,J=7 Hz), 5.65(2H,s), 5.84(1H,d,J=1.0 Hz), 5.85(1H,d,J=1.0 Hz), 6.03(1H,d,J=1.4 Hz), 6.06(1H,d,J=1.4 Hz), 6.68(1H,dd,J=1.5 Hz,8 Hz), 6.75 (1H,d,J=1.5 Hz), 6.86(1H,d,J=8 Hz), 7.19(1H,d,J=9 Hz), 7.60(1H,d,J=9 Hz), 8.67(1H,s); IR(KBr): 1725, 1665, 1625, 1480, 1450, 1275, 1225, 1120 cm$^{-1}$; Elemental Analysis for C$_{27}$H$_{25}$NO$_7$ Calcd.: C:68.20%, H:5.30%, N:2.95%; Found: C:68.00%, H:5.29%, N:2.83%.

EXAMPLE 95

Ethyl 11-(1,3-Benzodioxol-5-yl)-7,8,9,10-tetrahydro-1,3-benzodioxolo[4,5-g]-isoquinolin-7-one-8-acetate

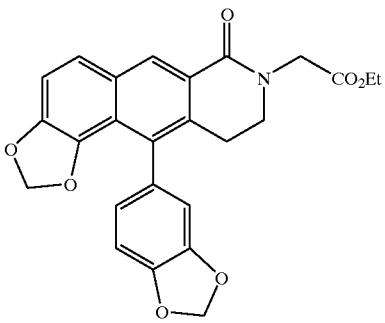

The entitled compound was obtained in a manner similar to that described in Example 6.

m.p.:149–151° C. (AcOEt-hexane); NMR(CDCl$_3$)δ: 1.29 (3H,t,J=7 Hz), 2.85–2.95(2H,m), 3.56(2H,t,J=6 Hz), 4.22 (2H,q,J=7 Hz), 4.37(2H,s), 5.84(1H,d,J=1.4 Hz), 5.85(1H, d,J=1.4 Hz), 6.03(1H,d,J=1.2 Hz), 6.06(1H,d,J=1.2 Hz), 6.70(1H,dd,J=1.6 Hz,8 Hz), 6.75(1H,d,J=1.6 Hz), 6.88(1H, d,J=8 Hz), 7.19(1H,d,J=9 Hz), 7.59(1H,d,J=9 Hz), 8.64(1H, s); IR(KBr): 1740, 1655, 1625, 1480, 1450, 1280, 1225, 1195 cm$^{-1}$; Elemental Analysis for C$_{25}$H$_{21}$NO$_7$ Calcd.: C:67.11%, H:4.73%, N:3.13%; Found: C:66.83%, H:4.74%, N:3.10%.

EXAMPLE 96

11-(1,3-Benzodioxol-5-yl)-7,8,9,10-tetrahydro-1,3-benzodioxolo[4,5-g]isoquinolin-7-one-8-acetic acid

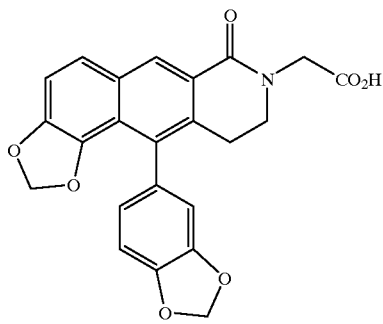

The entitled compound was obtained in a manner similar to that described in Example 7.

m.p.:231–233° C. (MeOH); Elemental Analysis for $C_{23}H_{17}NO_7 \cdot 0.7H_2O$ Calcd.: C:63.95%, H:4.29%, N:3.24%; Found: C:63.84%, H:4.13%, N:3.34%; NMR(CDCl$_3$)δ: 2.85–2.95(2H,m), 3.58(2H,t,J=7 Hz), 4.39(2H,s), 5.84(1H, d,J=1.4 Hz), 5.86(1H,d,J=1.4 Hz), 6.03(1H,d,J=1.4 Hz), 6.06(1H,d,J=1.4 Hz), 6.68(1H,dd,J=1.6 Hz,8 Hz), 6.73(1H, d,J=1.6 Hz), 6.86(1H,d,J=8 Hz), 7.19(1H,d,J=9 Hz), 7.59 (1H,d,J=9 Hz), 8.62(1H,s); IR(KBr): 3400, 1720, 1645, 1620, 1480, 1450, 1275, 1225 cm$^{-1}$.

EXAMPLE 97

N,N-diethyl-11-(1,3-benzodioxol-5-yl)-7,8,9,10-tetrahydro-1,3-benzodioxolo[4,5-g]isoquinolin-7-one-8-acetoamide

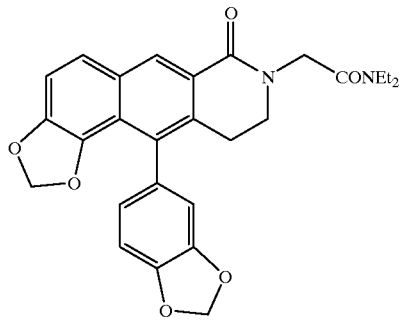

11-(1,3-Benzodioxol-5-yl)-7,8,9,10-tetrahydro-1.3-benzodioxolo[4,5-g]isoquinolin-7-one-8-acetic acid (220 mg) and N-methylmorpholine (69 μl) were dissolved in THF (2.5 ml) and isobutyl chloroformate (82 μl) was added dropwise thereto at −15° C. The mixture was stirred for 10 minutes and diethylamine (0.11 ml) was added therein, then stirred for 15 minutes. The mixture was stirred for 1 hour at room temperature and water was added thereto. The mixture was extracted with ethyl acetate. The extract was washed with saturated sodium chloride solution and dried with magnesium sulfate, then concentrated under reduced pressure. The obtained residue was recrystallized from ethyl acetate to give the entitled compound (149 mg) as pale-yellow crystals.

m.p.:169–171° C. (AcOEt); Elemental Analysis for $C_{27}H_{26}N_2O_6 \cdot 0.5H_2O$ Calcd.: C:67.07%, H:5.63%, N:5.79%; Found: C:67.30%, H:5.58%, N:5.78%; NMR (CDCl$_3$)δ:1.14(3H,t,J=7 Hz), 1.28(3H,t,J=7 Hz), 2.80–2.95 (2H,m), 3.40(4H,q,J=7 Hz), 3.61(2H,t,J=6 Hz), 3.39(1H,d, J=16 Hz), 3.47(1H,d,J=16 Hz), 5.84(1H,brs), 5.85(1H,brs), 6.03(1H,d,J=1.4 Hz), 6.06(1H,d,J=1.4 Hz), 6.70(1H,dd,J= 1.4 Hz,8 Hz), 6.75(1H,d,J=1.4 Hz), 6.86(1H,d,J=8 Hz), 7.18(1H,d,J=9 Hz), 7.58(1H,d,J=9 Hz), 8.62(1H,s); IR(KBr): 1645, 1620, 1480, 1450, 1280, 1225 cm$^{-1}$.

EXAMPLE 98

10-(1,3-Benzodioxol-5-yl)-8,9-dihydro-8-pivaloyl-7H-1,3-benzodioxolo[4,5-f]isoindol-7-one

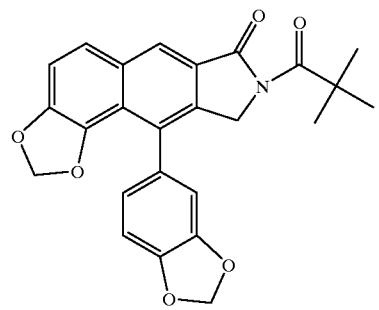

To the DMF (50 ml) solution of 10-(1,3-benzodioxol-5-yl)-8,9-dihydro-7H-1,3-benzodioxolo[4,5-f]isoindol-7-one (2.0 g) was added sodium hydride (253 mg) under ice cooling and stirred for 15 minutes at room temperature. The reaction mixture was cooled with ice and pivaloylchloride (0.9 ml) was added thereto, then stirred overnight at room temperature. To the reaction mixture was added water and extracted with ethyl acetate. The extract was washed with saturated sodium chloride solution and dried with magnesium sulfate, then concentrated under reduced pressure. The obtained residue was purified with column chromatography and recrystallized from ethyl acetate to give the entitled compound (76 mg) as a pale-yellow crystals.

m.p.:238–240° C. (AcOEt); NMR(CDCl$_3$)δ: 1.46(9H,s), 4.69(1H,d,J=18 Hz), 4.77(1H,d,J=18 Hz), 5.93(1H,d,J=1.4 Hz), 5.95(1H,d,J=1.4 Hz), 6.04(1H,d,J=1.4 Hz), 6.08(1H,d, J=1.4 Hz), 6.79(1H,dd,J=1.2 Hz,8 Hz), 6.81(1H,s), 6.86(1H, dd,J=1.2 Hz,8 Hz), 7.28(1H,d,J=9 Hz), 7.69(1H,d,J=9 Hz), 8.38(1H,s); IR(KBr): 1715, 1670, 1625, 1270, 1225, 1180, 1165, 1035 cm$^{-1}$; Elemental Analysis for $C_{25}H_{21}NO_6$ Calcd.: C: 69.60%, H:4.91%, N:3.25%; Found: C:69.34%, H:4.92%, N:3.21%.

EXAMPLE 99

Benzyl 3-[10-(1,3-Benzodioxol-5-yl)-8,9-dihydro-7H-1.3-benzodioxolo[4,5-f]isoindol-7-one-8-yl]carbonylpropionate

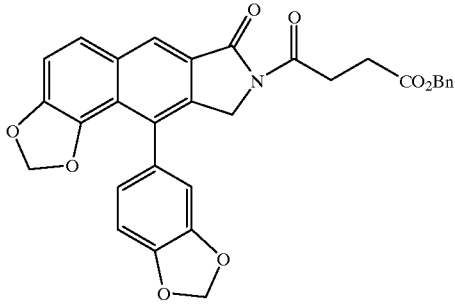

The entitled compound was obtained in a manner similar to that described in Example 98 m.p.:128–129° C. (AcOEt-hexane); Elemental Analysis for $C_{31}H_{23}NO_8 \cdot 0.5H_2O$ Calcd.: C:68.13%, H:4.43%, N:2.56%; Found: C:67.87%, H:4.32%, N:2.68%; NMR (CDCl$_3$)δ: 2.80(2H,t,J=6 Hz), 3.47(2H,t,J=6 Hz), 5.14(2H, s), 5.94(1H,d,J=1.4 Hz), 5.95(1H,d,J=1.4 Hz), 6.04(1H,d,J=1.2 Hz), 6,08(1H,d,J=1.2 Hz), 6.75–6.80(2H,m), 6.89(1H, d,J=9 Hz), 7.25–7.40(5H,m), 7.70(1H,d,J=9 Hz), 8.41(1H, s); IR(KBr): 1729, 1695, 1347, 1272, 1235, 1164 cm$^{-1}$.

EXAMPLE 100

3-[10-(1,3-Benzodioxol-5-yl)-8,9-dihydro-7H- 1,3-benzodioxolo[4,5-f]isoindol-7-one-8-yl]carbonylpropionic acid

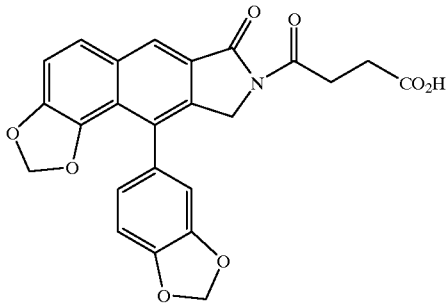

To an ethyl acetate (2 ml) solution of Benzyl 3-[10-(1,3-benzodioxol-5-yl)-8,9-dihydro-7H-1,3-benzodioxolo[4,5-f]isoindol-7-one-8-yl]carbonyl-propionate (50 mg) was added 10% palladium carbon (10 mg) and stirred overnight under hydrogen atmosphere. The catalysts were filtered off and the filtrate was concentrated under reduced pressure, then recrystallized from ethyl acetate-hexane to give the entitled compound (28 mg) as colorless crystals.

m.p.:231–233° C.; NMR(DMSO-d$_6$)δ: 2.57(2H,t,J=6 Hz), 3.25(2H,t,J=6 Hz), 4.59(2H,s), 5.99(1H,d,J=1.0 Hz), 6.01(1H,d,J=1.0 Hz), 6.09(1H,d,J=0.9 Hz), 6,14(1H,d,J=0.9 Hz), 6.88(1H,dd,J=1.6 Hz,8 Hz), 6.99(1H,d,J=8 Hz), 7.01 (1H,J=1.6 Hz), 7.48(1H,d,J=9 Hz), 7.94(1H,d,J=9 Hz), 8.56 (1H,s); IR(KBr): 1733, 1631, 1490, 1347, 1272, 1232, 1064 cm$^{-1}$; Elemental Analysis for $C_{24}H_{17}NO_8$ Calcd.: C:64.43%, H:3.83%, N:3.13%; Found: C:64.06%, H:4.03%, N:3.05%.

EXAMPLE 101

8,9-Dihydro-10-(4-hydroxyphenyl)-7H-1,3-benzodioxolo[4,5-f]isoindol-7-one

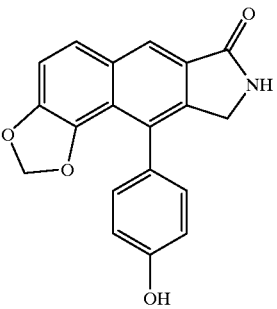

The entitled compound was obtained in a manner similar to that described in Example 100.

m.p.:300° C. (decomp.)(THF); NMR(DMSO-d$_6$)δ: 4.18 (2H,brs), 5.94(2H,brs), 6.81(2H,d,J=9 Hz), 7.22(2H,d,J=9 Hz), 7.42(1H,d,J=9 Hz), 7.84(2H,d,J=9 Hz), 8.27(1H,s), 8.59(1H,brs), 9.50(1H,s). IR(KBr): 1679, 151,3, 1459, 1297, 1276, 1245, 1070 cm$^{-1}$. Elemental Analysis for $C_{19}H_{13}NO_4 \cdot 0.3H_2O$ Calcd.: C:70.28%, H:4.22%, N:4.31%; Found: C:70.47%, H:4.32%, N:4.21%.

EXAMPLE 102

8,9-Dihydro-10-[4-(2-dimethylaminoethoxy)phenyl]-7H-1,3-benzodioxolo[4,5-f]isoindol-7-one oxalate

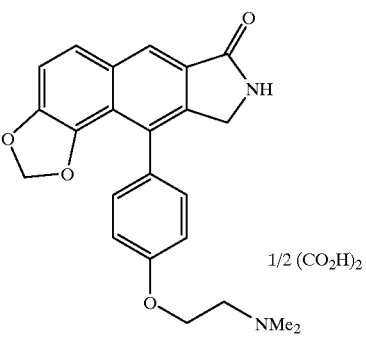

To a DMF (4 ml) solution of 8,9-dihydro-10-(4-hydroxyphenyl)-7H-1,3-benzodioxolo[4,5-f]isoindol-7-one (175 mg) was added 2-dimethylaminoethylcloride hydrochloride (95 mg), potassium carbonate (152 mg) and sodium iodide (8.3 mg) and stirred for 13 hours at 60° C. To the reaction mixture was added water and extracted with ethyl acetate. The basic component was extracted with 1N hydrochloric acid and pH of the mixture was adjusted to about 9 by 1N sodium hydroxide solution and then extracted with ethyl acetate. The extract was washed with saturated sodium chloride solution and dried with magnesium sulfate, then concentrated under reduced pressure. The obtained residue was suspended in THF and methanol (1 ml) solution of oxalic acid-dihydrate (3.8 mg). The reaction mixture was concentrated under reduced pressure and the obtained residue was dissolved in methanol. Methanol was distilled off under reduced pressure and the obtained powder was washed with THF to give the entitled compound (14 mg).

m.p.:209–210° C. (THF); NMR(DMSO-$d_6$)δ: 3.60(2H,t, J=7 Hz), 4.18(2H,brs), 4.34(2H,m), 5.92(2H,brs), 7.04(2H, d,J=8 Hz), 7.39(2H,d,J=8 Hz), 7.44(1H,d,J=9 Hz), 7.87(2H, d,J=9 Hz), 8.31(1H,s), 8.61(1H,brs); IR(KBr): 1685, 1637, 1511, 1457, 1280, 1241, 1068 cm$^{-1}$;

EXAMPLE 103

8,9-Dihydro-10-(4-hydroxy-3-methoxyphenyl)-7H-1,3-benzodioxolo[4,5-f]isoindol-7-one

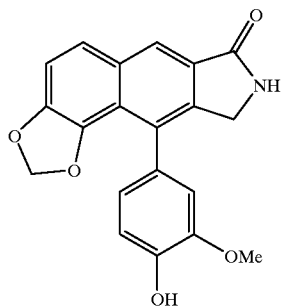

To a solution of 10-(4-benzyloxy-3-methoxyphenyl)-8,9-dihydro-7H-1,3-benzodioxolo[4,5-f]isoindol-7-one (3.0 g) in THF (100 ml) and DMF (30 ml) was added 10% palladium carbon (0.8 g) and stirred for 2 hours under hydrogen atmosphere. The catalysts were filtered off with Celite and the filtrate was concentrated under reduced pressure to give the entitled compound (2.7 g) as colorless crystals.

m.p.:280–282° C. (THF); NMR(CDCl$_3$)δ: 3.88 (3H, s), 4.25 (1H, d, J=17 Hz), 4.39 (1H, d, J=17 Hz), 5.90 (2H, d, J=1.4 Hz), 6.38 5 (1H, brs), 6.87 (2H, m), 6.99 (1H, d, J=8 Hz), 7.28 (1H, d, J=9 Hz), 7.68 (1H, d, J=9 Hz), 8.35 (1H, s); IR(KBr): 3200, 3064, 2881, 1695, 1634, 1515 cm$^{-1}$; Elemental Analysis for C$_{20}$H$_{15}$NO$_5$.0.2H$_2$O Calcd.: C:68.06%, H:4.71%, N:3.97%; Found: C:67.87%, H:5.04%, N:3.58%.

EXAMPLE 104

Methyl [4-(8,9-Dihydro-7H-1,3-benzodioxolo[4,5-f]isoindol-7-on-10-yl)-3-methoxyphenoxy]acetate

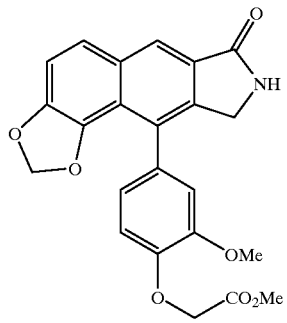

To a DMF (20 ml) solution of 8,9-dihydro-10-(4-hydroxy-3-methoxyphenyl)-7H-1,3-benzodioxolo[4,5-f]isoindol-7-one (600 mg) was added, potassium carbonate (360 mg) and methylbromoacetate (250 μl) and stirred overnight at room temperature. To the reaction mixture was added water and the mixture was extracted with ethyl acetate. The extract was washed with water and dried with magnesium sulfate, then the solvent was distilled off to give the entitled compound (290 mg) as colorless crystals.

m.p.:198–200° C. (THF); NMR(CDCl$_3$)δ: 3.86 (3H, s), 3.87 (3H, s), 4.24 (1H, d, J=17 Hz), 4.38 (1H, d, J=17 Hz), 4.79 (2H, s), 5.89 (2H, s), 6.42 (1H, b), 6.89 (3H, m), 7.29 (1H, d, J=8 Hz), 7.69 (1H, d, J=8 Hz), 8.36 (1H, s); IR(KBr): 3209, 2954, 2889, 1756, 1695, 1515 cm$^{-1}$; Elemental Analysis for C$_{23}$H$_{19}$NO$_7$.0.2H$_2$O Calcd.: C:64.00%, H:4.60%, N:3.30%; Found: C:64.26%, H:4.64%, N:3.24%.

EXAMPLE 105

2,3-Dihydro-6-hydroxy-4-(4-methoxyphenyl)-1H-benz[f]isoindol-1-one

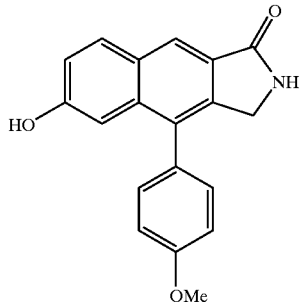

To a THF (20 ml) and ethanol (30 ml) solution of 6-benzyloxy-2,3-dihydro-4-(4-methoxyphenyl)-1H-benz[f]isoindol-1-one (0.8 g) was added 10% palladium carbon (0.2 g) and stirred for 2 hours under hydrogen atmosphere. The catalysts were filtered off by Celite, and the filtrate was concentrated to give the entitled compound (480 mg) as colorless crystals.

m.p.:249–251° C. (THF); NMR(CDCl₃)δ: 5 3.89 (3H, s), 4.29 (2H, s), 7.0–7.4 (7H, m), 7.91 (1H, d, J=9 Hz), 8.27 (1H, s), 9.25 (1H, brs); IR(KBr): 3215, 1683, 1616 cm⁻¹; Elemental Analysis for C₁₉H₁₅NO₃ Calcd.: C:74.74%, H:4.95%, N:4.59%; Found: C:74.42%, H:5.03%, N:4.59%.

EXAMPLE 106

6-Ethoxy-2,3-dihydro-4-(4-methoxyphenyl)-1H-benz[f]isoindol-1-one

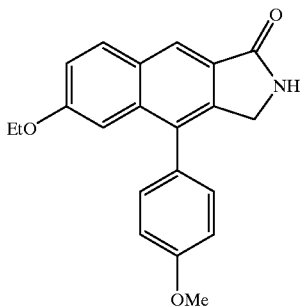

To a THF (10 ml) solution of 6-hydroxy-2,3-dihydro-4-(4-methoxyphenyl)-1H-benz[f]isoindol-1-one (80 mg) and potassium carbonate (60 mg) was added ethyliodide (150 μl) and heated under reflux for overnight. To the reaction mixture was added water and extracted with ethyl acetate. The extract was washed with water and dried with magnesium sulfate, then concentrated under reduced pressure to give the entitled compound (61 mg) as colorless crystals.

m.p.:235–238° C. (THF); NMR(CDCl₃)δ: 1.40 (3H, t, J 7 Hz), 3.92 (3H, s), 3.97 (2H, q, J=7 Hz), 4.33 (2H, s), 6.46 (1H, brs), 7.04 (1H, m), 7.07 (2H, d, J=9 Hz), 7.21 (1H, dd, J=3 Hz,9 Hz), 7.32 (2H, d, J=9 Hz), 7.96 (1H, d, J=9 Hz), 8.33 (1H, s); IR(KBr): 3209, 2979, 1695, 1616, 1506 cm⁻¹; Elemental Analysis for C₂₁H₁₉NO₃ Calcd.: C:75.66%, H:5.74%, N:4.20%; Found: C:75.23%, H:5.83%, N:4.15%.

EXAMPLE 107

2,3-Dihydro-6-isopropoxy-4-(4-methoxyphenyl)-1H-benz[f]isoindol-1-one

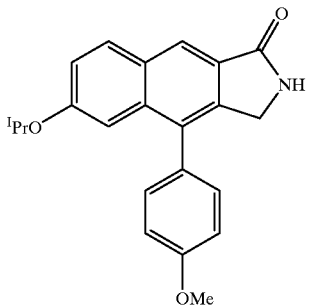

The entitled compound was obtained in a manner similar to that described in Example 106.

m.p.:212–215° C. (THF); NMR(CDCl₃)δ: 1,31 (6H, d, J=7 Hz), 3.92 (3H, s), 4.34 (2H, s), 4.50 (1H, m), 6.43 (1H, brs), 7.05 (1H, m), 7.07 (2H, d, J=9 Hz), 7.20 (1H, dd, J=3 Hz,9 Hz), 7.32 (2H, d, J=9 Hz), 7.96 (1H, d, J=9 Hz), 8.33 (1H, s); IR(KBr): 3222, 2977, 1695, 1616, 1506 cm⁻¹; Elemental Analysis for C₂₂H₂₁NO₃.0.2H₂O Calcd.: C:75.28%, H:6.15%, N:3.99%; Found: C:75.32%, H:6.33%, N:3.92%.

EXAMPLE 108

Methyl [2,3-Dihydro-4-(4-methoxyphenyl)-1H-benz[f]isoindol-1-one-6-yl]oxyacetate

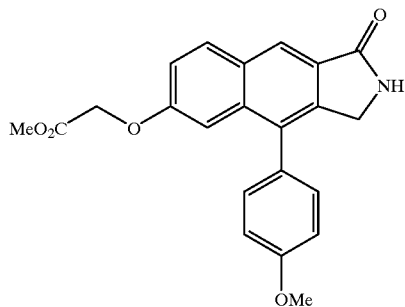

The entitled compound was obtained in a manner similar to that described in Example 106.

m.p.:202–203° C. (THF); NMR(CDCl₃)5: 3.77 (3H, s), 3.93 (3H, s), 4.34 (2H, s), 4.59 (2H, s), 6.48 (1H, brs), 7.00 (1H, d, J=3 Hz), 7.08 (2H, d, J=9 Hz), 7.29 (3H, m), 8.01 (1H, d, J=9 Hz), 8.35 (1H, s); IR(KBr): 3178, 3076, 2956, 1764, 1683, 1631 cm⁻¹; Elemental Analysis for C₂₂H₁₉NO₅ Calcd.: C:70.02%, H:5.07%, N:3.71%; Found: C:69.54%, H:5.09%, N:3.72%.

EXAMPLE 109

[2,3-Dihydro-4-(4-methoxyphenyl)-1H-benz[f]isoindol-1-one6-yl)oxyacetic acid

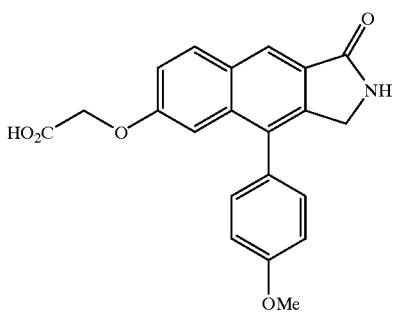

To a THF (5 ml) and methanol (1 ml) solution of methyl [2,3-dihydro-4-(4-methoxyphenyl)-1H-benz[f]isoindol-1-on-6-yl]oxyacetate (90 mg) was added 1N sodium hydroxide solution (3 ml) and stirred for 2 hours at room temperature. To the reaction mixture was added diluted hydrogen chloride and extracted with ethyl acetate-THF. The extract was washed with water and dried with magnesium sulfate, then concentrated under reduced pressure to give the entitled compound (48 mg) as colorless crystals.

m.p.:350–352° C. (THF); NMR(DMSO-d₆)δ: 3.86 (3H, s), 4.27 (2H, s), 4.64 (2H, s), 6.99 (1H, d, J=2 Hz), 7.11 (2H, d, J=8 Hz), 7.31 (1H, dd, J=2 Hz,9 Hz), 7.40 (2H, d, J=8 Hz), 8.15 (1H, d, J=9 Hz), 8.26 (1H, s), 8.60 (1H, brs); IR(KBr): 3336, 2842, 1733, 1714, 1616 cm$^{-1}$; Elemental Analysis for $C_{21}H_{17}NO_5.0.5H_2O$ Calcd.: C:67.74%, H:4.87%, N:3.76%; Found: C:67.50%, H:4.80%, N:3.75%.

EXAMPLE 110

12-(1,3-Benzodioxol-5-yl)-8,9,10,11-tetrahydro-7H-1,3-benzodioxolo[4,5-g][2]benzazepin-7-one

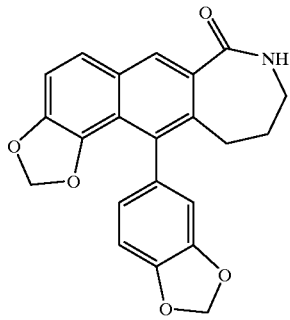

Methyl 8-(3-Aminopropyl)-9-(1,3-benzodioxol-5-yl)-naphtho[1,2-d]-1,3-dioxol-7-carboxylate (12 mg) was dissolved in toluene (5 ml), and heated under reflux for 8 hours. The reaction mixture was concentrated under reduced pressure and the obtained residue was purified with column chromatography (silica gel 1 g, eluent:ethyl acetate-hexane=2:1), then triturated with ether to give the entitled compound (3 mg).

m.p.:245–248° C.; NMR(CDCl$_3$)δ: 1.86(2H,quintet,J=7 Hz), 2.72(2H,t,J=7 Hz), 3.18(2H,quartet,J=7 Hz), 5.81(1H, d,J=1.4 Hz), 5.83(1H,d,J=1.4 Hz), 6.03(1H,d,J=1.4 Hz), 6.06(1H,d,J=1.4 Hz), 6.31(1H,brs), 6.69(1H,dd,J=1.5 Hz,8 Hz), 6.74(1H,d,J=1.5 Hz), 6.85(1H,d,J=8 Hz), 7.18(1H,d, J=9 Hz), 7.53(1H,d,J=9 Hz), 8.19(1H,s).

EXAMPLE 111

8,9-Dihydro-10-(4-pyridyl)-7H-1,3-benzodioxolo[4,5-f]isoindol-7-one hydrochloride

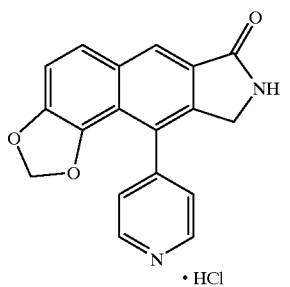

To a methanol (20 ml) solution of 8,9-dihydro-10-(4-pyridyl)-7H-1,3-benzodioxolo[4,5-f]isoindol-7-one (120 mg) was added 4N hydrogen chloride-ethyl acetate solution (4 ml) and stirred for 30 minutes. The resultant precipitates were collected by suction and washed with ethyl acetate to give the entitled compound (126 mg).

m.p.:325–328° C.; NMR(D$_2$O)δ: 4.28 (2H, s), 5.95 (2H, s), 7.30 (1H, m), 7.55 (1H, m), 8.00 (1H, s), 8.13 (2H, m), 8.91 (2H, m). IR(KBr): 3230, 3057, 2914, 1683, 1635 cm$^{-1}$; Elemental Analysis for $C_{18}H_{13}ClN_2O_3$. 0.3H$_2$O Calcd.: C:62.35%, H:3.97%, N:8.08%; Found: C:62.23%, H:4.08%, N:7.90%.

EXAMPLE 112

4-(8,9-Dihydro-7H-1,3-benzodioxolo[4,5-f]isoindol-7-on-10-yl)-1-methylpyridinium iodide

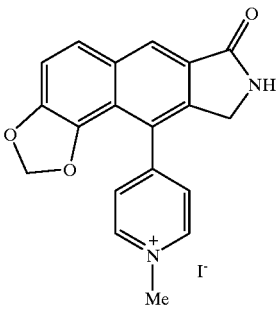

To a methanol (10 ml) solution of 8,9-dihydro-10-(4-pyridyl)-7H-1,3-benzodioxolo[4,5-f]isoindol-7-one (63 mg) was added methyl iodide (3 ml) and heated under reflux for 3 hours. The resultant precipitates were collected by suction and recrystallized from methanol-THF to give the entitled compound (51 mg) as yellow crystals.

m.p.:315–319° C.; NMR(DMSO-d$_6$)δ: 4.36 (2H, s), 4.42 (3H, s), 6.03 (2H, s), 7.57 (1H, d, J=9 Hz), 8.00 (1H, d, J=9 Hz), 8.33 (2H, d, J=7 Hz), 8.53 (1H, s), 8.79 (1H, brs), 9.05 (2H, d, J=7 Hz); IR(KBr): 3192, 3101, 1683, 1695 cm$^{-1}$; Elemental Analysis for $C_{19}H_{15}IN_2O_3.0.5H_2O$ Calcd.: C:50.13%, H:3.54%, N:6.15%; Found: C:50.00%, H:3.69%, N:6.11%.

EXAMPLE 113

8,9-Dihydro-10-(4-pyridyl)-7H-1,3-benzodioxolo[4,5-f]isoindol-7-one N-oxide

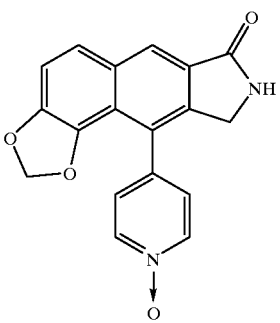

To a dichloromethane (100 ml) solution of 8,9-dihydro-10-(4-pyridyl)-7H-1,3-benzodioxolo[4,5-f]isoindol-7-one (200 mg) was added MCPBA (350 mg) and stirred for 2 hours at room temperature. To the reaction mixture was added water. The organic layer was taken and washed with sodium hydrogencarbonate solution and water. The mixture was dried with magnesium sulfate and concentrated to give the entitled compound (84 mg).

m.p.:270–274° C.; NMR(CDCl₃)δ: 4.32 (2H, s), 5.95 (2H, s), 7.3–7.4 (3H, m), 7.71 (2H, m), 8.29 (2H, d, J=7 Hz), 8.37 (1H, s). IR(KBr): 3416, 3107, 2902, 1695 cm⁻¹; Elemental Analysis for $C_{18}H_{12}N_2O_4 \cdot 0.5H_2O$ Calcd.: C:65.65%, H:3.98%, N:8.51%; Found: C:65.66%, H:4.29%, N:8.25%.

EXAMPLE 114

1,2-Dihydro-7-methoxy-2-(4-methoxybenzyl)-9-(4-methoxyphenyl)-3H-pyrrolo[3,4-b]quinolin-3-one

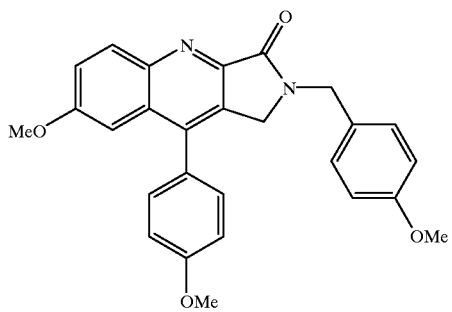

To 4-carbomethoxy-1-(4-methoxybenzyl)-2,3-dioxopyrrolidine (2.5 g, 9.1 mmol) was added 20% hydrochloric acid (150 ml) and heated under reflux for 30 minutes. The mixture was cooled to room temperature and extracted three times with a mixed solvent of THF and ethyl acetate (1:2). The organic layer was washed with saturated sodium chloride solution and dried with magnesium sulfate, then the solvent was distilled off. To the residue was added 2-amino-5-methoxyphenyl 4-methoxyphenyl ketone (670 mg, 2.60 mmol), acetic acid (100 ml), and concentrated sulfuric acid (0.5 ml) and heated under reflux for 40 minutes. The solvent was distilled off. To the residue was added water and potassium carbonate solution, then extracted twice with ethyl acetate. The organic layer was washed with saturated sodium chloride solution and dried with magnesium sulfate, then the solvent was distilled off. The residue was purified with silica gel column chromatography (eluent:ethyl acetate) to give the entitled compound (987 mg, 86%) as colorless crystals.

m.p.:191–192° C. (ethyl ether); NMR (CDCl₃)δ: 3.77 (6H, s), 3.91(3H, s), 4.19(2H, s), 4.82(2H, s), 6.81–7.35(9H, m), 7.42(1H, dd, J=3 Hz, 9 Hz), 8.31(1H, d, J=9 Hz); IR (KBr): 3001, 2912, 2839, 1700, 1623, 1513, 1463, 1289, 1243 cm⁻¹; Elemental Analysis for $C_{27}H_{24}N_2O_4 \cdot 0.2H_2O$ Calcd.:C:73.02%, H:5.54%, N:6.31%; Found: C:72.99%, H:5.57%, N:6.30%.

EXAMPLE 115

9-(4-Fluorophenyl)-1,2-dihydro-7-methoxy-2-(4-methoxybenzyl)-3H-pyrrolo[3,4-b]quinolin-3-one

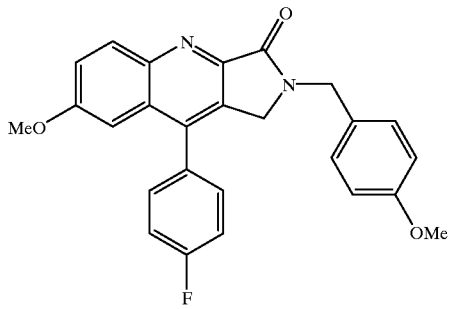

The entitled compound was obtained in a manner similar to that described in Example 114.

m.p.:170–173° C. (ethyl acetate-ether); NMR(CDCl₃)δ: 3.78(3H, s), 4.16(2H, s), 4.82(2H, s), 6.85(2H, d, J=7.8 Hz), 6.95(1H, m), 7.20–7.50(7H, m), 8.34(1H, d, J=9 Hz). IR(KBr): 2929, 1700, 1612, 1506, 1515, 1249, 1230 cm⁻¹; Elemental Analysis for $C_{26}H_{19}N_2O_4F \cdot 0.2H_2O$ Calcd.: C:72.28%, H:4.99%, N:6.48%; Found: C:72.39%, H:5.03%, N:6.10%.

EXAMPLE 116

1,2-Dihydro-7-methoxy-2-(4-methoxybenzyl)-9-(4-trifluoromethylphenyl)-3H-pyrrolo[3,4-b]quinolin-3-one

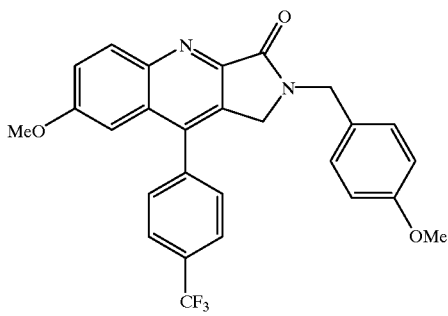

The entitled compound was obtained in a manner similar to that described in Example 114.

m.p. :140–142° C. (THF-ethyl acetate); NMR (200 MHz, CDCl₃) ppm: 3.78(3H, s), 4.15(2H, s), 4.82(2H, s), 6.80–6.90(3H, m), 7.20–7.30(2H, m), 7.40–7.50(1H, m), 7.52(2H, d, J=9.2 Hz), 7.83(2H, d, J=8.0 Hz), 8.36(1H, d, J=9.2 Hz)

EXAMPLE 117

3,4-Dihydro-7-methoxy-2-(4-methoxybenzyl)-5-(4-trifluoromethylphenyl)-benzo[b][1,7]naphthyridin-1(2H)-one

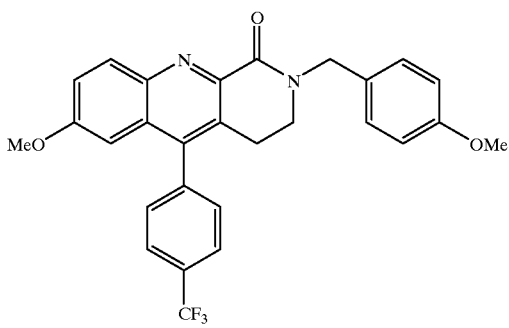

The entitled compound was obtained in a manner similar to that described in.Example 114 from 3,3-dimethoxy-1-(4-methoxybenzyl)-2-piperidone.

m.p.:234–236° C. (THF); NMR(CDCl$_3$)δ: 2.77 (2H, t, J=6 Hz), 3.43 (2H, t, J=6 Hz), 3.73 (3H, s), 3.78 (3H, s), 4.82 (2H, s), 6.59 (1H, d, J=3 Hz), 6.85 (2H, d, J=9 Hz), 7.32 (2H, d, J=9 Hz), 7.41 (3H, m), 7.82 (1H, d, J=8 Hz), 8.35 (1H, d, J=9 Hz); IR(KBr): 2964, 2933, 2835, 1661, 1621 cm$^{-1}$; Elemental Analysis for C$_{28}$H$_{23}$FN$_2$O$_3$ Calcd.: C:68.29%, H:4.71%, N:5.69%; Found: C:68.46%, H:4.78%, N:5.57%.

EXAMPLE 118

3,4-Dihydro-7-methoxy-2-(4-methoxybenzyl)-5-(4-methoxyphenyl)-benzo[b][1,7]naphthyridin-1(2H)-one

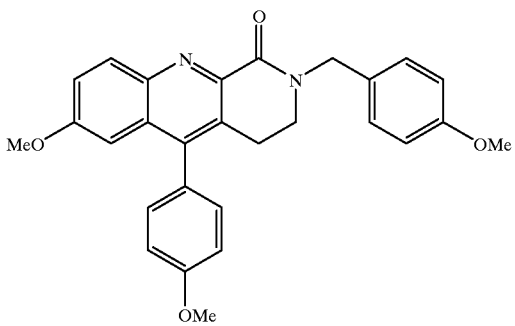

The entitled compound was obtained in a manner similar to that described in Example 117.

m.p.:132–134° C. (THF); NMR(CDCl$_3$)δ: 2.83 (2H, t, J=6 Hz), 3.41 (2H, t, J=6 Hz), 3.74 (3H, s), 3.78 (3H, s), 3.90 (3H, s), 4.82 (2H, s), 6.76 (1H, d, J=3 Hz), 6.85 (2H, d, J=9 Hz), 7.05 (2H, d, J=9 Hz), 7.18 (2H, d, J=9 Hz), 7.32 (2H, d, J=9 Hz), 7.36 (1H, dd, J=3 Hz,9 Hz), 8.32 (1H, d, J=9 Hz); IR(KBr):2958, 2935, 2837, 1662, 1616, 1515 cm$^{-1}$; Elemental Analysis for C$_{28}$H$_{26}$N$_2$O$_4$ Calcd.: C:73.99%, H:5.77%, N:6.16%; Found: C:73.52%, H:5.71%, N:6.14%.

EXAMPLE 119

1,2-Dihydro-7-methoxy-9-(4-methoxyphenyl)-3H-pyrrolo[3,4-b]quinolin-3-one

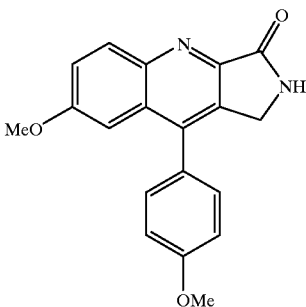

A mixture of 1,2-Dihydro-7-methoxy-2-(4-methoxybenzyl)-9-(4-methoxyphenyl)-3H-pyrrolo[3,4-b]quinolin-3-one (500 mg, 1.14mmol), diammonium cerium (IV) nitrate (3.9 g, 7.1 mmol), acetonitrile (30 ml), and water(30 ml) was stirred for 40 minutes at room temperature. The solvent was distilled off and water was added to the residue. The mixture was extracted twice with THF-ethyl acetate (1:1). The extract was washed with saturated sodium chloride solution and dried with magnesium sulfate, then the solvent was distilled off to give the entitled compound (75 mg) as colorless crystals.

m.p.:307° C. (Decomp.)(methanol-ethyl acetate); NMR (DMSO-d$_6$)δ: 3.77(3H, s), 3.87(3H, s), 4.37(2H, s), 7.00–7.25(3H, m), 7.40–7.70(3H, m), 8.16(1H, d, J=9 Hz), 9.13(1H, s); IR(KBr): 3186, 3101, 1716, 1687, 1608, 1508, 1463, 1253, 1230 cm$^{-1}$; Elemental Analysis for C$_{19}$H$_{16}$N$_2$O$_3$.0.2H$_2$O Calcd.: C:70.45%, H:5.10%, N:8.65%; Found: C:70.22%, H:5.04%, N:6.54%.

EXAMPLE 120

9-(4-Fluorophenyl)-1,2-dihydro-7-methoxy-3H-pyrrolo[3,4-b]quinolin-3-one

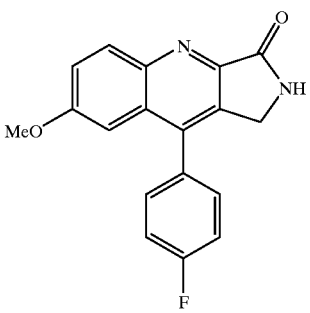

The entitled compound was obtained in a manner similar to that described in Example 119.

m.p.:284–286° C. (ethanol-ethyl acetate); NMR(CDCl$_3$) δ: 3.79(3H, s), 4.42(2H, s), 6.96(1H, m), 7.10–7.60(4H, m), 7.96(1H, brs), 8.29(1H, d, J=9 Hz); IR(KBr): 3280, 1733, 1625, 1506, 1463, 1232 cm$^{-1}$; Elemental Analysis for C$_{18}$H$_{11}$N$_2$O$_3$F.0.2H$_2$O Calcd.: C:66.34%, H:3.53%, N:8.60%; Found: C:66.70%, H:3.95%, N:8.60%.

EXAMPLE 121

1,2-Dihydro-7-methoxy-9-(4-trifluoromethylphenyl)-3H-pyrrolo[3,4-b]quinolin-3-one

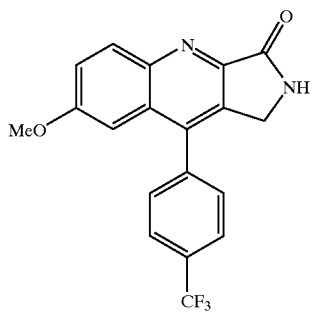

The entitled compound was obtained in a manner similar to that described in Example 119.

m.p.:305° C. (Decomp.)(THF-ethyl acetate); NMR (CDCl$_3$)δ: 3.80(3H, s), 4.41(2H, s), 6.91(1H, m), 7.20–7.65 (4H, m), 7.75–8.00(2H, m), 8.34(1H, d, J=9 Hz); IR(KBr): 3199, 1727, 1684, 1627, 1507, 1326, 1234 cm$^{-1}$; Elemental Analysis for C$_{19}$H$_{13}$N$_2$O$_2$F$_3$.0.4H$_2$O Calcd.: C:62.43%, H:3.81%, N:7.66%; Found: C:61.98%, H:3.47%, N:7.55%.

EXAMPLE 122

3,4-Dihydro-7-methoxy-5-(4-methoxyphenyl)-benzo[b][1,7)naphthyridine-1(2H)-one

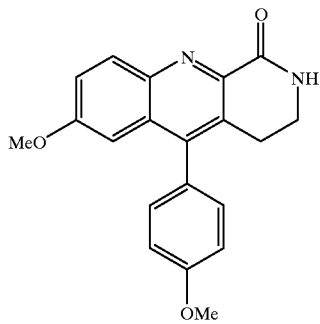

The entitled compound was obtained in a manner similar to that described in Example 119.

m.p.:287–288° C.; NMR(CDCl$_3$)δ: 2.95 (2H, d, J=6 Hz), 3.56 (2H, m), 3.74 (3H, s), 3.93 (3H, s), 6.77 (1H, d, J=3 Hz), 7.09 (2H, d, J=8 Hz), 7.23 (2H, d, J=8 Hz), 7.37 (1H, dd, J=3 Hz,9 Hz), 7.73 (1H, brs), 8.30 (1H, d, J=9 Hz); IR(KBr): 3257, 2995, 2952, 2873, 2831, 1695, 1662, 1616 cm$^{-1}$; Elemental Analysis for C$_{20}$H$_{18}$N$_2$O0.3H$_2$O Calcd.: C:70.57%, H:5.46%, N:8.23%; Found: C:70.44%, H:5.46%, N:7.83%.

EXAMPLE 123

Methyl (8,9-Dihydro-10-(4-methoxyphenyl)-7H-1,3-benzodioxolo[4,5-f]isoindol-7,9-dion-8-yl]acetate

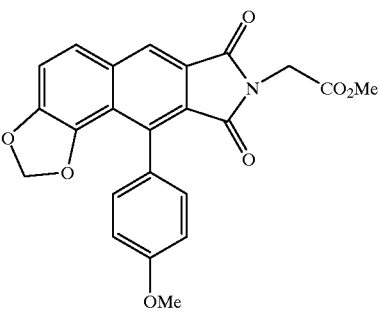

To a DMF (50 ml) solution of 8,9-dihydro-10-(4-methoxyphenyl)-7H-1,3-benzodioxolo[4,5-f]isoindol-7,9-dione (2.0 g) was added sodium hydride (60% in oil:0.3 g) under ice cooling and stirred for 1 hour at room temperature. To the mixture was added methyl bromoacetate (0.65 ml) and stirred for 1 hour at room temperature. To the reaction mixture was added water and extracted with ethyl acetate. The extract was washed with water and dried with magnesium sulfate, then the solvent was distilled off under reduced pressure to give the entitled compound (1.8 g) as yellow crystals.

m.p.:253–255° C. (THF-ethyl acetate); NMR(CDCl$_3$)δ: 3.73 (3H, s), 3.89 (3H, s), 4.37 (2H, s), 5.91 (2H, s), 6.97 (2H, d, J=9 Hz), 7.32 (2H, d, J=9 Hz), 7.35 (1H, d, J=8 Hz), 7.68 (1H, d, J=8 Hz), 8.30 (1H, s); IR(KBr): 2954, 2904, 1756, 1750, 1713, 1616, 1513 cm$^{-1}$; Elemental Analysis for C$_{23}$H$_{17}$NO$_7$ Calcd.: C:65.87%, H:4.09%, N:3.34%; Found: C:65.38%, H:4.16%, N:3.43%.

EXAMPLE 124

10-(1,3-Benzodioxol-5-yl)-8,9-dihydro-8-(2-pyridyl)-7H-1,3-benzodioxolo[4,5-f]isoindol-7-one

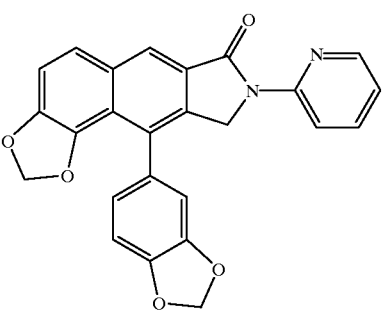

To a solution of 10-(1,3-Benzodioxol-5-yl)-8,9-dihydro-7H-1,3-benzodioxolo[4,5-f]isoindol-7-one (200 mg), which was obtained in Example 1, in DMF (5 ml) were added 2-bromopyridine (0.11 ml), CuI (121 mg), and potassium carbonate (159 mg). The reaction mixture was stirred overnight at 120° C. To the reaction mixture was added concentrated NH$_4$OH, and resultant precipitates were collected by suction. The precipitates were washed with methanol and ether, and then recrystallized from THF and ethanol to give the entitled compound (78 mg).

m.p.:305° C. (decomp.); NMR(DMSO-d$_6$)δ: 5 4.91(2H, s), 5.99(1H,d,J=1.0 Hz), 6.01(1H,d,J=1.0 Hz), 6.11(1H,d,J= 1.0 Hz), 6.16(1H,d,J=1.0 Hz), 6.94(1H,dd,J=1.6 Hz,8 Hz), 7.03(1H,d,J=8 Hz), 7.09(1H,d,J=1.6 Hz), 7.15–7.23(1H,m), 7.47(1H,d,J=9 Hz), 7.85–7.95(1H,m), 7.92(1H,d,J=9 Hz), 8.40(1H,m), 8.50(1H,s), 8.59(1H,d,J=8 Hz).

EXAMPLE 125

4-(1,3-Benzodioxol-5-yl)-5,7-dimethoxy-1H-benz[f]isoindol-1,3(2H)-dione

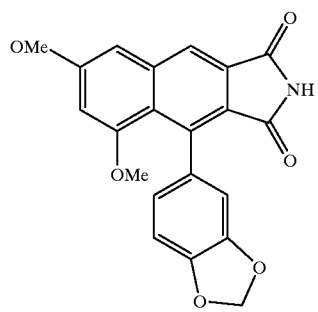

The entitled compound was obtained in a manner similar to that described in Example 14.

m.p.:265–267° C.; NMR(DMSO-d$_6$)δ: 3.51(3H,s), 3.97 (3H,s), 6.03(1H,brs), 6.05(1H,brs), 6.57(1H,d,J=2 Hz), 6.69 (1H,dd,J=1.6 Hz,8 Hz), 6.75(1H,d,J=1.6 Hz), 6.87(1H,d,J=8 Hz), 6.96(1H,d,J=2 Hz), 7.59(1H,brs), 8.16(1H,s); IR(KBr): 1756, 1718, 1610, 1361, 1312, 1232, 1212 cm$^{-1}$; Elemental Analysis for C$_{21}$H$_{15}$NO$_6$.0.4H$_2$O Calcd.: C:65.59%, H:4.14%, N:3.64%; Found: C:65.59%, H:4.30%, N:3.59%.

EXAMPLE 126

4-(1,3-Benzodioxol-5-yl)-2,3-dihydro-5,7-dimethoxy-1H-benz[f]isoindol-1-one

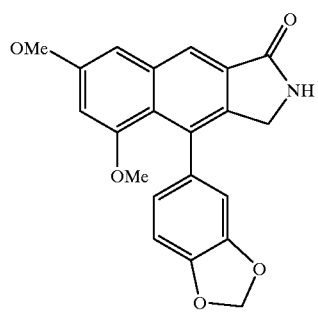

The entitled compound was obtained in a manner similar to that described in Example 53.

m.p.:252–254° C. (MeOH); NMR(CDCl$_3$)δ: 3.52(3H,s), 3.95(3H,s), 6.03(1H,brs), 4.15(1H,d,J=17 Hz), 4.22(1H,d,J= 17 Hz), 6.02(1H,brs), 6.03(1H,brs) 6.29(1H,brs), 6.54(1H, d,J=2 Hz), 6.68(1H,dd,J=1.8 Hz,8 Hz), 6.73(1H,d,J=1.8 Hz), 6.85(1H,d,J=8 Hz), 6.93(1H,d,J=2 Hz), 8.23(1H,s); IR(KBr): 1697, 1617, 1486, 1230, 1214, 1162 cm$^{-1}$;

Elemental Analysis for C$_{21}$H$_{17}$NO$_5$.0.6H$_2$O Calcd.: C:67.41%, H:4.90%, N:3.74%; Found: C:67.31%, H:4.79%, N:3.52%.

EXAMPLE 127

9-(1,3-Benzodioxol-5-yl)-6H-1,3-benzodioxolo[5,6-f]isoindol-6,8(7H)-dione

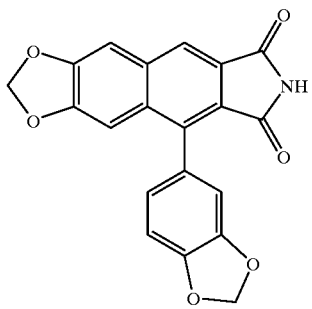

The entitled compound was obtained in a manner similar to that described in Example 14.

m.p.:299–301° C. (decomp.)(THF); NMR(CDCl$_3$)δ: 6.09 (2H,m), 6.13(2H,m), 6.81(2H,m), 6.98(1H,d,J=8 Hz), 7.14 (1H,s), 7.34(1H,s), 8.08(1H,brs), 8.16(1H,s); IR(KBr): 3168, 2920, 2783, 1768, 1724 cm$^{-1}$; Elemental Analysis for C$_{20}$H$_{11}$NO$_6$ Calcd.: C:66.49%, H:3.07%, N:3.88%; Found: C: 65.96%, H:3.33%, N:3.55%.

EXAMPLE 128

9-(1,3-Benzodioxol-5-yl)-7,8-dihydro-6H-1,3-benzodioxolo[5,6-f]isoindol-6-one

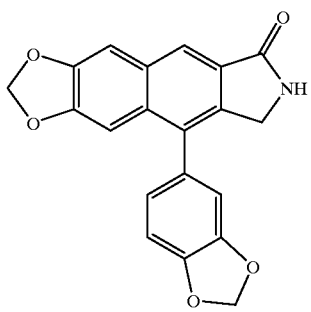

The entitled compound was obtained in a manner similar to that described in Example 53.

NMR(CDCl$_3$)δ: 4.31(2H,s), 6.07(2H,s), 6.08(2H,s), 6.53 (1H,brs), 6.80(2H,m), 6.96(1H,d,J=8 Hz), 7.05(1H,s), 7.31 (1H,s), 8.22(1H,s).

EXAMPLE 129

11-(4-Fluorophenyl)-7,8,9,10-tetrahydro-6-methyl-1,3-benzodioxolo[4,5-g]isoquinolin-7-one

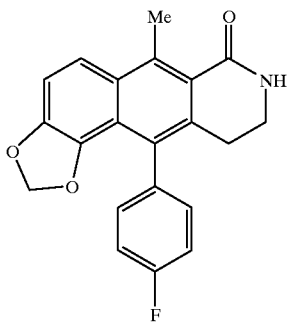

The entitled compound was obtained in a manner similar to that described in Example 11 from methyl 8-cyanomethyl-9-(p-fluorophenyl)-6-methylnaphtho[1,2-d]-1,3-dioxol-7-carboxylate, which was obtained in Reference Example 28.

m.p.:237–240° C.; NMR(CDCl$_3$)δ: 2.69(2H,t,J=6 Hz), 3.08(3H,s), 3.28–3.38(2H,m), 5.77(2H,s), 6.16(1H,brs), 7.04–7.27(5H,m), 7.88(1H,d,J=9 Hz); IR(KBr): 3202, 1659, 1507, 1447, 1285, 1069 cm$^{-1}$;

EXAMPLE 130

11-(4-Fluorophenyl)-7,8,9,10-tetrahydro-1,3-benzodioxolo[4,5-g]isoquinolin-7-one

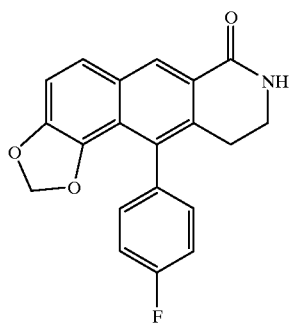

The entitled compound was obtained in a manner similar to that described in Example 11, from 8-cyanomethyl-9-(p-fluorophenyl)-naphtho[1,2-d]-1,3-dioxol-7-carboxylic acid, which was obtained in Reference Example 29.

m.p.:285–286 C.; NMR(CDCl$_3$)δ: 2.78(2H,t,J=6 Hz), 3.48(2H,dt,J=3 Hz,6 Hz), 5.80(2H,s), 6.16(1H,m), 7.05–7.30(5H,m), 7.61(1H,d,J=9 Hz), 8.65(1H,s); IR(KBr): 1672, 1630, 1505, 1481, 1454, 1282, 1074 cm$^{-1}$;

EXAMPLE 131

11-(1,3-Benzodioxol-5-yl)-7,8,9,10-tetrahydro-6-methyl-1,3-benzodioxolo[4,5-g]isoquinolin-7-one

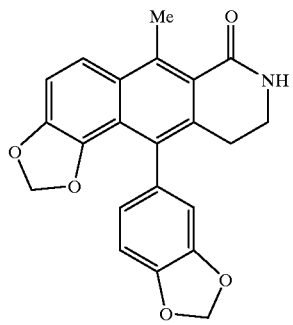

The entitled compound was obtained in a manner similar to that described in Example 11 from methyl 8-cyanomethyl-9-(1,3-benzodioxol-5-yl)-6-methylnaphtho[1,2-d]-1,3-dioxol-7-methylcarboxylate, which was obtained in Reference Example 30.

m.p.:239–241° C.; NMR(CDCl$_3$)δ: 2.74(2H,t,J=6 Hz), 3.30–3.40(2H,m), 5.82(1H,d,J=1.4 Hz), 5.83(1H,d,J=1.4 Hz), 6.02(1H,d,J=1.4 Hz), 6.06(1H,d,J=1.4 Hz), 6.67(1H,dd,J=1.4 Hz,8 Hz), 6.72(1H,d,J=1.4 Hz), 6.85(1H,d,J=8 Hz), 7.21(1H,d,J=,9 Hz), 7.87(1H,d,J=9 Hz); IR(KBr): 1655, 1489, 1437, 1287, 1233, 1065, 1039 cm$^{-1}$;

EXAMPLE 132

11-(4-Fluorophenyl)-8H-isoindolo[5,6-f]benz[b]-1,4-dioxan-8,10(9H)-dione

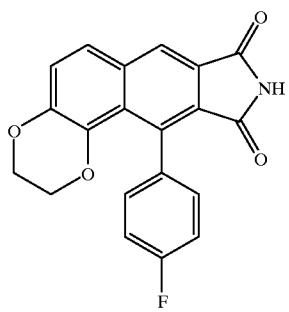

The entitled compound was obtained in a manner similar to that described in Example 14.

m.p.:274–276° C. (THF); NMR(CDCl$_3$)δ: 3.89(2H,m), 4.23(2H,m), 7.09(2H,t,J=9 Hz), 7.26(3H,m), 7.60(1H,d,J=9 Hz), 7.68(1H,brs), 8.25(1H,s); IR(KBr): 3214, 1759, 1717, 1605, 1508 cm$^{-1}$; Elemental Analysis for C$_{20}$H$_{12}$FNO$_4$ Calcd.: C:68.77%, H:3.46%, N:4.01%; Found: C:68.56%, H:3.24%, N:3.75%.

EXAMPLE 133

11-(4-Fluorophenyl)-9,10-dihydro-8H-isoindolo[5,6-f]benz[b]-1,4-dioxan-8-one

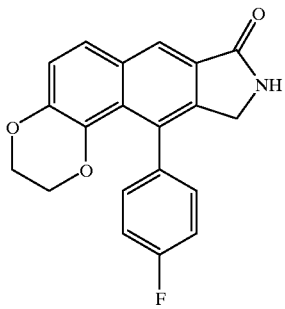

The entitled compound was obtained in a manner similar to that described in Example 53.

m.p.:276–278° C. (THF); NMR(CDCl$_3$)δ: 3.91(2H,m), 4.17(2H,s), 4.23(2H,m), 6.96(1H,brs), 7.09(2H,t,J=9 Hz), 7.21(3H,m), 7.59(1H,d,J=9 Hz), 8.31(1H,s); IR(KBr): 3196, 3086, 2890, 1694, 1617, 1508 cm$^{-1}$; Elemental Analysis for C$_{20}$H$_{14}$FNO$_3$ Calcd.: C:71.64%, H:4.21%, N:4.18%; Found: C:71.08%, H:4.60%, N:3.84%.

EXAMPLE 134

10-(1,3-Benzodioxol-5-yl)-2,3-dihydro-7H-benzofuro-[6,7-f]isoindol-7,9(8H)-dione

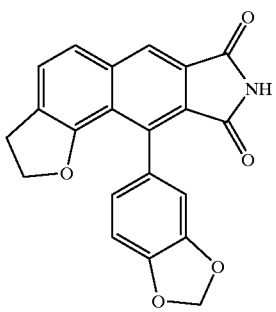

The entitled compound was obtained in a manner similar to that described in Example 14.

m.p.:>320° C. (THF); NMR(DMSO-d$_6$)δ: 3.26(2H,t,J=10 Hz), 4.39(2H,t,J=10 Hz), 6.09(2H,d,J=4 Hz), 6.71(1H,d,J=9 Hz), 6.86(1H,s), 6.88(1H,d,J=9 Hz), 7.66(1H,d,J=8 Hz), 7.78(1H,d,J=8 Hz), 8.37(1H,s), 11.30(1H,brs); IR(KBr): 3194, 3071, 2899, 1752, 1711 cm$^{-1}$; Elemental Analysis for C$_{21}$H$_{13}$NO$_5$.0.3H$_2$O Calcd.: C:69.04%, H:3.77%, N:3.83%; Found: C:68.82%, H:3.81%, N:4.01%.

EXAMPLE 135

10-(1,3-Benzodioxol-5-yl)-2,3-dihydrobenzofuro-[6,7-f]isoindol-7(9H)-one

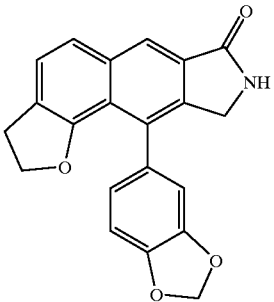

The entitled compound was obtained in a manner similar to that described in Example 53.

m.p.:275–277° C. (THF); NMR(CDCl$_3$)δ: 3.29(2H,t,J=9 Hz), 4.23(1H,d,J=17 Hz), 4.34(1H,d,J=17 Hz), 4.46(2H,t, J=9 Hz), 6.05(2H,t,J=6 Hz), 6.76(2H,m),6.87(1H,d,J=8 Hz), 7.32(1H,brs), 7.43(1H,d,J=8 Hz), 7.60(1H,d,J=8 Hz), 8.35 (1H,s); IR(KBr): 3225, 2892, 1698, 1489 cm$^{-1}$; Elemental Analysis for C$_{21}$H$_{15}$NO$_4$.0.12H$_2$O Calcd.: C:72.28%, H:4.45%, N:4.01%; Found: C:72.25%, H:4.47%, N:3.93%.

EXAMPLE 136

10-(4-Fluorophenyl)-2,3-dihydro-7H-benzofuro-[6,7-f]isoindol-7,9(8H)-dione

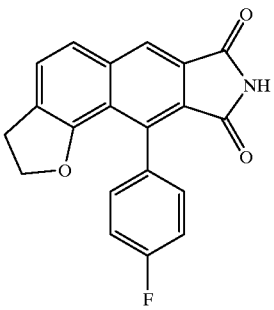

The entitled compound was obtained in a manner similar to that described in Example 14.

m.p.: >310° C. (THF); NMR(CDCl$_3$)δ: 3.29(2H,t,J=9 Hz), 4.42(2H,t,J=9 Hz), 7.12(2H,t,J=9 Hz), 7.27(2H,m), 7.56(1H,d,J=8 Hz), 7.63(1H,d,J=8 Hz), 7.69(1H,brs), 8.32 (1H,s). IR(KBr): 3193, 3052, 1767, 1721, 1508 cm$^{-1}$; Elemental Analysis for C$_{20}$H$_{12}$FNO$_3$.0.2H$_2$O Calcd.: C:71.30%, H:3.71%, N:4.16%; Found: C:70.93%, H:4.09%, N:3.82%.

EXAMPLE 137

10-(4-Fluorophenyl)-2,3-dihydrobenzofuro-[6,7-f]isoindol-7(9H)-one

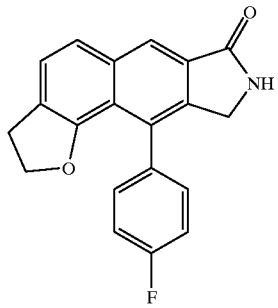

The entitled compound was obtained in a manner similar to that described in Example 53.

m.p.:302–305° C. (THF); NMR(CDCl$_3$)δ: 3.29(2H,J=9 Hz), 4.24(2H,s), 4.42(2H,t,J=9 Hz), 6.42(1H,brs), 7.12(3H, t,J=9 Hz), 7.29(2H,t,J=9 Hz), 7.44(1H,d,J=8 Hz), 7.62(1H, d,J=8 Hz), 8.38(1H,s); IR(KBr): 3194, 3085, 2894, 1713, 1694, 1508 cm$^{-1}$; Elemental Analysis for C$_{20}$H$_{14}$FNO$_2$ Calcd.: C:75.23%, H:4.42%, N:4.39%; Found: C:74.78%, H:4.40%, N:4.34%

EXAMPLE 138

6,7-Diethoxy-4-(4-pyridyl)-1H-benz[f]isoindol-1,3(2H)-dione

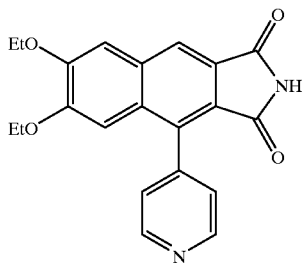

The entitled compound was obtained in a manner similar to that described in Example 46.

m.p.:210–213° C. (CHCl$_3$, AcOEt); NMR(DMSO-d$_6$)δ: 1.43(3H,t,J=7 Hz), 1.58(3H,t,J=7 Hz), 3.95(2H,q,J=7 Hz), 4.29(2H,q,J=7 Hz), 6.88(1H,s), 7.20–7.40(3H,m), 8.22(1H, s), 8.82(2H,m).

EXAMPLE 139

2,3-Dihydro-6,7-diethoxy-4-(4-pyridyl)-1H-benz[f]isoindol-1-one

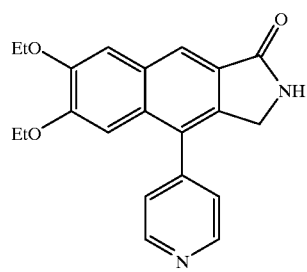

The entitled compound was obtained in a manner similar to that described in Example 53.

m.p.:169–172 C. (EtOH-Et$_2$O); NMR(DMSO-d$_6$)δ: 1.34 (3H,t,J=7 Hz), 1.46(3H,t,J=7 Hz), 3.88(2H,q,J=7 Hz), 4.18 (2H,q,J=7 Hz), 4.21(2H,s), 6.74(1H,brs), 6.79(1H,s), 7.17 (1H,s), 7.30(2H,brs), 8.17(1H,s), 8.73(1H,brs).

EXAMPLE 140

11-(4-Fluorophenyl)-7,8,9,10-tetrahydro-6-methyl-1,3-benzodioxolo[4,5-g]isoquinolin-7-one

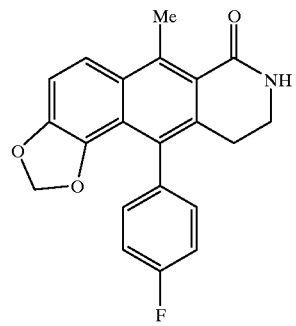

The entitled compound was obtained in a manner similar to that described in Example 11.

m.p.:237–240° C. (decomp.)(THF); NMR(DMSO-d$_6$)δ: 2.69(2H,t,J=6 Hz), 3.08(3H,s), 3.28–3.38(2H,m), 5.77(2H, s), 6.16(1H,brs), 7.04–7.27(5H,m), 7.88(1H,d,J=9 Hz); IR(KBr): 3200, 1659, 1507, 1287, 1069 cm$^{-1}$;

EXAMPLE 141

7,8,9,10-Tetrahydro-11-(4-methoxyphenyl)-1,3-benzodioxolo[4,5-g]isoquinolin-7-one

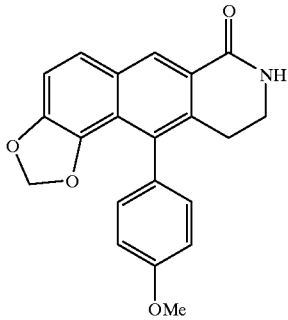

The entitled compound was obtained in a manner similar to that described in Example 11.

m.p.:245–247° C. (CHCl$_3$); NMR(DMSO-d$_6$)δ: 2.80(2H, t,J=7 Hz), 3.47(2H,dt,J=2 Hz,7 Hz), 3.90(3H,s), 5.81(2H,s), 6.20(2H,brs), 6.96(2H,d,J=9 Hz), 7.15–7.23(3H,m), 7.60 (1H,d,J=9 Hz), 8.63(1H,s); IR(KBr): 2890, 1669, 924 cm$^{-1}$;

EXAMPLE 142

7,8,9,10-Tetrahydro-11-(4-trifluoromethylphenyl)-1,3-benzodioxolo[4,5-g]isoquinolin-7-one

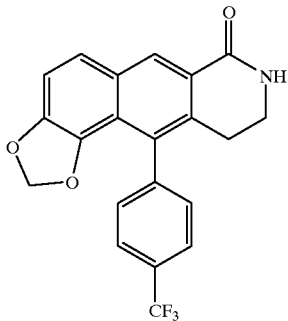

The entitled compound was obtained in a manner similar to that described in:Example 11.

m.p.:246–248° C.; NMR(DMSO-d$_6$)δ: 2.74(2H,t,J=6 Hz),3.48(2H,dt,J=3 Hz,6 Hz), 5.78(2H,s), 6.22(1H,brs), 7.21(1H,d,J=8 Hz), 7.40(2H,d,J=8 Hz), 7.62(1H,d,J=8 Hz), 7.68(2H,d,J=8 Hz), 8.68(1H,s); IR: 1672, 1456, 1325, 1071 cm$^{-1}$;

EXAMPLE 143

10-(1,3-Benzodioxol-5-yl)-8,9-dihydro-8-methoxy-7H-1,3-benzodioxolo[4,5-f]isoindol-7-one

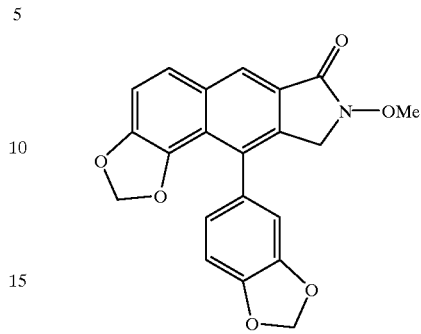

To a solution of methyl 9-(1,3-benzodioxol-5-yl)-8-methanesulfonyloxymethylnaphtho[1,2-d]-1,3-dioxole-7-carboxylate (400 mg), which was obtained in reference example 14, in DMF (4 ml) were added O-methylhydroxylamine hydrochloride (219 mg) and potassium carbonate (362 mg). The reaction mixture was stirred for 1 hour at room temperature and for 5 hours at 60° C. To the reaction mixture was added water. The resultant precipitates were collected by suction and dissolved in ethyl acetate. The solution was washed with brine, dried over magnesium sulfate, and concentrated under reduced pressure. The residue was purified by column chromatography (silica gel:30 g, eluent:ethyl acetate-hexane=1:2) and then recrystallized from ethyl acetate to give the entitled compound (130 mg).

m.p.:214–216° C.; NMR(DMSO-d$_6$)δ: 3.95(3H,s), 4.42 (1H,d,J=16 Hz), 4.49(1H,d,J=16 Hz), 5.92(1H,d,J=1.4 Hz), 5.94(1H,d,J=1.4 Hz), 6.05(1H,d,J=1.4 Hz), 6.08(1H,d,J=1.4 Hz), 6.78–6.94(3H,m), 7.27(1H,d,J=9 Hz), 7.65(1H,d,J=9 Hz), 8.33(1H,s); IR(KBr): 1713, 1489, 1458, 1439, 1273, 1235, 1063 cm$^1$; Elemental analysis for C$_{21}$H$_{15}$NO$_6$ Calcd.: C:66.84%, H:4.01%, N:3.71%; Found: C:66.73%, H:3.97%, N:3.66%.

Test Example 1

Induction of Alkaline Phosphatase (ALP) Production in Cultured Murine Osteoblasts The mouse-derived osteoblast cell line MC3T3-E1 in 10% fetal calf serum (FCS)-α-minimum essential medium (MEM) were seeded in a 96-well microtiter plate (8×10$^3$ cells/well). After 2 days when the growth had become confluent, the test substance diluted to various concentrations [Table 1] with the medium either containing or not containing 3 ng/ml of BMP-4/7 heterodimer (described in Japanese Patent Publication (Kokai) No. H7–265083) was added and the microtiter plate was further incubated for 72 hours. After the plate was washed once with phosphate buffered saline, the substrate solution was added and the plate was further incubated at room temperature for 15 minutes. The reaction was stopped by adding 0.05 N-sodium hydroxide and the absorbance at 405 nm was measured. It was found that, as shown in Tables 1–6, the compound of the invention enhances BMP activity, that is to say the induction of ALP production by BMP and that, regardless of the presence or absence of BMP, the compound of the invention by itself shows high ALP production inducing activity.

TABLE 1

Induction of alkaline phosphatase (ALP) production in mouse osteoblast cell line MC3T3-E1

| Example No. | Concentration of compound (μM) | ALP activity (1000 × A$_{405}$ ± SD) With BMP | Without BMP |
|---|---|---|---|
| 1 | 1 | 218 ± 38 | 133 ± 12* |
| | 0.1 | 515 ± 1* | 224 ± 9* |
| | 0.01 | 670 ± 24* | 227 ± 17* |
| | 0 (blank control) | 253 ± 4 | 64 ± 3 |
| 2 | 1 | 523 ± 29* | 172 ± 6* |
| | 0.1 | 587 ± 23* | 162 ± 18* |
| | 0.01 | 414 ± 29* | 112 ± 12* |
| | 0 (blank control) | 341 ± 23 | 74 ± 11 |
| 9 | 1 | 378 ± 39* | 199 ± 68 |
| | 0.1 | 306 ± 48* | 166 ± 71 |
| | 0.01 | 296 ± 34* | 152 ± 42 |
| | 0 (blank control) | 213 ± 34 | 106 ± 24 |
| 10 | 1 | 169 ± 37 | 80 ± 36 |
| | 0.1 | 402 ± 52* | 190 ± 33* |
| | 0.01 | 348 ± 34* | 171 ± 51 |
| | 0 (blank control) | 213 ± 34 | 106 ± 24 |
| 11 | 1 | 335 ± 13* | 214 ± 19* |
| | 0.1 | 630 ± 25* | 327 ± 16* |
| | 0.01 | 571 ± 34* | 251 ± 21* |
| | 0 (blank control) | 177 ± 10 | 76 ± 3 |
| 12 | 1 | 782 ± 10* | 362 ± 3* |
| | 0.1 | 699 ± 40* | 323 ± 18* |
| | 0.01 | 504 ± 78 | 236 ± 14 |
| | 0 (blank control) | 542 ± 25 | 213 ± 7 |
| 13 | 1 | 705 ± 27* | 341 ± 10* |
| | 0.1 | 603 ± 31* | 235 ± 17* |
| | 0.01 | 414 ± 8 | 181 ± 1 |
| | 0 (blank control) | 374 ± 21 | 139 ± 10 |
| 14 | 1 | 615 ± 7* | 307 ± 19* |
| | 0.1 | 673 ± 28* | 297 ± 5* |
| | 0.01 | 475 ± 16 | 223 ± 7* |
| | 0 (blank control) | 457 ± 16 | 195 ± 10 |

TABLE 2

| | | | |
|---|---|---|---|
| 31 | 1 | 714 ± 41* | 240 ± 10* |
| | 0.1 | 429 ± 4* | 160 ± 16 |
| | 0.01 | 319 ± 12 | 115 ± 1* |
| | 0 (blank control) | 295 ± 10 | 87 ± 3 |
| 53 | 1 | 453 ± 65 | 312 ± 31 |
| | 0.1 | 771 ± 35* | 393 ± 11* |
| | 0.01 | 819 ± 55* | 421 ± 8* |
| | 0 (blank control) | 492 ± 28 | 244 ± 5 |
| 55 | 1 | 1211 ± 54* | 422 ± 27* |
| | 0.1 | 751 ± 8* | 261 ± 9* |
| | 0.01 | 567 ± 10* | 205 ± 9* |
| | 0 (blank control) | 406 ± 28 | 149 ± 3 |
| 58 | 1 | 1082 ± 37* | 666 ± 15* |
| | 0.1 | 1018 ± 37* | 654 ± 22* |
| | 0.01 | 1005 ± 29* | 602 ± 65 |
| | 0 (blank control) | 709 ± 9 | 468 ± 11 |
| 59 | 1 | 1177 ± 32* | 482 ± 22* |
| | 0.1 | 1527 ± 57* | 601 ± 30* |
| | 0.01 | 956 ± 49* | 278 ± 17* |
| | 0 (blank control) | 399 ± 56 | 182 ± 3 |
| 60 | 1 | 1118 ± 46* | 430 ± 24* |
| | 0.1 | 1746 ± 106* | 574 ± 39* |
| | 0.01 | 1214 ± 61* | 314 ± 15* |
| | 0 (blank control) | 762 ± 51 | 202 ± 9 |
| 61 | 1 | 890 ± 21* | 276 ± 13* |
| | 0.1 | 597 ± 42* | 169 ± 6* |
| | 0.01 | 488 ± 19 | 147 ± 6 |
| | 0 (blank control) | 464 ± 16 | 155 ± 3 |
| 62 | 1 | 1663 ± 87* | 683 ± 13* |
| | 0.1 | 810 ± 69* | 235 ± 3* |
| | 0.01 | 667 ± 40 | 173 ± 10 |
| | 0 (blank control) | 678 ± 52 | 171 ± 9 |
| 63 | 1 | 1130 ± 37* | 688 ± 28* |
| | 0.1 | 1575 ± 24* | 599 ± 26* |
| | 0.01 | 1355 ± 76* | 469 ± 11* |
| | 0 (blank control) | 817 ± 35 | 211 ± 9 |

TABLE 3

| | | | |
|---|---|---|---|
| 64 | 1 | 453 ± 21* | 169 ± 10* |
| | 0.1 | 648 ± 17* | 194 ± 2* |
| | 0.01 | 692 ± 33* | 187 ± 6* |
| | 0 (blank control) | 420 ± 32 | 124 ± 3 |
| 65 | 1 | 354 ± 9 | 233 ± 12* |
| | 0.1 | 1427 ± 55* | 450 ± 6* |
| | 0.01 | 1513 ± 127* | 501 ± 14* |
| | 0 (blank control) | 795 ± 163 | 182 ± 2 |
| 66 | 1 | 803 ± 19 | 197 ± 5* |
| | 0.1 | 1460 ± 123* | 324 ± 6* |
| | 0.01 | 1587 ± 127* | 422 ± 10* |
| | 0 (blank control) | 780 ± 22 | 422 ± 10 |
| 67 | 1 | 261 ± 7 | 125 ± 3* |
| | 0.1 | 312 ± 9* | 142 ± 1* |
| | 0.01 | 427 ± 68* | 177 ± 11 |
| | 0 (blank control) | 244 ± 10 | 108 ± 4 |
| 68 | 1 | 348 ± 18* | 227 ± 6* |
| | 0.1 | 640 ± 7* | 355 ± 19* |
| | 0.01 | 419 ± 22* | 189 ± 12* |
| | 0 (blank control) | 152 ± 6 | 72 ± 6 |
| 69 | 1 | 298 ± 21* | 185 ± 7* |
| | 0.1 | 593 ± 21* | 309 ± 4* |
| | 0.01 | 671 ± 48* | 383 ± 12* |
| | 0 (blank control) | 152 ± 6 | 72 ± 6 |
| 70 | 1 | 598 ± 26* | 385 ± 27* |
| | 0.1 | 309 ± 10* | 162 ± 4* |
| | 0.01 | 199 ± 13* | 98 ± 2* |
| | 0 (blank control) | 158 ± 7 | 83 ± 4 |
| 72 | 1 | 433 ± 21 | 178 ± 8 |
| | 0.1 | 1543 ± 18* | 510 ± 21* |
| | 0.01 | 1610 ± 50* | 464 ± 12* |
| | 0 (blank control) | 745 ± 39 | 214 ± 12 |
| 73 | 1 | 805 ± 26* | 467 ± 4 |
| | 0.1 | 884 ± 43* | 538 ± 14* |
| | 0.01 | 974 ± 10* | 598 ± 33* |
| | 0 (blank control) | 695 ± 37 | 467 ± 19 |

TABLE 4

| | | | |
|---|---|---|---|
| 75 | 1 | 908 ± 12* | 313 ± 10* |
| | 0.1 | 1098 ± 45* | 294 ± 16* |
| | 0.01 | 974 ± 54* | 297 ± 7* |
| | 0 (blank control) | 451 ± 23 | 149 ± 4 |
| 76 | 1 | 586 ± 39* | 293 ± 9* |
| | 0.1 | 914 ± 36* | 359 ± 24* |
| | 0.01 | 1049 ± 10* | 478 ± 35* |
| | 0 (blank control) | 324 ± 8 | 101 ± 5 |
| 77 | 1 | 638 ± 36* | 356 ± 8* |
| | 0.1 | 886 ± 32* | 446 ± 20* |
| | 0.01 | 711 ± 32* | 347 ± 19* |
| | 0 (blank control) | 334 ± 29 | 135 ± 2 |
| 78 | 1 | 617 ± 54* | 358 ± 23* |
| | 0.1 | 555 ± 18* | 316 ± 6* |
| | 0.01 | 247 ± 16* | 125 ± 2* |
| | 0 (blank control) | 161 ± 7 | 79 ± 2 |
| 79 | 1 | 586 ± 12* | 306 ± 3* |
| | 0.1 | 662 ± 27* | 332 ± 14* |
| | 0.01 | 320 ± 43 | 136 ± 5* |
| | 0 (blank control) | 161 ± 7 | 79 ± 2 |
| 80 | 1 | 379 ± 80* | 224 ± 8* |
| | 0.1 | 201 ± 11* | 98 ± 6 |
| | 0.01 | 168 ± 8 | 82 ± 8 |
| | 0 (blank control) | 158 ± 8 | 83 ± 5 |
| 81 | 1 | 437 ± 30* | 175 ± 17* |
| | 0.1 | 611 ± 61* | 232 ± 2* |

TABLE 4-continued

|  |  |  |  |
|---|---|---|---|
|  | 0.01 | 483 ± 26* | 164 ± 12* |
|  | 0 (blank control) | 216 ± 3 | 67 ± 2 |
| 82 | 1 | 393 ± 11* | 177 ± 12* |
|  | 0.1 | 647 ± 34* | 264 ± 17* |
|  | 0.01 | 571 ± 6* | 206 ± 24* |
|  | 0 (blank control) | 201 ± 15 | 60 ± 4 |
| 83 | 1 | 352 ± 16* | 200 ± 10* |
|  | 0.1 | 585 ± 30* | 264 ± 4* |
|  | 0.01 | 639 ± 57* | 248 ± 22* |
|  | 0 (blank control) | 229 ± 19 | 71 ± 4 |

TABLE 5

|  |  |  |  |
|---|---|---|---|
| 87 | 1 | 293 ± 24 | 149 ± 8* |
|  | 0.1 | 400 ± 34* | 153 ± 12* |
|  | 0.01 | 328 ± 8* | 103 ± 8* |
|  | 0 (blank control) | 174 ± 2 | 45 ± 1 |
| 89 | 1 | 416 ± 30* | 109 ± 30* |
|  | 0.1 | 382 ± 26* | 90 ± 10* |
|  | 0.01 | 232 ± 14* | 47 ± 6 |
|  | 0 (blank control) | 151 ± 3 | 37 ± 3 |
| 90 | 1 | 87 ± 1 | 87 ± 1 |
|  | 0.1 | 368 ± 28 | 135 ± 6 |
|  | 0.01 | 535 ± 19* | 166 ± 7* |
|  | 0 (blank control) | 420 ± 32 | 124 ± 3 |
| 91 | 1 | 424 ± 4* | 276 ± 1* |
|  | 0.1 | 612 ± 28* | 326 ± 3* |
|  | 0.01 | 322 ± 11 | 119 ± 4* |
|  | 0 (blank control) | 158 ± 7 | 83 ± 4 |
| 93 | 1 | 183 ± 7* | 116 ± 1* |
|  | 0.1 | 641 ± 16* | 200 ± 6* |
|  | 0.01 | 675 ± 82* | 175 ± 10* |
|  | 0 (blank control) | 486 ± 18 | 132 ± 3 |
| 94 | 1 | 1487 ± 27* | 493 ± 12* |
|  | 0.1 | 925 ± 50* | 274 ± 18* |
|  | 0.01 | 656 ± 27* | 196 ± 9* |
|  | 0 (blank control) | 486 ± 18 | 153 ± 10 |
| 98 | 1 | 463 ± 38 | 176 ± 6* |
|  | 0.1 | 638 ± 59* | 194 ± 9* |
|  | 0.01 | 617 ± 31* | 181 ± 2* |
|  | 0 (blank control) | 421 ± 36 | 151 ± 3 |
| 99 | 1 | 907 ± 9* | 529 ± 9* |
|  | 0.1 | 903 ± 30* | 539 ± 10* |
|  | 0.01 | 930 ± 1* | 561 ± 6* |
|  | 0 (blank control) | 703 ± 1 | 443 ± 7 |
| 100 | 1 | 937 ± 25 | 539 ± 7* |
|  | 0.1 | 899 ± 31 | 571 ± 15* |
|  | 0.01 | 932 ± 21* | 579 ± 30* |
|  | 0 (blank control) | 703 ± 36 | 443 ± 7 |

TABLE 6

|  |  |  |  |
|---|---|---|---|
| 103 | 1 | 1473 ± 55* | 577 ± 18* |
|  | 0.1 | 1413 ± 21* | 361 ± 15* |
|  | 0.01 | 926 ± 65* | 206 ± 5* |
|  | 0 (blank control) | 678 ± 52 | 171 ± 9 |
| 104 | 1 | 848 ± 66* | 203 ± 4* |
|  | 0.1 | 720 ± 26 | 184 ± 6 |
|  | 0.01 | 748 ± 44 | 172 ± 1 |
|  | 0 (blank control) | 696 ± 31 | 172 ± 9 |
| 105 | 1 | 368 ± 8* | 282 ± 18* |
|  | 0.1 | 300 ± 30* | 153 ± 6* |
|  | 0.01 | 182 ± 10 | 89 ± 2 |
|  | 0 (blank control) | 158 ± 8 | 83 ± 5 |
| 106 | 1 | 589 ± 32 | 243 ± 6* |
|  | 0.1 | 409 ± 25* | 132 ± 5* |
|  | 0.01 | 288 ± 13* | 100 ± 4* |
|  | 0 (blank control) | 215 ± 33 | 69 ± 7 |
| 112 | 1 | 706 ± 39* | 442 ± 8* |
|  | 0.1 | 588 ± 26* | 362 ± 12* |
|  | 0.01 | 464 ± 24* | 303 ± 17 |
|  | 0 (blank control) | 423 ± 16 | 284 ± 7 |
| 113 | 1 | 729 ± 18* | 553 ± 21* |
|  | 0.1 | 613 ± 16* | 472 ± 28* |

TABLE 6-continued

|  |  |  |  |
|---|---|---|---|
|  | 0.01 | 568 ± 22* | 430 ± 18 |
|  | 0 (blank control) | 520 ± 15 | 410 ± 15 |
| 119 | 1 | 1165 ± 82* | 637 ± 35* |
|  | 0.1 | 671 ± 72* | 291 ± 7* |
|  | 0.01 | 395 ± 20 | 163 ± 10* |
|  | 0 (blank control) | 334 ± 23 | 123 ± 4 |
| 124 | 1 | 680 ± 18* | 244 ± 4* |
|  | 0.1 | 558 ± 3 | 193 ± 4* |
|  | 0.01 | 461 ± 29 | 164 ± 3* |
|  | 0 (blank control) | 478 ± 44 | 142 ± 2 |

*: Statistically significant (p<0.05 vs. control; t-test)

Test Example 2

Action on Neurite Extension in the Rat Pheochromocytoma Cell Line

To a suspension of PC12 cells (rat pheochromocytoma cell line; 2000 cells/well) in 10% FCS-Dulbecco's MEM was added NGF (2 ng/ml) as well as the test substance of varying concentration and the mixture was seeded in a 96-well microtiter plate and incubated for 3 days. The medium was then discarded and the cells were stained with hematoxylin-eosin using a commercial kit (Difquick R, Kokusai Shiyaku K.K.). The outgrowth of neurites was observed under the microscope and compared with the drug-free control involving addition of NGF (2 ng/ml) alone. The case in which a definite neurite out growth was observed was rated + and the case in which no definite difference from the control was found was rated –. As shown in [Table 7], the compound of the invention was found to have high nerve growth factor agonist activity.

TABLE 7

Neurite extending activity in the rat pheocromocytoma cell line

| Example No. | Concentration of compound ($\mu$M) | Enhancement of NGF activity |
|---|---|---|
| 1 | 1 | + |
|  | 0.1 | + |
|  | 0.01 | + |
| 4 | 1 | + |
|  | 0.1 | – |
|  | 0.01 | – |
| 5 | 1 | + |
|  | 0.1 | – |
|  | 0.01 | – |
| 11 | 1 | + |
|  | 0.1 | + |
|  | 0.01 | + |
| 12 | 1 | + |
|  | 0.1 | + |
|  | 0.01 | – |
| 16 | 1 | + |
|  | 0.1 | + |
|  | 0.01 | + |
| 124 | 1 | + |
|  | 0.1 | – |
|  | 0.01 | – |

FORMULATION EXAMPLE 1

By mixing the following components (1)–(6) and compressing the mixture with a tablet machine, about 1,000 uncoated tablets measuring 6.5 mm in diameter and containing 5 mg of the compound of Example 1 per tablet can be manufactured. Then, by coating those tablets using the following components (7)–(9), film-coated tablets each measuring 6.6 mm in diameter can be provided.

| (1) Compound of Example 1 | 5 g |
|---|---|
| (2) Lactose | 82.5 g |
| (3) Hydroxypropylcellulose | 2.8 g |
| (4) Magnesium stearate | 0.4 g |
| (5) Hydroxypropylmethylcellulose 2910 | 2.994 g |
| (6) Corn starch | 19.3 g |
| (7) Macrogol 6000 | 0.6 g |
| (8) Titanium dioxide | 0.4 g |
| (9) Iron sesquioxide | 0.006 g |

FORMULATION EXAMPLE 2

By suspending or dissolving the following components (1), (3), (4), (5), (6), (7), and (8) in purified water and coating a granular core material (2), shown below, with the suspension or solution, uncoated fine granules can be provided. By coating these fine granules using the following components (9)–(11) and mixing the resulting coated granules with the following component (12), about 500 g of 1% fine granules of the compound of Example 1 can be manufactured. The fine granules are dispensed in packets, 500 mg per packet.

| (1) Compound of Example 1 | 5 g |
|---|---|
| (2) Lactose-crystalline cellulose (granular) | 330 g |
| (3) D-mannitol | 29 g |
| (4) Low-substitution-degree hydroxypropyl-cellulose | 20 g |
| (5) Talc | 25 g |
| (6) Hydroxypropylcellulose | 50 g |
| (7) Aspartame | 3 g |
| (8) Dipotassium glycyrrhizinate | 3 g |
| (9) Hydroxypropylmethylcellulose 2910 | 30 g |
| (10) Titanium dioxide | 3.5 g |
| (11) Yellow iron sesquioxide | 0.5 g |
| (12) Light silicic anhydride | 1 g |

INDUSTRIAL APPLICABILITY

The cell differentiation inducing composition or the cell differentiation factor activity enhancing composition comprising compound [I] or salt according to the present invention has high bone morphogenetic protein-like activity or enhances bone morphogenetic protein activity and, as such, acts on bone tissues to increase bone mass and bone strength. Therefore, the composition of the invention is of value for the treatment and prevention of bone diseases such as osteoporosis and for the acceleration of bone fracture healing and bone remodeling. Furthermore, this composition has neurotrophic factor-like activity or enhancing neurotrphoc factor activity and, as such, finds application in the treatment and prevention of various nerve diseases such as Alzheimer type dementia, senile dementia in general, motor neuronal diseases (e.g. amyotrophic lateral sclerosis) and diabetic peripheral neuropathy, among other diseases.

We claim:
1. A compound of the formula:

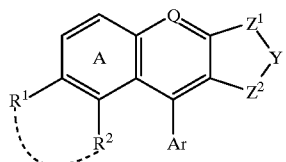

wherein

Q is an optionally substituted carbon atom;

Y is an optionally substituted imino group;

$Z^1$

$Z^2$ is a $C_{1-3}$ alkylene group optionally substituted by hydroxy or oxo;

Ar is an optionally substituted carbocyclic group or an optionally substituted heterocyclic group;

$R^1$ and $R^2$ taken together with adjacent —C=C— form a $C_{1-6}$ alkyleneoxy or $C_{1-6}$ alkylenedioxy group; and ring A is a benzene ring which may be substituted in addition to $R^1$ and $R^2$;

or a salt thereof.

2. A compound as claimed in claim 1 wherein

Q is (A) $CR^4$ wherein $R^4$ is (1) a hydrogen atom, (2) a halogen atom, (3) a $C_{1-16}$ acyclic or cyclic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{3-6}$ cycloalkyl, (vii) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (viii) a $C_{1-6}$ alkylthio optionally having 1 to 3 halogen atoms, (ix) a hydroxyl, (x) an amino, (xi) a mono-$C_{1-6}$ alkylamino, (xii) a di-$C_{1-6}$ alkylamino, (xiii) a $C_{1-6}$ alkyl-carbonyl, (xiv) a $C_{1-6}$ alkyl-carbonyloxy, (xv) a $C_{1-6}$ alkyl-carbonyloxy-$C_{1-3}$ alkyl, (xvi) a carboxyl, (xvii) a $C_{1-6}$ alkoxy-carbonyl, (xviii) a mono-$C_{1-6}$ alkylamino-carbonyl, (xix) a di-$C_{1-6}$ alkylamino-carbonyl, (xx) a carbamoyl, (xxi) a mono-$C_{1-6}$ alkyl-carbamoyl, (xxii) a di-$C_{1-6}$ alkyl-carbamoyl, (xxiii) a sulfo, (xxiv) a $C_{1-6}$ alkylsulfonyl, (xxv) a $C_{6-10}$ aryl, (xxvi) a $C_{6-10}$ aryloxy, (xxvii) a 5- to 7-membered heterocyclic group having 1 to 4 hetero atoms selected from the group consisting of nitrogen, oxygen and sulfur, said heterocyclic group being optionally fused with a benzene ring, (xxviii) thiocarbamoyl, (xxix) mono-$C_{1-6}$ alkylthio-carbamoyl, (xxx) di-$C_{1-6}$ alkylthio-carbamoyl, (xxxi) $C_{6-10}$ aryl-carbamoyl and (xxxii) $C_{6-10}$ aryl-thiocarbamoyl; or (4) a hydroxyl group which may be substituted with a $C_{1-16}$ acyclic or cyclic hydrocarbon group which may have 1 to 5 substituents selected from the group consisting of (i) a halogen, (ii) a $C_{1-3}$ alkylenedioxy, (iii) a nitro, (iv) a cyano, (v) a C1,6 alkyl optionally having 1 to 3 halogen atoms, (vi) a $C_{3-6}$ cycloalkyl, (vii) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (viii) a $C_{1-6}$ alkylthio optionally having 1 to 3 halogen atoms, (ix) a hydroxyl, (x) an amino, (xi) a mono-$C_{1-6}$ alkylamino, (xii) a di-$C_{1-6}$ alkylamino, (xiii) a $C_{1-6}$ alkyl-carbonyl, (xiv) a $C_{1-6}$ alkyl-carbonyloxy, (xv) a $C_{1-6}$ alkyl-carbonyloxy-$C_{1-3}$ alkyl, (xvi) a carboxyl, (xvii) a $C_{1-6}$ alkoxy-carbonyl, (xviii) a mono-$C_{1-6}$ alkylamino-carbonyl, (xix) a di-$C_{1-6}$ alkylamino-carbonyl, (xx) a carbamoyl, (xxi) a mono-$C_{1-6}$ alkyl-carbamoyl, (xxii) a di-$C_{1-6}$ alkyl-carbamoyl, (xxiii) a sulfo, (xxiv) a $C_{1-6}$ alkylsulfonyl, (xxv) a $C_{6-10}$ aryl, (xxvi) a $C_{6-10}$ aryloxy, (xxvii) a 5- to 7-membered heterocyclic group having 1 to 4 hetero atoms selected from the group consisting of nitrogen, oxygen and sulfur, said heterocyclic group being optionally fused with a benzene ring, (xxviii) thiocarbamoyl, (xxix) mono-$C_{1-6}$ alkylthio carbamoyl, (xxx) di-$C_{1-6}$ alkylthio-carbamoyl, (xxxi) $C_{6-10}$ aryl-carbamoyl and (xxxii) $C_{6-10}$ aryl-thiocarbamoyl;

Y is =$NR^5$ wherein $R^5$ is (i) a hydrogen, (ii) a $C_{1-6}$ acyclic or cyclic hydrocarbon group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a $C_{1-6}$ alkyl-carbonyl, (n) a $C_{1-6}$ alkyl carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from the group consisting of nitrogen, oxygen and sulfur, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl, (iii) —(C=O)—$R^7$ wherein $R^7$ is hydrogen or a $C_{1-6}$ acyclic or cyclic hydrocarbon group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a 5- or 6-membered cyclic amino optionally having hydroxyl or oxo, (n) —NHCOOR$^6$ wherein $R^6$ is a $C_{1-6}$ acyclic or cyclic hydrocarbon group which may have 1 to 5 substituents selected from the group consisting of (n-1) a halogen, (n-2) a $C_{1-3}$ alkylenedioxy, (n-3) a nitro, (n-4) a cyano, (n-5) a $C_{1-6}$ alkyl optionally having 1 to 3 halogen atoms, (n-6) a $C_{3-6}$ cycloalkyl, (n-7) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (n-8) a $C_{1-6}$ alkylthio optionally having 1 to 3 halogen atoms, (n-9) a hydroxyl, (n-10) an amino, (n-11) a mono-$C_{1-6}$ alkylamino, (n-12) a di-$C_{1-6}$ alkylamino, (n-13) a $C_{1-6}$ alkyl-carbonyl, (n-14) a $C_{1-6}$ alkyl-carbonyloxy, (n-15) a $C_{1-6}$ alkyl-carbonyloxy-$C_{1-3}$ alkyl, (n-16) a carboxyl, (n-17) a $C_{1-6}$ alkoxy-carbonyl, (n-18) a mono-$C_{1-6}$ alkylamino-carbonyl, (n-19) a di-$C_{1-6}$ alkylamino-carbonyl, (n-20) a carbamoyl, (n-21) a mono-$C_{1-6}$ alkyl-carbamoyl, (n-22) a di-$C_{1-6}$ alkyl-carbamoyl, (n-23) a sulfo, (n-24) a $C_{1-6}$ alkylsulfonyl, (n-25) a $C_{6-10}$ aryl, (n-26) a $C_{6-10}$ aryloxy, (n-27) a 5- to 7-membered heterocyclic group having 1 to 4 hetero atoms selected from the group consisting of nitrogen, oxygen and sulfur, said heterocyclic group being optionally fused with a benzene ring, (n-28) thiocarbamoyl, (n-29) mono-$C_{1-6}$ alkylthio-carbamoyl, (n-30) di-$C_{1-6}$ alkylthio-carbamoyl, (n-31) $C_{6-10}$ aryl-carbamoyl and (n-32) $C_{6-10}$ aryl-thiocarbamoyl, (o) —NHCONHR$^6$ (p) —NHCOR$^6$, (q) —NHSO$_2$R$^6$, (r) a $C_{1-6}$ alkyl-carbonyl, (s) a $C_{1-6}$ alkyl-carbonyloxy, (t) a $C_{1-6}$ alkyl-carbonyloxy-$C_{1-3}$ alkyl, (u) a carboxyl, (v) a $C_{1-6}$ alkoxy-carbonyl, (w) a mono-$C_{1-6}$ alkylamino-carbonyl, (x) a di-$C_{1-6}$ alkylamino-carbonyl, (y) a carbamoyl, (z) a mono-$C_{1-6}$ alkyl-carbamoyl, (aa) a di-$C_{1-6}$ alkyl-carbamoyl, (bb) a sulfo, (cc) a $C_{1-6}$ alkylsulfonyl, (dd) a $C_{6-10}$ aryl, (ee) a $C_{6-10}$ aryloxy, (ff) a 5- to 7-membered heterocyclic group having 1 to 4 hetero atoms selected from the group consisting of nitrogen, oxygen and sulfur, said heterocyclic group being optionally fused with a benzene ring, (gg) $C_{7-11}$ aralkyloxy-carbonyl, (hh) thiocarbamoyl, (ii) mono-$C_{1-6}$ alkylthio-carbamoyl, (jj) di-$C_{1-6}$ alkylthio-carbamoyl, (kk) $C_{6-10}$ aryl-carbamoyl and (11) $C_{6-10}$ aryl-thiocarbamoyl, (iv) —SO$_2$—$R^7$; (v) —SO—$R^7$, (vi) —(C=O)NR$^8$—$R^7$ wherein $R^8$ is hydrogen or $C_{1-6}$ alkyl or (vii) —(C=O)O—$R^7$;

Ar is (1) a 3- to 14-membered monocyclic or fused polycyclic nonaromatic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{2-6}$ alkenyl optionally having 1 to 3 halogen atoms, (vii) a $C_{2-6}$ alkynyl optionally having 1 to 3 halogen atoms, (viii) a $C_{3-6}$ cycloalkyl, (ix) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (x) a $C_{1-6}$ alkylthio optionally having 1 to 3 halogen atoms, (xi) a hydroxyl, (xii) an amino, (xiii) a mono-$C_{1-6}$ alkylamino, (xiv) a di-$C_{1-6}$ alkylamino, (xv) a 5- or 6-membered cyclic amino, (xvi) —NHCOOR$^6$, (xvii) —NHCONHR$^6$, (xviii) —NHCOR$^6$, (xix) —NHSO$_2$R$^6$, (xx) a $C_{1-6}$ alkyl-carbonyl, (xxi) a carboxyl, (xxii) a $C_{1-6}$ alkoxy-carbonyl, (xxiii) a carbamoyl, (xxiv) a mono-$C_{1-6}$ alkyl-carbamoyl, (xxv) a di-$C_{1-6}$ alkyl-carbamoyl, (xxvi) a $C_{6-10}$ aryl-carbamoyl, (xxvii) a sulfo, (xxviii) a $C_{1-6}$ alkylsulfonyl, (xxvix) a $C_{6-10}$ aryl, (xxx) a $C_{6-10}$ aryloxy, (xxxi) $C_{7-16}$ aralkyloxy, (xxxii) thiocarbamoyl, (xxxiii) mono-$C_{1-6}$ alkylthio-carbamoyl, (xxxiv) di-$C_{1-6}$ alkylthio-carbamoyl, (xxxv) $C_{6-10}$ aryl-carbamoyl and (XXXVi) $C_{6-10}$ aryl-thiocarbamoyl, (2) a 6- to 14-membered monocyclic or fused polycyclic aromatic hydrocarbon group, which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{2-6}$ alkenyl optionally having 1 to 3 halogen atoms, (vii) a $C_{2-6}$ alkynyl optionally having 1 to 3 halogen atoms, (viii) a $C_{3-6}$ cycloalkyl, (ix) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (x) a $C_{1-6}$ alkylthio optionally having 1 to 3 halogen atoms, (xi) a hydroxyl, (xii) an amino, (xiii) a mono-$C_{1-6}$ alkylamino, (xiv) a di-$C_{1-6}$ alkylamino, (xv) a 5- or 6-membered cyclic amino, (xvi) —NHCOOR$^6$, (xvii) —NHCONHR$^6$, (xviii) —NHCOR$^6$, (xix) —NHSO$_2$R$^6$, (xx) a $C_{1-6}$ alkyl-carbonyl, (xxi) a carboxyl, (xxii) a $C_{1-6}$ alkoxy-carbonyl, (xxiii) a carbamoyl, (xxiv) a mono-$C_{1-6}$ alkyl-carbamoyl, (xxv) a di-$C_{1-6}$ alkyl-carbamoyl, (xxvi) a $C_{6-10}$ aryl-carbamoyl, (xxvii) a sulfo, (xxviii) a $C_{1-6}$ alkylsulfonyl, (xxvix) a $C_{6-10}$ aryl, (xxx) a $C_{6-10}$ aryloxy, (xxxi) $C_{7-16}$ aralkyloxy, (xxxii) thiocarbamoyl, (xxxiii) mono-$C_{1-6}$ alkylthio-carbamoyl, (xxxiv) di-$C_{1-6}$ alkylthio-carbamoyl, (xxxv) $C_{6-10}$ aryl-carbamoyl and (XXXVi) $C_{6-10}$ aryl-thiocarbamoyl, (3) a 5- to 10-membered monocyclic nonaromatic heterocyclic group having 1 to 4 hetero atoms selected from the group consisting of nitrogen, oxygen and sulfur, said heterocyclic group being optionally fused with a benzene ring, which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{2-6}$ alkenyl optionally having 1 to 3 halogen atoms, (vii) a $C_{2-6}$ alkynyl optionally having 1 to 3 halogen atoms, (viii) a $C_{3-6}$ cycloalkyl, (ix) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (x) a $C_{1-6}$ alkylthio optionally having 1 to 3 halogen atoms, (xi) a hydroxyl, (xii) an amino, (xiii) a mono-$C_{1-6}$ alkylamino, (xiv) a di-$C_{1-6}$ alkylamino, (xv) a 5- or 6-membered cyclic amino, (xvi) —NHCOOR$^6$, (xvii) —NHCONHR$^6$, (xviii) —NHCOR$^6$, (xix) —NHSO$_2$R$^6$, (xx) a $C_{1-6}$ alkyl-carbonyl, (xxi) a carboxyl group, (xxii) a $C_{1-6}$ alkoxy-carbonyl, (xxiii) a carbamoyl, (xxiv) a mono-$C_{1-6}$ alkyl-carbomoyl, (xxv) a di-$C_{1-6}$ alkyl-carbamoyl, (xxvi) a $C_{6-10}$ aryl-carbamoyl, (xxvii) a sulfo, (xxviii) a $C_{1-6}$ alkylsulfonyl, (xxix) a $C_{6-10}$ aryl, (xxx) a $C_{6-10}$ aryloxy, (xxxi) $C_{7-16}$ aralkyloxy, (xxxii) thiocarbamoyl, (xxxiii) mono-$C_{1-6}$ alkylthio-carbamoyl, (xxxiv) di-$C_{1-6}$ alkylthio-carbamoyl, (xxxv) $C_{6-10}$ aryl-carbamoyl and (xxxvi) $C_{6-10}$ aryl-thiocarbamoyl, or (4) 5- to 10-membered monocyclic aromatic heterocyclic group having 1 to 4 hetero atoms selected from the group consisting of nitrogen, oxygen and sulfur, said heterocyclic group being optionally fused with a benzene ring, which may have 1 to 5 substituents selected from a group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{2-6}$ alkenyl optionally having 1 to 3 halogen atoms, (vii) a $C_{2-6}$ alkynyl optionally having 1 to 3 halogen atoms, (viii) a $C_{3-6}$ cycloalkyl, (ix) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (x) a $C_{1-6}$ alkylthio optionally having 1 to 3 halogen atoms, (xi) a hydroxyl, (xii) an amino, (xiii) a mono-$C_{1-6}$ alkylamino, (xiv) a di-$C_{1-6}$ alkylamino, (xv) a 5- or 6-membered cyclic amino, (xvi) —NHCOOR$^6$, (xvii) —NHCONHR$^6$, (xviii) —NHCOR$^6$, (xix) —NHSO$_2$R$^6$, (xx) a $C_{1-6}$ alkyl-carbonyl, (xxi) a carboxyl, (xxii) a $C_{1-6}$ alkoxy-carbonyl, (xxiii) a carbamoyl, (xxiv) a mono-$C_{1-6}$ alkyl-carbamoyl, (xxv) a di-$C_{1-6}$ alkyl-carbamoyl, (xxvi) a $C_{6-10}$ aryl-carbamoyl, (xxvii) sulfo, (xxviii) a $C_{1-6}$ alkylsulfonyl, (xxix) a $C_{6-10}$ aryl, (xxx) a $C_{6-10}$ aryloxy, (xxxi) $C_{7-16}$ aralkyloxy, (xxxii) thiocarbamoyl, (xxxiii) mono-$C_{1-6}$ alkylthio-carbamoyl, (xxxiv) di-$C_{1-6}$ alkylthio-carbamoyl, (xxxv) $C_{6-10}$ aryl-carbamoyl and (xxxvi) $C_{6-10}$ aryl-thiocarbamoyl;

$R^1$ and $R^2$ together form a $C_{1-6}$ alkyleneoxy or $C_{1-6}$ alkylenedioxy group;

ring A is a benzene ring which may have 1 or 2 substituents selected from the group consisting of (1) hydrogen, (2) a halogen, (3) a $C_{1-16}$ acyclic or cyclic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{3-6}$ cycloalkyl, (vii) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (viii) a $C_{1-6}$ alkylthio optionally having 1 to 3 halogen atoms, (ix) a hydroxyl, (x) an amino, (xi) a mono-$C_{1-6}$ alkylamino, (xii) a di-$C_{1-6}$ alkylamino, (xiii) a $C_{1-6}$ alkyl-carbonyl, (xiv) a $C_{1-6}$ alkyl-carbonyloxy, (xv) a $C_{1-6}$ alkyl-carbonyloxy-$C_{1-3}$ alkyl, (xvi) a carboxyl, (xvii) a $C_{1-6}$ alkoxy-carbonyl, (xviii) a mono-$C_{1-6}$ alkylamino-carbonyl, (xix) a di-$C_{1-6}$ alkylamino-carbonyl, (xx) a carbamoyl, (xxi) a mono-$C_{1-6}$ alkyl-carbamoyl, (xxii) a di-$C_{1-6}$ alkyl-carbamoyl, (xxiii) a sulfo, (xxiv) a $C_{1-6}$ alkylsulfonyl, (xxv) a $C_{6-10}$ aryl, (xxvi) a $C_{6-10}$ aryloxy, (xxvii) a 5- to 7-membered heterocyclic group having 1 to 4 hetero atoms selected from the group consisting of nitrogen, oxygen and sulfur, said heterocyclic group being optionally fused with a benzene ring, (xxviii) thiocarbamoyl, (xxix) mono-$C_{1-6}$ alkylthio-carbamoyl, (xxx) di-$C_{1-6}$ alkylthio-carbamoyl, (xxxi) $C_{6-10}$ aryl-carbamoyl and (xxxii) $C_{6-10}$ aryl-thiocarbamoyl.

3. A compound of the formula:

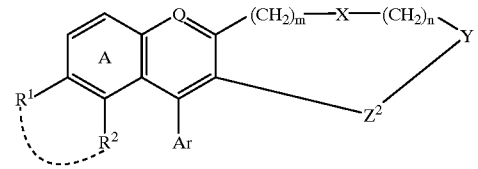

wherein

Q is CR$^4$ wherein R$^4$ is (i) a hydrogen atom, (ii) a halogen atom, (iii) an optionally substituted hydrocarbon group or (iv) an optionally substituted hydroxyl group;

X is C═O;

Y is NR$^5$ wherein R$^5$ is (i) a hydrogen atom, (ii) an optionally substituted hydrocarbon group or (iii) an acyl group;

$Z^2$ is a $C_{1-3}$ alkylene group optionally substituted by hydroxy or oxo;

m and n each represent 0;

Ar is an optionally substituted carbocyclic group or an optionally substituted heterocyclic group;

$R^1$ and $R^2$ together with adjacent —C═C— form a $C_{1-6}$ alkyleneoxy or $C_{1-6}$ alkylenedioxy group; and ring A is a benzene ring which may be substituted in addition to $R^1$ and $R^2$.

4. A compound as claimed in claim 3 wherein Q is CR$^4$ wherein R$^4$ is (1) a hydrogen atom, (2) a halogen atom, (3)

a $C_{1-16}$ acyclic or cyclic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{3-6}$ cycloalkyl, (vii) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (viii) a $C_{1-6}$ alkylthio optionally having 1 to 3 halogen atoms, (ix) a hydroxyl, (x) an amino, (xi) a mono-$C_{1-6}$ alkylamino, (xii) a di-$C_{1-6}$ alkylamino, (xiii) a $C_{1-6}$ alkyl-carbonyl, (xiv) a $C_{1-6}$ alkyl-carbonyloxy, (xv) a $C_{1-6}$ alkyl-carbonyloxy-$C_{1-3}$ alkyl, (xvi) a carboxyl, (xvii) a $C_{1-6}$ alkoxy-carbonyl, (xviii) a mono-$C_{1-6}$ alkylamino-carbonyl, (xix) a di-$C_{1-6}$ alkylamino-carbonyl, (xx) a carbamoyl, (xxi) a mono-$C_{1-6}$ alkyl-carbamoyl, (xxii) a di-$C_{1-6}$ alkyl-carbamoyl, (xxiii) a sulfo, (xxiv) a $C_{1-6}$ alkylsulfonyl, (xxv) a $C_{6-10}$ aryl, (xxvi) a $C_{6-10}$ aryloxy, (xxvii) a 5- to 7-membered heterocyclic group having 1 to 4 hetero atoms selected from nitrogen, oxygen and sulfur in addition to carbon atoms, said heterocyclic group being optionally fused with a benzene ring, (xxviii) thiocarbamoyl, (xxix) mono-$C_{1-6}$ alkylthio-carbamoyl, (xxx) di-$C_{1-6}$ alkylthio-carbamoyl, (xxxi) $C_{6-10}$ aryl-carbamoyl and (xxxii) $C_{6-10}$ aryl-thiocarbamoyl, or (4) a hydroxyl group which may be substituted with a $C_{1-16}$ acyclic or cyclic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{3-6}$ cycloalkyl, (vii) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (viii) a $C_{1-6}$ alkylthio optionally having 1 to 3 halogen atoms, (ix) a hydroxyl, (x) an amino, (xi) a mono-$C_{1-6}$ alkylamino, (xii) a di-$C_{1-6}$ alkylamino, (xiii) a $C_{1-6}$ alkyl-carbonyl, (xiv) a $C_{1-6}$ alkyl-carbonyloxy, (xv) a $C_{1-6}$ alkyl-carbonyloxy-$C_{1-3}$ alkyl, (xvi) a carboxyl, (xvii) a $C_{1-6}$ alkoxy-carbonyl, (xviii) a mono-$C_{1-6}$ alkylamino-carbonyl, (xix) a di-$C_{1-6}$ alkylamino-carbonyl, (xx) a carbamoyl, (xxi) a mono-$C_{1-6}$ alkyl-carbamoyl, (xxii) a di-$C_{1-6}$ alkyl-carbamoyl, (xxiii) a sulfo, (xxiv) a $C_{1-6}$ alkylsulfonyl, (xxv) a $C_{6-10}$ aryl, (xxvi) a $C_{6-10}$ aryloxy, (xxvii) a 5- to 7-membered heterocyclic group having 1 to 4 hetero atoms selected from nitrogen, oxygen and sulfur in addition to carbon atoms, said heterocyclic group being optionally fused with a benzene ring, (xxviii) thiocarbamoyl, (xxix) mono-$C_{1-6}$ alkylthio-carbamoyl, (xxx) di-$C_{1-6}$ alkylthio-carbamoyl, (xxxi) $C_{6-10}$ aryl-carbamoyl and (xxxii) $C_{6-10}$ aryl-thiocarbamoyl; Y is $NR^5$ wherein $R^5$ is (i) a hydrogen, (ii) a $C_{1-16}$ acyclic or cyclic hydrocarbon group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (l) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from nitrogen, oxygen and sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl, (iii) —(C=O)—$R^7$ wherein $R^7$ is a hydrogen or a $C_{1-16}$ acyclic or cyclic hydrocarbon group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamiho, (l) a di-$C_{1-6}$ alkylamino, (m) 5- or 6-membered cyclicamino optionally having carboxyl or oxo, (n) —NHCOOR$^6$ wherein $R^6$ is a $C_{1-16}$ acyclic or cyclic hydrocarbon group which may have 1 to 5 substituents selected from the group consisting of (n-1) a halogen, (n-2) a $C_{1-3}$ alkylenedioxy, (n-3) a nitro, (n-4) a cyano, (n-5) a $C_{1-6}$ alkyl optionally having 1 to 3 halogen atoms, (n-6) a $C_{3-6}$ cycloalkyl, (n-7) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (n-8) a C1-6 alkylthio optionally having 1 to 3 halogen atoms, (n-9) a hydroxyl, (n-10) an amino, (n-11) a mono-$C_{1-6}$ alkylamino, (n-12) a di-$C_{1-6}$ alkylamino, (n-13) a $C_{1-6}$ alkyl-carbonyl, (n-14) a $C_{1-6}$ alkyl-carbonyloxy, (n-15) a $C_{1-6}$ alkyl-carbonyloxy-$C_{1-3}$ alkyl, (n-16) a carboxyl, (n-17) a $C_{1-6}$ alkoxy-carbonyl, (n-18) a mono-$C_{1-6}$ alkylamino-carbonyl, (n-19) a di-$C_{1-6}$ alkylamino-carbonyl, (n-20) a carbamoyl, (n-21) a mono-$C_{1-6}$ alkyl-carbamoyl, (n-22) a di-$C_{1-6}$ alkyl-carbamoyl, (n-23) a sulfo, (n-24) a $C_{1-6}$ alkylsulfonyl, (n-25) a $C_{6-10}$ aryl, (n-26) a $C_{6-10}$ aryloxy, (n-27) a 5- to 7-membered heterocyclic group having 1 to 4 hetero atoms selected from nitrogen, oxygen and sulfur in addition to carbon atoms, said heterocyclic group being optionally fused with a benzene ring, (n-28) thiocarbamoyl, (n-29) mono-$C_{1-6}$ alkylthio-carbamoyl, (n-30) di-$C_{1-6}$ alkylthio-carbamoyl, (n-31) $C_{6-10}$ aryl-carbamoyl and (n-32) $C_{6-10}$ aryl-thiocarbamoyl, (o) —NHCONHR$^6$ wherein $R^6$ is as defined above, (p) —NHCOR$^6$ wherein $R^6$ is as defined above, (q) —NHSO$_2$R$^6$ wherein $R^6$ is as defined above, (r) a $C_{1-6}$ alkyl-carbonyl, (s) a $C_{1-6}$ alkyl-carbonyloxy, (t) a $C_{1-6}$ alkyl-carbonyloxy-$C_{1-3}$ alkyl, (u) a carboxyl, (v) a $C_{1-6}$ alkoxy-carbonyl, (w) a mono-$C_{1-6}$ alkylamino-carbonyl, (x) a di-$C_{1-6}$ alkylamino-carbonyl, (y) a carbamoyl, (z) a mono-$C_{1-6}$ alkyl-carbamoyl, (aa) a di-$C_{1-6}$ alkyl-carbamoyl, $C_{6-10}$ aryl-carbamoyl, (bb) a sulfo, (cc) a $C_{1-6}$ alkylsulfonyl, (dd) a $C_{6-10}$ aryl, (ee) a $C_{6-10}$ aryloxy, (ff) a 5- to 7-membered heterocyclic group having 1 to 4 hetero atoms selected from nitrogen, oxygen and sulfur in addition to carbon atoms, said heterocyclic group being optionally fused with a benzene ring, (gg) $C_{7-11}$ aralkyloxy-carbonyl, (hh) thiocarbamoyl, (ii) mono-$C_{1-6}$ alkylthio-carbamoyl, (jj) di-$C_{1-6}$ alkylthio-carbamoyl, (kk) $C_{6-10}$ aryl-carbamoyl and (11) $C_{6-10}$ aryl-thiocarbamoyl, (iv) —SO$_2$—$R^7$ wherein $R^7$ is as defined above, (v) —SO—$R^7$ wherein $R^7$ is as defined above, (vi) —(C=O)$NR^8$—$R^7$ wherein $R^7$ is as defined above, $R^8$ is hydrogen or $C_{1-6}$ alkyl or (vii) —(C=O)O—$R^7$ wherein $R^7$ is as defined above.

5. A compound as claimed in claim 3 wherein Ar is 3- to 14-membered aromatic group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{2-6}$ alkenyl optionally having 1 to 3 halogen atoms, (vii) a $C_{2-6}$ alkynyl optionally having 1 to 3 halogen atoms, (viii) a $C_{3-6}$ cycloalkyl, (ix) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (x) a $C_{1-6}$ alkylthio optionally having 1 to 3 halogen atoms, (xi) a hydroxyl, (xii) an amino, (xiii) a mono-$C_{1-6}$ alkylamino, (xiv) a di-$C_{1-6}$ alkylamino, (xv) 5- or 6-membered cyclic amino, (xvi) —NHCOO$R^6$ wherein $R^6$ is a $C_{1-16}$ acyclic or cyclic hydrocarbon group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (1) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from the group consisting of a nitrogen, an oxygen and a sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl, (xvii) —NHCON$HR^6$ wherein $R^6$ is as defined above, (xviii) —NHCO$R^6$ wherein R is as defined above, (xix) —NHSO$_2R^6$ wherein $R^6$ is as defined above, (xx) a $C_{1-6}$ alkyl-carbonyl, (xxi) a carboxyl, (xxii) a $C_{1-6}$ alkoxy-carbonyl, (xxiii) a carbamoyl, (xxiv) a mono-$C_{1-6}$ alkyl-carbamoyl, (xxv) a di-$C_{1-6}$ alkyl-carbamoyl, (xxvi) a $C_{6-10}$ aryl-carbamoyl, (xxvii) a sulfo, (xxviii) a $C_{16}$ alkylsulfonyl, (xxix) a $C_{6-10}$ aryl, (xxx) a $C_{6-10}$ aryloxy, (xxxi) $C_{7-16}$ aralkyloxy, (xxxii) thiocarbamoyl, (xxxiii) mono-$C_{1-6}$ alkylthio-carbamoyl, (xxxiv) di-$C_{1-6}$ alkylthio-carbamoyl, (xxxv) $C_{6-10}$ aryl-carbamoyl and (xxxvi) $C_{6-10}$ aryl-thiocarbamoyl.

6. A compound as claimed in claim 4 wherein Ar is a phenyl group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{2-6}$ alkenyl optionally having 1 to 3 halogen atoms, (vii) a $C_{2-6}$ alkynyl optionally having 1 to 3 halogen atoms, (viii) a $C_{3-6}$ cycloalkyl, (ix) a $C_{1-6}$ alkoxy which may be substituted with amino, mono- or di-$C_{1-6}$ alkylamino or $C_{16}$ alkoxycarbonyl, and optionally having 1 to 3 halogen atoms, (x) a $C_{1-6}$ alkylthio optionally having 1 to 3 halogen atoms, (xi) a hydroxyl, (xii) an amino, (xiii) a mono-$C_{1-6}$ alkylamino, (xiv) a di-$C_{1-6}$ alkylamino, (xv) 5- or 6-membered cyclic amino, (xvi) —NHCOO$R^6$ wherein $R^6$ is a $C_{1-16}$ acyclic or cyclic hydrocarbon group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (1) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 4 hetero atoms selected from the group consisting of a nitrogen, an oxygen and a sulfur in addition to carbon atoms, said heterocyclic group being optionally fused with a benzene ring, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl, (xvii) —NHCON$HR^6$ wherein $R^6$ is as defined above, (xviii) —NHCO$R^6$ wherein $R^6$ is as defined above, (xix) —NHSO$_2R^6$ wherein $R^6$ is as defined above, (xx) a $C_{1-6}$ alkyl-carbonyl, (xxi) a carboxyl, (xxii) a $C_{1-6}$ alkoxy-carbonyl, (xxiii) a carbamoyl, (xxiv) a mono-$C_{1-6}$ alkyl-carbamoyl, (xxv) a di-$C_{1-6}$ alkyl-carbamoyl, (xxvi) a $C_{6-10}$ aryl-carbamoyl, (xxvii) a sulfo, (xxviii) a $C_{1-6}$ alkylsulfonyl, (xxix) a $C_{6-10}$ aryl, (xxx) a $C_{6-10}$ aryloxy, (xxxi) $C_{7-16}$ aralkyloxy, (xxxii) thiocarbamoyl, (xxxiii) mono-$C_{1-6}$ alkylthio-carbamoyl, (xxxiv) di-$C_{1-6}$ alkylthio-carbamoyl, (xxxv) $C_{6-10}$ aryl-carbamoyl and (xxxvi) $C_{6-10}$ aryl-thiocarbamoyl.

7. A compound as claimed in claim 4, wherein is

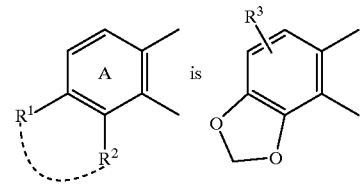

wherein $R^3$ is (1) a hydrogen atom, (2) a halogen atom, (3) a $C_{1-16}$ acyclic or cyclic hydrocarbon group which may have 1 to 5 substituents selected from the group consisting of (a) a halogen, (b) a $C_{1-3}$ alkylenedioxy, (c) a nitro, (d) a cyano, (e) a $C_{1-6}$ alkyl optionally having 1 to 3 halogen atoms, (f) a $C_{3-6}$ cycloalkyl, (g) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (h) a $C_{1-6}$ alkylthio optionally having 1 to 3 halogen atoms, (i) a hydroxyl, (j) an amino, (k) a mono-$C_{1-6}$ alkylamino, (1) a di-$C_{1-6}$ alkylamino, (m) a $C_{1-6}$ alkyl-carbonyl, (n) a $C_{1-6}$ alkyl-carbonyloxy, (o) a $C_{1-6}$ alkyl-carbonyloxy-$C_{1-3}$ alkyl, (p) a carboxyl, (q) a $C_{1-6}$ alkoxy-carbonyl, (r) a mono-$C_{1-6}$ alkylamino-carbonyl, (s) a di-$C_{1-6}$ alkylamino-carbonyl, (t) a carbamoyl, (u) a mono-$C_{1-6}$ alkyl-carbamoyl, (v) a di-$C_{1-6}$ alkyl-carbamoyl, (w) a sulfo, (x) a $C_{1-6}$ alkylsulfonyl, (y) a $C_{6-10}$ aryl, (z) a $C_{6-10}$ aryloxy, (aa) a 5- to 7-membered heterocyclic group having 1 to 3 hetero atoms selected from nitrogen, oxygen and sulfur in addition to carbon atoms, said heterocyclic group being optionally fused with a benzene ring, an optionally substituted hydrocarbon group, (bb) thiocarbamoyl, (cc) mono-$C_{1-6}$ alkylthio-carbamoyl, (dd) di-$C_{1-6}$ alkylthio-carbamoyl, (ee) $C_{6-10}$ aryl-carbamoyl and (ff) $C_{6-10}$ aryl-thiocarbamoyl or (4) a hydroxyl group which may be substituted with a $C_{1-16}$ acyclic or cyclic hydrocarbon group which may have 1 to 5 substituents selected from the group consisting of (i) a halogen, (ii) a $C_{1-3}$ alkylenedioxy, (iii) a nitro, (iv) a cyano, (v) a $C_{1-6}$ alkyl optionally having 1 to 3 halogen atoms, (vi) a $C_{3-6}$ cycloalkyl, (vii) a $C_{1-6}$ alkoxy which may be substituted with amino, mono- or di-$C_{1-6}$ alkylamino or $C_{1-6}$ alkoxycarbonyl, and optionally having 1 to 3 halogen atoms, (viii) a $C_{1-6}$ alkylthio optionally having 1 to 3 halogen atoms, (ix) a hydroxyl, (x) an amino, (xi) a mono-$C_{1-6}$ alkylamino, (xii) a di-$C_{1-6}$ alkylamino, (xiii) a $C_{1-6}$ alkyl-carbonyl, (xiv) a $C_{1-6}$ alkyl-carbonyloxy, (xv) a $C_{1-6}$ alkyl-carbonyloxy-$C_{1-3}$ alkyl, (xvi) a carboxyl, (xvii) a $C_{1-6}$ alkoxy-carbonyl, (xviii) a mono-$C_{1-6}$ alkylamino-carbonyl, (xvix) a di-$C_{1-6}$ alkylamino-carbonyl, (xx) a carbamoyl, (xxi) a mono-$C_{1-6}$ alkyl-carbamoyl, (xxii) a di-$C_{1-6}$ alkyl-carbamoyl, (xxiii) a sulfo, (xxiv) a $C_{1-6}$ alkylsulfonyl, (xxv) a $C_{6-10}$ aryl, (xxvi) a $C_{6-10}$ aryloxy, (xxvii) a 5- to 7-membered heterocyclic group having 1 to 3 hetero atoms selected from nitrogen, oxygen and sulfur in addition to carbon atoms, said heterocyclic group being optionally fused with a benzene ring, (xxviii) thiocarbamoyl, (xxix) mono-$C_{1-6}$ alkylthio-carbamoyl, (xxx) di-$C_{1-6}$ alkylthio-carbamoyl, (xxxi) $C_{6-10}$ aryl-carbamoyl and (xxxii) $C_{6-10}$ aryl-thiocarbamoyl.

8. A compound as claimed in claim 7 wherein $R^3$ is a hydrogen.

9. A compound as claimed in claim 3, wherein

Q is $CR^{4'}$ wherein $R^{4'}$ is (i) a $C_{1-6}$ alkyl group which may be substituted with a di-$C_{1-6}$ alkylamino group, (ii) a halogen atom, or (iii) a $C_{1-6}$ alkoxy group;

Y is $NR^{5'}$ wherein $R^{5'}$ is (i) hydrogen, (ii) a $C_{1-6}$ alkyl group which may be substituted with (a) a morpholino, (b) a carboxyl, (c) a $C_{1-6}$ alkoxy-carbonyl, or (d) a phenyl which may be substituted with $C_{1-6}$ alkoxy, or (iii) $COR^{7''}$ wherein $R^{7''}$ is (a) a hydrogen, (b) $C_{1-6}$ alkyl which may be substituted with a carboxyl or a benzyloxycarbonyl, or a di-$C_{1-6}$ alkylamino;

m and n each represent 0;

$Z^2$ is (1) C=O, (2) $CH_2$, (3) $(CH_2)_2$, (4) $(CH_2)_3$, or (5) CH—OH;

Ar is (1) a phenyl group which may be substituted with (a) a halogen, (b) a $C_{1-6}$ alkylenedioxy, (c) a $C_{1-6}$ alkoxy which may be substituted with (c-1) a halogen, (c-2) a di-$C_{1-6}$ alkylamino or (c-3) a $C_{1-6}$ alkoxy-carbonyl, (d) a $C_{7-11}$ aralkyloxy, (e) $C_{1-6}$ alkyl which may be substituted with a halogen or (f) hydroxyl, (2) an optionally oxidized pyridyl group, or (3) a pyridinium group which may be substituted with $C_{1-6}$ alkyl;

$R^1$ and $R^2$ together with adjacent —C=C— form a $C_{1-6}$ alkylenedioxy group or a $C_{1-6}$ alkyleneoxy group; and ring A is a benzene ring which may have a $C_{1-6}$ alkoxy group in addition to $R^1$ and $R^2$, and a $C_{1-6}$ alkoxy group on ring A and a $C_{1-6}$ alkoxy group of $R^1$ may be taken together form a $C_{1-6}$ alkylenedioxy group.

10. A compound as claimed in claim 9 wherein

Q is CH;

$Z^2$ is $CH_2$; and $R^1$ and $R^2$ together with adjacent —C=C— form a $C_{1-6}$ alkylenedioxy group.

11. A compound as claimed in claim 3, which is 10-(1,3-Benzodioxol-5-yl)-8,9-dihydro-7H-1,3,-benzodioxolo[4,5-f]isoindol-7-one, 11-(1,3-Benzodioxol-5-yl)-7,8,9,10-tetrahydro-1,3,-benzodioxolo[4,5-g]isoquinolin-7-one, 4-(1,3-Benzodioxol-5-yl)-2,3-dihydro-5-methoxy-1H-benz[f]isoindol-1-one, 8,9-Dihydro-10-(4-trifluoromethylphenyl)-7H-1,3-benzodioxolo[4,5-f]isoindol-7-one, 11-(1,3-Benzodioxol-5-yl)-9,10-dihydro-8H-isoindolo[5,6-f]benz[b]-1,4-dioxan-8-one, 10-(4-Fluorophenyl)-8,9,-dihydro-7H-1,3-benzodioxolo[4,5-f]isoindol-7-one, 10-(1,3-Benzodioxol-5-yl)-8,9-dihydro-6-methyl-7H-1,3-benzodioxolo[4,5-f]isoindol-7-one, 10-(4-Fluorophenyl)-8,9-dihydro-6-methyl-7H-1,3-benzodioxolo[4,5-f]isoindol-7-one, 8,9-Dihydro-6-methyl-10-(4-trifluoromethylphenyl)-7H-1,3-benzodioxolo[4,5-f]isoindol-7-one, 10-(1,3-Benzodixol-5-yl)-8,9-dihydro-6-ethyl-7H-1,3-benzodioxolo[4,5-f]isoindol-7-one, 4-(1,3-Benzodioxol-5-yl)-2,3-dihydro-6-methoxy-1H-benz[f]isoindol-1-one, 2,3-Dihydro-6-methoxy-4-(4-methoxypheny)-1H-benz[f]isoindol-1-one, 2,3-Dihydro-6-methoxy-4-(4-trifluoromethylphenyl)-1H-benz[f]isoindol-1-one, 4-(4-Fluorophenyl)-2,3-dihydro-6-methoxy-9-methyl-1H-benz[f]isoindol-1-one, 4-(4-Methoxyphenyl)-2,3-dihydro-6-methoxy-9-methyl-1H-benz[f]isoindol-1-one.

12. A process for producing a compound of the formula:

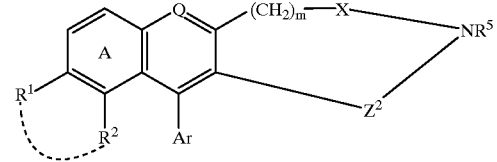

as claim 3, or a salt thereof, which comprises subjecting a compound of the formula:

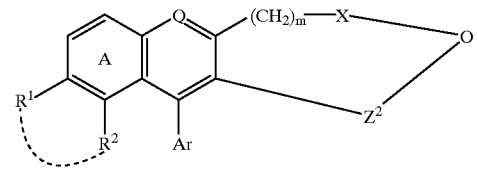

or a salt thereof, to lactamization reaction, optionally followed by introducing a substituent $R^5$ into the resulting lactam.

13. A pharmaceutical composition comprising a compound of claim 1 and a pharmaceutically acceptable carrier.

14. A composition of claim 13 which enhances cell differentiation inducing factor.

15. A process of enhancing cell differentiation inducing factor comprising administering to a patient in need thereof a compound of the formula:

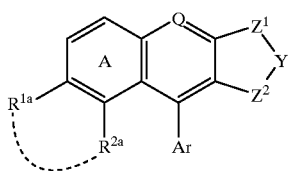

wherein

Q is an optionally substituted carbon atom;

Y is an optionally substituted imino group;

$Z^1$ is

$Z^2$ is a $C_{1-3}$ alkylene group optionally substituted by hydroxy or oxo;

Ar is an optionally substituted carbocyclic group or an optionally substituted heterocyclic group;

one of $R^{1a}$ and $R^{2a}$ is a hydrogen atom, an optionally substituted $C_{1-6}$ alkyl group or an optionally substituted $C_{1-6}$ alkoxy group;

the other of $R^{1a}$ and $R^2$ is an optionally substituted $C_{1-6}$ alkyl group or an optionally substituted $C_{1-6}$ alkoxy group; or $R^{1a}$ and $R^{2a}$ together with adjacent —C=C— form a $C_{1-6}$ alkyleneoxy or $C_{1-6}$ alkylenedioxy group; and ring A is a benzene ring which may be substituted in addition to $R^{1a}$ and $R^{2a}$;

or a salt thereof.

16. A method of treating or preventing neuropathy or bone-and-joint disease which comprises administering to a mammal in need thereof an effective amount of compound of the formula:

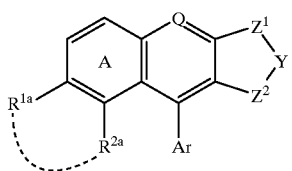

wherein

Q is an optionally substituted carbon atom;

Y is an optionally substituted imino group;

$Z^1$

$Z^2$ is a $C_{1-3}$ alkylene group optionally substituted by hydroxy or oxo;

Ar is an optionally substituted carbocyclic group or an optionally substituted heterocyclic group;

one of $R^{1a}$ and $R^{2a}$ is a hydrogen atom, an optionally substituted $C_{1-6}$ alkyl group or an optionally substituted $C_{1-6}$ alkoxy group;

the other of $R_{1a}$ and $R^{2a}$ is an optionally substituted $C_{1-6}$ alkyl group or an optionally substituted $C_{1-6}$ alkoxy group; or $R^{1a}$ and $R^{2a}$ together with adjacent —C=C— form a $C_{1-6}$ alkyleneoxy or $C_{1-6}$ alkylenedioxy group; and ring A is a benzene ring which may be which may be substituted in addition to $R^{1a}$ and $R^{2a}$;

or a salt thereof.

17. A process of treating or preventing neuropathy or bone-and-joint disease which comprises administering to a patient in need thereof a compound of the formula:

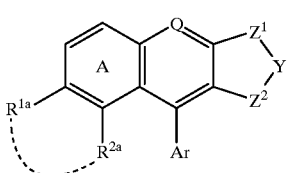

wherein

Q is an optionally substituted carbon atom;

Y is an optionally substituted imino group;

$Z^1$

$Z^2$ is a $C_{1-3}$ alkylene group optionally substituted by hydroxy or oxo;

Ar is an optionally substituted carbocyclic group or an optionally substituted heterocyclic group;

one of $R^{1a}$ and $R^{2a}$ is a hydrogen atom, an optionally substituted $C_{1-6}$ alkyl group or an optionally substituted $C_{1-6}$ alkoxy group;

the other of $R^{1a}$ and $R^{2a}$ is an optionally substituted $C_{1-6}$ alkyl group or an optionally substituted $C_{1-6}$ alkoxy group; or $R^{1a}$ and $R^{2a}$ together with adjacent —C=C— form a $C_{1-6}$ alkyleneoxy or $C_{1-6}$ alkylenedioxy group; and ring A is a benzene ring which may be substituted in addition to $R^{1a}$ and $R^{2a}$;

or a salt thereof.

18. A process of claim 17 which promotes bone formation.

19. A process of claim 17 which inhibits disruption of cartilage.

* * * * *

UNITED STATES PATENT AND TRADEMARK OFFICE
CERTIFICATE OF CORRECTION

PATENT NO. : 6,030,967
DATED : February 29, 2000
INVENTOR(S) : Shogo Marui et al.

It is certified that error appears in the above-identified patent and that said Letters Patent is hereby corrected as shown below:

Title page,
Item [56] FOREIGN PATENT DOCUMENTS

| "2149545 | should read | -- 2-149545 -- |
|---|---|---|
| 2160248 | | 2-160248 |
| 2160583 | | 2-160583 |
| 3081274 | | 3-081274 |
| 4211609 | | 4-211609 |
| 4321681 | | 4-321681 --. |

Column 2,
Line 33, "proteins,." should read -- proteins, --.

Column 7,
Line 28, "even." should read -- even --.

Column 10,
Lines 55-60,

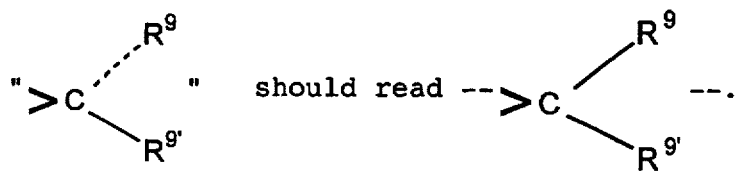

Column 11,
Line 11-15,

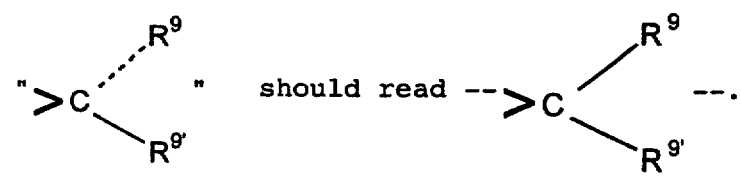

Column 15,
Line 51, "alkoxy;which" should read -- alkoxy which --.

Column 17,
Line 51, "mono-$C_1l_2$" should read -- mono-$C_{1-6}$ --;
Line 59, "aryloxy; (xxvii)" should read -- aryloxy, (xxvii) --.

UNITED STATES PATENT AND TRADEMARK OFFICE
CERTIFICATE OF CORRECTION

PATENT NO. : 6,030,967
DATED : February 29, 2000
INVENTOR(S) : Shogo Marui et al.

It is certified that error appears in the above-identified patent and that said Letters Patent is hereby corrected as shown below:

Column 18
Line 35, "item 3" should read -- item 3, --.

Column 20
Line 44, "item 3" should read -- item 3, --;
Line 46, "item 3" should read -- item 3, --;
Line 49, "item 3" should read -- item 3, --;
Line 51, "item 3" should read -- item 3, --;
Line 54, "item 3" should read -- item 3, --.

Column 21,
Line 38, "item 4" should read -- item 4, --.

Column 23,
Line 24, "item 11" should read -- item 11, --;
Line 28, "item 3" should read -- item 3, --;
Line 29, "CR4" should read -- $CR^{4'}$ --;
Line 66, "item 13" should read -- item 13, --.

Column 29,
Line 6, "$C_{26}$" should read -- $C_{2-6}$ --.

Column 32,
Lines 25-30,

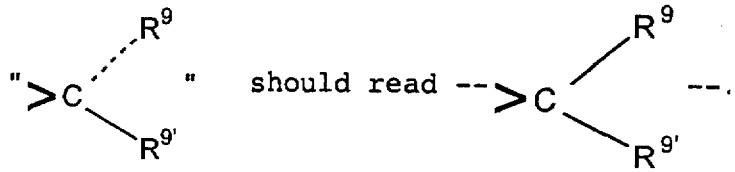

Column 33,
Line 5,

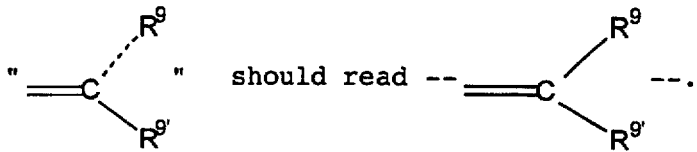

UNITED STATES PATENT AND TRADEMARK OFFICE
CERTIFICATE OF CORRECTION

PATENT NO. : 6,030,967
DATED : February 29, 2000
INVENTOR(S) : Shogo Marui et al.

It is certified that error appears in the above-identified patent and that said Letters Patent is hereby corrected as shown below:

Column 35,
Line 32, "are" should read -- is --; and "the " (second occurrence) should read -- of the --;
Line 35, "preferred" should read -- preferred substituent--;
Line 40, "are should read -- is --.

Column 36,
Line 28, "$CR^4$" should read -- $CR^4$ --;
Line 50, a "C16" should read -- $C_{1-6}$ --.

Column 41,
Lines 15-24,

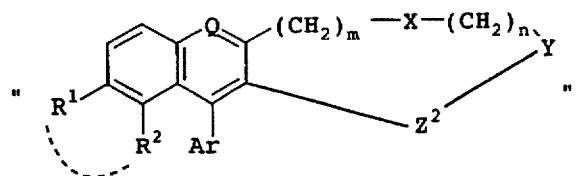

should read

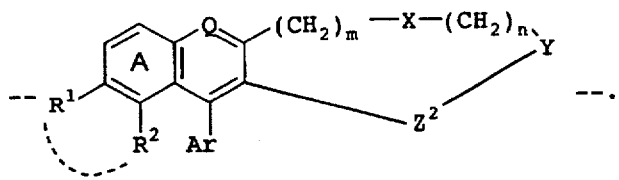

Column 44,
Lines 6-15,

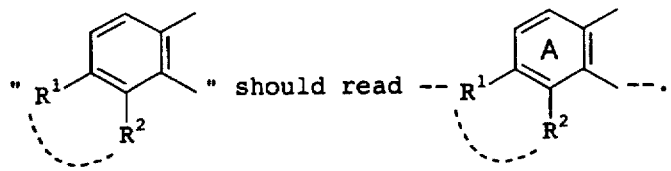

Column 46,
Line 33,"Schema 2. '" should read --Schema 2. ¶
Schema 2 --.

UNITED STATES PATENT AND TRADEMARK OFFICE
CERTIFICATE OF CORRECTION

PATENT NO.   : 6,030,967
DATED        : February 29, 2000
INVENTOR(S)  : Shogo Marui et al.

It is certified that error appears in the above-identified patent and that said Letters Patent is hereby corrected as shown below:

Column 59,
Line 56, "obtained" should read -- obtained.--.

Column 65,
Line 38, 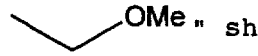

Column 67,
Line 34, "were" should read -- was --.

Column 68,
Line 33, 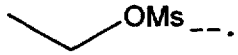

Column 73,
Line 50, "WSC" should read -- To a DME (200 ml) solution of 3-(4-Methylphenyl) propiolic acid (10.0g) was gradually added WSC --.

Column 76,
Line 46, 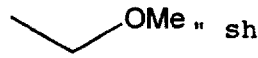

Column 80,
Line 24, "$^9$-(p-" should read -- 9-(p- --.

Column 81,
Line 42, "1048" should read -- 1048, --.

Column 82,
Line 50, "a" should be deleted.

Column 86,
Line 24, "added-to" should read -- added to --.

Column 89,
Line 47, "Methyl .8-" should read -- Methyl 8- --.

UNITED STATES PATENT AND TRADEMARK OFFICE
CERTIFICATE OF CORRECTION

PATENT NO. : 6,030,967
DATED : February 29, 2000
INVENTOR(S) : Shogo Marui et al.

It is certified that error appears in the above-identified patent and that said Letters Patent is hereby corrected as shown below:

Column 97,
Line 65, "6:2.71" should read -- δ:2.71 --.

Column 99,
Line 44, "C:69.11, H:4.25, N:3,84; Found: C:69.06, H:4.19, " should read -- C:69.11%, H:4.25%, N:3.84%; Found C:69.06%, H:4.19%, --;
Line 45, "N:3.77" should read -- N:3.77% --.

Column 100,
Line 26, "H:4.00" should read -- H:4.00% --.

Column 101,
Line 29, "toluene." should read -- toluene --.

Column 109,
Line 29, "1277 cm$^{31}$ $^1$;" should read -- 1277 cm$^{-1}$.
Line 64, "1277 cm$^{31}$ $^1$;" should read -- 1277 cm$^{-1}$. --.

Column 110,
Line 32, "1280 cm$^{31}$ $^1$; " should read -- 1280 cm$^{-1}$. --.

Column 117,
Line 49, "(100 ml)" should read -- (100 ml) --;
Line 52, "(10 ml)" should read -- (100 ml) --.

Column 120,
Line 31, "1228 cm$^{31}$ $^1$; " should read -- 1228 cm$^{-1}$. --.

Column 122,
Line 30, "$_{Calcd.:C:}$ 67.17%," should read -- Calcd.: 67.17%, --.

Column 139,
Line 6, " O'Pr " should read -- OiPr --.

Column 140,
Line 26, "Found:°" should read -- Found: --.

UNITED STATES PATENT AND TRADEMARK OFFICE
CERTIFICATE OF CORRECTION

PATENT NO. : 6,030,967
DATED : February 29, 2000
INVENTOR(S) : Shogo Marui et al.

It is certified that error appears in the above-identified patent and that said Letters Patent is hereby corrected as shown below:

Column 149,
Line 53, "$^{i}Pro^{/}$" should read -- $^{i}Pro^{/}$ --.

Column 155,
Line 23, "in. Example" should read -- in Example --.

Column 157,
Line 64, should read "$C_{20}H_{18}N_2OO.3H_2O$" should read -- $C_{20}H_{18}N_2O_3 \cdot O.3H_2O$ --.

Column 165,
Line 34, "N:4.34%" should read -- N:4.34%. --.

Column 167,
Line 59, "in:Example 11." should read -- in Example 11. --.

Column 173,
Line 61, "neurotr-" should read -- neurotro --;
Line 62, "phoc" should read -- phic --.

Column 174,
Line 3, "claim 1" should read -- claim 1, --;
Lines 15-20, "$Z^1$" should read -- $Z^1$ is --;
Line 64, "C1,6" should read -- $C_{1-6}$ --.

Column 178,
Line 66, "claim 3" should read -- claim 3, --; and "Q" should read -- ¶ Q --.

Column 180,
Line 30, "C1-6" should read -- $C_{1-6}$ --.

Column 181,
Line 5, "claim 3" should read -- claim 3, --
Line 57, "claim 4" should read -- claim 4, --;
Line65, "$C_{16}$" should read -- $C_{1-6}$ --.

UNITED STATES PATENT AND TRADEMARK OFFICE
CERTIFICATE OF CORRECTION

PATENT NO. : 6,030,967
DATED : February 29, 2000
INVENTOR(S) : Shogo Marui et al.

It is certified that error appears in the above-identified patent and that said Letters Patent is hereby corrected as shown below:

Column 182,
Line 40, "is" should be deleted.

Column 183,
Line 4, "ring,an" should read -- ring, an --;
Line 33, "claim 7" should read -- claim 7, --;
Line 64, "claim 9" should read -- claim 9, --.

Column 184,
Line 11, "11-" should read -- ¶ 11 --;
Line 46, "as" should read -- as in --;
Line 35, -one." should read -- one, ¶ or a salt thereof. --;
Line 62, "claim 13" should read -- claim 13, --.

Column 185,
Line 52, "$z^1$" should read -- $z^1$ is --.

Column 186
Line 31, "$Z^1$" should read -- $Z^1$ is --;
Line 55, "claim 17" should read -- claim 17, --;
Line 57, "claim 17" should read -- claim 17, --.

Signed and Sealed this

Fourth Day of December, 2001

Attest:

NICHOLAS P. GODICI
Attesting Officer
Acting Director of the United States Patent and Trademark Office